(12) United States Patent
Suwa

(10) Patent No.: US 12,312,419 B2
(45) Date of Patent: May 27, 2025

(54) HEMIASTERLIN DERIVATIVE HAVING CYSTEINE RESIDUE

(71) Applicant: Sumitomo Pharma Co., Ltd., Osaka (JP)

(72) Inventor: Atsushi Suwa, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 962 days.

(21) Appl. No.: 17/429,429

(22) PCT Filed: Feb. 12, 2020

(86) PCT No.: PCT/JP2020/005307
§ 371 (c)(1),
(2) Date: Aug. 9, 2021

(87) PCT Pub. No.: WO2020/166600
PCT Pub. Date: Aug. 20, 2020

(65) Prior Publication Data
US 2022/0144889 A1 May 12, 2022

(30) Foreign Application Priority Data

Feb. 13, 2019 (JP) .................. 2019-023960

(51) Int. Cl.
| A61K 38/00 | (2006.01) |
| A61K 47/68 | (2017.01) |
| A61P 35/00 | (2006.01) |
| C07K 5/08 | (2006.01) |
| C07K 5/10 | (2006.01) |

(52) U.S. Cl.
CPC ............ *C07K 5/08* (2013.01); *A61K 47/6811* (2017.08); *A61P 35/00* (2018.01); *C07K 5/10* (2013.01); *A61K 38/00* (2013.01)

(58) Field of Classification Search
CPC ........ C07K 5/08; C07K 5/10; A61K 47/6811; A61K 38/00; A61P 35/00
See application file for complete search history.

(56) References Cited

U.S. PATENT DOCUMENTS

| 6,153,590 A | 11/2000 | Andersen et al. |
| 7,579,323 B1 | 8/2009 | Andersen et al. |
| 2004/0229819 A1 | 11/2004 | Kowalczyk et al. |
| 2005/0171014 A1 | 8/2005 | Tarasova et al. |
| 2009/0136526 A1 | 5/2009 | McDonagh et al. |
| 2011/0171125 A1 | 7/2011 | Elkins et al. |
| 2015/0366990 A1 | 12/2015 | Park et al. |
| 2017/0007714 A1 | 1/2017 | Kontermann et al. |
| 2017/0008945 A1 | 1/2017 | Madsen et al. |
| 2017/0335284 A1 | 11/2017 | Masuda et al. |
| 2022/0202948 A1* | 6/2022 | Suwa ............... A61K 47/6849 |

FOREIGN PATENT DOCUMENTS

| CN | 101336249 A | 12/2008 |
| CN | 105358174 A | 2/2016 |
| EP | 3666787 A1 | 6/2020 |
| JP | H11-505211 A | 5/1999 |
| JP | 2005-530717 A | 10/2005 |
| JP | 2007-537136 A | 12/2007 |
| JP | 2011-500725 A | 1/2011 |
| JP | 2012-522513 A | 9/2012 |
| JP | 2016-504355 A | 2/2016 |
| JP | 2016-516063 A | 6/2016 |
| JP | 2017-502047 A | 1/2017 |

(Continued)

OTHER PUBLICATIONS

Extended European Search Report issued in corresponding European Patent Application No. 20755570.7 dated Oct. 10, 2022.

(Continued)

*Primary Examiner* — Amanda L. Aguirre
(74) *Attorney, Agent, or Firm* — Morgan, Lewis & Bockius LLP

(57) ABSTRACT

A compound represented by formula (1):

[Chemical Formula 1]

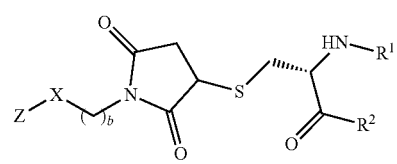

(1)

wherein
b represents an integer of 1 to 5;
X represents —NH— or —CO—;
Z represents a group represented, for example, by formula (Z-1);
$R^1$ represents a hydrogen atom or $(AB)_m$;
AB represents a particular amino acid residue, and when there is a plurality of ABs, each AB may be the same as or different from each other and ABs are bonded to each other via an amide bond;
m represents an integer of 1 to 9;
$R^2$ represents a hydroxy group or $(AC)_g$;
AC represents a particular amino acid residue, and when there is a plurality of ACs, each AC may be the same as or different from each other and ACs are bonded to each other via an amide bond; and
g represents an integer of 1 to 9,
or a salt thereof.

26 Claims, 1 Drawing Sheet
Specification includes a Sequence Listing.

(56) References Cited

FOREIGN PATENT DOCUMENTS

| | | | |
|---|---|---|---|
| JP | 2017-506234 A | 3/2017 | |
| JP | 2017-508741 A | 3/2017 | |
| WO | 96/033211 A1 | 10/1996 | |
| WO | 03/082268 A2 | 10/2003 | |
| WO | 2004/026293 A2 | 4/2004 | |
| WO | 2005/030794 A2 | 4/2005 | |
| WO | 2009/052431 A2 | 4/2009 | |
| WO | 2010/114940 A1 | 10/2010 | |
| WO | 2013/173393 A1 | 11/2013 | |
| WO | 2014/057436 A2 | 4/2014 | |
| WO | 2014/107024 A1 | 7/2014 | |
| WO | 2014/144871 A1 | 9/2014 | |
| WO | 2015/095952 A1 | 7/2015 | |
| WO | 2015/095953 A1 | 7/2015 | |
| WO | 2015/128403 A2 | 9/2015 | |
| WO | 2015/151079 A2 | 10/2015 | |
| WO | 2016/072519 A1 | 5/2016 | |
| WO | 2016/123582 A1 | 8/2016 | |
| WO | 2019/031614 A1 | 2/2019 | |
| WO | 2019/031615 A1 | 2/2019 | |

OTHER PUBLICATIONS

Talpir et al., "Hemiasterlin and Geodiamolide TA; Two New Cytotoxic Peptides from the Marine Sponge Hemiasterella Minor (Kirkpatrick)," Tetrahedron Letters, 35 (25): 4453-4456 (1994).

Zask et al., "D-piece modifications of the hemiasterlin analog HTI-286 produce potent tubulin inhibitors," Bioorganic & Medicinal Chemistry Letters, 14: 4353-4358 (2004).

Zask et al., "Synthesis and Biological Activity of Analogues of the Antimicrotubule Agent N, B, B-Trimethyl -L-phenylalanyl-N1-[ (IS, 2E) -3- carboxy-1-isopropylbut-2-enyl]-N1, 3-dimethyl-L-valinamide (HTI-286)," Journal of Medicinal Chemistry, 47 (19): 4774-4786 (2004).

Yamashita et al., "Synthesis and activity of novel analogs of hemiasterlin as inhibitors of tubulin polymerization: modification of the A segment," Bioorganic & Medicinal Chemistry Letters, 14: 5317-5322 (2004).

Nieman et al., "Synthesis and Antimitotic/Cytotoxic Activity of Hemiasterlin Analogues," Journal of Natural Products, 66: 183-199 (2003).

Rocha-Lima et al., "A Phase 1 Trial of E7974 Administered on Day 1 of a 21-Day Cycle in Patients With Advanced Solid Tumors," Cancer, 4262-4270 (2012).

Doronina et al., "Enhanced Activity of Monomethylauristatin F through Monoclonal Antibody Delivery: Effects of Linker Technology on Efficacy and Toxicity," Bioconjugate Chemistry, 17 (1): 114-124 (2006).

International Search Report issued in corresponding International Application No. PCT/JP2020/005307 dated May 12, 2020.

International Preliminary Report on Patentability and Written Opinion issued in corresponding International Application No. PCT/JP2020/005307 dated Aug. 26, 2021.

International Search Report issued in related International Patent Application No. PCT/JP2020/005369 dated Apr. 21, 2020.

Erickson et al., "Antibody-Maytansinoid Conjugates Are Activated in Targeted Cancer Cells by Lysosomal Degradation and Linker-Dependent Intracellular Processing", Cancer Research, 66 (8): 4426-4433 (2006).

International Search Report issued in related International Patent Application No. PCT/JP2020/005291 dated May 12, 2020.

Alley et. al., "Contribution of Linker Stability to the Activities of Anticancer Immunoconjugates," Bioconjugate Chemistry, 19: 759-765 (2008).

Baldwin et. al., "Tunable Degradation of Maleimide—Thiol Adducts in Reducing Environments", Bioconjugate Chemistry, 22: 1946-1953 (2011).

International Search Report issued in corresponding International Patent Application No. PCT/JP2018/030143 dated Nov. 13, 2018. (046124-5509).

Toki et al., "Protease-Mediated Fragmentation of p-Amidobenzyl Ethers: A New Strategy for the Activation of Anticancer Prodrugs," The Journal of Organic Chemistry, 67: 1866-1872 (2002).

International Search Report issued in corresponding International Patent Application No. PCT/JP2018/030144 dated Nov. 13, 2018. (046124-5508).

* cited by examiner

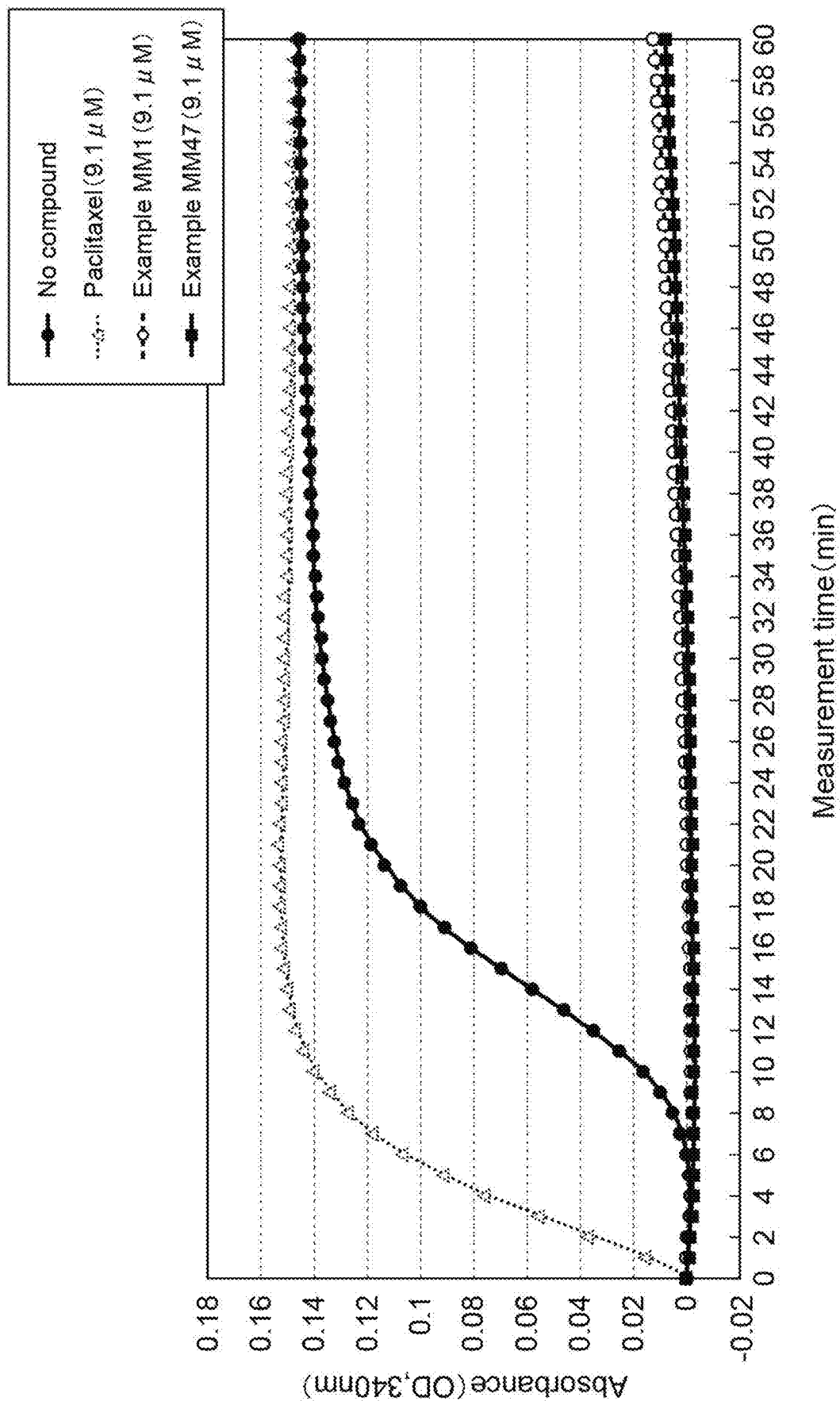

HEMIASTERLIN DERIVATIVE HAVING CYSTEINE RESIDUE

SEQUENCE LISTING SUBMISSION VIA EFS-WEB

A computer readable text file, entitled "SequenceListing.txt," created on Jul. 19, 2021 with a file size of 1,228 bytes contains the sequence listing for this application and is hereby incorporated by reference in its entirety.

TECHNICAL FIELD

The present invention relates to hemiasterlin derivatives having cysteine residue.

BACKGROUND ART

Hemiasterlin is a naturally occurring compound having a tripeptide structure, isolated from marine sponges, and is involved in microtubule depolymerization and mitotic arrest in cells (Non Patent Literature 1).

Several groups have so far conducted structural modification of hemiasterlin derivatives, and have found hemiasterlin derivatives exhibiting strong cytotoxicity and antimitotic effects for treatment for diseases such as cancer (Patent Literatures 1 to 5 and Non Patent Literatures 2 to 5). However, these hemiasterlin derivatives have been reported to be systemically delivered because of the lack of targeting properties, and exhibit cytotoxicity even to normal cells and show side effects (Non Patent Literature 6).

Antibody-drug conjugates are conjugates formed by conjugating an antibody and a drug directly or via an appropriate linker. Such antibody-drug conjugates have a characteristic to prevent systemic exposure to a drug and enhance the drug efficacy to target cells through delivering the drug to target cells via an antibody that binds to an antigen expressed on the target cells.

In addition, several groups have so far reported conjugates in which a hemiasterlin derivative having a maleimide group and a cysteine residue of an antibody or the like form thiosuccinimide (Patent Literatures 4 and 6 to 8).

Further, several other groups have reported that an antibody-drug conjugate formed by directly conjugating a cysteine residue of an antibody and a drug releases the Cys-drug moiety of the antibody-drug conjugate in cells through metabolism of the antibody (Non Patent Literature 7).

CITATION LIST

Patent Literature

Patent Literature 1: International Publication No. WO 2004/026293
Patent Literature 2: International Publication No. WO 96/33211
Patent Literature 3: U.S. Pat. No. 7,579,323
Patent Literature 4: International Publication No. WO 2014/144871
Patent Literature 5: International Publication No. WO 2003/082268
Patent Literature 6: International Publication No. WO 2015/095952
Patent Literature 7: International Publication No. WO 2015/095953
Patent Literature 8: International Publication No. WO 2014/057436

Non Patent Literature

Non Patent Literature 1: Talpir, R. et al., Tetrahedron Lett., 1994, 35, 4453-4456.
Non Patent Literature 2: Zask, A. et. al., Bioorg. Med. Chem. Lett., 2004, 14, 4353-4358.
Non Patent Literature 3: Zask, A. et. al., J. Med. Chem., 2004, 47, 4774-4786.
Non Patent Literature 4: Yamashita, A. et. al., Bioorg. Med. Chem. Lett., 2004, 14, 5317-5322.
Non Patent Literature 5: Nieman, J. A. et. al., J, Nat. Prod., 2003, 66, 183-199.
Non Patent Literature 6: Rocha-Lima, C. M. et. al., Cancer, 2012, 118, 4262-4270.
Non Patent Literature 7: Doronina S. O. et. al., Bioconjugate. Chem. 2006, 17, 114-124.

SUMMARY OF INVENTION

Technical Problem

An object of the present invention is to provide a hemiasterlin derivative that provide cell damage specifically to target cells while suppressing cytotoxicity to normal cells.

Solution to Problem

As a result of diligent studies, the present inventors have found that a hemiasterlin derivative having cysteine residue represented by formula (1) exhibits strong antitumor activity while having low cytotoxicity to normal cells, thereby completing the present invention.

That is, the present invention is as follows:
[Item 1]
A compound represented by formula (1):

[Chemical Formula 1]

(1)

wherein
b represents an integer of 1 to 5;
X represents —NH— or —CO—;
Z represents a group represented by formula (Z-1), formula (Z-2), formula (Z-3), formula (Z-4), formula (Z-5), formula (Z-6), formula (Z-7), formula (Z-8), formula (Z-9), formula (Z-10) or formula (Z-11):

[Chemical Formula 2]

(Z-1)

where n represents an integer of 0 to 2;

p represents an integer of 1 to 3;

AA represents a glutamic acid residue (Glu), an aspartic acid residue (Asp) or a lysine residue (Lys), and when there is a plurality of AAs, each AA may be the same as or different from each other and AAs are bonded to each other via an amide bond, and an N-terminal nitrogen atom of $(AA)_n$ or $(AA)_p$ forms an amide bond together with carbonyl group (a);

G represents —O— or —NH—; and

W represents a group represented by formula (W-1) or formula (W-2):

[Chemical Formula 3]

where $R^{6a}$ and $R^{6b}$ each independently represent a hydrogen atom or a methyl group;

$R^7$ represents a $C_{1-6}$ alkyl group; and

Q represents a group represented by formula (Q-1), formula (Q-2), formula (Q-3), formula (Q-4), formula (Q-5), formula (Q-6) or formula (Q-7):

[Chemical Formula 4]

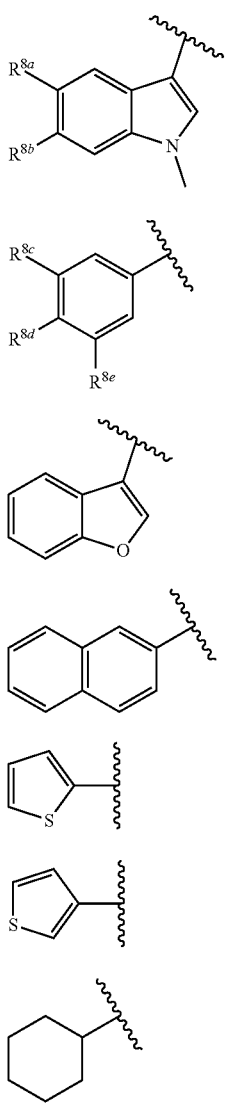

where
R$^{8a}$ and R$^{8b}$ each independently represent a hydrogen atom, a halogen atom, a C$_{1-6}$ alkyl group or a C$_{1-6}$ alkoxy group; and
R$^{8c}$, R$^{8d}$ and R$^{8e}$ each independently represent a hydrogen atom, a halogen atom, a hydroxy group, a cyano group, an amino group, a carboxyl group, a phenyl group, or a C$_{1-6}$ alkyl group, a C$_{1-6}$ alkoxy group or a C$_{1-6}$ alkyl ester group optionally substituted with 1 to 3 fluorine atoms;

R$^3$ represents —(CH$_2$)$_u$—COR$^9$;
u represents 1 or 2;
R$^4$ and R$^9$ each independently represent a hydroxy group or AD;
AD represents Glu, Asp or Lys, and an N-terminal nitrogen atom of AD forms an amide bond together with a neighboring carbonyl group;
with a proviso that when R$^4$ or R$^9$ is AD, n is 0 or 1; and
R$^{5a}$ and R$^{5b}$ each independently represent a hydrogen atom or a methyl group;

with a proviso that when X is —NH—, Z is formula (Z-1), formula (Z-2), formula (Z-3), formula (Z-4) or formula (Z-5), and when X is —CO—, Z is formula (Z-6), formula (Z-7), formula (Z-8), formula (Z-9), formula (Z-10) or formula (Z-11);

R$^1$ represents a hydrogen atom or (AB)$_m$;

AB represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ABs, each AB may be the same as or different from each other and ABs are bonded to each other via an amide bond;

m represents an integer of 1 to 9;

R$^2$ represents a hydroxy group or (AC)$_g$;

AC represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ACs, each AC may be the same as or different from each other and ACs are bonded to each other via an amide bond; and g represents an integer of 1 to 9;

with a proviso that when R$^1$ is (AB)$_m$ and R$^2$ is (AC)$_g$, a sum of m and g is an integer of 2 to 10, or a salt thereof.

[Item 2]

The compound according to item 1, wherein formula (1) is represented by formula (1-1):

[Chemical Formula 5]

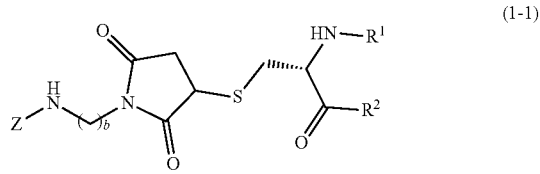

(1-1)

wherein
b represents an integer of 1 to 5;
Z represents a group represented by formula (Z-1), formula (Z-2), formula (Z-3), formula (Z-4) or formula (Z-5):

[Chemical Formula 6]

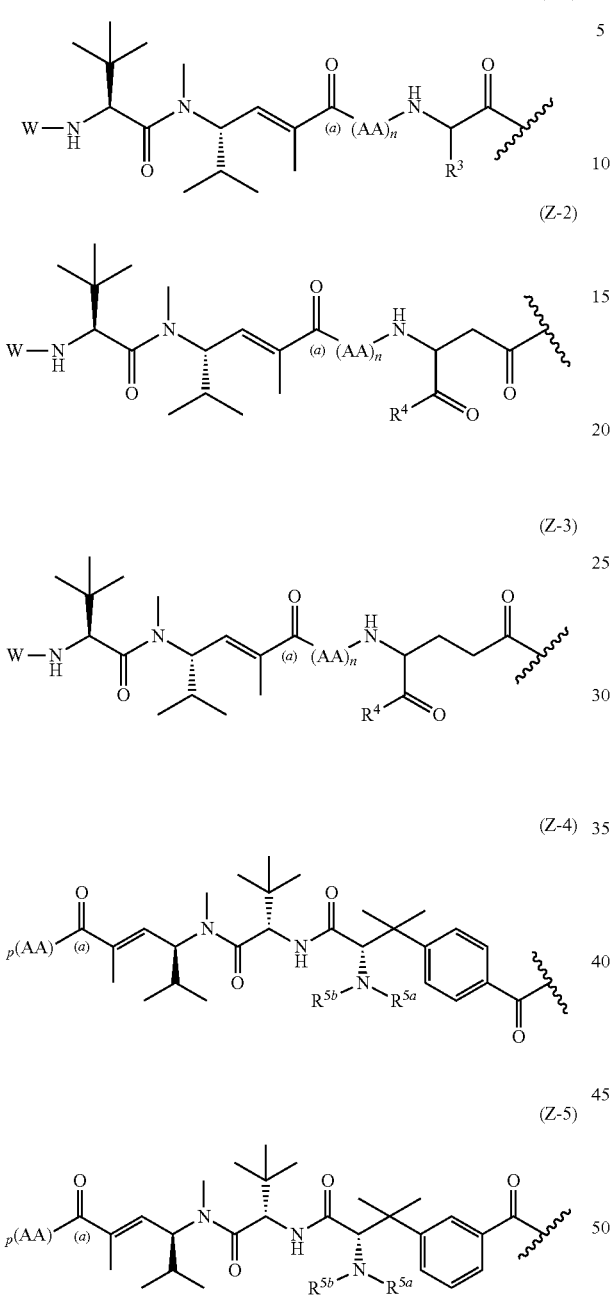

where
n represents an integer of 0 to 2;
p represents an integer of 1 to 3;
AA represents a glutamic acid residue (Glu), an aspartic acid residue (Asp) or a lysine residue (Lys), and when there is a plurality of AAs, each AA may be the same as or different from each other and AAs are bonded to each other via an amide bond, and an N-terminal nitrogen atom of $(AA)_n$ or $(AA)_p$ forms an amide bond together with carbonyl group (a); and
W represents a group represented by formula (W-1) or formula (W-2):

[Chemical Formula 7]

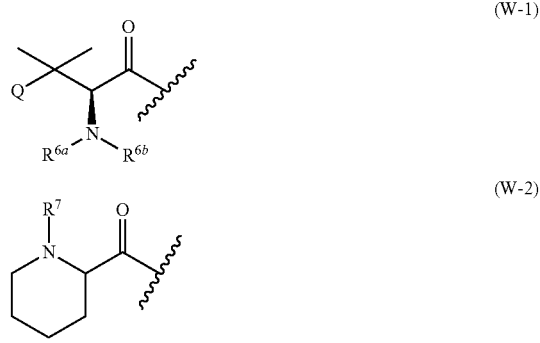

where
$R^{6a}$ and $R^{6b}$ each independently represent a hydrogen atom or a methyl group;
$R^7$ represents a $C_{1-6}$ alkyl group; and
Q represents a group represented by formula (Q-1), formula (Q-2), formula (Q-3), formula (Q-4), formula (Q-5), formula (Q-6) or formula (Q-7):

[Chemical Formula 8]

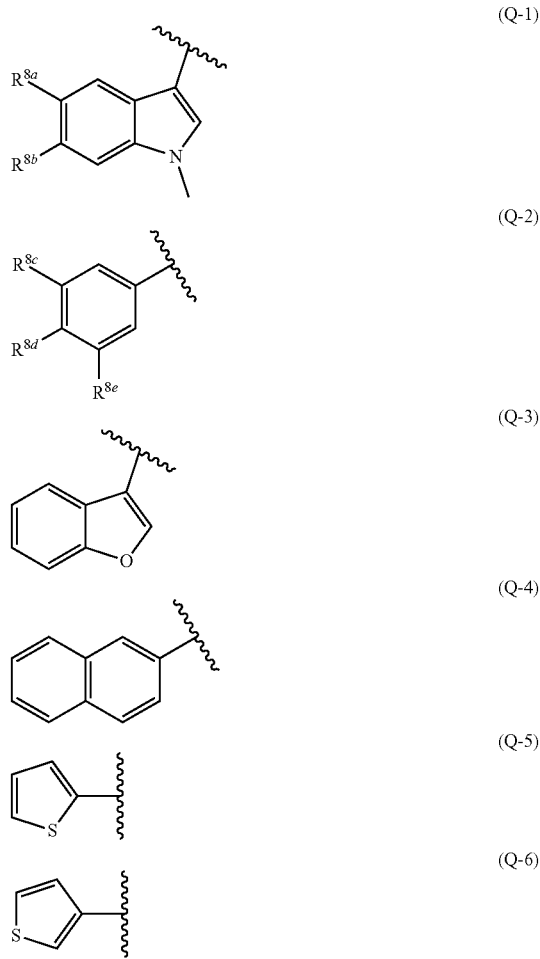

-continued (Q-7)

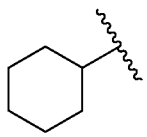

where
R$^{8a}$ and R$^{8b}$ each independently represent a hydrogen atom, a halogen atom, a C$_{1-6}$ alkyl group or a C$_{1-6}$ alkoxy group; and
R$^{8c}$, R$^{8d}$ and R$^{8e}$ each independently represent a hydrogen atom, a halogen atom, a hydroxy group, a cyano group, an amino group, a carboxyl group, a phenyl group, or a C$_{1-6}$ alkyl group, a C$_{1-6}$ alkoxy group or a C$_{1-6}$ alkyl ester group optionally substituted with 1 to 3 fluorine atoms;
R$^3$ represents —(CH$_2$)$_u$—COR$^9$;
u represents 1 or 2;
R$^4$ and R$^9$ each independently represent a hydroxy group or AD;
AD represents Glu, Asp or Lys, and an N-terminal nitrogen atom of AD forms an amide bond together with a neighboring carbonyl group;
with a proviso that when R$^4$ or R$^9$ is AD, n is 0 or 1; and
R$^{5a}$ and R$^{5b}$ each independently represent a hydrogen atom or a methyl group;
R$^1$ represents a hydrogen atom or (AB)$_m$;
AB represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ABs, each AB may be the same as or different from each other and ABs are bonded to each other via an amide bond;
m represents an integer of 1 to 9;
R$^2$ represents a hydroxy group or (AC)$_g$;
AC represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ACs, each AC may be the same as or different from each other and ACs are bonded to each other via an amide bond; and
g represents an integer of 1 to 9;
with a proviso that when R$^1$ is (AB)$_m$ and R$^2$ is (AC)$_g$, a sum of m and g is an integer of 2 to 10,
or a salt thereof.
[Item 3]
The compound according to item 2, wherein
IV is a methyl group or an isopropyl group; and
Q is formula (Q-1), formula (Q-2), formula (Q-4), formula (Q-6) or formula (Q-7),
or a salt thereof.
[Item 4]
The compound according to item 2 or 3, wherein
p is 1;
W is formula (W-1);
Q is formula (Q-1) or formula (Q-2);
R$^{8a}$ and R$^{8b}$ are each independently a hydrogen atom, a fluorine atom or a methoxy group;
R$^{8c}$, R$^{8d}$ and R$^{8e}$ are each independently a hydrogen atom, a fluorine atom, a hydroxy group, a cyano group, an amino group, a carboxyl group, a methyl group, a trifluoromethyl group or a methoxy group; and
R$^4$ and R$^9$ are each a hydroxy group, or a salt thereof.
[Item 5]
The compound according to any one of items 2 to 4, wherein
Z is formula (Z-1), formula (Z-2) or formula (Z-3);
W is formula (W-1);
Q is formula (Q-1) or formula (Q-2);
R$^{8a}$ and R$^{8b}$ are each a hydrogen atom;
R$^{8c}$, R$^{8d}$ and R$^{8e}$ are each a hydrogen atom; and
R$^4$ and R$^9$ are each a hydroxy group,
or a salt thereof.
[Item 6]
The compound according to any one of items 2 to 5, wherein b is 2,
or a salt thereof.
[Item 7]
The compound according to item 1, wherein formula (1) is represented by formula (1-2):

[Chemical Formula 9]

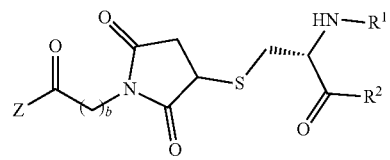

(1-2)

wherein
b represents an integer of 1 to 5;
Z represents a group represented by formula (Z-6), formula (Z-7), formula (Z-8), formula (Z-9), formula (Z-10) or formula (Z-11):

[Chemical Formula 10]

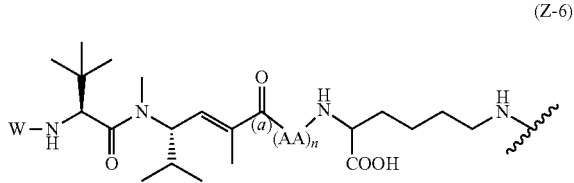

(Z-6)

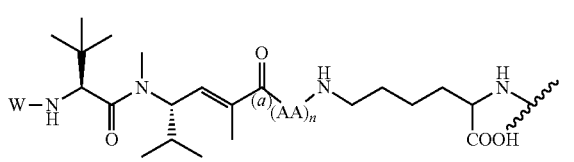

(Z-7)

-continued

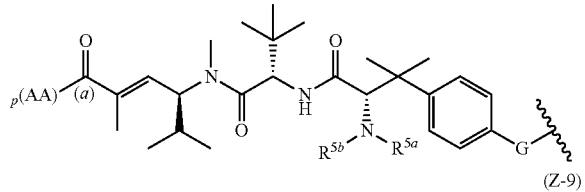
(Z-8)

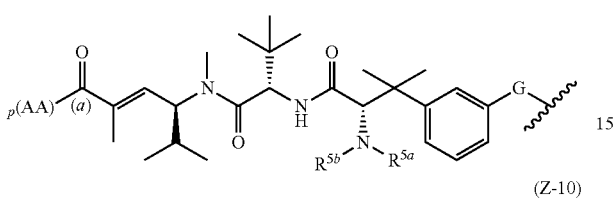
(Z-9)

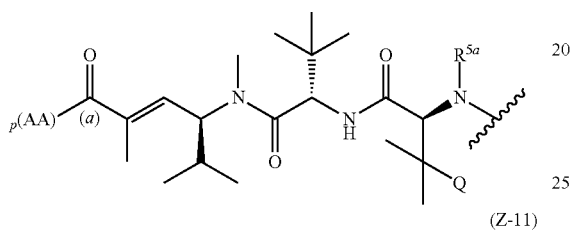
(Z-10)

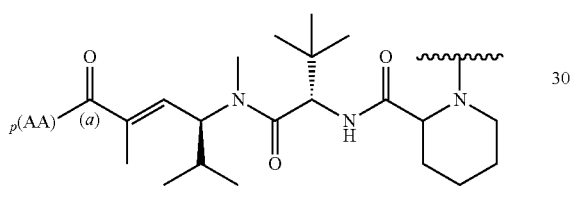
(Z-11)

where
n represents an integer of 0 to 2;
p represents an integer of 1 to 3;
AA represents a glutamic acid residue (Glu), an aspartic acid residue (Asp) or a lysine residue (Lys), and when there is a plurality of AAs, each AA may be the same as or different from each other and AAs are bonded to each other via an amide bond;
an N-terminal nitrogen atom of $(AA)_n$ or $(AA)_p$ forms an amide bond together with carbonyl group (a);
G represents —O— or —NH—; and
W represents a group represented by formula (W-1) or formula (W-2):

[Chemical Formula 11]

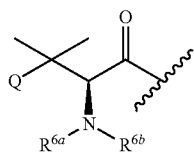
(W-1)

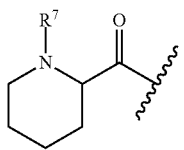
(W-2)

where
$R^{6a}$ and $R^{6b}$ each independently represent a hydrogen atom or a methyl group;
$R^7$ represents a $C_{1-6}$ alkyl group; and
Q represents a group represented by formula (Q-1), formula (Q-2), formula (Q-3), formula (Q-4), formula (Q-5), formula (Q-6) or formula (Q-7):

[Chemical Formula 12]

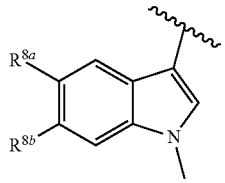
(Q-1)

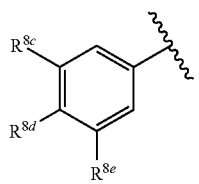
(Q-2)

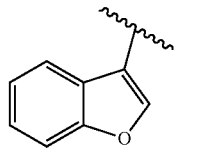
(Q-3)

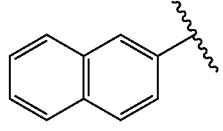
(Q-4)

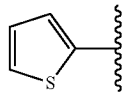
(Q-5)

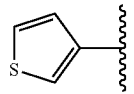
(Q-6)

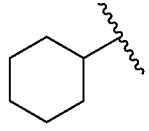
(Q-7)

where
$R^{8a}$ and $R^{8b}$ each independently represent a hydrogen atom, a halogen atom, a $C_{1-6}$ alkyl group or a $C_{1-6}$ alkoxy group; and
$R^{8c}$, $R^{8d}$ and $R^{8e}$ each independently represent a hydrogen atom, a halogen atom, a hydroxy group, a cyano group, an amino group, a carboxyl group, a phenyl group, or a $C_{1-6}$ alkyl group, a $C_{1-6}$ alkoxy group or a $C_{1-6}$ alkyl ester group optionally substituted with 1 to 3 fluorine atoms; and
$R^{5a}$ and $R^{5b}$ each independently represent a hydrogen atom or a methyl group; and
$R^1$ represents a hydrogen atom or $(AB)_m$;

AB represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ABs, each AB may be the same as or different from each other and ABs are bonded to each other via an amide bond;

m represents an integer of 1 to 9;

$R^2$ represents a hydroxy group or $(AC)_g$;

AC represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ACs, each AC may be the same as or different from each other and ACs are bonded to each other via an amide bond; and g represents an integer of 1 to 9;

with a proviso that when $R^1$ is $(AB)_m$ and $R^2$ is $(AC)_g$, a sum of m and g is an integer of 2 to 10, or a salt thereof.

[Item 8]

The compound according to item 7, wherein

Z is formula (Z-6), formula (Z-7), formula (Z-8) or formula (Z-9);

$R^7$ is a methyl group or an isopropyl group; and

Q is formula (Q-1), formula (Q-2), formula (Q-4), formula (Q-6) or formula (Q-7), or a salt thereof.

[Item 9]

The compound according to item 7 or 8, wherein

Z is formula (Z-6) or formula (Z-7);

W is formula (W-1);

Q is formula (Q-1) or formula (Q-2);

$R^{8a}$ and $R^{8b}$ are each independently a hydrogen atom, a fluorine atom or a methoxy group; and $R^{8c}$, $R^{8d}$ and $R^{8e}$ are each independently a hydrogen atom, a fluorine atom, a hydroxy group, a cyano group, an amino group, a carboxyl group, a methyl group, a trifluoromethyl group or a methoxy group, or a salt thereof.

[Item 10]

The compound according to any one of items 7 to 9, wherein $R^{8a}$ and $R^{8b}$ are each a hydrogen atom; and $R^{8c}$, $R^{8d}$ and $R^{8e}$ are each a hydrogen atom, or a salt thereof.

[Item 11]

The compound according to any one of items 7 to 10, wherein b is 3, or a salt thereof.

[Item 12]

The compound according to any one of items 1 to 11, wherein $(AB)_m$ is an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr), a valine residue (Val), $*^1$-(Glu)-(Gly), $*^1$-(Glu)-(Gly)-(Arg), $*^1$-(Glu)-(Gly)-(Arg)-(Asn), $*^1$-(Glu)-(Gly)-(Arg)-(Asn)-(Phe), $*^1$-(Glu)-(Gly)-(Arg)-(Asn)-(Phe)-(Ser), $*^1$-(Glu)-(Gly)-(Arg)-(Asn)-(Phe)-(Ser)-(Lys), $*^1$-(Glu)-(Gly)-(Arg)-(Asn)-(Phe)-(Ser)-(Lys)-(Thr) or $*^1$-(Glu)-(Gly)-(Arg)-(Asn)-(Phe)-(Ser)-(Lys)-(Thr)-(Val), where terminus $*^1$ represents amide bonding to a cysteine residue; and $(AC)_g$ is a glycine residue (Gly) or a proline residue (Pro), or a salt thereof.

[Item 13]

The compound according to any one of items 1 to 11, wherein $(AB)_m$ is an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val); and $(AC)_g$ is a glycine residue (Gly), or a salt thereof.

[Item 14]

The compound according to any one of items 1 to 13, wherein $R^1$ is a hydrogen atom; and $R^2$ is a hydroxy group, or a salt thereof.

[Item 15]

The compound according to any one of items 1 to 14, wherein $(AA)_n$ is a group represented by formula (A-1):

[Chemical Formula 13]

(A-1)

where $AA_1$ and $AA_2$ each independently represent Glu, Asp or Lys, or a salt thereof.

[Item 16]

The compound according to any one of items 1 to 14, wherein $(AA)_n$ is a group represented by formula (A-2):

[Chemical Formula 14]

(A-2)

15
where
AA₁ and AA₂ each independently represent Glu, Asp or Lys,
or a salt thereof.
16
[Item 17]
The compound according to any one of items 1 to 14, wherein n is 0 or 1, or a salt thereof.
[Item 18]
The compound according to item 1, wherein the compound is selected from following:
[Chemical Formula 15]
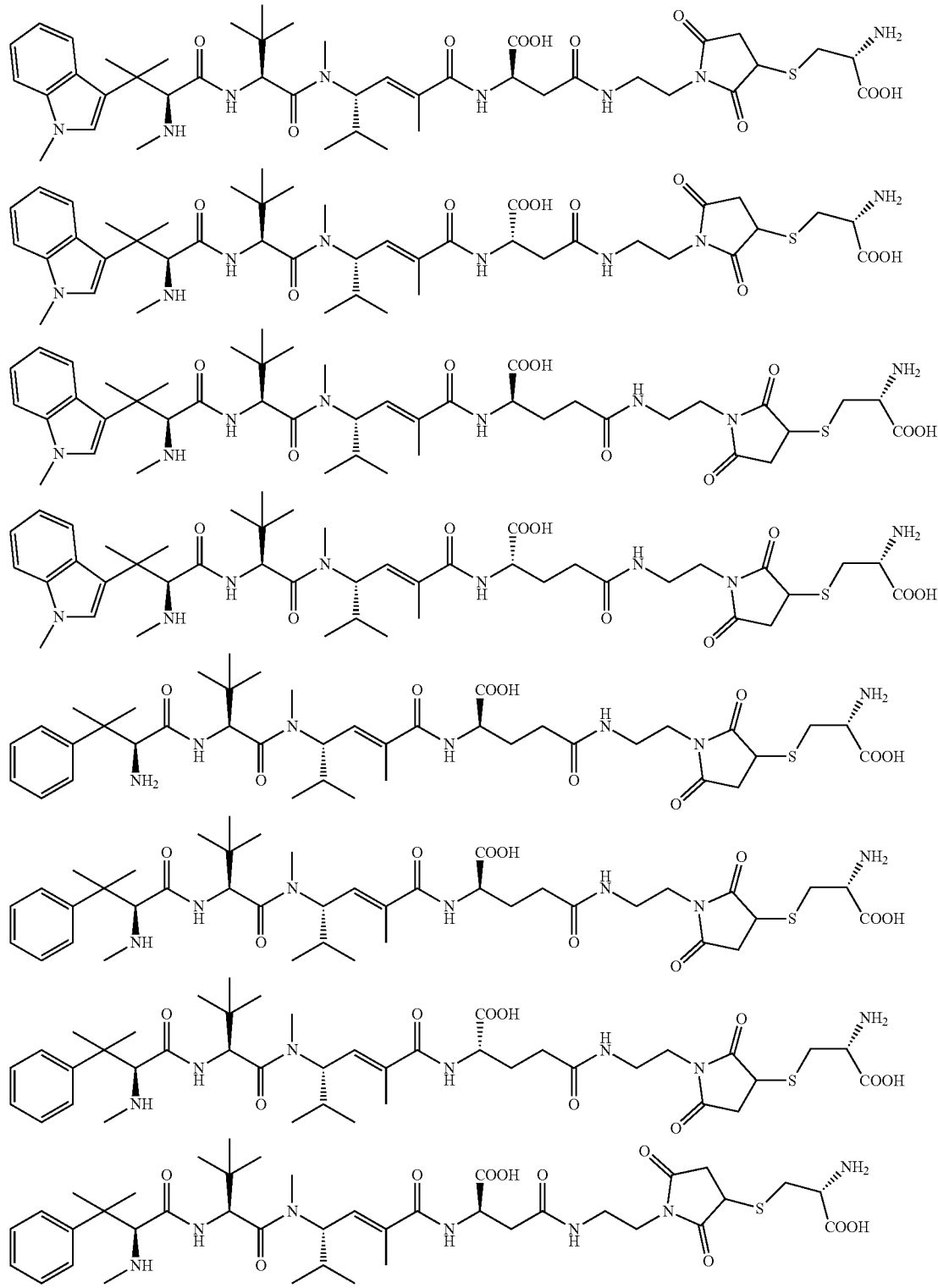

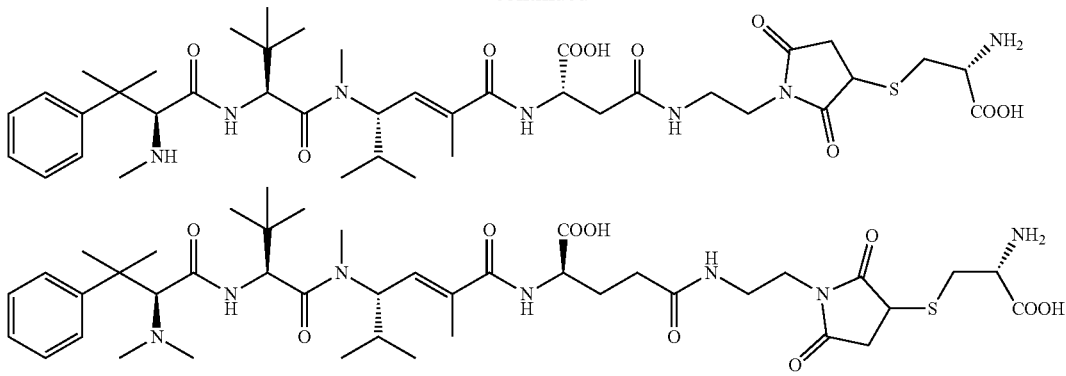

or a salt thereof.

[Item 19]

The compound according to item 1, wherein the compound is selected from following:

[Chemical Formula 16]

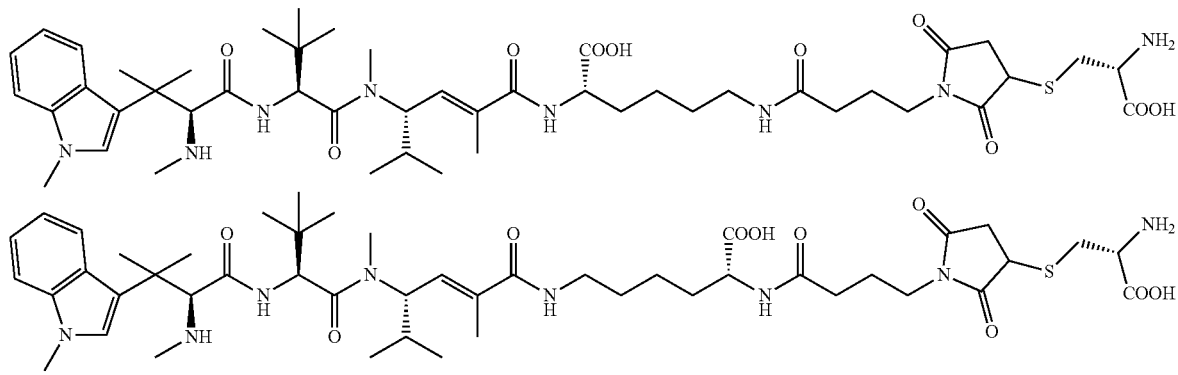

or a salt thereof.

Advantageous Effects of Invention

The hemiasterlin derivatives according to the present invention exhibit cytotoxic activity specifically to antigen-expressing cells and have low cytotoxicity in normal cells other than the antigen-expressing cells, and therefore, can be anticancer agents excellent in safety.

BRIEF DESCRIPTION OF DRAWINGS

FIG. 1 shows activities of Examples MM1 and MM47 to inhibit polymerization of porcine tubulins.

DESCRIPTION OF EMBODIMENTS

In the present specification, the "$C_{1-6}$ alkyl group" means a linear or branched saturated hydrocarbon group having 1 to 6 carbon atoms. Examples of the "$C_{1-6}$ alkyl group" preferably include a "$C_{1-4}$ alkyl group", more preferably include a "$C_{1-3}$ alkyl group", further preferably include a methyl group, an ethyl group, a propyl group or an isopropyl group, and particularly preferably include a methyl group or an ethyl group.

Specific examples of the "$C_{1-3}$ alkyl group" include a methyl group, an ethyl group, a propyl group and an isopropyl group. Specific examples of the "$C_{1-4}$ alkyl group" include a butyl group, a 1,1-dimethylethyl group, a 1-methylpropyl group and a 2-methylpropyl group in addition to those mentioned as the specific examples of the "$C_{1-3}$ alkyl group". Specific examples of the "$C_{1-6}$ alkyl group" include a pentyl group, a 3-methylbutyl group, a 2-methylbutyl group, a 2,2-dimethylpropyl group, a 1-ethylpropyl group, a 1,1-dimethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group and a 1,2-dimethylbutyl group in addition to those mentioned as the specific examples of the "$C_{1-4}$ alkyl group".

In the present specification, the "$C_{1-6}$ alkyl ester" means an ester, in which R' of the ester (—COOR') is the above "$C_{1-6}$ alkyl group". Examples of the "$C_{1-6}$ alkyl ester" preferably include a "$C_{1-4}$ alkyl ester", more preferably include a "$C_{1-3}$ alkyl ester", further preferably include a methyl ester, an ethyl ester, an isopropyl ester or a tert-butyl ester, and particularly preferably include a methyl ester or an ethyl ester.

Specific examples of the "$C_{1-3}$ alkyl ester" include a methyl ester, an ethyl ester, a propyl ester and an isopropyl ester. Specific examples of the "$C_{1-4}$ alkyl ester" include a butyl ester and a tert-butyl ester in addition to those mentioned as the specific examples of the "$C_{1-3}$ alkyl ester". Specific examples of the "$C_{1-6}$ alkyl ester" include a pentyl ester, a 3-methylbutyl ester, a 2-methylbutyl ester, a 2,2-dimethylpropyl ester, a 1-ethylpropyl ester, a 1,1-dimethylpropyl ester, a hexyl ester, a 4-methylpentyl ester, a 3-methylpentyl ester, a 2-methylpentyl ester, a 1-methylpentyl ester, a 3,3-dimethylbutyl ester, a 2,2-dimethylbutyl ester, a 1,1-dimethylbutyl ester and a 1,2-dimethylbutyl ester in addition to those mentioned as the specific examples of the "$C_{1-4}$ alkyl ester".

In the present specification, the "$C_{1-6}$ alkoxy group" means an oxy group substituted with a "$C_{1-6}$ alkyl group". Examples of the "$C_{1-6}$ alkoxy group" preferably include a "$C_{1-4}$ alkoxy group", more preferably include a "$C_{1-3}$ alkoxy group", further preferably include a methoxy group, an ethoxy group, a propoxy group or a 1-methylethoxy group, and particularly preferably include a methoxy group or an ethoxy group.

Specific examples of the "$C_{1-3}$ alkoxy group" include a methoxy group, an ethoxy group, a propoxy group or a 1-methylethoxy group. Specific examples of the "$C_{1-4}$ alkoxy group" include a butoxy group, a 1,1-dimethylethoxy group, a 1-methylpropoxy group and a 2-methylpropoxy group in addition to those mentioned as the specific examples of the "$C_{1-3}$ alkoxy group". Specific examples of the "$C_{1-6}$ alkoxy group" include a pentyloxy group, a 3-methylbutoxy group, a 2-methylbutoxy group, a 2,2-dimethylpropoxy group, a 1-ethylpropoxy group, a 1,1-dimethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group and a 1,2-dimethylbutoxy group in addition to those mentioned as the specific examples of the "$C_{1-4}$ alkoxy group".

In the present specification, examples of the "halogen atom" include a fluorine atom, a chlorine atom, a bromine atom or an iodine atom. Preferably, examples thereof include a fluorine atom or a chlorine atom, and more preferably, examples thereof include a fluorine atom.

A compound represented by formula (1) and a salt thereof (hereinafter, may be referred to as the "hemiasterlin derivative according to the present invention") are as follows:

[Chemical Formula 17]

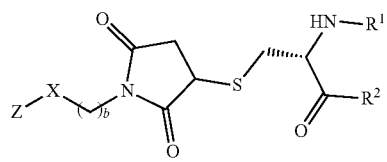

(1)

In the formula, b represents an integer of 1 to 5. That is, b is 1, 2, 3, 4 or 5. Examples of one aspect of b include an integer of 1 to 4; examples of another aspect thereof include an integer of 1 to 3; and examples of another aspect thereof include 2 or 3.

In the formula, X represents —NH— or —CO—. Examples of one aspect of X include —NH—, and another aspect thereof include —CO—.

In the formula, Z represents a group represented by formula (Z-1), formula (Z-2), formula (Z-3), formula (Z-4), formula (Z-5), formula (Z-6), formula (Z-7), formula (Z-8), formula (Z-9), formula (Z-10) or formula (Z-11):

[Chemical Formula 18]

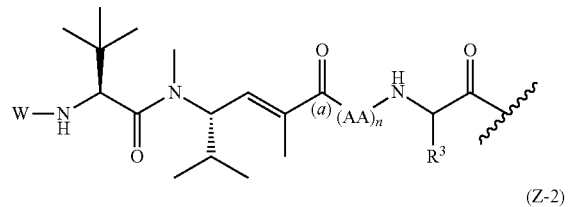
(Z-1)

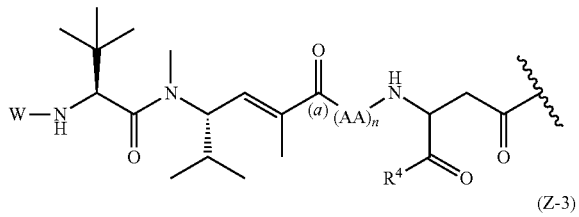
(Z-2)

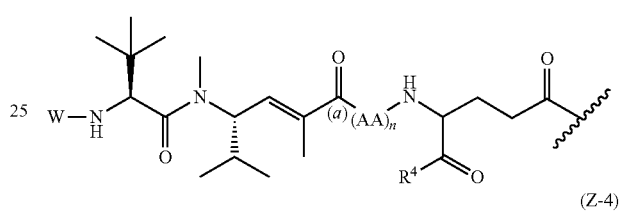
(Z-3)

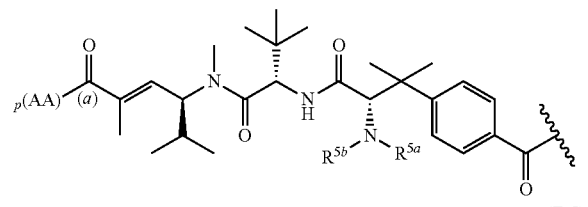
(Z-4)

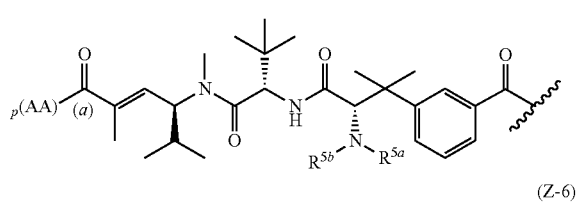
(Z-5)

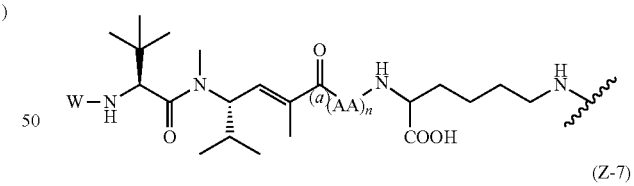
(Z-6)

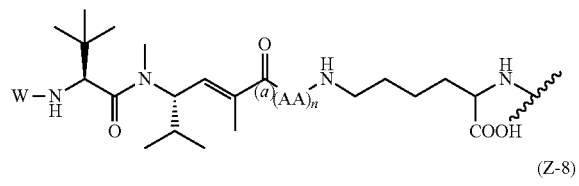
(Z-7)

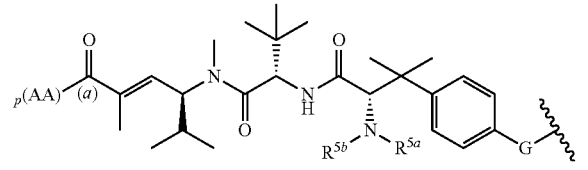
(Z-8)

-continued

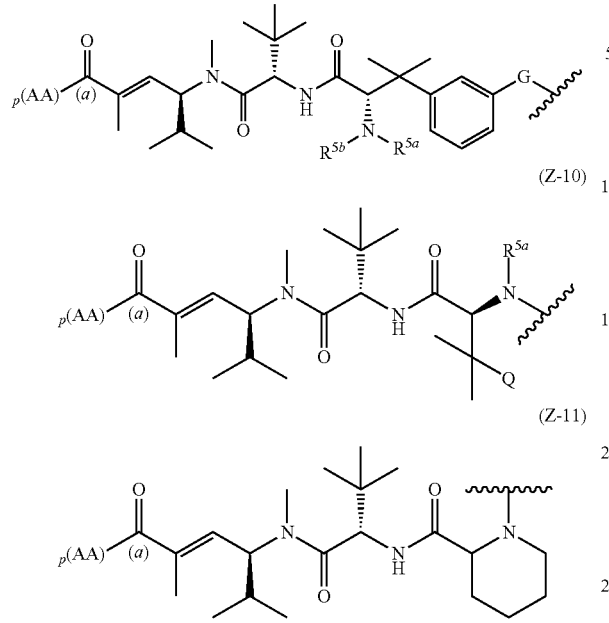

(Z-9)

(Z-10)

(Z-11)

In these formulas, AA represents a glutamic acid residue, an aspartic acid residue or a lysine residue, and examples thereof preferably include a glutamic acid residue or an aspartic acid residue.

In the present specification, except when it is particularly necessary to make distinction, the three letter abbreviated notations shown below may be used for representing both α-amino acids and corresponding amino acid residues. In addition, the optical activity of the α-amino acids may include any of DL form, D form and L form unless otherwise specified. For example, "glutamic acid" or "Glu" represents DL-glutamic acid or a residue thereof, D-glutamic acid or a residue thereof, or L-glutamic acid or a residue thereof.

Ala: alanine, Arg: arginine, Asn: asparagine, Asp: aspartic acid, Cys: cysteine, Gln: glutamine, Glu: glutamic acid, Gly: glycine, His: histidine, Ile: isoleucine, Leu: leucine, Lys: lysine, Met: methionine, Phe: phenylalanine, Pro: proline, Ser: serine, Trp: tryptophan, Thr: threonine, Tyr: tyrosine, Val: valine.

In these formulas, n represents an integer of 0 to 2. That is, n is 0, 1 or 2. Examples of one aspect of n include an integer of 0 or 1; examples of another aspect thereof include 0; examples of another aspect thereof include 1 or 2; examples of another aspect thereof include 1; and examples of another aspect thereof include 2.

In these formulas, p represents an integer of 1 to 3. That is, p is 1, 2 or 3. Examples of one aspect of p include 1 or 2; examples of another aspect thereof include 2 or 3; examples of another aspect thereof include 1; examples of another aspect thereof include 2; and examples of another aspect thereof include 3.

When there is a plurality of AAs, each AA may be the same as or different from each other and AAs are bonded to each other via an amide bond. "AAs are bonded to each other via an amide bond" means that the carboxyl group of one amino acid and the amino group of another amino acid are condensed to form an amide bond. For example, when n is 2 and two AAs are both Glu, nitrogen atom (d) of one Glu and carbonyl group (c) of the other Glu may be linked by forming an amide bond, as represented by the following formula:

[Chemical Formula 19]

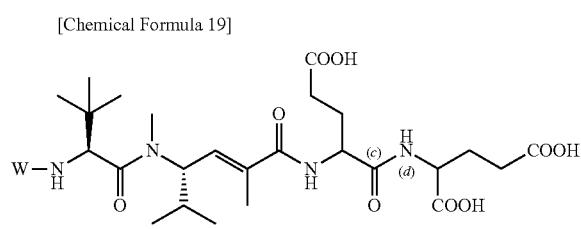

The N-terminal nitrogen atom of $(AA)_n$ or $(AA)_p$ forms an amide bond together with carbonyl group (a). "The N-terminal nitrogen atom of AA forms an amide bond together with carbonyl group (a)" means that, for example, when AA is Asp, nitrogen atom (b) of Asp and carbonyl group (a) are linked to form an amide bond, as represented by the following formula:

[Chemical Formula 20]

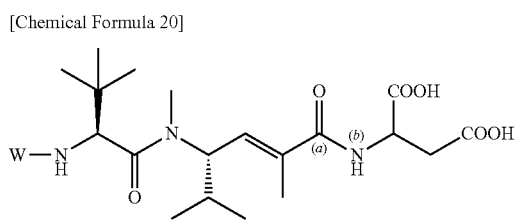

Examples of one aspect of $(AA)_n$ include a group represented by formula (A-1) or formula (A-2), wherein n is 2.

[Chemical Formula 21]

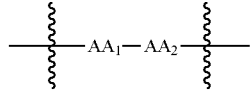

(A-1)

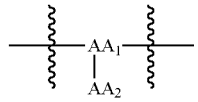

(A-2)

In these formulas, $AA_1$ and $AA_2$ each independently represent Glu, Asp or Lys.

Examples of one aspect of $(AA)_p$ include a group represented by formula (A-3) or formula (A-4), wherein p is 3.

[Chemical Formula 22]

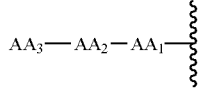

(A-3)

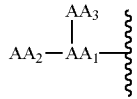

(A-4)

In these formulas, $AA_1$, $AA_2$ and $AA_3$ each independently represent Glu, Asp or Lys.

In formula (Z-1), formula (Z-2), formula (Z-3), formula (Z-6) and formula (Z-7), W represents a group represented by formula (W-1) or formula (W-2):

[Chemical Formula 23]

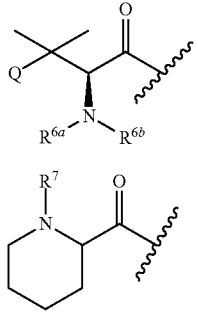

(W-1)

(W-2)

In formula (W-1), $R^{6a}$ and $R^{6b}$ each independently represent a hydrogen atom or a methyl group. In formula (W-2), $R^7$ represents a $C_{1-6}$ alkyl group. $R^7$ may be, for example, a methyl group, an ethyl group, a propyl group or an isopropyl group.

In formula (Z-10) and formula (W-1), Q represents a group represented by formula (Q-1), formula (Q-2), formula (Q-3), formula (Q-4), formula (Q-5), formula (Q-6) or formula (Q-7):

[Chemical Formula 24]

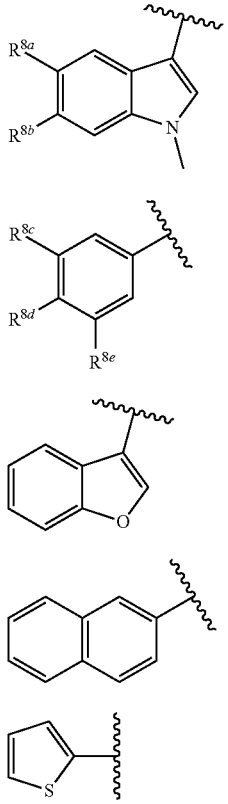

(Q-1)

(Q-2)

(Q-3)

(Q-4)

(Q-5)

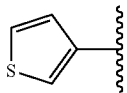

(Q-6)

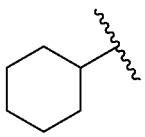

(Q-7)

In formula (Q-1), $R^{8a}$ and $R^{8b}$ each independently represent a hydrogen atom, a halogen atom, a $C_{1-6}$ alkyl group or a $C_{1-6}$ alkoxy group. In formula (Q-2), $R^{8c}$, $R^{8d}$ and $R^{8e}$ each independently represent a hydrogen atom, a halogen atom, a hydroxy group, a cyano group, an amino group, a carboxyl group, a phenyl group, or a $C_{1-6}$ alkyl group, a $C_{1-6}$ alkoxy group or a $C_{1-6}$ alkyl ester group optionally substituted with 1 to 3 fluorine atoms. The halogen atom may be, for example, a fluorine atom, a chlorine atom or a bromine atom.

Q may be a group represented by formula (Q-1) or formula (Q-2). $R^{8a}$ and $R^{8b}$ may be each a hydrogen atom, and $R^{8c}$, $R^{8d}$ and $R^{8e}$ may be each a hydrogen atom.

In formula (Z-4), formula (Z-5), formula (Z-8), formula (Z-9) and formula (Z-10), $R^{5a}$ and $R^{5b}$ each independently represent a hydrogen atom or a methyl group.

In the present specification, a hydrogen atom may be $^1H$ or $^2H(D)$. That is, for example, a deuterated product in which one or two or more $^1H$ of the compound represented by formula (1) are converted into $^2H(D)$ is also encompassed in the compound represented by formula (1).

In formula (1), $R^1$ represents a hydrogen atom or $(AB)_m$. Here, m is an integer of 1 to 9, that is, 1, 2, 3, 4, 5, 6, 7, 8 or 9. AB represents Ala, Arg, Asn, Asp, Cys, Gln, Glu, Gly, His, Ile, Leu, Lys, Met, Phe, Pro, Ser, Trp, Thr, Tyr or Val, and when there is a plurality of ABs, each AB may be the same as or different from each other and ABs are bonded to each other via an amide bond. Examples of one aspect of m include 1, 2, 3, 4 or 5; examples of another aspect thereof include 1; examples of another aspect thereof include 2; examples of another aspect thereof include an integer of 1 to 3; and examples of another aspect thereof include 3.

Examples of one aspect of $(AB)_m$ in formula (1) include $*^1$-(Glu)-(Gly), $*^1$-(Glu)-(Gly)-(Arg), $*^1$-(Glu)-(Gly)-(Arg)-(Asn), $*^1$-(Glu)-(Gly)-(Arg)-(Asn)-(Phe), $*^1$-(Glu)-(Gly)-(Arg)-(Asn)-(Phe)-(Ser), $*^1$-(Glu)-(Gly)-(Arg)-(Asn)-(Phe)-(Ser)-(Lys), $*^1$-(Glu)-(Gly)-(Arg)-(Asn)-(Phe)-(Ser)-(Lys)-(Thr) or $*^1$-(Glu)-(Gly)-(Arg)-(Asn)-(Phe)-(Ser)-(Lys)-(Thr)-(Val). Here, terminus $*^1$ represents amide bonding to a cysteine residue.

In formula (1), $R^2$ represents a hydroxy group or $(AC)_g$. Here, g is an integer of 1 to 9, that is, 1, 2, 3, 4, 5, 6, 7, 8 or 9. AC represents Ala, Arg, Asn, Asp, Cys, Gln, Glu, Gly, His, Ile, Leu, Lys, Met, Phe, Pro, Ser, Trp, Thr, Tyr or Val. When there is a plurality of ACs, each AC may be the same as or different from each other and ACs are bonded to each other via an amide bond. Examples of one aspect of g include 1, 2, 3, 4 or 5; examples of another aspect thereof include an integer of 1 to 3; examples of another aspect thereof include 1; examples of another aspect thereof include 2; and examples of another aspect thereof include 3.

Examples of one aspect of $(AC)_g$ in formula (1) include Gly or Pro.

When $R^1$ is $(AB)_m$ and $R^2$ is $(AC)_g$, the sum of m and g is an integer of 2 to 10, that is, 2, 3, 4, 5, 6, 7, 8, 9 or 10. Examples of one aspect of the sum of n and p include an integer of 2 to 5; examples of one aspect thereof include 2 or 3; and examples of one aspect thereof include 2.

In formula (Z-1), $R^3$ represents —$(CH_2)_u$—$COR^9$. Here, u is 1 or 2. $R^9$ represents a hydroxy group or AD, and more preferably is a hydroxy group. Here, AD represents Glu, Asp or Lys, and the N-terminal nitrogen atom of AD forms an amide bond together with the neighboring carbonyl group.

In formula (Z-2) or formula (Z-3), $R^4$ represents a hydroxy group or AD, and more preferably is a hydroxy group. Here, AD represents Glu, Asp or Lys, and the N-terminal nitrogen atom of AD forms an amide bond together with the neighboring carbonyl group.

When $R^4$ or $R^9$ is AD, n is 0 or 1. Examples of one aspect of n include 0, and examples of another aspect thereof include 1.

The compound represented by formula (1) may cause isomerization as shown in the following formula to become a compound represented by formula (1'). Hence, the hemiasterlin derivative according to the present invention encompasses the compound represented by formula (1').

[Chemical Formula 25]

The compound represented by formula (1') may be competitively generated when an antibody-drug conjugate is metabolized and the compound represented by formula (1) is generated in an organism, and may also be generated when the compound represented by formula (1) is generated in an organism and then causes the above isomerization. In chemical aspects, the compound represented by formula (1) causes the above isomerization in the presence of an acid or base catalyst. The compound represented by formula (1') is expected to exhibit activity for inhibiting microtubule polymerization or cellular toxicity as the compound represented by formula (1).

Examples of one aspect of the hemiasterlin derivative according to the present invention include the following (1-A).

(1-A)
A compound, wherein, in formula (1),
b is 2, 3 or 4;
X is —NH—;
Z is a group represented by formula (Z-1), formula (Z-2) or formula (Z-3);
W is a group represented by formula (W-1);
Q is a group represented by formula (Q-1) or formula (Q-2);
$R^{8a}$ and $R^{8b}$ are each a hydrogen atom;
$R^{8c}$, $R^{8d}$ and $R^{8e}$ are each a hydrogen atom;
$R^{6a}$ is a methyl group;
$R^{6b}$ is a hydrogen atom;
n is 0;
$R^3$ is —$(CH_2)_u$—$COR^9$;
u is 1 or 2;
$R^9$ is a hydroxy group;
$R^4$ is a hydroxy group;
$R^1$ is a hydrogen atom or $(AB)_m$;
$(AB)_m$ is Ala, Arg, Asn, Asp, Cys, Gln, Glu, Gly, His, Ile, Leu, Lys, Met, Phe, Pro, Ser, Thr, Trp, Tyr, Val, *¹-(Glu)-(Gly), *¹-(Glu)-(Gly)-(Arg), *¹-(Glu)-(Gly)-(Arg)-(Asn), *¹-(Glu)-(Gly)-(Arg)-(Asn)-(Phe), *¹-(Glu)-(Gly)-(Arg)-(Asn)-(Phe)-(Ser), *¹-(Glu)-(Gly)-(Arg)-(Asn)-(Phe)-(Ser)-(Lys), *¹-(Glu)-(Gly)-(Arg)-(Asn)-(Phe)-(Ser)-(Lys)-(Thr) or *¹-(Glu)-(Gly)-(Arg)-(Asn)-(Phe)-(Ser)-(Lys)-(Thr)-(Val); and
$R^2$ is a hydroxy group, Gly or Pro,
or a salt thereof.

Examples of one aspect of the hemiasterlin derivative according to the present invention include the following (1-B).

(1-B)
A compound, wherein, in formula (1),
b is 2, 3 or 4;
X is —NH—;
Z is a group represented by formula (Z-1), formula (Z-2) or formula (Z-3);
W is a group represented by formula (W-1);
Q is a group represented by formula (Q-1) or formula (Q-2);
$R^{8a}$ and $R^{8b}$ are each a hydrogen atom;
$R^{8c}$, $R^{8d}$ and $R^{8e}$ are each a hydrogen atom;
$R^{6a}$ is a methyl group;
$R^{6b}$ is a hydrogen atom;
n is 0 or 1;
AA is Glu or Asp;
$R^3$ is —$(CH_2)_u$—$COR^9$;
u is 1 or 2;
$R^9$ is a hydroxy group;
$R^4$ is a hydroxy group;
$R^1$ is a hydrogen atom or $(AB)_m$;
$(AB)_m$ is Ala, Arg, Asn, Asp, Gln, Glu, Gly, His, Ile, Leu, Lys, Met, Phe, Pro, Ser, Thr, Trp, Tyr, Val or *¹-(Glu)-(Gly); and
$R^2$ is a hydroxy group,
or a salt thereof.

Examples of one aspect of the hemiasterlin derivative according to the present invention include the following (1-C).

(1-C)
A compound, wherein, in formula (1),
b is 2, 3, 4 or 5;
X is —CO—;
Z is a group represented by formula (Z-6) or formula (Z-7);
W is a group represented by formula (W-1) or formula (W-2);
$R^7$ is an isopropyl group;
Q is a group represented by formula (Q-1) or formula (Q-2);
$R^{8a}$ and $R^{8b}$ are each a hydrogen atom;
$R^{8c}$, $R^{8d}$ and $R^{8e}$ are each a hydrogen atom;
$R^{6a}$ is a methyl group;
$R^{6b}$ is a hydrogen atom;
n is 0 or 1;

AA is Glu or Asp;
$R^3$ is $-(CH_2)_u-COR^9$;
u is 1 or 2;
$R^9$ is a hydroxy group;
$R^4$ is a hydroxy group;
$R^1$ is a hydrogen atom; and
$R^2$ is a hydroxy group,
or a salt thereof.

Examples of one aspect of the hemiasterlin derivative according to the present invention include the following (1-D).
(1-D)
A compound, wherein, in formula (1),
b is 2, 3, 4 or 5;
X is —NH—;
Z is a group represented by formula (Z-4) or formula (Z-5);
p is 1;
AA is Glu, Asp or Lys;
$R^{5a}$ is a methyl group;
$R^{5b}$ is a hydrogen atom;
$R^1$ is a hydrogen atom; and
$R^2$ is a hydroxy group,
or a salt thereof.

Examples of one aspect of the hemiasterlin derivative according to the present invention include the following (1-E).
(1-E)
A compound, wherein, in formula (1),
b is 2, 3, 4 or 5;
X is —CO—;
Z is a group represented by formula (Z-8) or formula (Z-9);
G is —O— or —NH—;
p is 1;
AA is Glu, Asp or Lys;
$R^{5a}$ is a methyl group;
$R^{5b}$ is a hydrogen atom;
$R^1$ is a hydrogen atom; and
$R^2$ is a hydroxy group,
or a salt thereof.

An antibody-drug conjugate is, as shown below, a conjugate in which the antibody moiety derived from an antibody molecule and a drug moiety derived from a drug molecule are covalently bonded in a direct fashion. In the present specification, the "antibody-drug conjugate" may be referred to as "ADC".

[Chemical Formula 26]

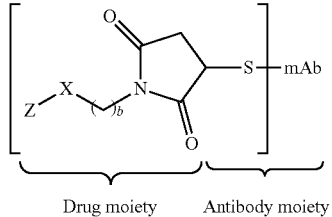

Drug moiety    Antibody moiety q indicates the drug antibody ratio (alternatively, referred to as DAR) in the antibody-drug conjugate. Drug antibody ratio q means the number of drug molecules per antibody molecule in one molecule of the antibody-drug conjugate, that is, per antibody-drug conjugate molecule. Note that antibody-drug conjugates obtained through chemical synthesis are often a mixture of a plurality of antibody-drug conjugate molecules that may have different drug antibody ratio q. In the present specification, the overall drug antibody ratio in such a mixture of antibody-drug conjugates (that is, the average value of drug antibody ratio q of each antibody-drug conjugate) is referred to as the "average drug antibody ratio" or "average DAR".

q is 1, 2, 3, 4, 5, 6, 7 or 8. Examples of one aspect of q include an integer of 2 to 8; examples of another aspect thereof include an integer of 2 to 6; examples of another aspect thereof include an integer of 4 to 8; examples of another aspect thereof include an integer of 6 to 8; examples of another aspect thereof include 2 or 4; examples of another aspect thereof include 6 or 8; and examples of another aspect thereof include 8.

Examples of one aspect of the average DAR include 2 to 8; examples of another aspect thereof include 3.5 to 4.5; and examples of another aspect thereof include 1 to 2, 2 to 3, 3 to 4, 4 to 5, 5 to 6, 6 to 7 or 7 to 8. It is possible to determine the average DAR by methods conventionally used to determine the average DAR, such as SDS-PAGE, mass spectrometry, ELISA (enzyme-linked immunosorbent assay) and HPLC (high performance liquid chromatography). It is possible to separate, purify and characterize an antibody-drug conjugate of a particular DAR from a mixture of a plurality of antibody-drug conjugates having different DARs by methods such as hydrophobic interaction chromatography (HIC) HPLC, reversed phase HPLC and electrophoresis.

mAb represents an "antibody". Here, it is sufficient that the "antibody" be an antibody including at least a heavy chain variable domain and a light chain variable domain, and it may be a complete antibody or a fragment of a complete antibody that is an antigen-binding fragment having an antigen-recognition site. The complete antibody has two full length light chains and two full length heavy chains, and respective light chains and heavy chains are linked by disulfide bonds. The complete antibody includes IgA, IgD, IgE, IgM and IgG, and IgG includes $IgG_1$, $IgG_2$, $IgG_3$ and $IgG_4$ as subtypes. In addition, it is preferable that the antibody be a monoclonal antibody. The antibody moiety and the drug moiety are linked via a sulfhydryl group obtained by reducing a disulfide bond in the antibody.

The antibody mAb is not particularly limited as long as it is an antibody that can recognize antigens present on the surface of target cells. It is sufficient that the target cell be a cell in need of treatment with a hemiasterlin derivative, and it is preferable that the target cell be a cancer cell. It is preferable that the antigen present on the surface of target cells be an antigen specific for the target cells, not expressed or expressed in a small amount in normal cells. Examples of one aspect of mAb include the known antibodies recited above; examples of another aspect thereof include brentuximab, trastuzumab, inotuzumab, gemtuzumab, glembatumumab, labetuzumab, sacituzumab, lifastuzumab, indusatumab, polatuzumab, pinatuzumab, coltuximab, indatuximab, milatuximab, rovalpituzumab, anetumab, tisotumab, lorvotuzumab, rituximab, depatuxizumab, denintuzumab, enfortumab, telisotuzumab, vandortuzumab, sofituzumab, vorsetuzumab, mirvetuximab, naratuximab, cantuzumab, laprituximab, bivatuzumab, vadastuximab, lupartumab, aprutumab, abagovomab, abciximab, abituzumab, abrilumab, actoxumab, adalimumab, adecatumumab, aducanumab, afasevikumab, afelimomab, alacizumab, alemtuzumab, alirocumab, altumomab, amatuximab, anatumomab, anifrolumab, anrukinzumab, apolizumab, arcitumomab, ascrinvacumab, aselizumab, atezolizumab, atinumab, atorolimumab, avelumab, azintuxizumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bleselumab, blinatumomab, bloblontuvetmab, blosozumab, bococizumab, brazikumab, briakinumab, brodalumab, brolucizumab, brontictuzumab, burosumab, cabiralizumab, camrelizumab, caplacizumab, capromab, carlumab, carotuximab, catumaxomab, cedelizumab, certolizumab, cetuximab, citatuzumab, cixutumumab, clenoliximab, clivatuzumab, codrituzumab, conatumumab, concizumab, cosfroviximab, crenezumab, crizanlizumab, crotedumab, dacetuzumab, daclizumab, dalotuzumab, dapirolizumab, daratumumab, dectrekumab, demcizumab, denosumab, detumomab, dezamizumab, dinutuximab, diridavumab, domagrozumab, dorlimomab, drozitumab, duligotuzumab, dupilumab, durvalumab, dusigitumab, duvortuxizumab, ecromeximab, eculizumab, edobacomab, edrecolomab, efalizumab, efungumab, eldelumab, elezanumab, elotuzumab, elsilimomab, emactuzumab, emapalumab, emibetuzumab, emicizumab, enavatuzumab, enlimomab, enoblituzumab, enokizumab, enoticumab, ensituximab, epitumomab, epratuzumab, eptinezumab, erenumab, erlizumab, ertumaxomab, etaracizumab, etrolizumab, evinacumab, evolocumab, exbivirumab, faralimomab, farletuzumab, fasinumab, felvizumab, fezakinumab, ficlatuzumab, figitumumab, firivumab, flanvotumab, fletikumab, fontolizumab, foralumab, foravirumab, fremanezumab, fresolimumab, frunevetmab, fulranumab, futuximab, galcanezumab, galiximab, ganitumab, gantenerumab, gatipotuzumab, gavilimomab, gedivumab, gevokizumab, gilvetmab, girentuximab, golimumab, guselkumab, ibalizumab, ibritumomab, icrucumab, idarucizumab, ifabotuzumab, igovomab, imalumab, imciromab, imgatuzumab, inclacumab, inebilizumab, infliximab, inolimomab, intetumumab, ipilimumab, iratumumab, isatuximab, itolizumab, ixekizumab, keliximab, lacnotuzumab, lampalizumab, lanadelumab, landogrozumab, larcaviximab, lebrikizumab, lemalesomab, lenzilumab, lerdelimumab, lesofavumab, letolizumab, lexatumumab, libivirumab, lifatuzumab, ligelizumab, lilotomab, lintuzumab, lirilumab, lodelcizumab, lokivetmab, lucatumumab, lulizumab, lumretuzumab, lutikizumab, mapatumumab, margetuximab, maslimomab, matuzumab, mavrilimumab, mepolizumab, metelimumab, minretumomab, mitumomab, modotuximab, mogamulizumab, monalizumab, morolimumab, motavizumab, moxetumomab, muromonab, nacolomab, namilumab, naptumomab, namatumab, natalizumab, navicixizumab, navivumab, nebacumab, necitumumab, nemolizumab, nerelimomab, nesvacumab, nimotuzumab, nivolumab, obiltoxaximab, obinutuzumab, ocaratuzumab, ocrelizumab, odulimomab, ofatumumab, olaratumab, oleclumab, olendalizumab, olokizumab, omalizumab, onartuzumab, ontuxizumab, opicinumab, oportuzumab, oregovomab, orticumab, otelixizumab, otlertuzumab, oxelumab, ozanezumab, ozoralizumab, pagibaximab, palivizumab, pamrevlumab, panitumumab, panobacumab, parsatuzumab, pascolizumab, pasotuxizumab, pateclizumab, patritumab, pembrolizumab, perakizumab, pertuzumab, pexelizumab, pidilizumab, placulumab, plozalizumab, ponezumab, porgaviximab, prezalumab, priliximab, pritoxaximab, pritumumab, quilizumab, racotumomab, radretumab, rafivirumab, ralpancizumab, ramucirumab, ranevetmab, ranibizumab, raxibacumab, refanezumab, regavirumab, remtolumab, reslizumab, rilotumumab, rinucumab, risankizumab, rivabazumab, robatumumab, roledumab, romosozumab, rontalizumab, rosmantuzumab, rovelizumab, rozanolixizumab, ruplizumab, samalizumab, sarilumab, satralizumab, satumomab, secukinumab, selicrelumab, seribantumab, setoxaximab, sevirumab, sibrotuzumab, sifalimumab, siltuximab, simtuzumab, siplizumab, sirukumab, solanezumab, solitomab, sontuzumab, stamulumab, sulesomab, suptavumab, suvizumab, suvratoxumab, tabalumab, tadocizumab, talizumab, tamtuvetmab, tanezumab, taplitumomab, tarextumab, tavolixizumab, fanolesomab, nofetumomab, pintumomab, tefibazumab, telimomab, telisotuzumab, tenatumomab, teneliximab, teplizumab, teprotumumab, tesidolumab, tezepelumab, tigatuzumab, tildrakizumab, timigutuzumab, timolumab, tocilizumab, tomuzotuximab, toralizumab, tosatoxumab, tositumomab, tovetumab, tralokinumab, tregalizumab, tremelimumab, trevogrumab, tucotuzumab, tuvirumab, ublituximab, ulocuplumab, urelumab, urtoxazumab, ustekinumab, utomilumab, vantictumab, vanucizumab, vapaliximab, varisakumab, varlilumab, vatelizumab, vedolizumab, veltuzumab, vepalimomab, vesencumab, visilizumab, vobarilizumab, volociximab, vonlerolizumab, votumumab, vunakizumab, tacatuzumab, zalutumumab, zanolimumab, ziralimumab, zolimomab or anti-embigin antibody; examples of another aspect thereof include brentuximab, trastuzumab, inotuzumab, gemtuzumab, labetuzumab, polatuzumab, coltuximab, indatuximab, anetumab, rituximab, denintuzumab, laprituximab, vadastuximab, glembatumumab, cetuximab, alemtuzumab, or depatuxizumab; examples of another aspect thereof include brentuximab, trastuzumab, rituximab or anti-embigin antibody; and examples of another aspect thereof include brentuximab or trastuzumab, preferably brentuximab.

Examples of mAb include anti-19A antibody, anti-AXL antibody, anti-BCMA antibody, anti-C4.4a antibody, anti-CA6 antibody, anti-CA9 antibody, anti-CA-125 antibody, anti-cadherin-6 antibody, anti-CD166 antibody, anti-CD19 antibody, anti-CD20 antibody, anti-CD22 antibody, anti-CD25 antibody, anti-CD27 antibody, anti-CD30 antibody, anti-CD33 antibody, anti-CD37 antibody, anti-CD40 antibody, anti-CD41 antibody, anti-CD44v6 antibody, anti-CD51 antibody, anti-CD52 antibody, anti-CD56 antibody, anti-CD70 antibody, anti-CD74 antibody, anti-CD79 antibody, anti-CD79b antibody, anti-CEACAM5 antibody, anti-c-Met antibody, anti-DLL3 antibody, anti-DPEP3 antibody, anti-EGFR antibody, anti-EGFRvIII antibody, anti-ENPP3 antibody, anti-EpCAM antibody, anti-EphA4 antibody, anti-FGFR2 antibody, anti-FGFR3 antibody, anti-FTL3 antibody, anti-folate receptor a antibody, anti-gripican 3 antibody, anti-gpNMB antibody, anti-HER2 antibody, anti-HER3 antibody, anti-IL-3RA antibody, anti-LAMP1 antibody, anti-LIV-1 antibody, anti-LRRC15 antibody, anti-Ly6E antibody, anti-mesothelin antibody, anti-MUC-16 antibody, anti-NaPi2b antibody, anti-nectin-4 antibody, anti-CD352 antibody, anti-P-cadherin antibody, anti-PMSA antibody, anti-protein tyrosine kinase 7 antibody, anti-SLITRK antibody, anti-STEAP1 antibody, anti-CD138 antibody, anti-tissue factor antibody, anti-CD71 antibody, anti-TIM-1 antibody, anti-Trop2 antibody, anti-5T4 antibody, anti-B7-H3 antibody, anti-CD163 macrophage receptor antibody, anti-CD38 antibody, anti-CD48 antibody, anti-cKit antibody, anti-guanylate cyclase C antibody, anti-gastrin releasing peptide antibody, anti-solute carrier antibody, anti-tumor-associated MUC-1 antibody, anti-GD2 antibody, anti-α4β7 integrin antibody or anti-embigin antibody. Examples of another aspect of mAb include anti-CD19 antibody, anti-CD20 antibody, anti-CD22 antibody, anti-CD30 antibody, anti-CD33 antibody, anti-CD52 antibody, anti-CD70 antibody, anti- CD79b antibody, anti-CEACAM5 antibody, anti-EGFR antibody, anti-EGFRvIII antibody, anti-gpNMB antibody, anti-HER2 antibody, anti-mesothelin antibody, anti-CD138 antibody, anti-CD38 antibody or anti-GD2 antibody. Examples of another aspect of mAb include anti-CD19 antibody, anti-CD20 antibody, anti-CD22 antibody, anti-CD30 antibody, anti-CD33 antibody, anti-CD52 antibody, anti-CD79b antibody, anti-CEACAM5 antibody, anti-EGFR antibody, anti-EGFRvIII antibody, anti-gpNMB antibody, anti-HER2 antibody, anti-mesothelin antibody or anti-CD138 antibody.

The "antibody of AMG 595" means anti-EGFRvIII antibody that can be obtained by the method described in Mol. Cancer Ther., 2015, 14, 1614-1624.

In general, it is possible to carry out production and analysis of the antibody-drug conjugate by an arbitrary technique known to a person having ordinary skill in the art. Examples of such a method include the method described in Antibody-Drug Conjugates (edited by Laurent Ducry, published by Humana Press, 2013).

The antibody-drug conjugate may be formed by, for example, reducing a disulfide bond in the antibody into a sulfhydryl group and allowing this sulfhydryl group to react with the hemiasterlin derivative.

The antibody-drug conjugate undergoes metabolism of the antibody in target cells (antigen-expressing cells), and a structure including a part of the antibody (antibody fragment) and the drug moiety may be released as an active metabolite. For example, it is disclosed in Non Patent Literature 7 that the Cys-drug moiety of an antibody-drug conjugate is released in cells through metabolism of the antibody.

It is speculated that the antibody-drug conjugate is delivered specifically into particular antigen-expressing cells through uptake into cells utilizing antibody-antigen reaction, and then releases the active metabolite through the mechanisms mentioned above, thereby exerting drug efficacy only in the particular cells. The antibody-drug conjugate can be taken up specifically into cancer cells, and therefore, can be expected to exert strong drug efficacy against cancer cells.

On the other hand, it is believed that some antibody-drug conjugates may be broken down by protease or the like contained in the blood before being delivered to target cells, releasing the active metabolite into the blood. At that time, in case of conventional antibody-drug conjugates, the active metabolite released in the blood acts also on normal cells. As a result, unintentional systemic exposure is caused, which is unfavorable because side effects tend to occur.

Further, after being specifically delivered into particular antigen-expressing cells, the antibody-drug conjugate releases the active metabolite through the above-described mechanism, and as a result the active metabolite may be released from the inside of the cells to the outside of the cells or into the blood through cell death or the like. At that time, in case of conventional antibody-drug conjugates, the active metabolite released in the blood acts also on normal cells. As a result, unintentional systemic exposure is caused, which is unfavorable because side effects tend to occur.

In contrast, the active metabolite corresponding to the hemiasterlin derivative according to the present invention, as reported in Non Patent Literature 7, is unlikely to act on normal cells and is quickly metabolized and excreted, even if the active metabolite is released in the blood before or after reaching target cells; therefore, it can be expected that side effects due to systemic exposure is small.

That is, because of being produced through metabolism of the antibody-drug conjugate, the hemiasterlin derivative according to the present invention is expected to exert drug efficacy specifically to cancer cells, and also to have small influence on normal cells and high safety.

The "salt" is a suitable salt of the hemiasterlin derivative according to the present invention and is a salt thereof acceptable as a pharmaceutical raw material, and is preferably a pharmaceutically acceptable salt. For the "salt", for example, in addition to acid addition salts such as organic acid salts (for example, acetate, trifluoroacetate, maleate, fumarate, citrate, tartrate, methanesulfonate, benzenesulfonate, formate, p-toluenesulfonate or the like) and inorganic acid salts (for example, hydrochloride, hydrobromide, hydroiodide, sulfate, nitrate, phosphateor the like); salts with amino acids (for example, arginine, aspartic acid, glutamic acid or the like); metal salts such as alkali metal salts (for example, sodium salt, potassium salt or the like) and alkaline earth metal salts (for example, calcium salt, magnesium salt or the like); ammonium salts; or organic base salts (for example, trimethylamine salt, triethylamine salt, pyridine salt, picoline salt, dicyclohexylamine salt, N,N'-dibenzylethylenediamine salt or the like), a person having ordinary skill in the art may select appropriate salts as appropriate.

Examples of the "pharmaceutically acceptable salt" include acid addition salts and base addition salts. Examples of the acid addition salt include inorganic acid salts such as hydrochloride, hydrobromide, sulfate, hydroiodide, nitrate and phosphate, or organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate and camphorsulfonate. In addition, examples of the base addition salt include inorganic base salts such as sodium salt, potassium salt, calcium salt, magnesium salt, barium salt and aluminum salt, or organic base salts such as trimethylamine, triethylamine, pyridine, picoline, 2,6-lutidine, ethanolamine, diethanolamine, triethanolamine, tromethamine[tris(hydroxymethyl)methyl amine], tert-butylamine, cyclohexylamine, dicyclohexylamine and N,N-dibenzylethylamine. Furthermore, examples of the "pharmaceutically acceptable salt" include salts (amino acid salts) with basic amino acids or acidic amino acids such as arginine, lysine, ornithine, aspartic acid and glutamic acid.

When it is desired to acquire a salt of the hemiasterlin derivative according to the present invention, if the target compound is obtained in the form of salt, that compound may be purified as is, and if the target compound is obtained in the free form, that compound may be dissolved or suspended in an appropriate organic solvent, to which an acid or base is added to form a salt by a conventional method.

The hemiasterlin derivative according to the present invention may be present in the form of hydrates and/or solvates (ethanolate and the like) with various solvents, and these hydrates and/or solvates are also included in the hemiasterlin derivative according to the present invention. Furthermore, all modes of crystal forms of the hemiasterlin derivative according to the present invention are also included in the present invention.

Among the hemiasterlin derivative according to the present invention, some may have optical isomers based on the optically active center, atropisomers based on axial or planar chirality caused by restraint of intramolecular rotation, and all of the other stereoisomers, tautomers and geometrical isomers, and all possible isomers including the above are encompassed within the scope of the present invention.

In particular, optical isomers and atropisomers may be obtained as racemate, and when optically active starting materials or intermediates are used, optically active substances may be obtained, respectively. If necessary, at an appropriate stage in the following production methods, corresponding raw material, intermediate or racemate, the final product, may be optically resolved into optical enantiomers physically or chemically through known separation methods such as a method using an optically active column and fractional crystallization method. Specifically, for example, in diastereomer method, two diastereomers are formed from racemate through a reaction using an optically active resolving agent. In general, these different diastereomers have different physical properties, and thus, can be optically resolved by known methods such as fractional crystallization.

Production methods for the hemiasterlin derivative according to the present invention will be mentioned below. The hemiasterlin derivative according to the present invention represented by formula (1) may be produced by, for example, the following production method A to P or T.

Production Method A

When X is —NH—; Z is a group represented by formula (Z-1); W is a group represented by formula (W-1); Q is a group represented by formula (Q-1); $R^{6a}$ is a methyl group; $R^{6b}$ is a hydrogen atom or a methyl group; and $R^3$ is —$(CH_2)_u$—COOH, the compound represented by formula (1) may be produced by, for example, the following production method:

[Chemical Formula 27]

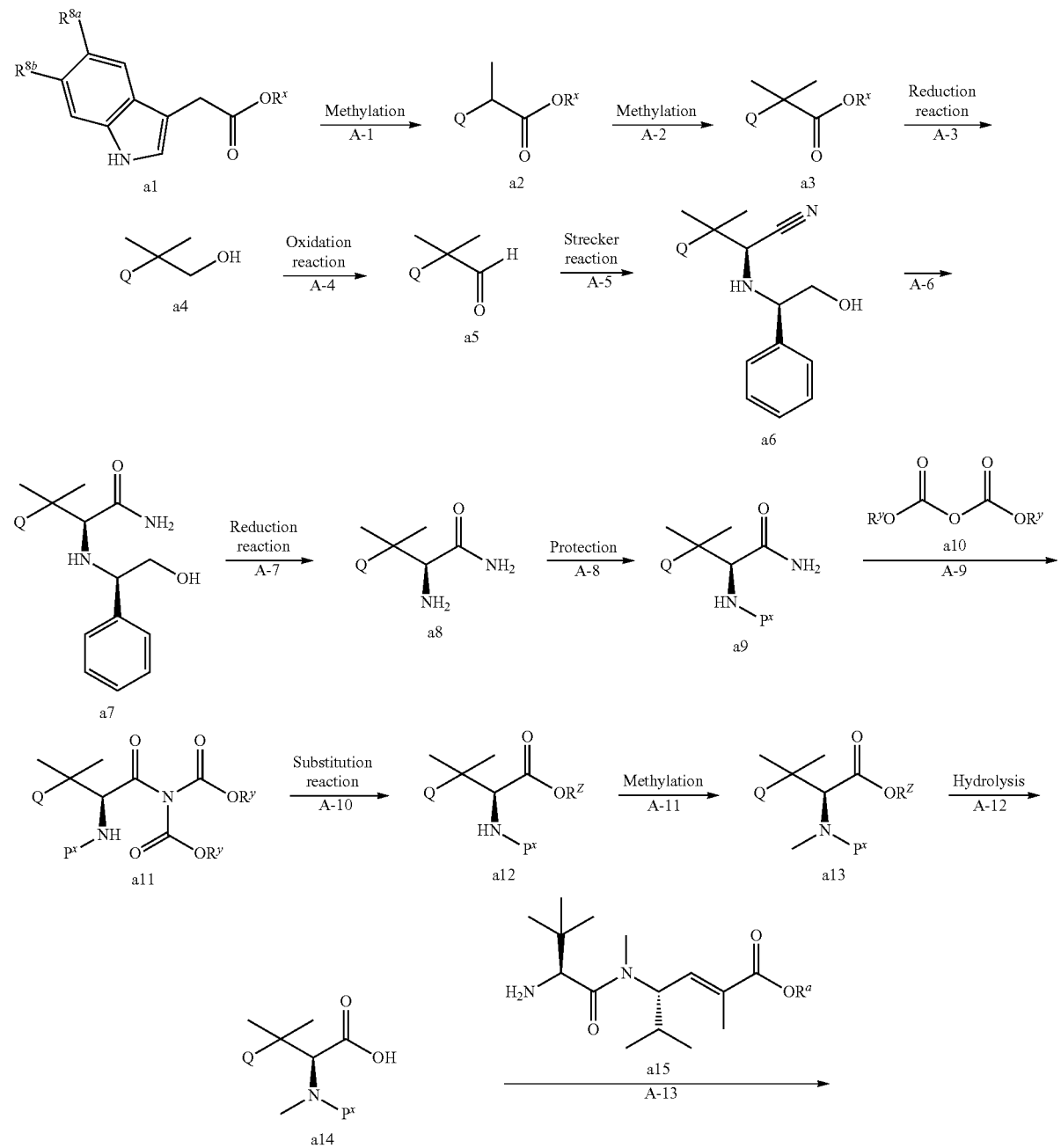

-continued
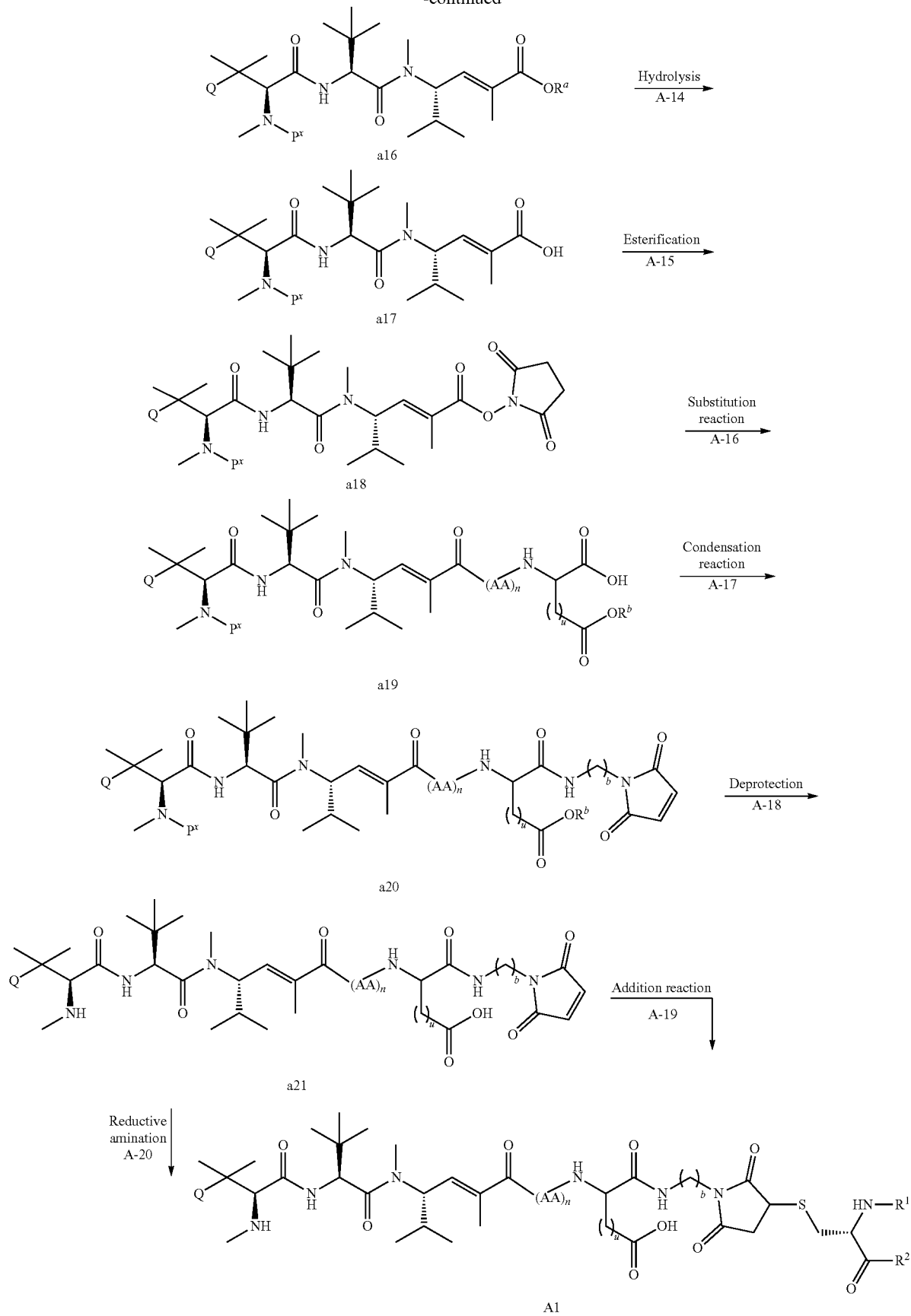

-continued

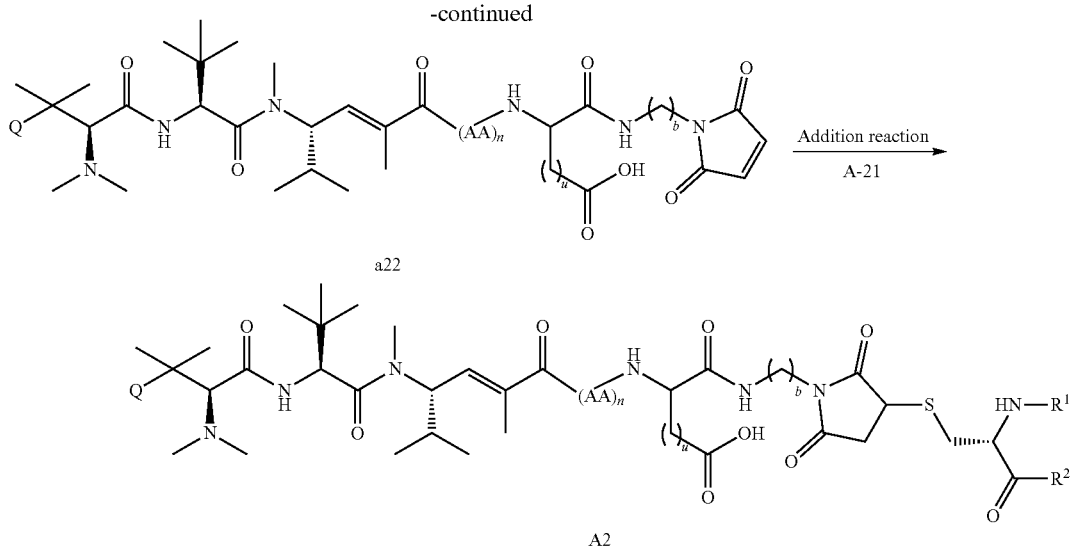

a22

A2 wherein, $R^1$, $R^2$, $R^{8a}$, $R^{8b}$, AA, u, b and n are as defined in item 1; $R^a$, $R^b$, $R^x$, $R^y$ and $R^z$ each independently represent a $C_{1-6}$ alkyl group or a benzyl group; and $P^X$ represents a protecting group for the amino group.

As the above protecting group for the amino group, represented by $P^X$, the protecting groups described in Protective Groups in Organic Synthesis (authored by Theodora W. Greene, Peter G. M. Wuts, issued by John Wiley & Sons, Inc., 1999) and the like may be used.

Compound a1 may be produced by the method described in, for example, J. Med. Chem., 2007, 50, 4329-4339 and the like, or may be purchased as a commercial product. Compound a15 may be produced by the method described in, for example, Tetrahedron Lett., 1997, 38, 317-320 and the like, or may be purchased as a commercial product.

[A-1 Step]

Compound a2 may be produced by allowing compound a1 to react with various methylating reagents in an appropriate solvent in the presence of an appropriate base. Examples of the methylating reagent include methyl halide, and preferably include methyl iodide, methyl bromide and methyl chloride. Examples of the base preferably include potassium hexamethyldisilazide. Examples of the solvent preferably include tetrahydrofuran. The reaction time is normally 5 minutes to 48 hours, and is preferably 10 minutes to 2 hours. The reaction temperature is normally −78° C. to 100° C., and is preferably −78° C. to 10° C. This step may be carried out in accordance with the method described in J. Nat. Prod. 2003, 66, 183-199 and the like.

[A-2 Step]

Compound a3 may be produced from compound a2 in accordance with the method described in the above A-1 step.

[A-3 Step]

Compound a4 may be produced by allowing compound a3 to react with an appropriate reducing agent in an appropriate solvent. The reducing agent is selected from reducing agents used in usual organic synthesis reactions as appropriate, and examples thereof preferably include diisobutylaluminum hydride. Examples of the solvent preferably include diethyl ether. The reaction time is normally 5 minutes to 48 hours, and is preferably 10 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[A-4 Step]

Compound a5 may be produced by oxidizing compound a4 using an appropriate oxidizing agent in an appropriate solvent. The oxidizing agent may be selected from oxidizing agents used in usual organic synthesis reactions as appropriate, and examples thereof preferably include tetrapropylammonium perruthenate. Examples of the solvent preferably include dichloromethane. The reaction time is normally 5 minutes to 72 hours, and is preferably 30 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[A-5 Step]

Compound a6 may be produced by α-aminocyanating the aldehyde of the compound a5 in an appropriate solvent. Examples of the solvent preferably include toluene and dichloromethane. The reaction time is normally 5 minutes to 96 hours, and is preferably 24 hours to 72 hours. The reaction temperature is normally 0° C. to 200° C., and is preferably 0° C. to 100° C. This step may be carried out in accordance with the method described in Org. Lett. 2002, 4, 695-697 and the like.

[A-6 Step]

Compound a7 may be produced from compound a6 by using an appropriate oxidizing agent in an appropriate solvent in the presence of or in the absence of an appropriate base. The oxidizing agent may be selected from oxidizing agents used in usual organic synthesis reactions as appropriate, and examples thereof preferably include hydrogen peroxide. Examples of the base preferably include potassium carbonate. Examples of the solvent preferably include methanol. The reaction time is normally 5 minutes to 72 hours, and is preferably 30 minutes to 24 hours. The reaction temperature is normally 0° C. to 200° C., and is preferably 0° C. to 60° C. This step may be carried out in accordance with the method described in J. Org. Chem. 2001, 66, 7355-7364 and the like.

[A-7 Step]

Compound a8 may be produced by reducing compound a7 using an appropriate reducing agent in an appropriate solvent in the presence of an appropriate catalyst. The reducing agent may be selected from reducing agents used in usual organic synthesis reactions as appropriate, and examples thereof preferably include hydrogen, formate such as ammonium formate, or hydrazine. Examples of the catalyst include transition metals such as palladium, nickel, rhodium, cobalt and platinum, salts thereof or complexes thereof, or supports such as polymer having the above transition metals supported thereon. Examples of the solvent preferably include ethanol or methanol. The reaction time is normally 5 minutes to 72 hours, and is preferably 30 minutes to 24 hours. The reaction temperature is normally 0° C. to 200° C., and is preferably 0° C. to 100° C. This step may be carried out in accordance with the method described in J. Org. Chem. 2001, 66, 7355-7364 and the like.

[A-8 Step]

Compound a9 may be produced by protecting the amino group of compound a8 with protecting group $P^X$. This step may be carried out in accordance with the method described in Protective Groups in Organic Synthesis (authored by Theodora W. Greene, Peter G. M. Wuts, issued by John Wiley & Sons, Inc., 1999) and the like.

[A-9 Step]

Compound a11 may be produced by allowing compound a9 to react with various acylating reagents (for example, compound a10) in an appropriate solvent in the presence of or in the absence of an appropriate base. Examples of the acylating reagent include carboxylic halide and carboxylic anhydride, and preferably include di-tert-butyl dicarbonate. Examples of the base preferably include diisopropylethylamine. Examples of the solvent preferably include chloroform. The reaction time is normally 5 minutes to 72 hours, and is preferably 30 minutes to 24 hours. The reaction temperature is normally 0° C. to 200° C., and is preferably 0° C. to 50° C.

[A-10 Step]

Compound a12 may be produced by allowing compound a11 to react with an appropriate alkali metal alkoxide in an appropriate solvent. The alkali metal alkoxide may be selected from alkali metal alkoxides used in usual organic synthesis reactions as appropriate, and examples thereof preferably include lithium methoxide or lithium ethoxide. Examples of the solvent preferably include methanol or ethanol. The reaction time is normally 5 minutes to 72 hours, and is preferably 30 minutes to 6 hours. The reaction temperature is normally −78° C. to 200° C., and is preferably −78° C. to 50° C.

[A-11 Step]

Compound a13 may be produced by allowing compound a12 to react with various methylating reagents in an appropriate solvent in the presence of an appropriate base. Examples of the methylating reagent include methyl halide, and preferably include methyl iodide, methyl bromide and methyl chloride. Examples of the base preferably include sodium hydride. Examples of the solvent preferably include tetrahydrofuran. The reaction time is normally 5 minutes to 48 hours, and is preferably 10 minutes to 2 hours. The reaction temperature is normally −78° C. to 100° C., and is preferably −78° C. to 10° C.

[A-12 Step]

Compound a14 may be produced by hydrolyzing the ester of compound a13, in an appropriate solvent in the presence of an appropriate base. Examples of the base preferably include lithium hydroxide. Examples of the solvent preferably include water or methanol. The reaction time is normally 5 minutes to 72 hours, and is preferably 30 minutes to 24 hours. The reaction temperature is normally 0° C. to 200° C., and is preferably 0° C. to 100° C.

[A-13 Step]

Compound a16 may be produced by condensing compound a14 and compound a15 using various condensing agents in an appropriate solvent in the presence of an appropriate base. As the condensing agent, various condensing agents used in usual organic synthesis reactions may be used, and examples thereof preferably include (1-ethyl-3-(3-dimethylaminopropyl)carbodiimide or bromotripyrrolidinophosphonium hexafluorophosphate. In addition a carbonyl activating reagent such as 1-hydroxybenzotriazole may be used together as necessary, in order to improve efficiency of the condensation reaction. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally −78° C. to 200° C., and is preferably 0° C. to 100° C. This step may be carried out in accordance with the method described in Tetrahedron Lett., 1997, 38, 317-320 and the like.

[A-14 Step]

Compound a17 may be produced by hydrolyzing the ester of compound a16, in accordance with the method described in the above A-12 step. This step may be carried out in accordance with the method described in Tetrahedron Lett., 1997, 38, 317-320 and the like.

[A-15 Step]

Compound a18 may be produced by allowing compound a17 to react with N-hydroxysuccinimide using various condensing agents in an appropriate solvent in the presence of an appropriate base. As the condensing agent, various condensing agents used in usual organic synthesis reactions may be used, and examples thereof preferably include (1-ethyl-3-(3-dimethylaminopropyl)carbodiimide or bromotripyrrolidinophosphonium hexafluorophosphate. In addition, a carbonyl activating reagent such as 1-hydroxybenzotriazole may be used together as necessary, in order to improve efficiency of the reaction. Examples of the base preferably include diisopropylethylamine Examples of the solvent preferably include N,N-dimethylformamide. The reaction time is normally 5 minutes to 72 hours, and is preferably 30 minutes to 24 hours. The reaction temperature is normally −78° C. to 200° C., and is preferably 0° C. to 100° C.

[A-16 Step]

Compound a19 may be produced by allowing compound a18 to react with an ester of an amino acid or peptide in an appropriate solvent in the presence of an appropriate base. Examples of the base preferably include diisopropylethylamine Examples of the solvent preferably include N,N-dimethylformamide. The reaction time is normally 5 minutes to 72 hours, and is preferably 30 minutes to 24 hours. The reaction temperature is normally 0° C. to 200° C., and is preferably 0° C. to 100° C.

[A-17 Step]

Compound a20 may be produced by condensing compound a19 and an aminoalkylmaleimide compound in accordance with the method described in the above A-13 step.

[A-18 Step]

Compound a21 may be produced by deprotection of the protecting group $P^X$ for the amino group of compound a20 and hydrolysis of the ester (—$COOR^b$). This step may be carried out in accordance with the method described in Protective Groups in Organic Synthesis (authored by Theodora W. Greene, Peter G. M. Wuts, issued by John Wiley & Sons, Inc., 1999) and the like.

In addition, when $(AA)_n$ has an ester or a protected amino group, hydrolysis of the ester and deprotection of the protecting group for the amino group may also be carried out as necessary in the present deprotecting step.

[A-19 Step]

Compound A1 may be produced by allowing compound a21 and a cysteine derivative to react together in an appropriate solvent. Examples of the solvent preferably include water, dimethylsulfoxide and dimethylformamide. The reaction time is normally 5 minutes to 72 hours, and is preferably 30 minutes to 24 hours. The reaction temperature is normally 0° C. to about 200° C., and is preferably 0° C. to 40° C.

[A-20 Step]

Compound a22 may be produced by allowing compound a21 and formaldehyde to react together with an appropriate reducing agent in an appropriate solvent. Examples of the solvent preferably include acetonitrile. As the reducing agent, various reducing agents used in usual organic synthesis reactions may be used, and examples thereof preferably include sodium triacetoxyborohydride. The reaction time is normally 5 minutes to 72 hours, and is preferably 30 minutes to 24 hours. The reaction temperature is normally 0° C. to about 200° C., and is preferably 0° C. to 100° C.

[A-21 Step]

Compound A2 may be produced from compound a22 in accordance with the method described in the above A-19 step.

Production Method B

When X is —NH—; Z is a group represented by formula (Z-1); W is a group represented by formula (W-1); Q is a group represented by formula (Q-2); $R^{8c}$, $R^{8d}$ and $R^{8e}$ are each a hydrogen atom; $R^{6a}$ is a methyl group; $R^{6b}$ is a hydrogen atom or a methyl group; and $R^3$ is —$(CH_2)_u$—COOH, the compound represented by formula (1) may be produced by, for example, the following production method:

[Chemical Formula 28]

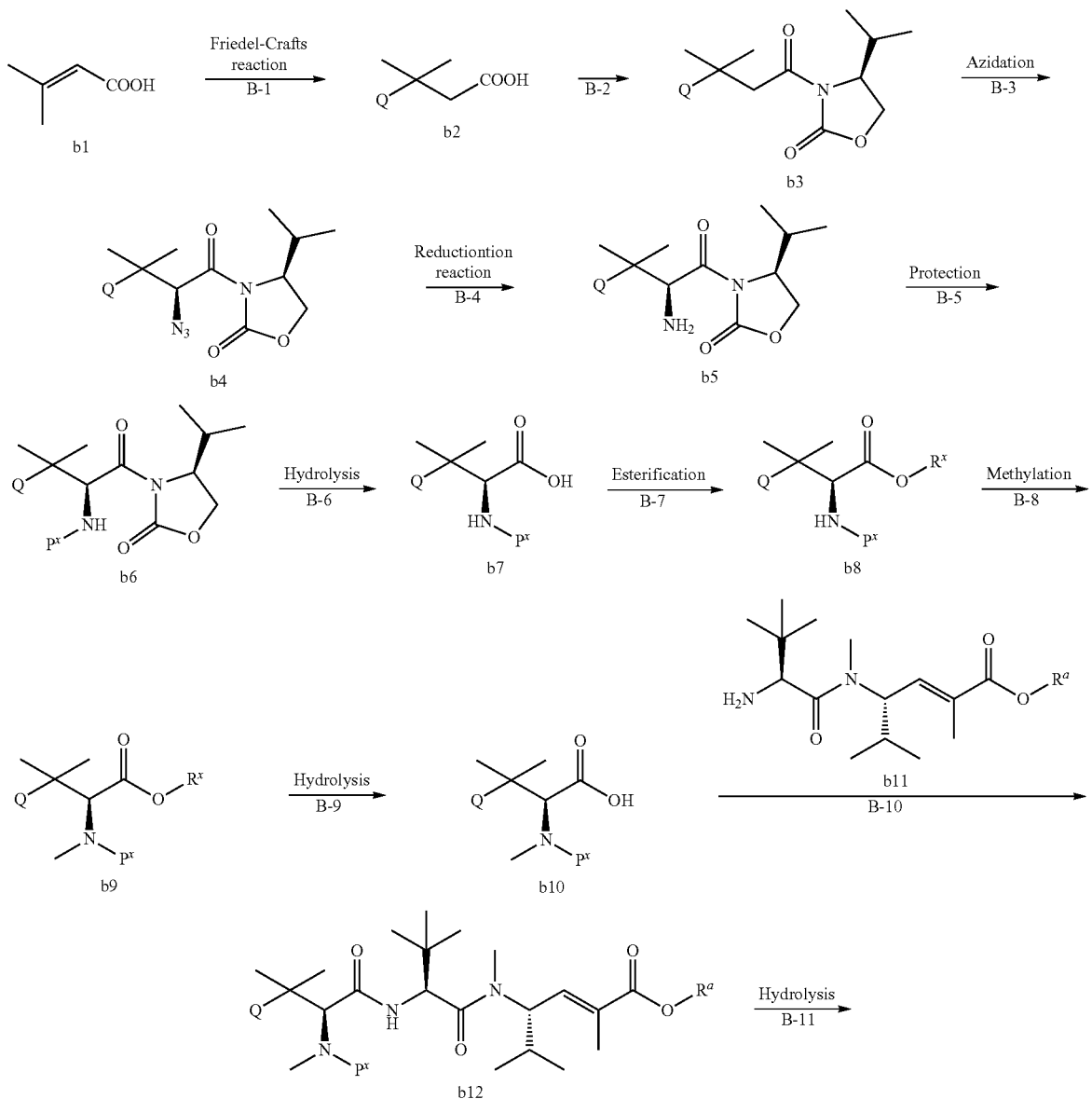

-continued
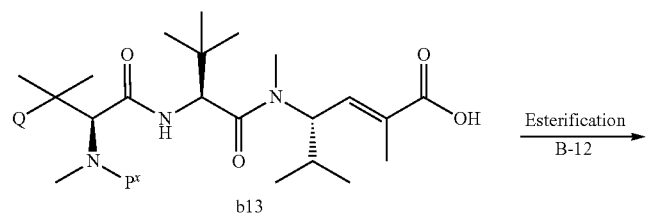
b13 → Esterification B-12
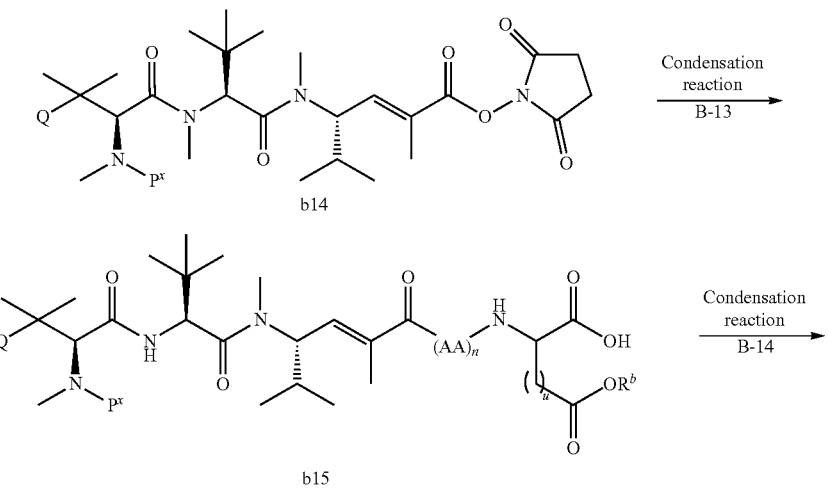
b14 → Condensation reaction B-13
b15 → Condensation reaction B-14
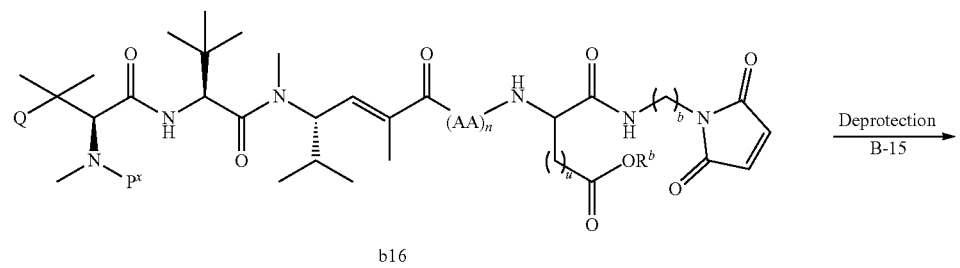
b16 → Deprotection B-15
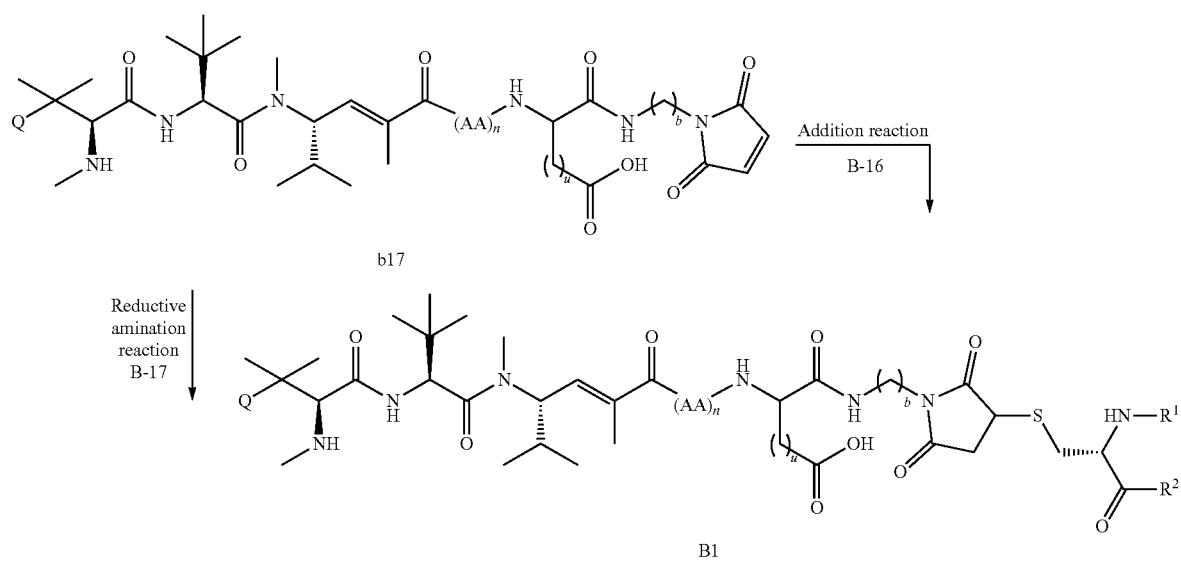
b17 → Addition reaction B-16
↓ Reductive amination reaction B-17
B1

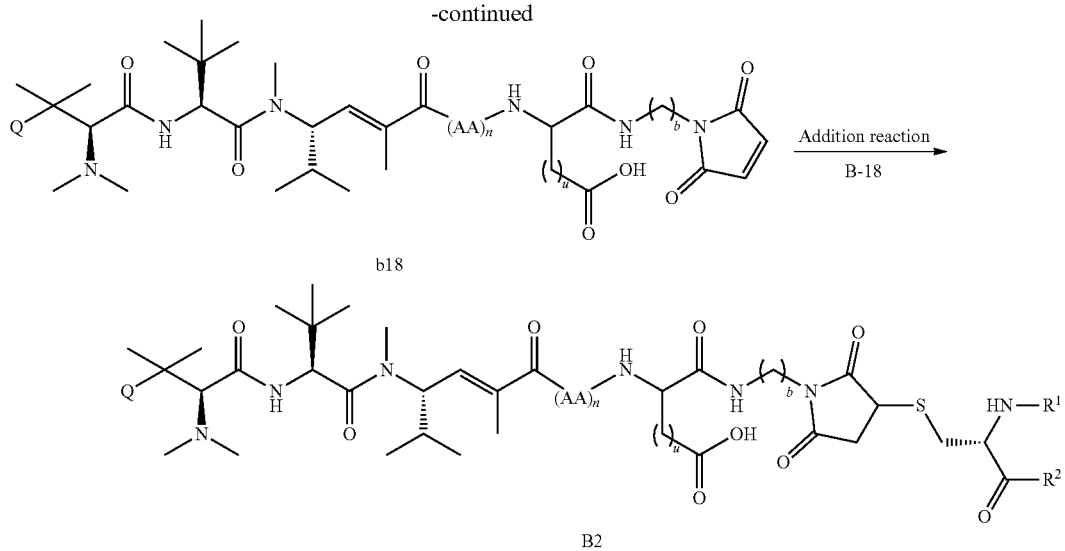

b18

B2 wherein, $R^1$, $R^2$, AA, u, b and n are as defined in item 1; $R^a$, $R^b$ and $R^x$ represent a $C_{1-6}$ alkyl group or a benzyl group; and $P^x$ means a protecting group for the amino group.

Compound b1 may be, for example, purchased as a commercial product. Compound b11 may be produced by the methods described in, for example, Tetrahedron Lett., 1997, 38, 317-320 and the like, or may be purchased as a commercial product.

[B-1 Step]

Compound b2 may be produced by allowing compound b1 to react with benzene in the presence of various Lewis acids. Examples of the Lewis acid include boron halide, aluminum halide, gallium halide, iron halide and titanium halide, and preferably include aluminum chloride and iron chloride. The reaction time is normally 5 minutes to 48 hours, and is preferably 30 minutes to 4 hours. The reaction temperature is normally −78° C. to 200° C., and is preferably 50° C. to 150° C. This step may be carried out in accordance with the method described in J. Nat. Prod. 2003, 66, 183-199 and the like.

[B-2 Step]

Compound b3 may be produced by allowing compound b2 to react with various carboxylic halides and then to react with an alkali metallized 4-alkyl-2-oxazolidinone in an appropriate solvent in the presence of an appropriate base. Examples of the base preferably include triethylamine or diisopropylethylamine Examples of the solvent preferably include tetrahydrofuran. Examples of the carboxylic halide include carboxylic chloride, and preferably include pivaloyl chloride. Examples of the alkali metallized 4-alkyl-2-oxazolidinone include 4-alkyl-2-oxazolidinone lithium and 4-alkyl-2-oxazolidinone sodium, and preferably include 4-isopropyl-2-oxazolidinone lithium. The reaction time is normally 5 minutes to 48 hours, and is preferably 10 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[B-3 Step]

Compound b4 may be produced by allowing compound b3 to react with various azidating reagents in an appropriate solvent in the presence of an appropriate base. Examples of the azidating reagent include sodium azide, trimethylsilyl azide and diphenylphosphoryl azide, and preferably include trimethylsilyl azide. Examples of the base preferably include potassium hexamethyldisilazide. Examples of the solvent preferably include tetrahydrofuran. The reaction time is normally 5 minutes to 72 hours, and is preferably 30 minutes to 24 hours. The reaction temperature is normally −78° C. to 200° C., and is preferably −78° C. to 75° C. This step may be carried out in accordance with the method described in J. Nat. Prod. 2003, 66, 183-199 and the like.

[B-4 Step]

Compound b5 may be produced from compound b4 in accordance with the method described in the above A-7 step.

[B-5 Step]

Compound b6 may be produced from compound b5 in accordance with the method described in the above A-8 step.

[B-6 Step]

Compound b7 may be produced from compound b6 by using an appropriate oxidizing agent in an appropriate solvent in the presence of an appropriate base. Examples of the base preferably include lithium hydroxide. Examples of the solvent preferably include methanol, tetrahydrofuran or water. The oxidizing agent may be selected from oxidizing agents used in usual organic synthesis reactions as appropriate, and examples thereof preferably include hydrogen peroxide. The reaction time is normally 5 minutes to 72 hours, and is preferably 30 minutes to 24 hours. The reaction temperature is normally 0° C. to 200° C., and is preferably 0° C. to 60° C. This step may be carried out in accordance with the method described in J. Nat. Prod. 2003, 66, 183-199 and the like.

[B-7 Step]

Compound b8 may be produced by allowing compound b7 to react with various alkylating reagents in an appropriate solvent in the presence of an appropriate base. Examples of the alkylating reagent include alkyl halide, and preferably include alkyl iodide, alkyl bromide and alkyl chloride. Examples of the base preferably include sodium carbonate and potassium carbonate. Examples of the solvent preferably include N,N-dimethylformamide. The reaction time is normally 5 minutes to 48 hours, and is preferably 10 minutes to 2 hours. The reaction temperature is normally −78° C. to 100° C., and is preferably −10° C. to 25° C. This step may be carried out in accordance with the method described in Protective Groups in Organic Synthesis (authored by Theodora W. Greene, Peter G. M. Wuts, issued by John Wiley & Sons, Inc., 1999) and the like.

[B-8 Step]

Compound b9 may be produced from compound b8 in accordance with the method described in the above A-11 step.

[B-9 Step]

Compound b10 may be produced from compound b9 in accordance with the method described in the above A-12 step.

[B-10 Step]

Compound b12 may be produced from compound b10 and compound b11 in accordance with the method described in the above A-13 step.

[B-11 Step]

Compound b13 may be produced by hydrolyzing the ester of compound b12 in accordance with the method described in the above A-12 step.

[B-12 Step]

Compound b14 may be produced from compound b13 in accordance with the method described in the above A-15 step.

[B-13 Step]

Compound b15 may be produced from compound b14 in accordance with the method described in the above A-16 step.

[B-14 Step]

Compound b16 may be produced from compound b15 in accordance with the method described in the above A-17 step.

[B-15 Step]

Compound b17 may be produced from compound b16 in accordance with the method described in the above A-18 step.

[B-16 Step]

Compound B1 may be produced from compound b17 in accordance with the method described in the above A-19 step.

[B-17 Step]

Compound b18 may be produced from compound b17 in accordance with the method described in the above A-20 step.

[B-18 Step]

Compound B2 may be produced from compound b18 in accordance with the method described in the above A-19 step.

Production Method C

When X is —NH—; Z is a group represented by formula (Z-1); W is a group represented by formula (W-1); $R^{6a}$ is a methyl group; $R^{6b}$ is a hydrogen atom or a methyl group; and $R^3$ is —$(CH_2)_u$—COOH, the compound represented by formula (1) may be produced by, for example, the following production method:

[Chemical Formula 29]

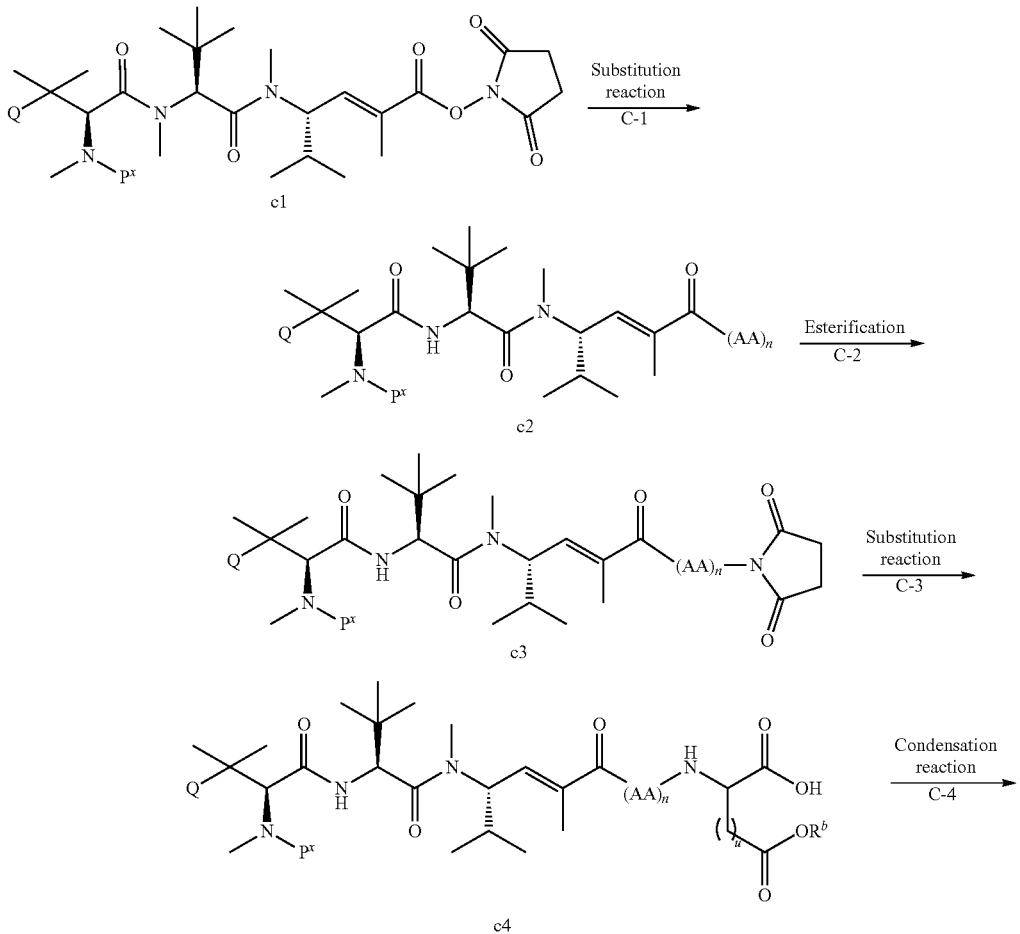

-continued

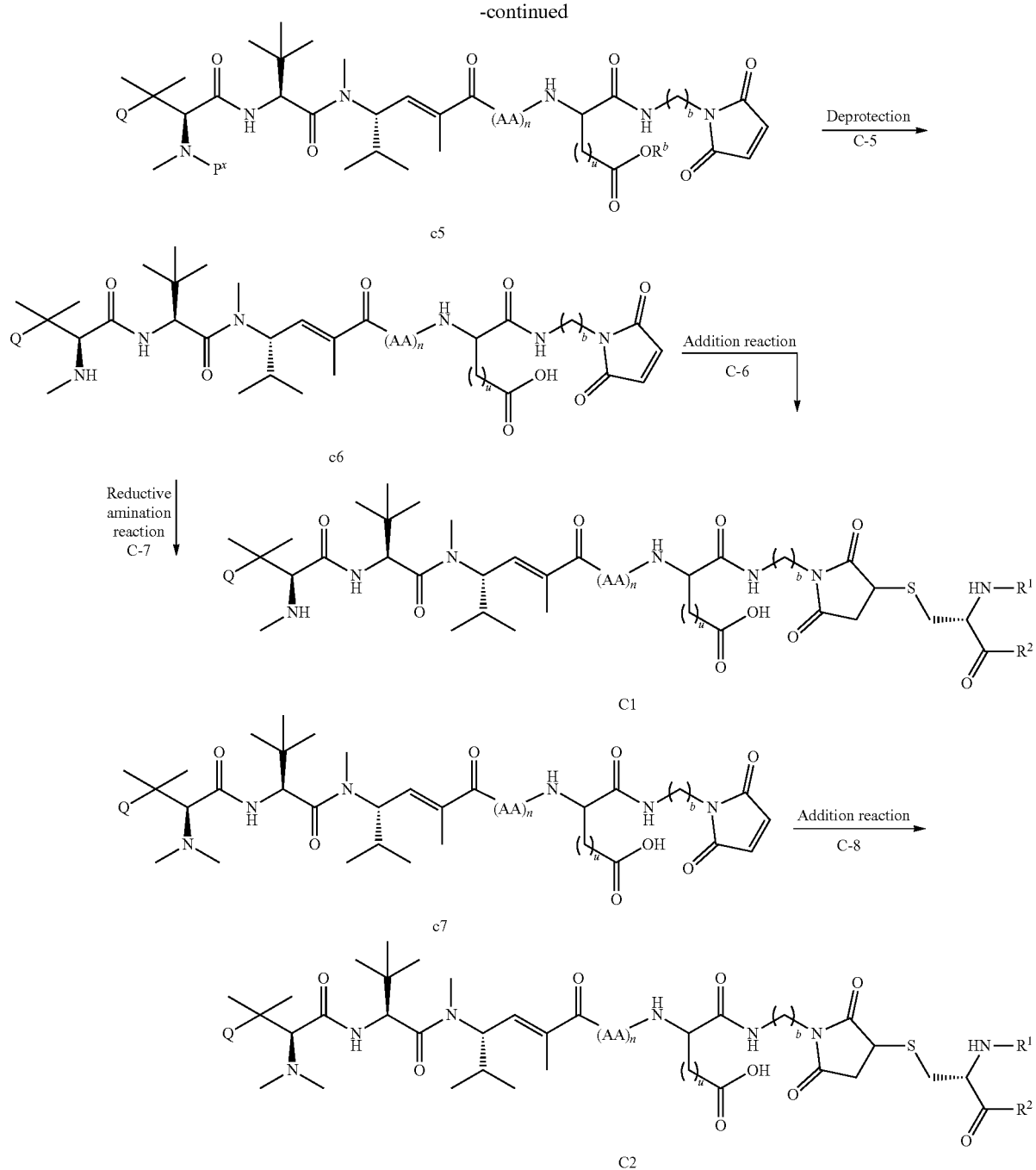

wherein, R', R², AA, u, b and n are as defined in item 1; and R$^b$ and P$^x$ are as defined above.

Compound c1 represents compound a18 of Production Method A or compound b14 of Production Method B.

[C-1 Step]

Compound c2 may be produced from compound c1 in accordance with the method described in the above A-16 step.

[C-2 Step]

Compound c3 may be produced from compound c2 in accordance with the method described in the above A-15 step.

[C-3 Step]

Compound c4 may be produced from compound c3 in accordance with the method described in the above A-16 step.

[C-4 Step]

Compound c5 may be produced from compound c4 in accordance with the method described in the above A-17 step.

[C-5 Step]

Compound c6 may be produced from compound c5 in accordance with the method described in the above A-18 step.

[C-6 Step]

Compound $C_1$ may be produced from compound c6 in accordance with the method described in the above A-19 step.

[C-7 Step]

Compound c7 may be produced from compound c6 in accordance with the method described in the above A-20 step.

[C-8 Step]

Compound C2 may be produced from compound c7 in accordance with the method described in the above A-19 step.

Production Method D

When X is —NH—; Z is a group represented by formula (Z-1); W is a group represented by formula (W-1); $R^{6a}$ is a methyl group; $R^{6b}$ is a hydrogen atom or a methyl group; $R^3$ is —$(CH_2)_u$—$COR^9$; $R^5$ is AD; and n is 1, the compound represented by formula (1) may be produced by, for example, the following production method:

[Chemical Formula 30]

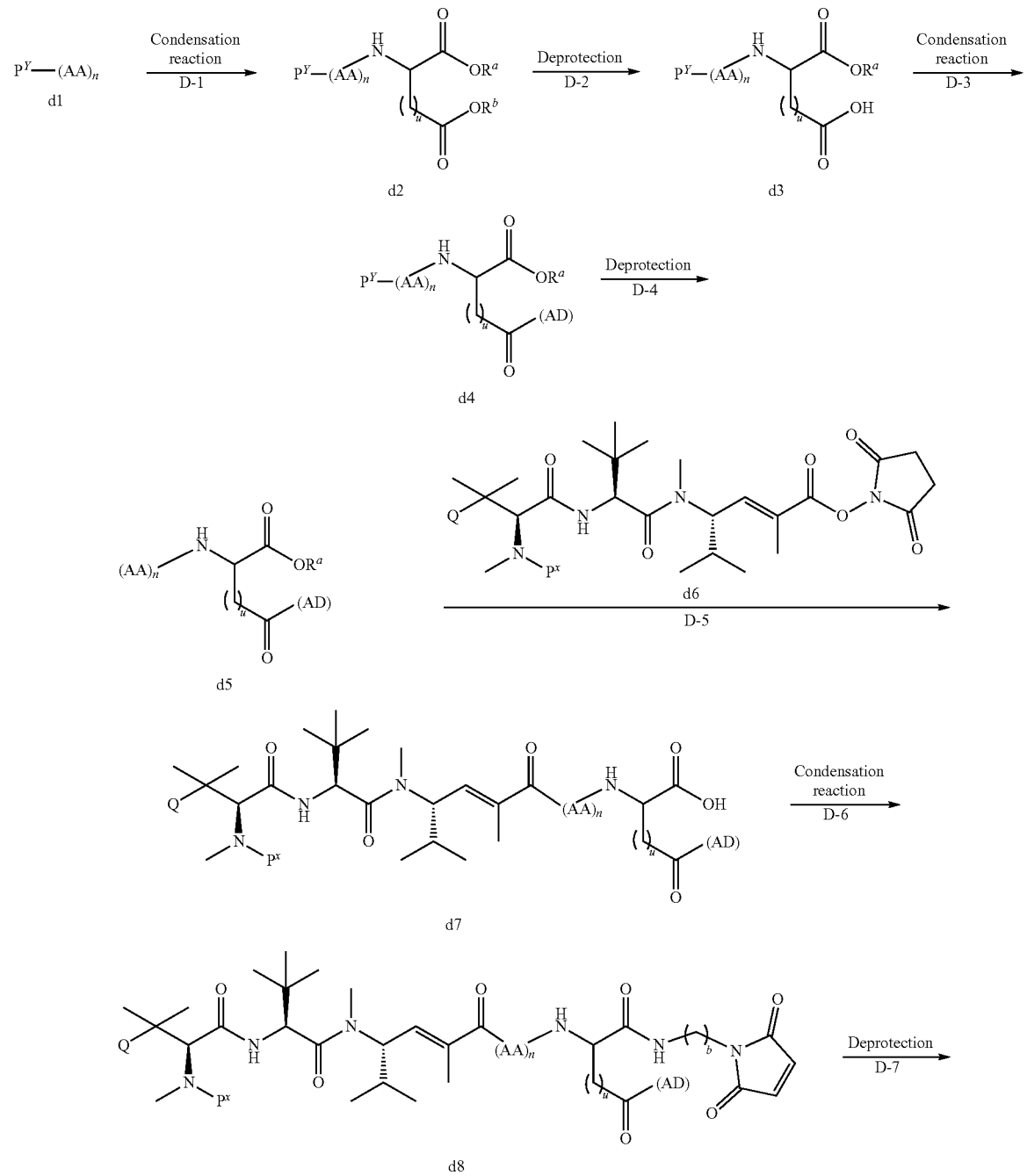

-continued

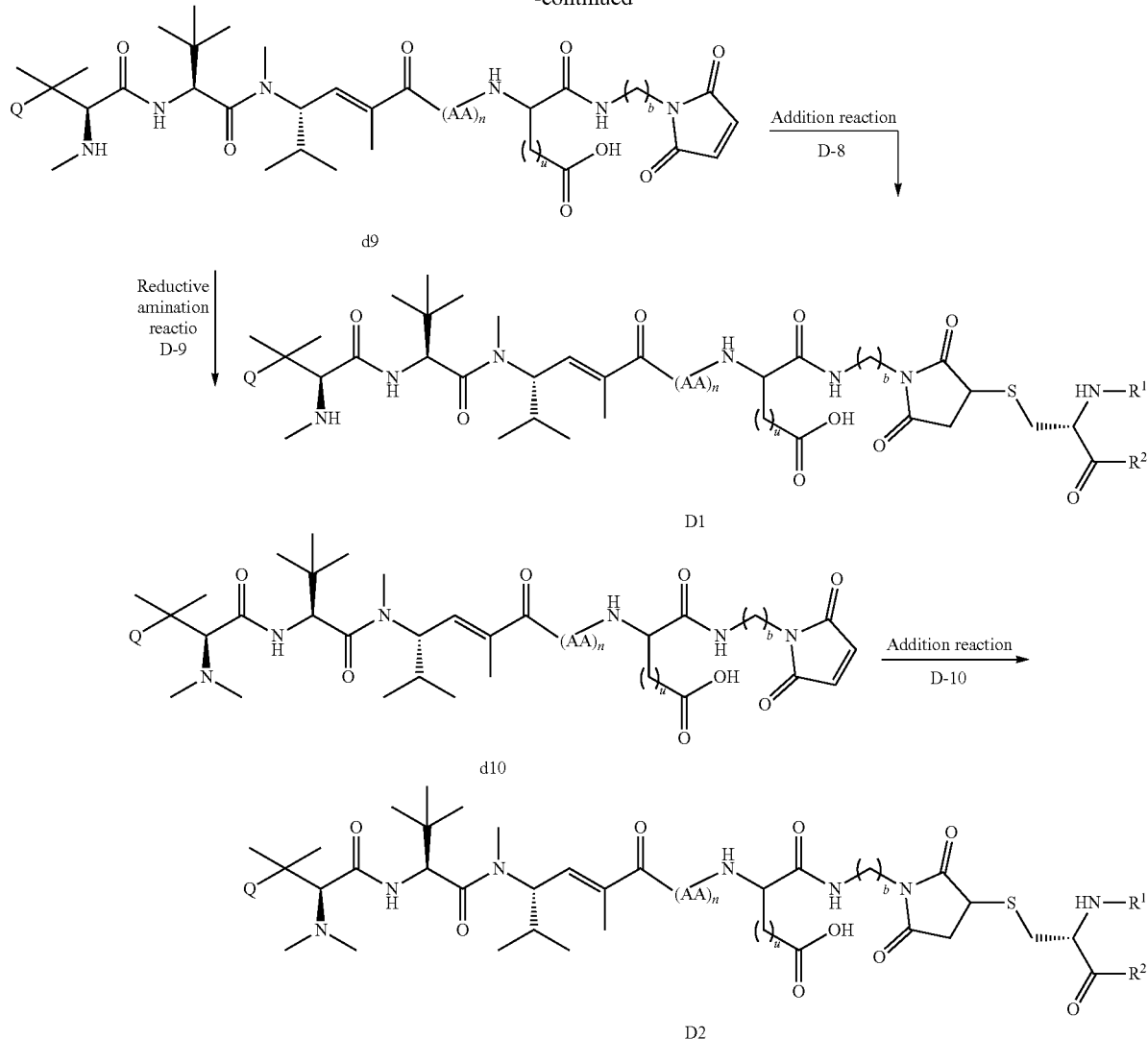

wherein, $R^1$, $R^2$, Q, AA, AD, u and b are as defined in item 1; $P^Y$ means a protecting group for the amino group; and $R^1$, $R^b$ and $P^X$ are as defined above.

As the above protecting group for the amino group, represented by $P^Y$, the protecting groups described in Protective Groups in Organic Synthesis (authored by Theodora W. Greene, Peter G. M. Wuts, issued by John Wiley & Sons, Inc., 1999) and the like may be used.

Compound d1 may be, for example, purchased as a commercial product. Compound d6 represents compound a18 of Production Method A or compound b14 of Production Method B.

[D-1 Step]
Compound d2 may be produced by condensing compound d1 and aspartic acid diester or glutamic acid diester in accordance with the method described in the above A-13 step.

[D-2 Step]
Compound d3 may be produced by hydrolyzing the ester of compound d2 in accordance with the method described in the above A-12 step.

[D-3 Step]
Compound d4 may be produced by condensing compound d3 and (AD) in accordance with the method described in the above A-13 step.

[D-4 Step]
Compound d5 may be produced by carrying out hydrolysis of the ester of compound d4 and deprotection of the protecting group for the amino group in accordance with the method described in the above A-18 step. In addition, when (AD) has an ester or a protected amino group, hydrolysis of the ester and deprotection of the protecting group for amino may also be carried out in the present deprotecting step, as necessary.

[D-5 Step]
Compound d7 may be produced from compound d5 and compound d6 in accordance with the method described in the above A-16 step.

[D-6 Step]
Compound d8 may be produced from compound d7 in accordance with the method described in the above A-17 step.

[D-7 Step]
Compound d9 may be produced from compound d8 in accordance with the method described in the above A-18 step.

[D-8 Step]

Compound D1 may be produced from compound d9 in accordance with the method described in the above A-19 step.

[D-9 Step]

Compound d10 may be produced from compound d9 in accordance with the method described in the above A-20 step.

[D-10 Step]

Compound D2 may be produced from compound d10 in accordance with the method described in the above A-19 step.

Production Method E

When X is —NH—; Z is a group represented by formula (Z-2) or formula (Z-3); W is a group represented by formula (W-1); $R^{6a}$ is a methyl group; $R^{6b}$ is a hydrogen atom or a methyl group; and $R^4$ is a hydroxy group, the compound represented by formula (1) may be produced by, for example, the following production method:

[Chemical Formula 31]

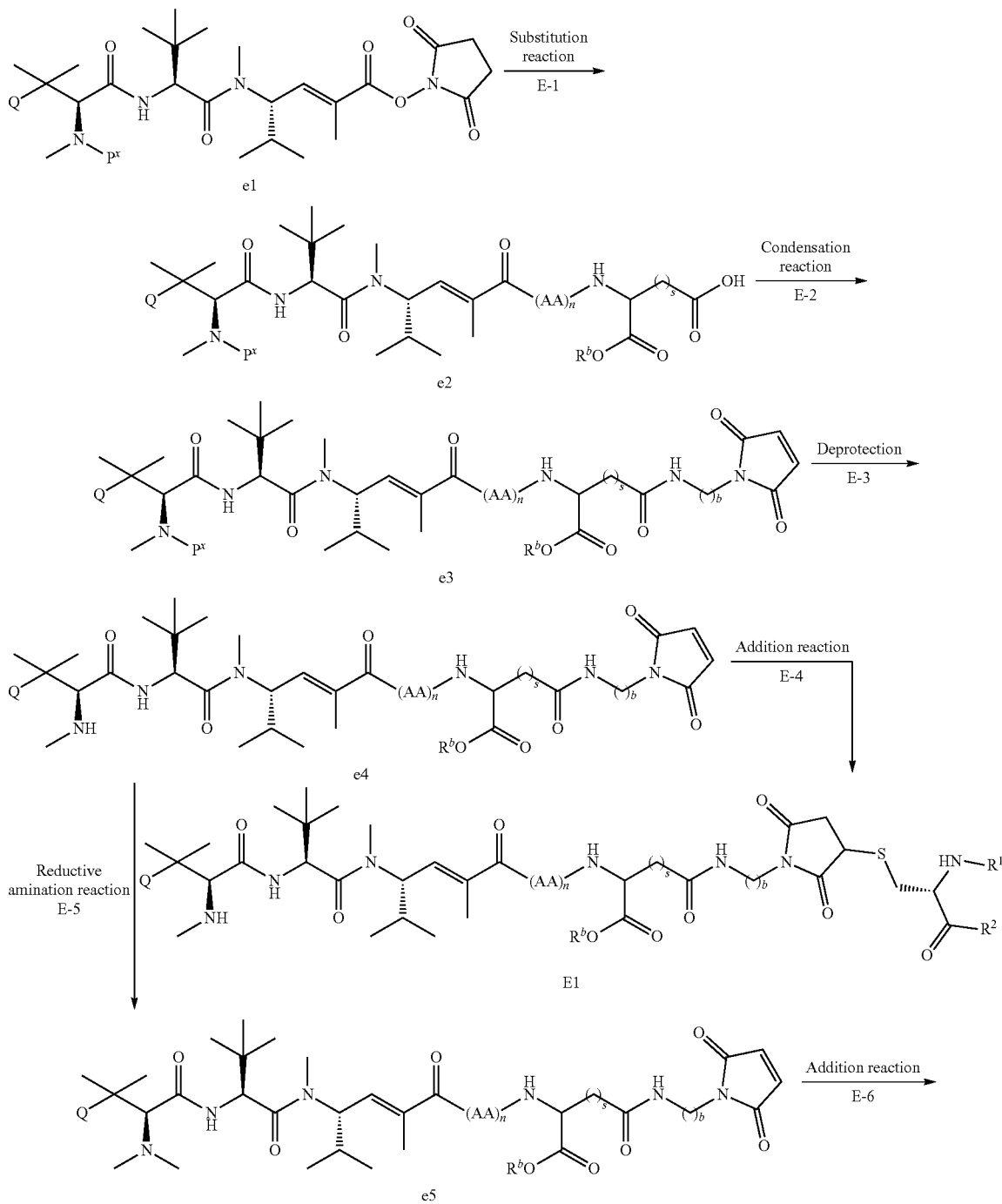

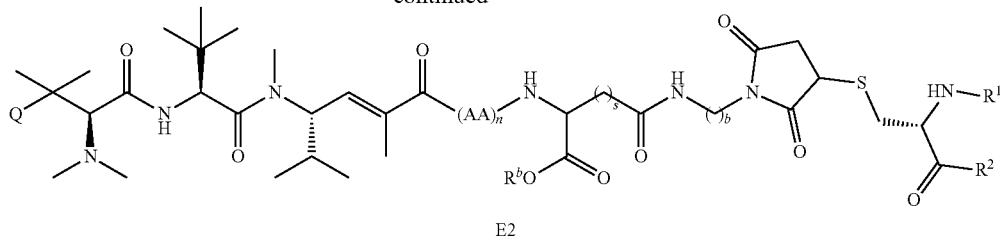

E2 wherein, $R^1$, $R^2$, Q, AA, b and n are as defined in item 1; s represents 1 or 2; and $R^b$ and $P^x$ are as defined above.

Compound e1 represents compound a18 of Production Method A or compound b14 of Production Method B.

[E-1 Step]

Compound e2 may be produced from compound e1 in accordance with the method described in the above A-16 step.

[E-2 Step]

Compound e3 may be produced from compound e2 in accordance with the method described in the above A-17 step.

[E-3 Step]

Compound e4 may be produced from compound e3 in accordance with the method described in the above A-18 step.

[E-4 Step]

Compound E1 may be produced from compound e4 in accordance with the method described in the above A-19 step.

[E-5 Step]

Compound e5 may be produced from compound e4 in accordance with the method described in the above A-20 step.

[E-6 Step]

Compound E2 may be produced from compound e5 in accordance with the method described in the above A-19 step.

Production Method F

When X is —NH—; Z is a group represented by formula (Z-2) or formula (Z-3); W is a group represented by formula (W-1); $R^{6a}$ is a methyl group; $R^{6b}$ is a hydrogen atom or a methyl group; and $R^4$ is a hydroxy group, the compound represented by formula (1) may be produced by, for example, the following production method:

[Chemical Formula 32]

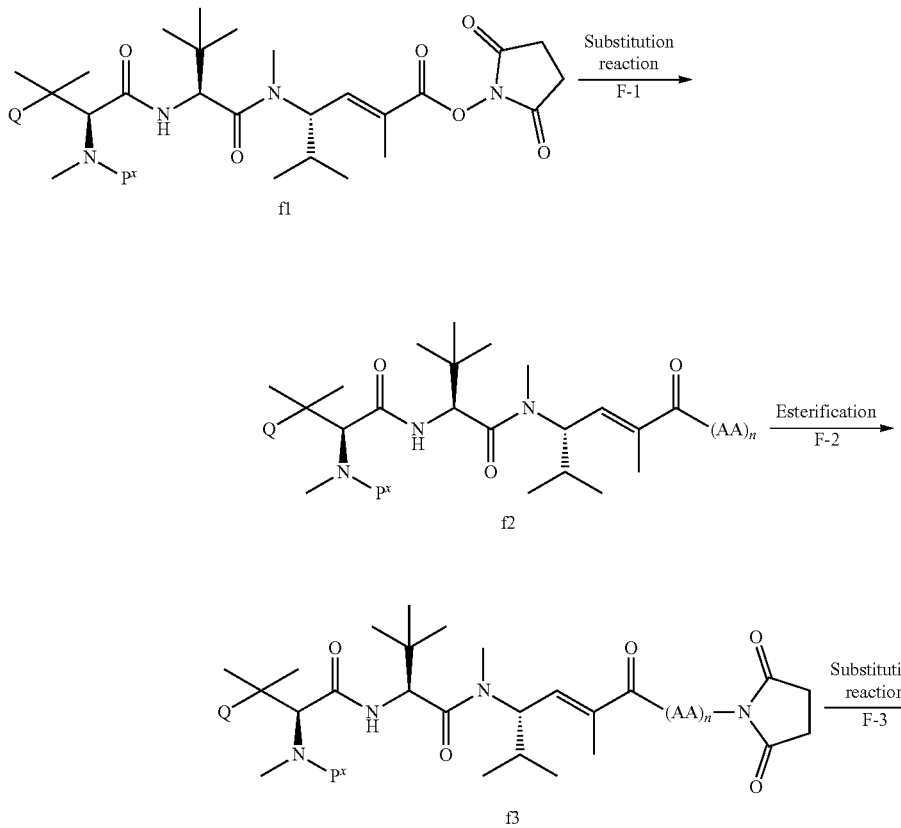

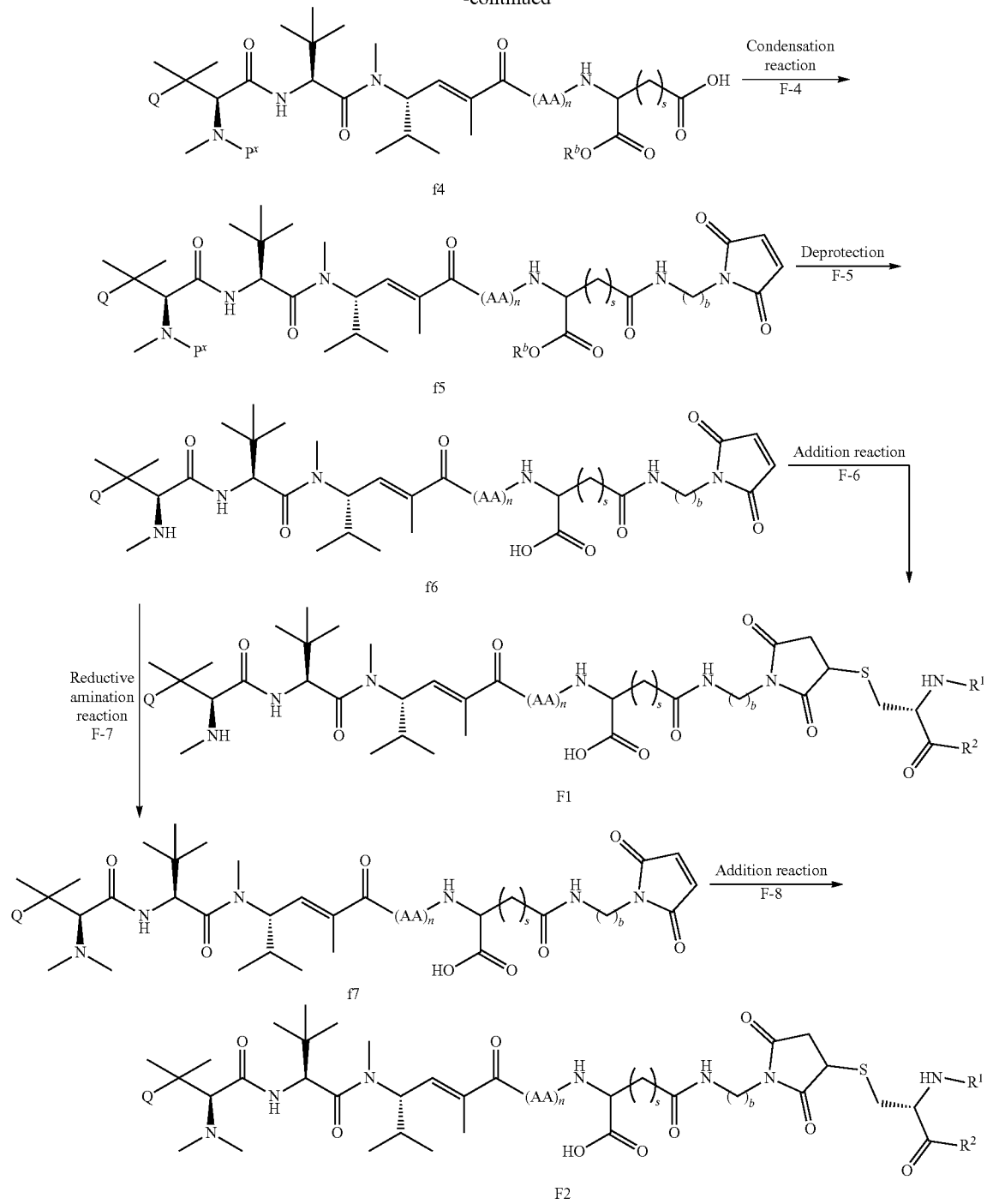

wherein, $R^1$, $R^2$, Q, AA b and n are as defined in item 1; and s, $R^b$ and $P^x$ are as defined above.

Compound f1 represents compound a18 of Production Method A or compound b14 of Production Method B.

[F-1 Step]

Compound f2 may be produced from compound f1 in accordance with the method described in the above A-16 step.

[F-2 Step]

Compound f3 may be produced from compound f2 in accordance with the method described in the above A-15 step.

[F-3 Step]

Compound f4 may be produced from compound f3 in accordance with the method described in the above A-16 step.

[F-4 Step]

Compound f5 may be produced from compound f4 in accordance with the method described in the above A-17 step.

[F-5 Step]

Compound f6 may be produced from compound f5 in accordance with the method described in the above A-18 step.

[F-6 Step]

Compound F1 may be produced from compound f6 in accordance with the method described in the above A-19 step.

[F-7 Step]

Compound f7 may be produced from compound f6 in accordance with the method described in the above A-20 step.

[F-8 Step]

Compound F2 may be produced from compound f7 in accordance with the method described in the above A-19 step.

Production Method G

When X is —NH—; Z is a group represented by formula (Z-2) or formula (Z-3); W is a group represented by formula (W-1); $R^{6a}$ is a methyl group; $R^{6b}$ is a hydrogen atom or a methyl group; and $R^4$ is AD, the compound represented by formula (1) may be produced by, for example, the following production method:

[Chemical Formula 33]

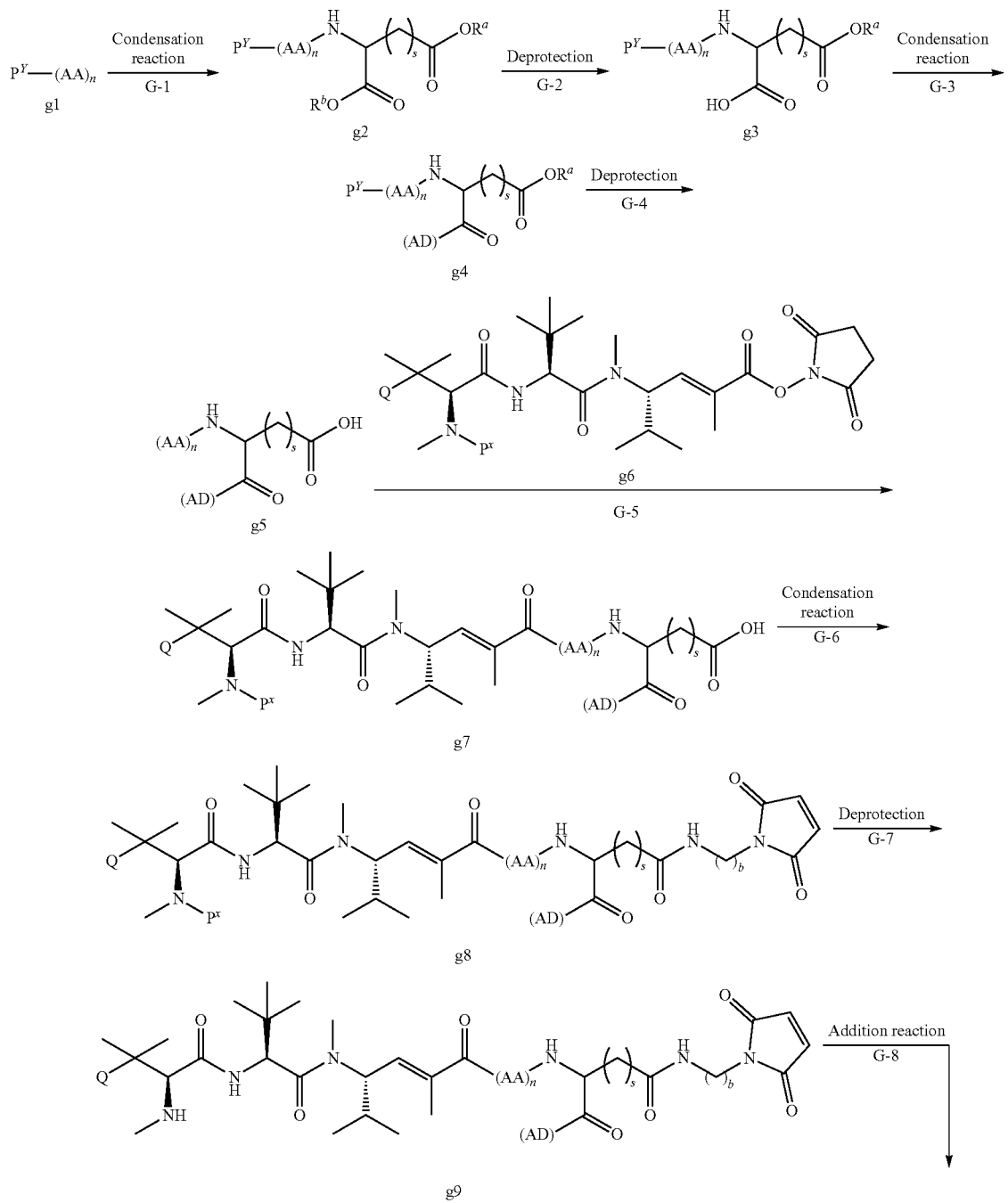

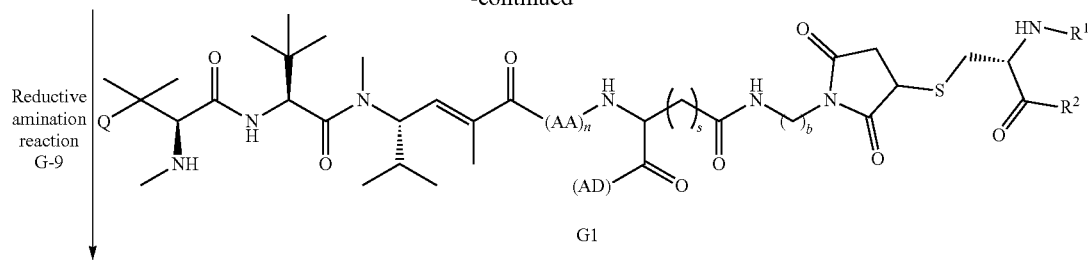

G1

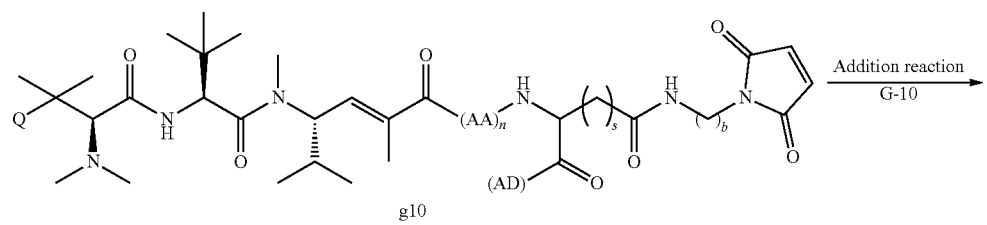

g10

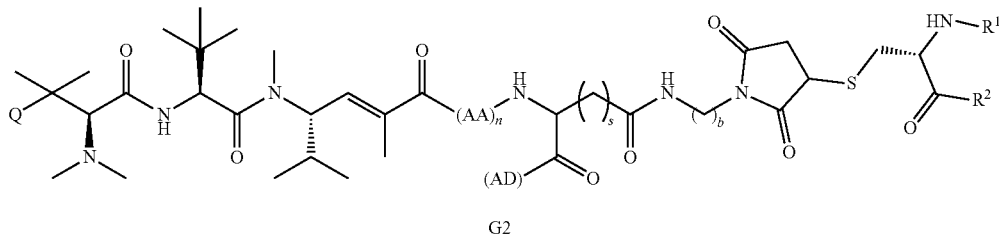

G2 wherein, $R^1$, $R^2$, Q, AA, AD, b and n are as defined in item 1; s, $R^a$, $R^b$, $P^X$ and $P^Y$ are as defined above.

Compound g1 may be, for example, purchased as a commercial product. Compound g6 represents compound a18 of Production Method A or compound b14 of Production Method B.

[G-1 Step]

Compound g2 may be produced by condensing compound g1 and aspartic acid diester or glutamic acid diester in accordance with the method described in the above A-13 step.

[G-2 Step]

Compound g3 may be produced by hydrolyzing the ester of compound g2 in accordance with the method described in the above A-12 step.

[G-3 Step]

Compound g4 may be produced from compound g3 and (AD) in accordance with the method described in the above A-13 step.

[G-4 Step]

Compound g5 may be produced by carrying out hydrolysis of the ester of compound g4 and deprotection of the protecting group for amino in accordance with the method described in the above A-18 step. In addition, when (AD) has an ester or a protected amino group, hydrolysis of the ester and deprotection of the protecting group for the amino group may also be carried out in the present deprotecting step, as necessary.

[G-5 Step]

Compound g7 may be produced from compound g5 and compound g6 in accordance with the method described in the above A-16 step.

[G-6 Step]

Compound g8 may be produced from compound g7 in accordance with the method described in the above A-17 step.

[G-7 Step]

Compound g9 may be produced from compound g8 in accordance with the method described in the above A-18 step.

[G-8 Step]

Compound G1 may be produced from compound g9 in accordance with the method described in the above A-19 step.

[G-9 Step]

Compound g10 may be produced from compound g9 in accordance with the method described in the above A-20 step.

[G-10 Step]

Compound G2 may be produced from compound g10 in accordance with the method described in the above A-19 step.

Production Method H

When X is —C(O)—; Z is a group represented by formula (Z-6); W is a group represented by formula (W-1); $R^{6a}$ is a methyl group; and $R^{6b}$ is a hydrogen atom or a methyl group, the compound represented by formula (1) may be produced by, for example, the following production method:

[Chemical Formula 34]
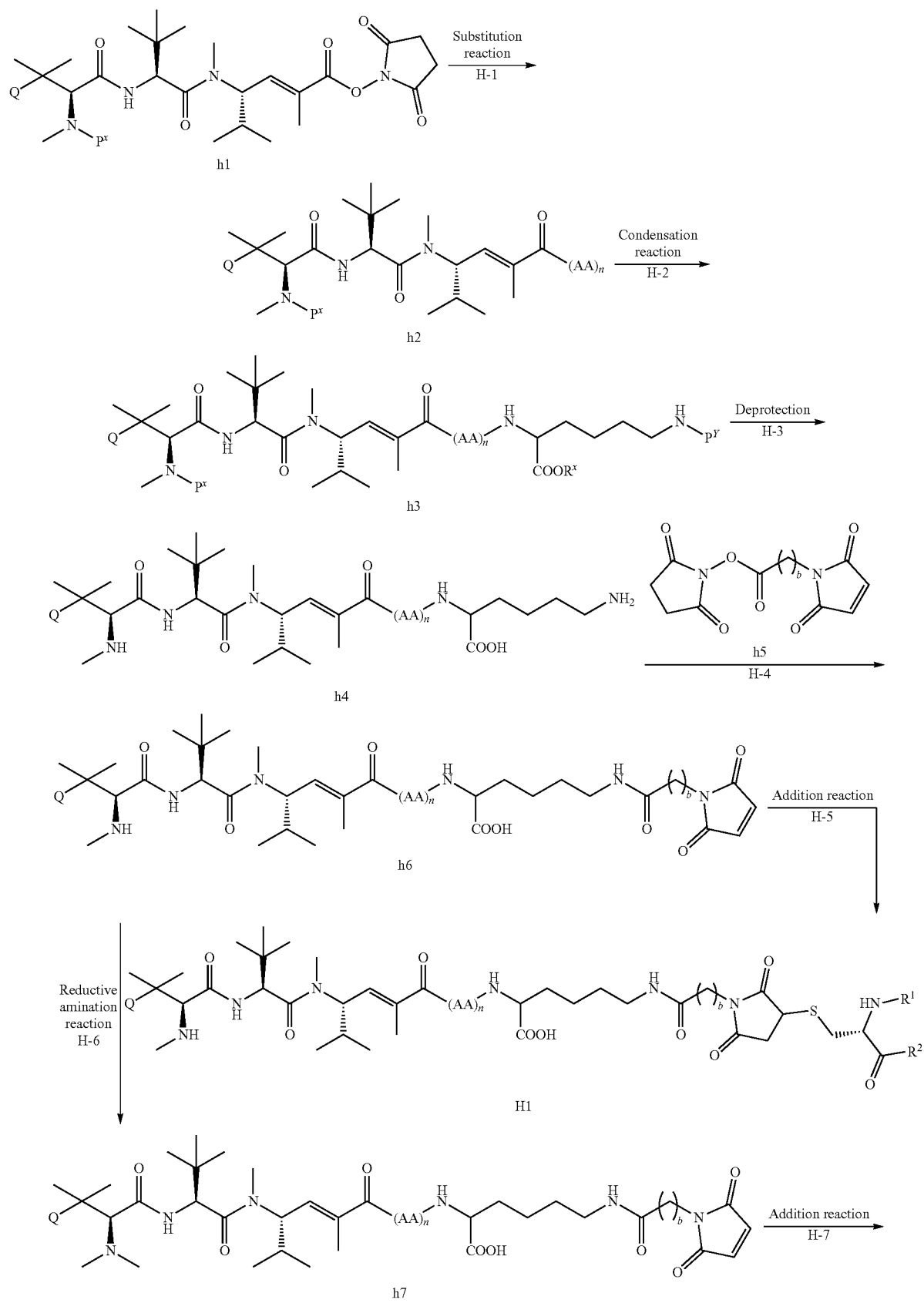

-continued

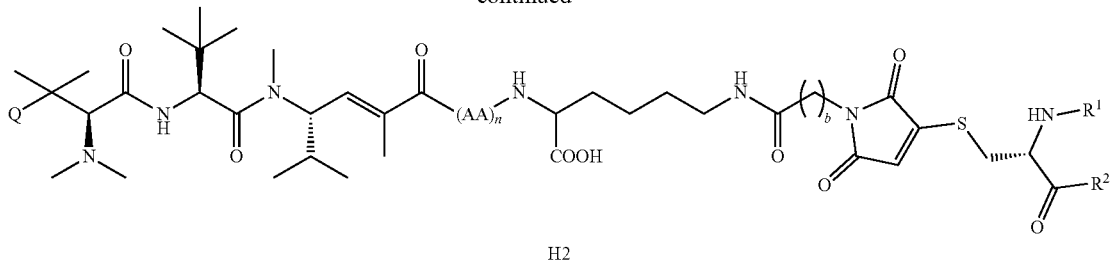

H2 wherein, $R^1$, $R^2$, Q, AA, b and n are as defined in item 1; and $R^x$, $P^X$ and $P^Y$ are as defined above.

Compound h1 represents compound a18 of Production Method A or compound b14 of Production Method B. Compound h5 may be, for example, purchased as a commercial product.

[H-1 Step]

Compound h2 may be produced from compound h1 in accordance with the method described in the above A-16 step.

[H-2 Step]

Compound h3 may be produced by condensing compound h2 and a lysine derivative in accordance with the method described in the above A-13 step.

[H-3 Step]

Compound h4 may be produced from compound h3 in accordance with the method described in the above A-18 step.

[H-4 Step]

Compound h6 may be produced from compound h4 and compound h5 in accordance with the method described in the above A-16 step.

[H-5 Step]

Compound H1 may be produced from compound h6 in accordance with the method described in the above A-19 step.

[H-6 Step]

Compound h7 may be produced from compound h6 in accordance with the method described in the above A-20 step.

[H-7 Step]

Compound H2 may be produced from compound h7 in accordance with the method described in the above A-19 step.

Production Method I

When X is —C(O)—; Z is a group represented by formula (Z-7); W is a group represented by formula (W-1); $R^{6a}$ is a methyl group; and $R^{6b}$ is a hydrogen atom or a methyl group, the compound represented by formula (1) may be produced by, for example, the following production method:

[Chemical Formula 35]

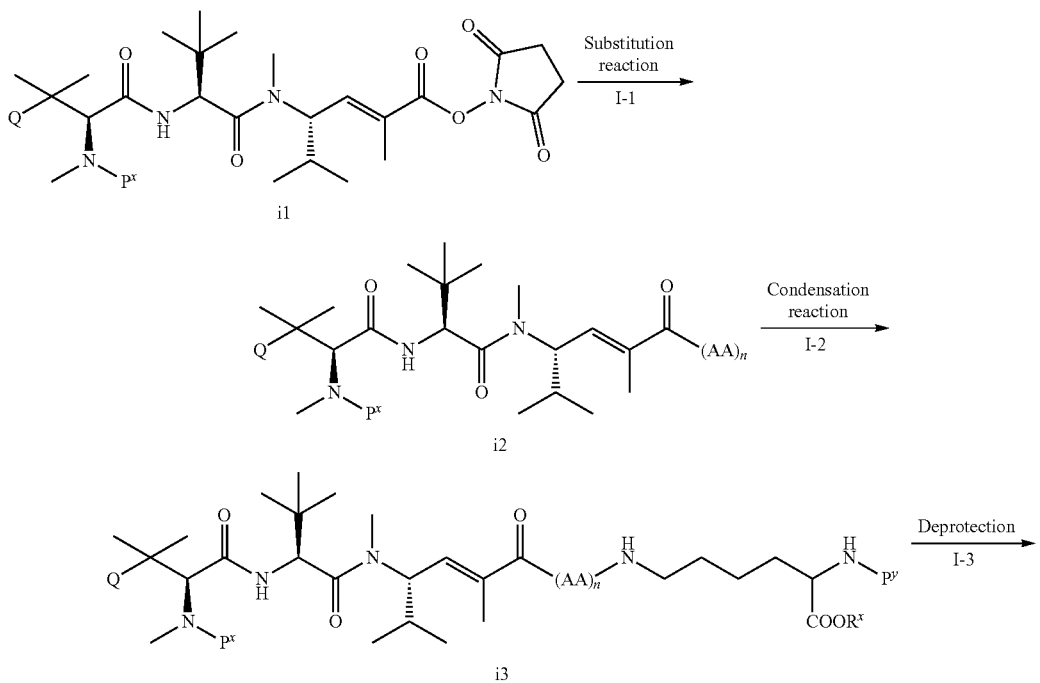

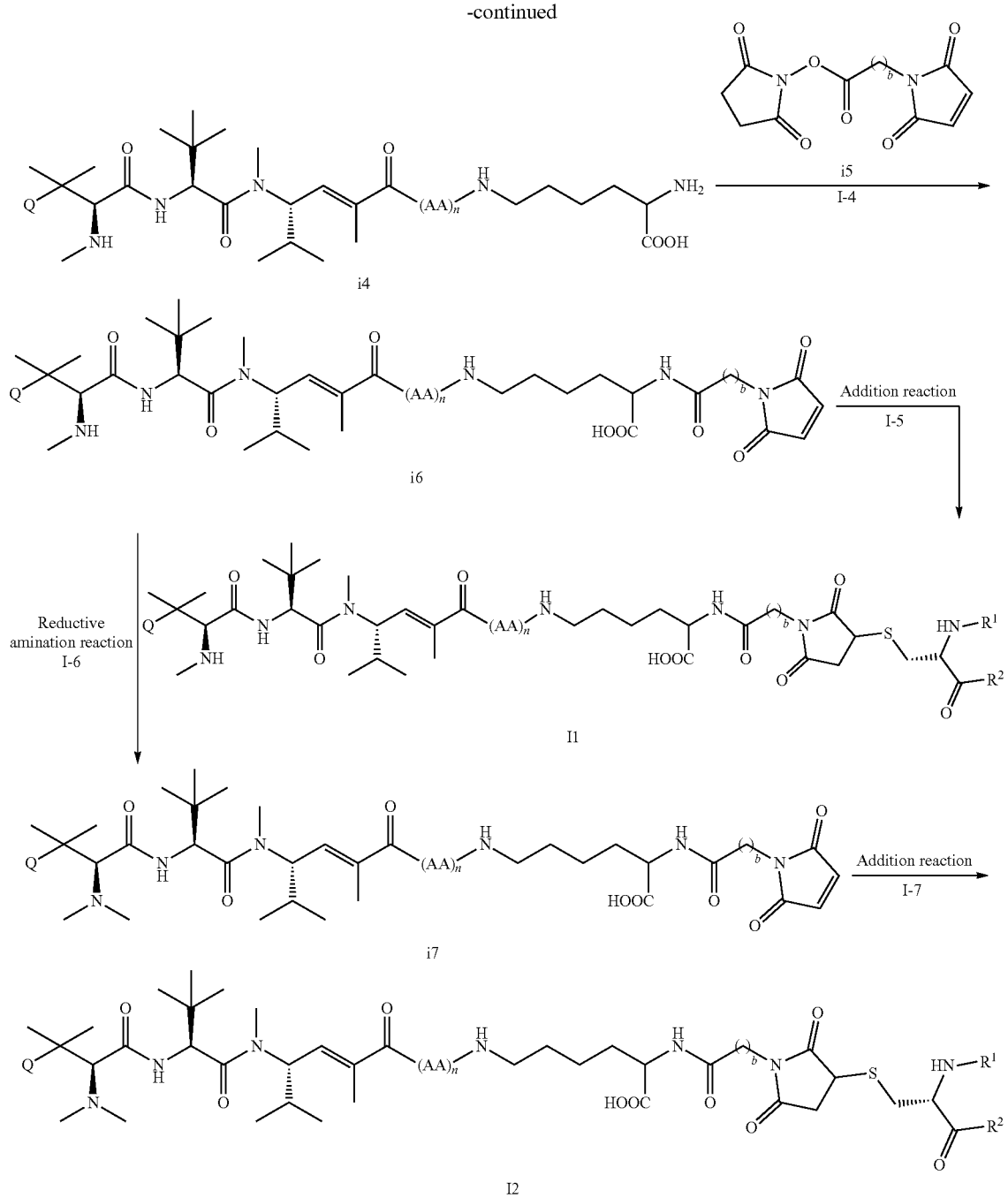

wherein, $R^1$, $R^2$, Q, AA, b and n are as defined in item 1; and $R^x$, $P^X$ and $P^Y$ are as defined above.

Compound i1 represents compound a18 of Production Method A or compound b14 of Production Method B. Compound i5 may be, for example, purchased as a commercial product.

[I-1 Step]

Compound i2 may be produced from compound i1 in accordance with the method described in the above A-16 step.

[I-2 Step]

Compound i3 may be produced by condensing compound i2 and a lysine derivative in accordance with the method described in the above A-13 step.

[I-3 Step]

Compound i4 may be produced from compound i3 in accordance with the method described in the above A-18 step.

[I-4 Step]

Compound i6 may be produced from compound i4 and compound i5 in accordance with the method described in the above A-16 step.

[I-5 Step]

Compound I1 may be produced from compound i6 in accordance with the method described in the above A-19 step.

[I-6 Step]

Compound i7 may be produced from compound i6 in accordance with the method described in the above A-20 step.

[I-7 Step]

Compound I2 may be produced from compound i7 in accordance with the method described in the above A-19 step.

Production Method J

Compound j6 is a production intermediate of compound J1, wherein, in formula (1), X is —NH—, Z is a group represented by formula (Z-1), formula (Z-2) or formula (Z-3), W is a group represented by formula (W-1), and Q is a group represented by formula (Q-1), formula (Q-2), formula (Q-3), formula (Q-4), formula (Q-5) or formula (Q-6). Compound j6 may be produced by, for example, the following production method. In addition, compound J1 may be produced from compound j6 in accordance with the production method described in A-16 step to A-21 step of Production Method A:

[Chemical Formula 36]

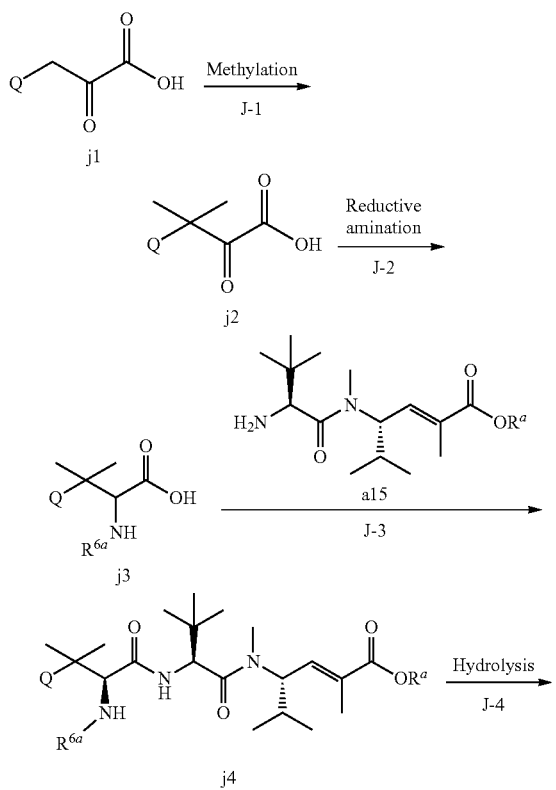

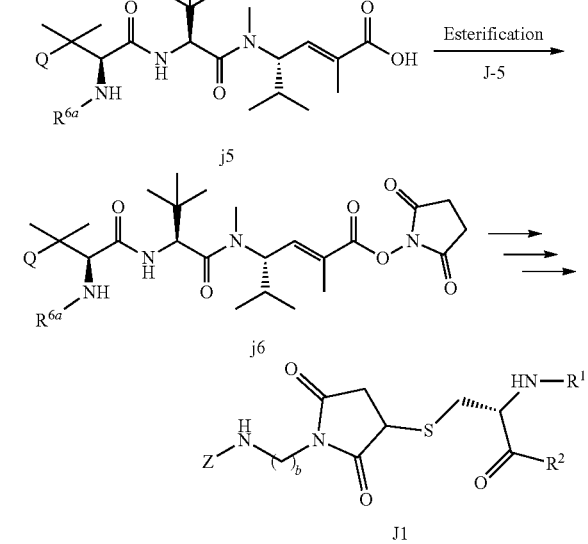

wherein, $R^1$, $R^2$, $R^{6a}$, and b are as defined in item 1; and $R^a$ represents a $C_{1-6}$ alkyl group.

Compound j1 may be, for example, purchased as a commercial product. Compound a15 may be produced by, for example, the method described in Production Method A.

[J-1 Step]

Compound j2 may be produced in accordance with the method described in, for example, Bioorg. Med. Chem. Lett. 14 (2004) 5317-5322 and the like.

[J-2 Step]

Compound j3 may be produced in accordance with the method described in, for example, Bioorg. Med. Chem. Lett. 14 (2004) 5317-5322 and the like.

[J-3 Step]

Compound j4 may be produced in accordance with the method described in, for example, Bioorg. Med. Chem. Lett. 14 (2004) 5317-5322 and the like.

[J-4 Step]

Compound j5 may be produced from compound j4 in accordance with A-14 step of Production Method A.

[J-5 Step]

Compound j6 may be produced from compound j5 in accordance with A-15 step of Production Method A.

Production Method K

When X is —C(O)—; and Z is a group represented by formula (Z-10), the compound represented by formula (1) may be produced by, for example, the following production method:

[Chemical Formula 37]

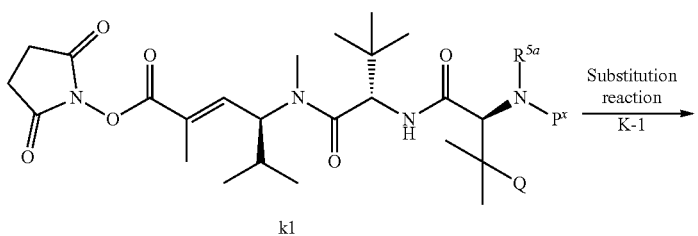

-continued

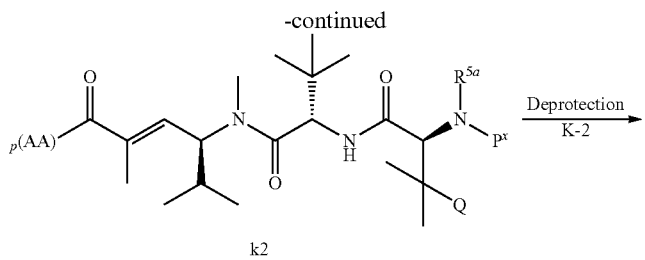

k2

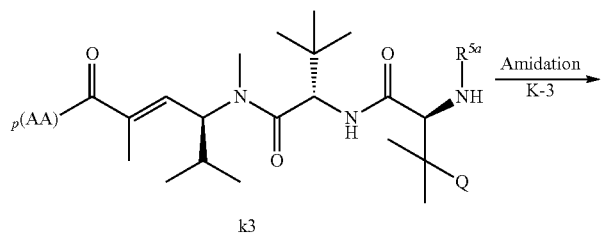

k3

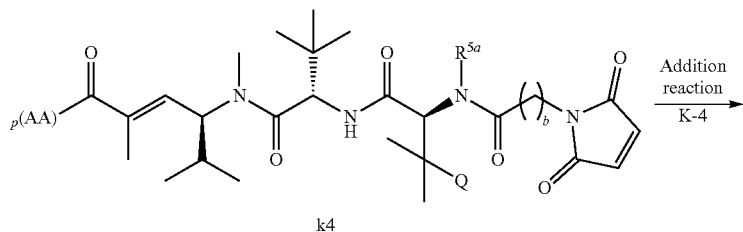

k4

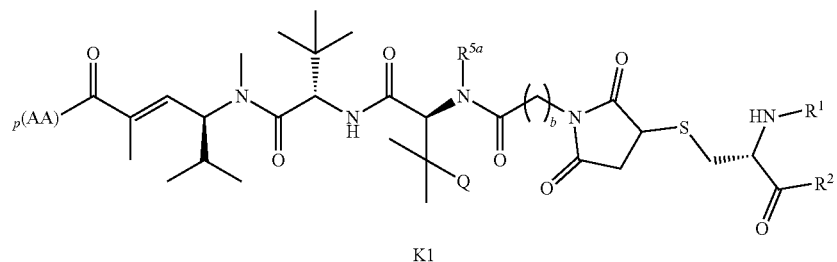

K1 wherein, $R^1$, $R^2$, AA, b, Q, p and $R^{5a}$ are as defined in item 1; and $P^x$ represents a protecting group for the amino group.

Compound k1 represents compound a18 of Production Method A or compound b14 of Production Method B.

[K-1 Step]

Compound k2 may be produced from compound k1 in accordance with the method described in the above A-16 step.

[K-2 Step]

Compound k3 may be produced from compound k2 in accordance with the method described in the above A-18 step.

[K-3 Step]

Compound k4 may be produced from compound k3 in accordance with the method described in the above A-13 or A-16 step.

[K-4 Step]

Compound K1 may be produced from compound k4 in accordance with the method described in the above A-19 step.

Production Method L

When X is —C(O)—; and Z is a group represented by formula (Z-11), the compound represented by formula (1) may be produced by, for example, the following production method:

[Chemical Formula 38]

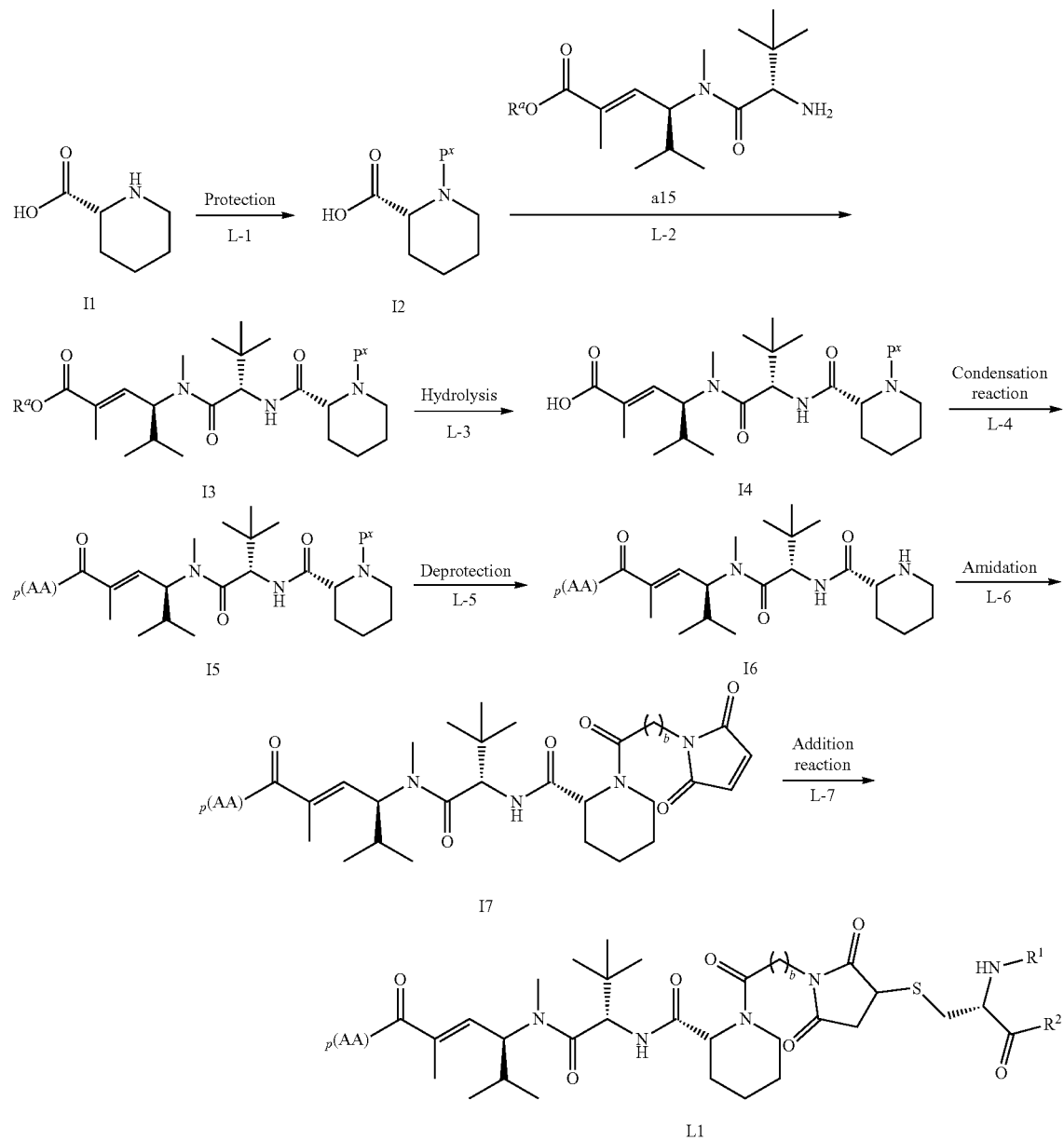

wherein, $R^1$, $R^2$, AA, b and p are as defined in item 1; $P^x$ is a protecting group for the amino group; and $R^a$ represents a $C_{1-6}$ alkyl group.

Compound I1 may be, for example, purchased as a commercial product. Compound a15 may be produced by, for example, the method described in Production Method A.

[L-1 Step]
Compound I2 may be produced by protecting the amino group of compound I1 with the protecting group $P^x$. This step may be carried out in accordance with the method described in Protective Groups in Organic Synthesis (authored by Theodora W. Greene, Peter G. M. Wuts, issued by John Wiley & Sons, Inc., 1999) and the like.

[L-2 Step]
Compound I3 may be produced from compound I2 in accordance with the method described in the above A-13 step.

[L-3 Step]
Compound I4 may be produced from compound I3 in accordance with the method described in the above A-14 step.

[L-4 Step]
Compound I5 may be produced from compound I4 in accordance with the method described in the above A-13 step.

[L-5 Step]
Compound I6 may be produced by deprotecting the protecting groups $P^x$ of compound I5. This step may be carried out in accordance with the methods described in Protective Groups in Organic Synthesis (authored by Theodora W. Greene, Peter G. M. Wuts, issued by John Wiley & Sons, Inc., 1999), Tetrahedron Lett. 45 (2004) 495-499 and the like. In addition, when $(AA)_p$ has an ester or a protected amino group, hydrolysis of the ester and deprotection of the protecting group for the amino group may also be carried out in the present deprotecting step, as necessary.

[L-6 Step]

Compound 17 may be produced from compound 16 in accordance with the method described in the above A-13 or A-16 step.

[L-7 Step]

Compound L1 may be produced from compound 17 in accordance with the method described in the above A-19 step.

Production Method M

Compound m7 is a production intermediate of compound Ma1, wherein, in formula (1), X is —NH—, Z is a group represented by formula (Z-1), formula (Z-2) or formula (Z-3), W is a group represented by formula (W-1), and Q is a group represented by formula (Q-7). Compound m7 may be produced by, for example, the following production method: In addition, compound Ma1 may be produced from compound m7 in accordance with the production method described in A-16 step to A-21 step of Production Method A:

[Chemical Formula 39]

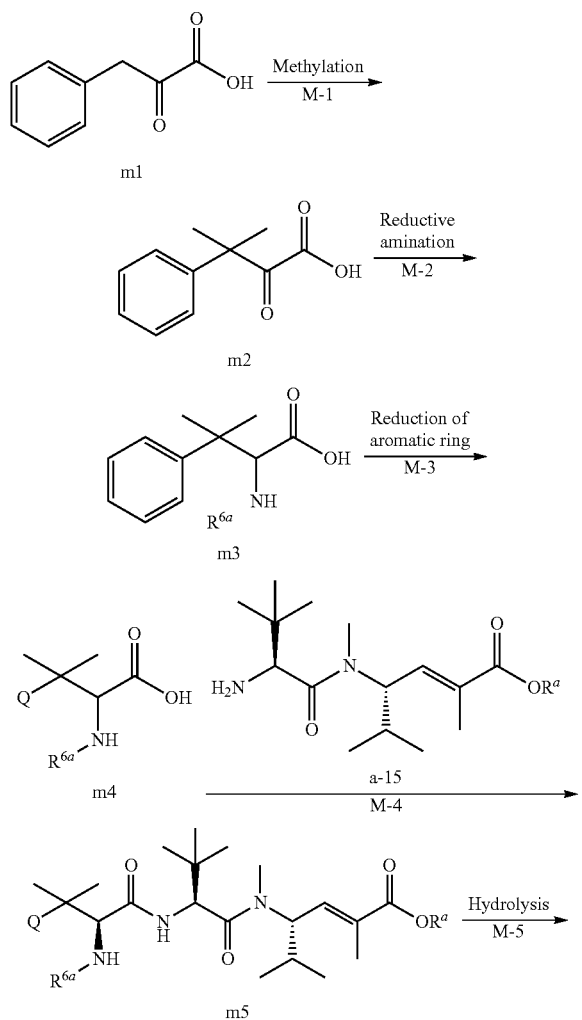

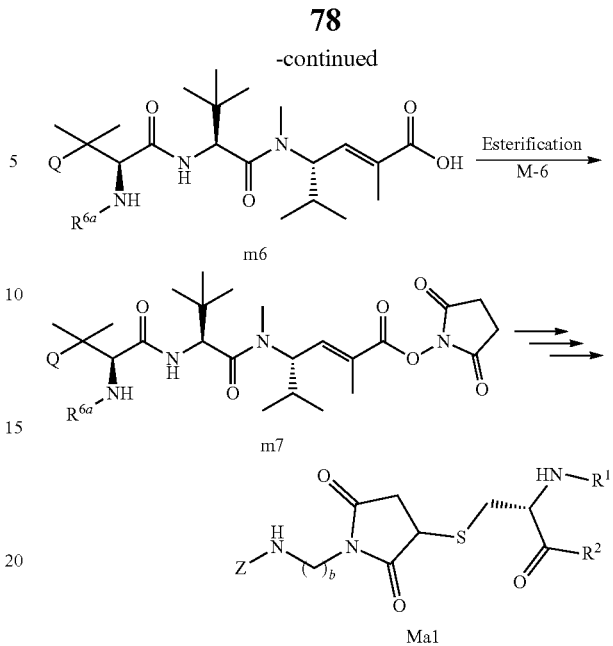

wherein, $R^1$, $R^2$, $R^{6a}$, and b are as defined in item 1; and $R^a$ represents a $C_{1-6}$ alkyl group.

Compound m1 may be, for example, purchased as a commercial product. Compound a15 may be produced by, for example, the method described in Production Method A.

[M-1 Step]

Compound m2 may be produced in accordance with the method described in, for example, Bioorg. Med. Chem. Lett. 14 (2004) 5317-5322 and the like.

[M-2 Step]

Compound m3 may be produced in accordance with the method described in, for example, Bioorg. Med. Chem. Lett. 14 (2004) 5317-5322 and the like.

[M-3 Step]

Compound m4 may be produced in accordance with the method described in, for example, J. Med. Chem. 2004, 47, 4774-4786 and the like.

[M-4 Step]

Compound m5 may be produced in accordance with the method described in, for example, Bioorg. Med. Chem. Lett. 14 (2004) 5317-5322 and the like.

[M-5 Step]

Compound m6 may be produced from compound m5 in accordance with A-14 step of Production Method A.

[M-6 Step]

Compound m7 may be produced from compound m6 in accordance with A-15 step of Production Method A.

Production Method N

Compound n5 is a production intermediate of compound N1, wherein, in formula (1), X is —NH—, Z is a group represented by formula (Z-1), formula (Z-2) or formula (Z-3), and W is a group represented by formula (W-2). Compound n5 may be produced by, for example, the following production method. In addition, compound N1 may be produced from compound n5 in accordance with the production method described in A-16 step to A-19 step of Production Method A:

[Chemical Formula 40]

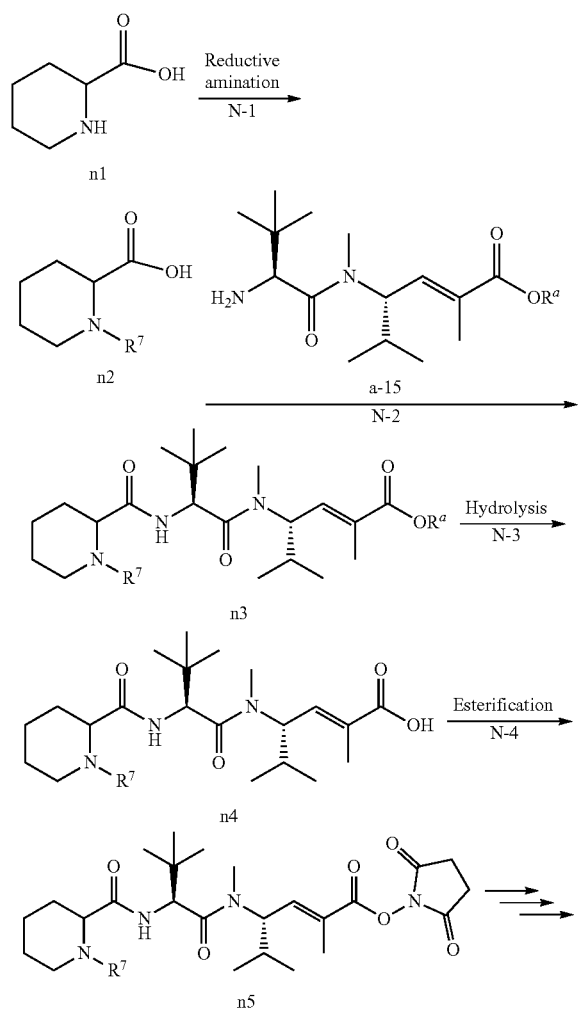

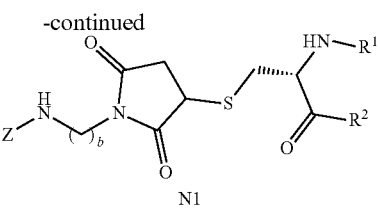

wherein, $R^1$, $R^2$, IV, and b are as defined in item 1; and $R^a$ represents a $C_{1-6}$ alkyl group.

Compound n1 may be, for example, purchased as a commercial product. Compound a15 may be produced by, for example, the method described in Production Method A.

[N-1 Step]

Compound n2 may be produced in accordance with the method described in, for example, International Publication No. WO 2003/082268 and the like.

[N-2 Step]

Compound n3 may be produced from compound n2 in accordance with the method described in A-13 step.

[N-3 Step]

Compound n4 may be produced from compound n3 in accordance with the method described in A-14 step.

[N-4 Step]

Compound n5 may be produced from compound n4 in accordance with A-15 step of Production Method A.

Production Method O

When X is —NH—; and Z is a group represented by formula (Z-4) or formula (Z-5), the compound represented by formula (1) may be produced by, for example, the following production method:

[Chemical Formula 41]

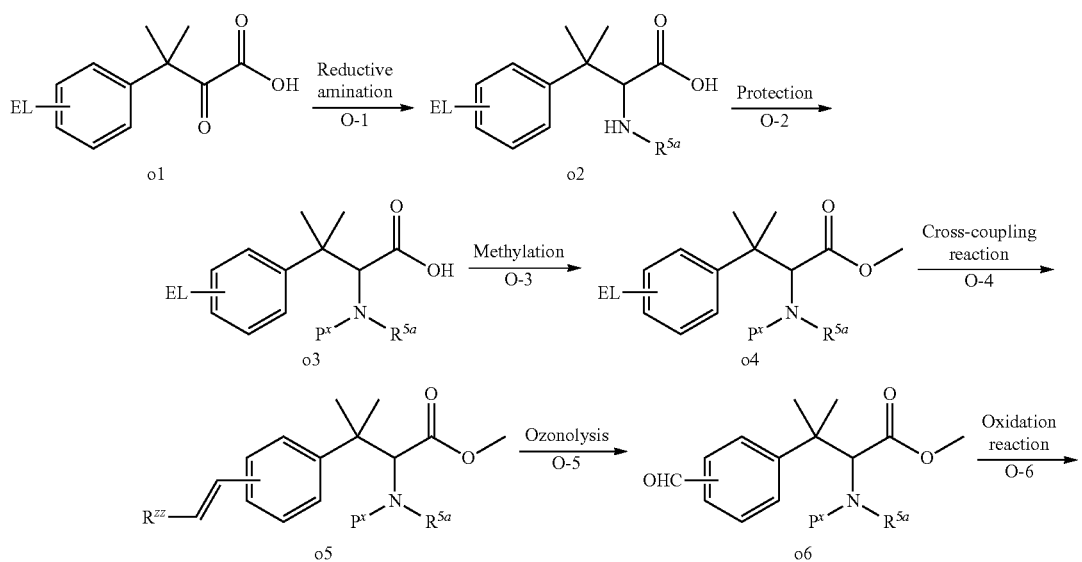

-continued
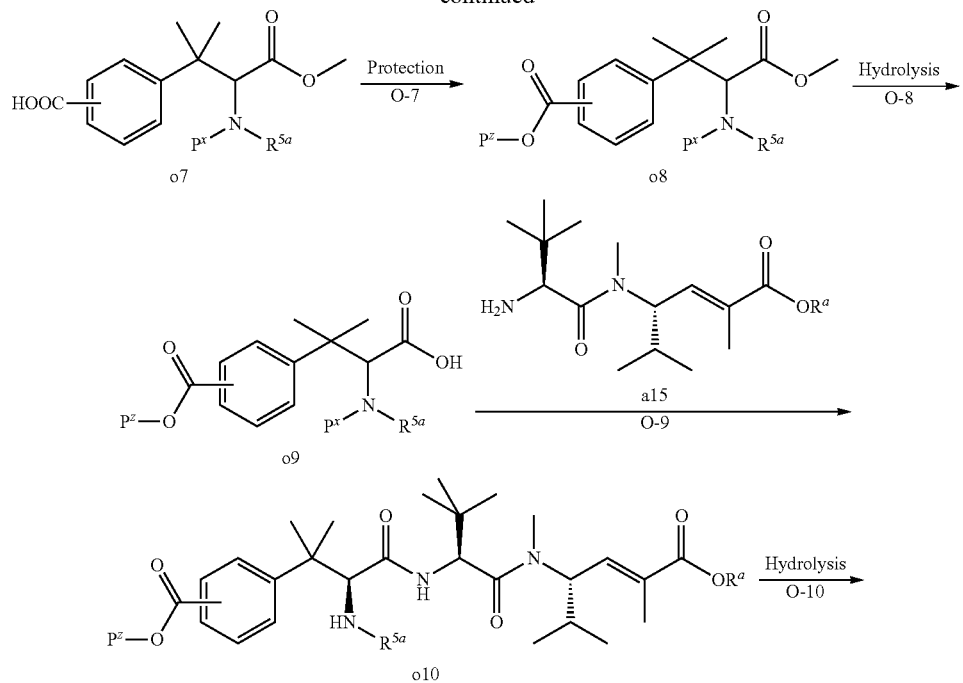
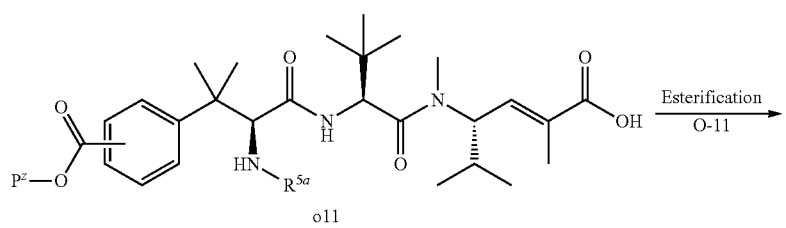
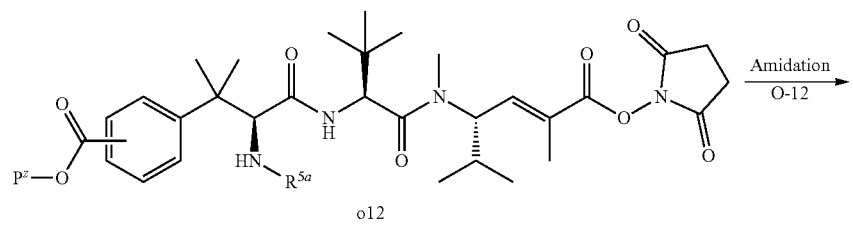
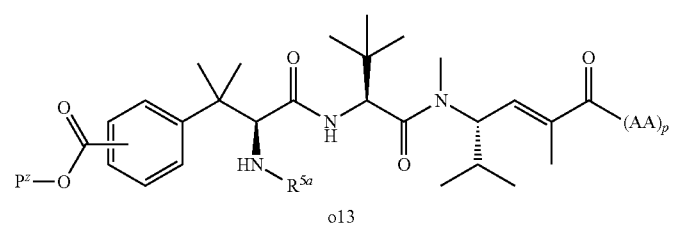
Deprotection
O-13
Reductive amination reaction
O-16

-continued

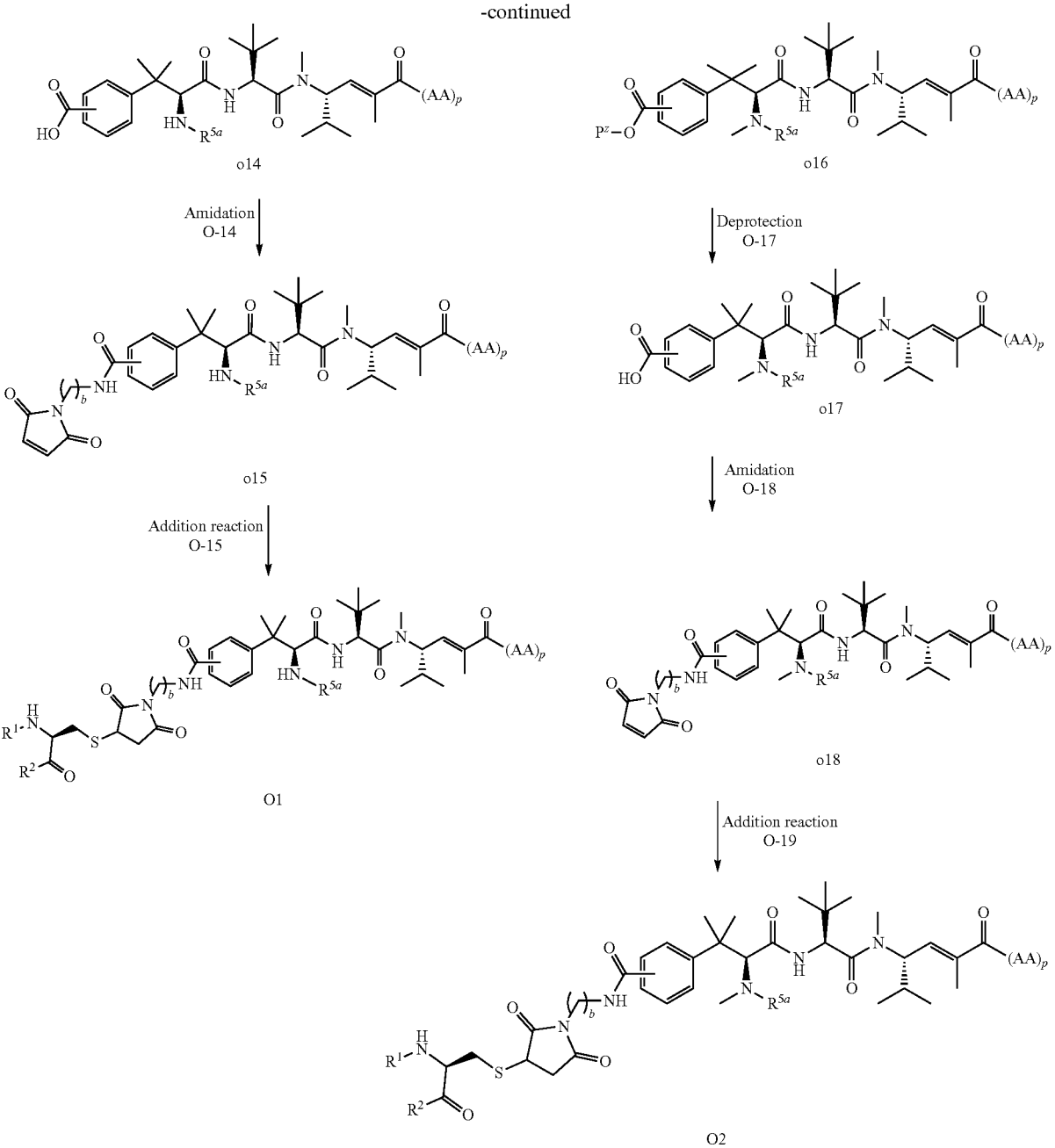

wherein, $R^1$, $R^2$, AA, $R^{5a}$, b and p are as defined in item 1; EL represents a chlorine atom, a bromine atom, an iodine atom, a trifluoromethylsulfonyl group or a tosyl group; $R^{zz}$ represents a hydrogen atom or —$COOR^a$; $P^x$ represents a protecting group for the amino group; $P^z$ represents a protecting group for the carboxyl group; and $R^a$ represents a $C_{1-6}$ alkyl group.

Compound o1 may be produced by the methods described in, for example, International Publication No. WO 2004/026293, International Publication No. WO 2016/123582 and the like, or may be purchased as a commercial product. Compound a15 may be produced by, for example, the method described in Production Method A.

[O-1 Step]

Compound o2 may be produced from compound o1 in accordance with the methods described in, for example, International Publication No. WO 2004/026293; Bioorg. Med. Chem. Lett. 14 (2004) 5317-5322; and the like.

[O-2 Step]

Compound o3 may be produced from compound o2 in accordance with the method described in the above A-8 step.

[O-3 Step]

Compound o4 may be produced from compound o3 in accordance with the method described in the above A-11 step.

[O-4 Step]

Compound o5 may be produced from compound o4 by the method described in, for example, International Publication No. WO 2004/026293 and the like.

[O-5 Step]

Compound o6 may be produced from compound o5 by the method described in, for example, International Publication No. WO 2004/026293 and the like.

[O-6 Step]

Compound o7 may be produced from compound o6 by the method described in, for example, International Publication No. WO 2004/026293 and the like.

[O-7 Step]

Compound o8 may be produced by protecting the carboxyl group of compound o7 with the protecting group $P^z$. This step may be carried out in accordance with the method described in Protective Groups in Organic Synthesis (authored by Theodora W. Greene, Peter G. M. Wuts, issued by John Wiley & Sons, Inc., 1999) and the like.

[O-8 Step]

Compound o9 may be produced from compound o8 in accordance with the method described in the above A-12 step.

[O-9 Step]

Compound o10 may be produced from compound o9 in accordance with the method described in the above A-13 step.

[O-10 Step]

Compound o11 may be produced from compound o10 in accordance with the method described in the above A-14 step.

[O-11 Step]

Compound o12 may be produced from compound o11 in accordance with the method described in the above A-15 step.

[O-12 Step]

Compound o13 may be produced from compound o12 in accordance with the method described in the above A-16 step.

[O-13 Step]

Compound o14 may be produced from compound o13 by deprotecting the protecting group W. This step may be carried out in accordance with the method described in Protective Groups in Organic Synthesis (authored by Theodora W. Greene, Peter G. M. Wuts, issued by John Wiley & Sons, Inc., 1999) and the like.

[O-14 Step]

Compound o15 may be produced from compound o14 in accordance with the method described in the above A-17 step.

[O-15 Step]

Compound O1 may be produced from compound o15 in accordance with the methods described in the above A-19 step.

[O-16 Step]

Compound o16 may be produced from compound o13 in accordance with the method described in the above A-20 step.

[O-17 Step]

Compound o17 may be produced from compound o16 in accordance with the method described in the above O-13 step.

[O-18 Step]

Compound o18 may be produced from compound o17 in accordance with the method described in the above O-14 step.

[O-19 Step]

Compound O2 may be produced from compound o18 in accordance with the method described in the above A-19 step.

Production Method P

When X is —C(O)—; Z is a group represented by formula (Z-8) or formula (Z-9); and G is —O—, the compound represented by formula (1) may be produced by, for example, the following production method:

[Chemical Formula 42]

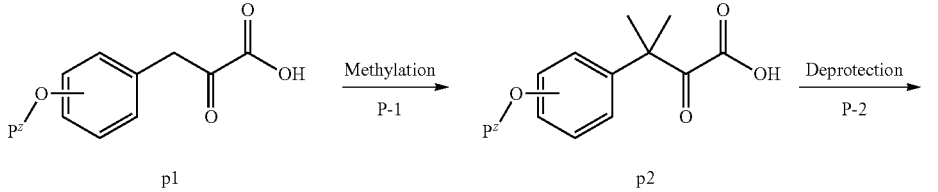

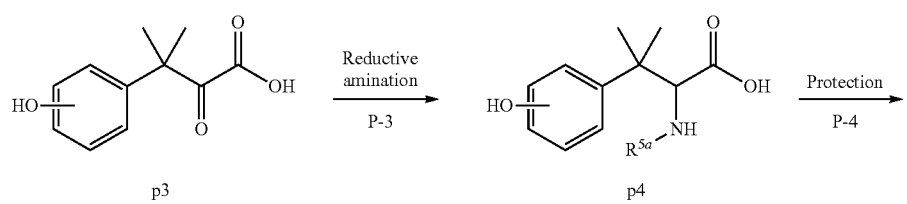

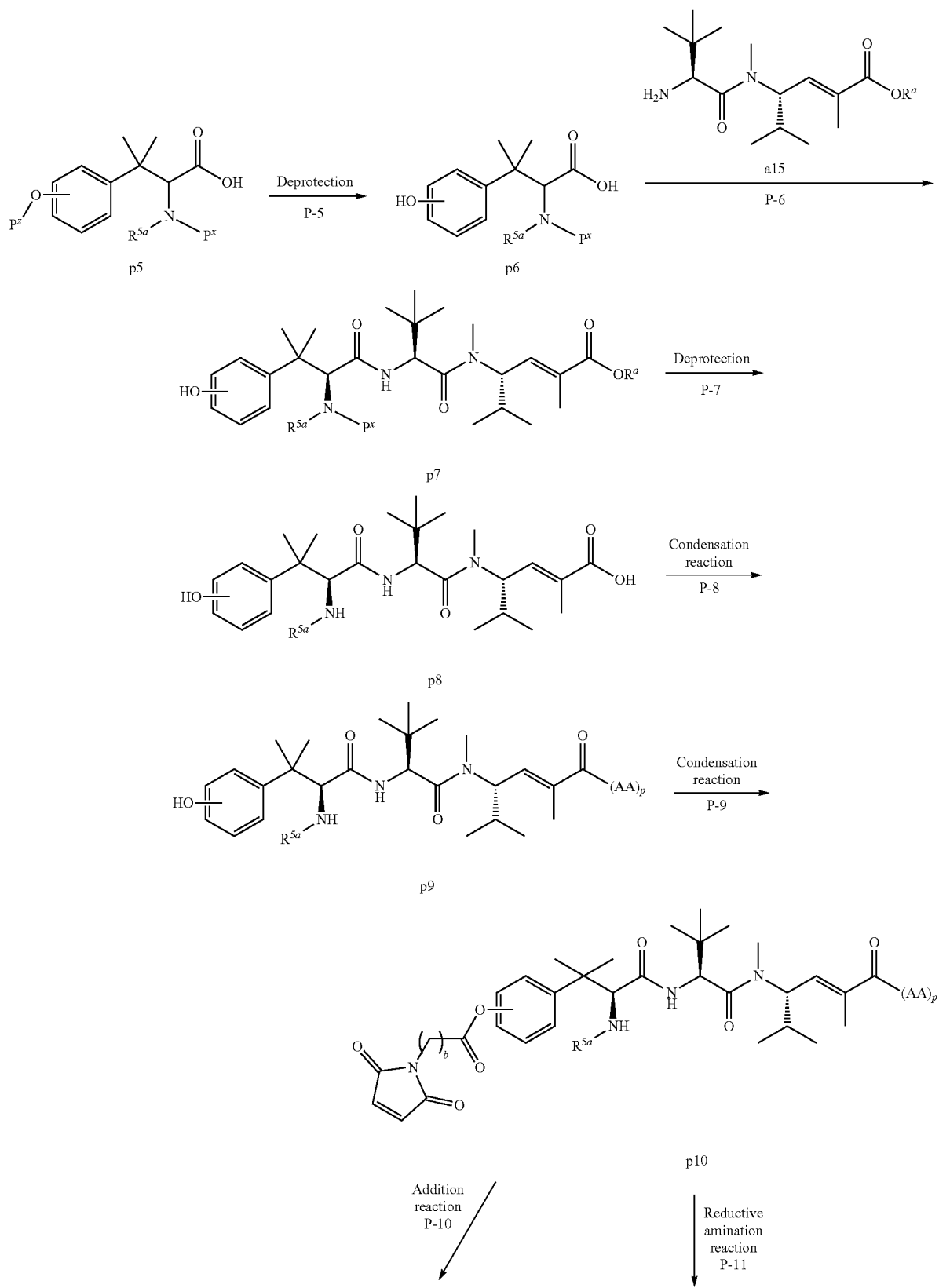

-continued

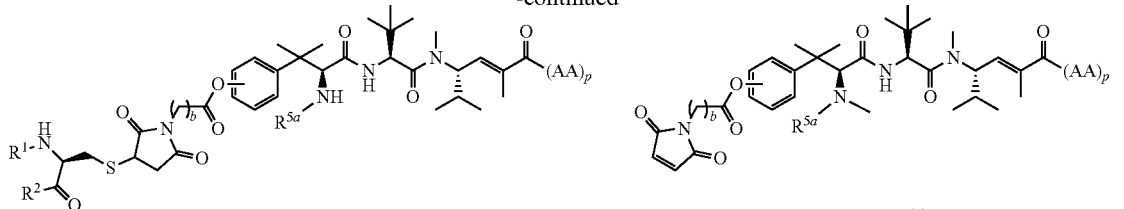

P1 p11

↓ Addition reaction P-12

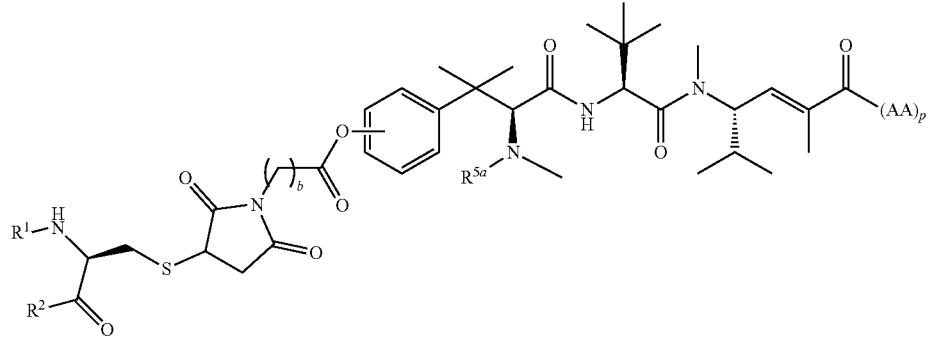

P2 wherein, $R^1$, $R^2$, AA, p, b and $R^5$ are as defined in item 1; $P^x$ represents a protecting group for the amino group; $P^z$ represents a protecting group for the hydroxy group; and $R^a$ represents a $C_{1-6}$ alkyl group.

Compound p1 may be, for example, purchased as a commercial product. Compound a15 may be produced by, for example, the method described in Production Method A.

[P-1 Step]

Compound p2 may be produced from compound p1 in accordance with the method described in, for example, International Publication No. WO 2004/026293 and the like.

[P-2 Step]

Compound p3 may be produced from compound p2 by deprotecting the protecting group $P^z$. This step may be carried out in accordance with the method described in Protective Groups in Organic Synthesis (authored by Theodora W. Greene, Peter G. M. Wuts, issued by John Wiley & Sons, Inc., 1999) and the like.

[P-3 Step]

Compound p4 may be produced from compound p3 in accordance with the method described in, for example, International Publication No. WO 2004/026293 and the like.

[P-4 Step]

Compound p5 may be produced by protecting the amino group and the hydroxy group of compound p4 with protecting group $P^x$ and protecting group $P^z$, respectively. This step may be carried out in accordance with the method described in Protective Groups in Organic Synthesis (authored by Theodora W. Greene, Peter G. M. Wuts, issued by John Wiley & Sons, Inc., 1999) and the like.

[P-5 Step]

Compound p6 may be produced from compound p5 by deprotecting the protecting group $P^z$. This step may be carried out in accordance with the method described in Protective Groups in Organic Synthesis (authored by Theodora W. Greene, Peter G. M. Wuts, issued by John Wiley & Sons, Inc., 1999), or Tetrahedron Lett. 45 (2004) 495-499 and the like.

[P-6 Step]

Compound p7 may be produced from compound p6 in accordance with the method described in A-13 step.

[P-7 Step]

Compound p8 may be produced from compound p7 in accordance with the method described in the above A-18 step.

[P-8 Step]

Compound p9 may be produced from compound p8 by condensing in accordance with the method described in the above A-13 step. In addition, when $(AA)_p$ has an ester or a protected amino group, hydrolysis of the ester and deprotection of the protecting group for the amino group may also be carried out as necessary after the condensation reaction, in accordance with the method described in Protective Groups in Organic Synthesis (authored by Theodora W. Greene, Peter G. M. Wuts, issued by John Wiley & Sons, Inc., 1999) and the like.

[P-9 Step]

Compound p10 may be produced from compound p9 and a succinimide derivative by condensing in accordance with the method described in the above A-16 step.

[P-10 Step]

Compound P1 may be produced from compound p10 in accordance with the method described in the above A-19 step.

[P-11 Step]

Compound p11 may be produced from compound p10 in accordance with the method described in the above A-20 step.

[P-12 Step]
Compound P2 may be produced from compound p11 in accordance with the method described in the above A-19 step.
Production Method T
When X is —C(O)—; Z is a group represented by formula (Z-8) or formula (Z-9); and G is —NH—, the compound represented by formula (1) may be produced by, for example, the following production method:
[Chemical Formula 43]
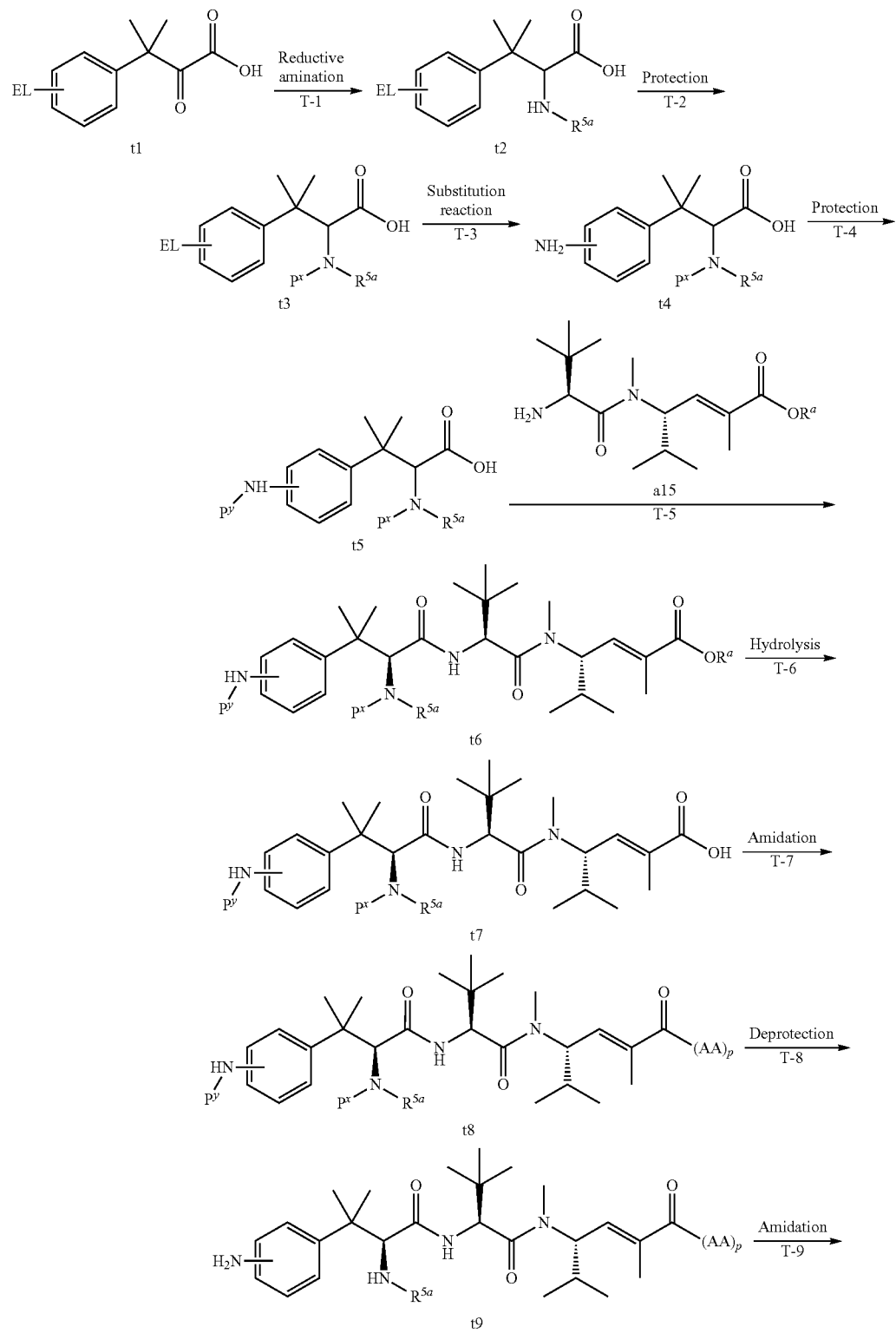

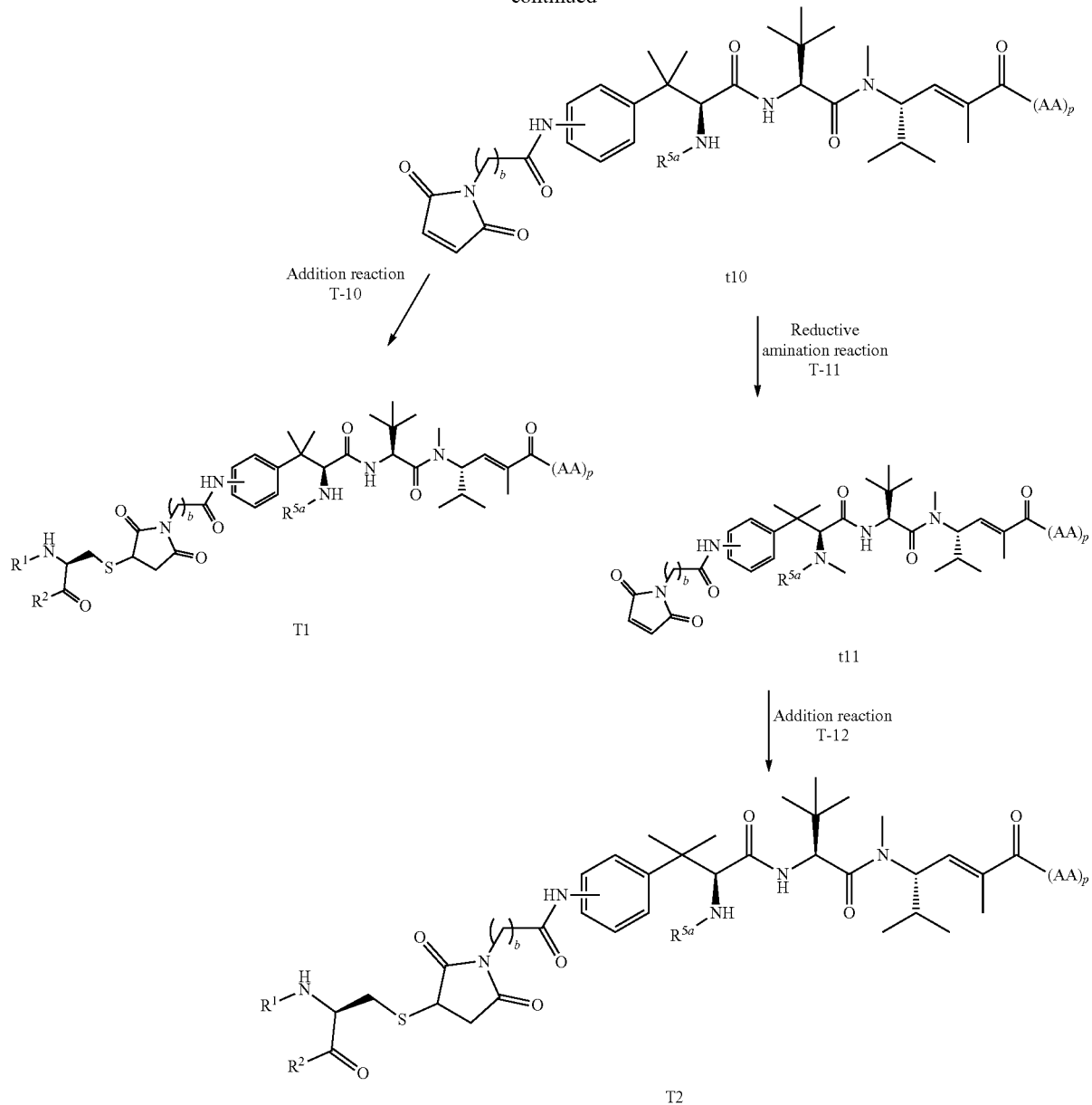

wherein, $R^1$, $R^2$, AA, p, b and $R^{5a}$ are as defined in item 1; EL represents a chlorine atom, a bromine atom, an iodine atom, a trifluoromethylsulfonyl group or a tosyl group; $P^x$ and $P^y$ represent a protecting group for the amino group; and $R^a$ represents a $C_{1-6}$ alkyl group.

Compound t1 may be produced by the methods described in, for example, International Publication No. WO 2004/026293, International Publication No. WO 2016/123582 and the like, or may be purchased as a commercial product. Compound a15 may be produced by, for example, the method described in Production Method A.

[T-1 Step]

Compound t2 may be produced from compound t1 in accordance with the methods described in, for example, International Publication No. WO 2004/026293; Bioorg. Med. Chem. Lett. 14 (2004) 5317-5322; and the like.

[T-2 Step]

Compound t3 may be produced from compound t2 in accordance with the method described in the above A-8 step.

[T-3 Step]

Compound t4 may be produced from compound t3 by the method described in, for example, International Publication No. WO 2016/123582 and the like.

[T-4 Step]

Compound t5 may be produced by protecting the amino group of compound t4 with protecting group P. This step may be carried out in accordance with the method described in Protective Groups in Organic Synthesis (authored by Theodora W. Greene, Peter G. M. Wuts, issued by John Wiley & Sons, Inc., 1999) and the like.

[T-5 Step]

Compound t6 may be produced from compound t5 in accordance with the method described in the above A-13 step.

[T-6 Step]

Compound t7 may be produced from compound t6 in accordance with the method described in the above A-14 step.

[T-7 Step]

Compound t8 may be produced from compound t7 in accordance with the method described in the above A-13 step.

[T-8 Step]

Compound t9 may be produced by deprotecting the protecting groups $P^x$ and $P^y$ of compound t8. This step may be carried out in accordance with the methods described in Protective Groups in Organic Synthesis (authored by Theodora W. Greene, Peter G. M. Wuts, issued by John Wiley & Sons, Inc., 1999), Tetrahedron Lett. 45 (2004) 495-499 and the like. In addition, when $(AA)_p$ has an ester or a protected amino group, hydrolysis of the ester and deprotection of the protecting group for the amino group may also be carried out in the present deprotecting step, as necessary.

[T-9 Step]

Compound t10 may be produced from compound t9 in accordance with the method described in the above A-13 step or the above A-16 step.

[T-10 Step]

Compound T1 may be produced from compound t10 in accordance with the method described in the above A-19 step.

[T-11 Step]

Compound t11 may be produced from compound t10 in accordance with the method described in the above A-20 step.

[T-12 Step]

Compound T2 may be produced from compound t11 in accordance with the method described in the above A-19 step.

The production methods for the hemiasterlin derivative according to the present invention have been shown in the above. However, the hemiasterlin derivative according to the present invention may also be produced even by a method other than those, for example, by appropriately combining methods known to a person having ordinary skill in the art.

Appropriate bases used in each step of the above production methods should be selected as appropriate depending on reactions, types of raw material compounds and the like, and examples thereof include alkali bicarbonates such as sodium bicarbonate and potassium bicarbonate; alkali carbonates such as sodium carbonate and potassium carbonate; metal hydrides such as sodium hydride and potassium hydride; alkali metal hydroxides such as sodium hydroxide and potassium hydroxide; alkali metal alkoxides such as sodium methoxide and sodium t-butoxide; organometallic bases such as butyllithium and lithium diisopropylamide; and organic bases such as triethylamine, diisopropylethylamine, pyridine, 4-dimethylaminopyridine (DMAP) and 1,8-diazabicyclo[5.4.0]-7-undecene (DBU).

Appropriate solvents used in each step of the above production methods should be selected as appropriate depending on reactions, types of raw material compounds and the like, and examples thereof include alcohols such as methanol, ethanol and isopropanol; ketones such as acetone and methyl ketone; halogenated hydrocarbons such as methylene chloride and chloroform; ethers such as tetrahydrofuran (THF) and dioxane; aromatic hydrocarbons such as toluene and benzene; aliphatic hydrocarbons such as hexane and heptane; esters such as ethyl acetate and propyl acetate; amides such as N,N-dimethylformamide (DMF) and N-methyl-2-pyrrolidone; sulfoxides such as dimethylsulfoxide (DMSO); nitriles such as acetonitrile; distilled water; and the like, and one of these solvents may be used singly, or two or more of them may be mixed for use. In addition, depending on the type of reactions, organic bases such as triethylamine, diisopropylethylamine and pyridine may be used as the solvent.

The hemiasterlin derivative according to the present invention may be separated and purified by methods known to a person having ordinary skill in the art. Examples thereof include extraction, partitioning, reprecipitation, column chromatography (for example, silica gel column chromatography, ion exchange column chromatography or preparative liquid chromatography) or recrystallization.

As the recrystallization solvent, for example, alcohol solvents such as methanol, ethanol and 2-propanol; ether solvents such as diethyl ether; ester solvents such as ethyl acetate; aromatic hydrocarbon solvents such as benzene and toluene; ketone solvents such as acetone; halogenated solvents such as dichloromethane and chloroform; hydrocarbon solvents such as hexane; aprotic solvents such as dimethylformamide, acetonitrile; water; or mixed solvents thereof may be used.

As other purification method, the method described in The Experimental Chemistry (edited by The Chemical Society of Japan, Maruzen), vol. 1 and the like may be used. In addition, determination of the molecular structure of the hemiasterlin derivative according to the present invention may be readily carried out by spectroscopic approaches such as nuclear magnetic resonance, infrared absorption technique and circular dichroism spectroscopy, or mass spectrometry, with reference to the structure derived from their respective raw material compounds.

In addition, intermediates or final products in the above production methods may also be derivatized into other compounds included in the present invention by converting their functional groups as appropriate, in particular, by extending various side chains using an amino group, hydroxy group, carbonyl group, halogen atom or the like as the basis, and upon this, by carrying out protection and deprotection of the above functional groups as necessary. The conversion of functional groups and extension of side chains may be carried out by general methods that are conventionally performed (for example, see Comprehensive Organic Transformations, R. C. Larock, John Wiley & Sons Inc. (1999) and the like).

The hemiasterlin derivative according to the present invention may have asymmetry or may have a substituent having an asymmetric carbon, and optical isomers are present in such compounds. Optical isomers may be produced in accordance with conventional methods. Examples of the production method include a method of using a raw material having an asymmetric point or a method of introducing asymmetry in the midway stage. For example, in the case of optical isomers, optical isomers may be obtained by using optically active raw materials or by carrying out optical resolution or the like at an appropriate stage during the production process. When the hemiasterlin derivative according to the present invention has a basic functional group, examples of the optical resolution method include a diastereomer method, in which a salt is formed using an optically active acid (for example, monocarboxylic acids such as mandelic acid, N-benzyloxyalanine and lactic acid; dicarboxylic acids such as tartaric acid, o-diisopropylidene tartaric acid and malic acid; sulfonic acids such as camphorsulfonic acid and bromocamphorsulfonic acid) in an inert solvent (for example, an alcohol solvent such as methanol, ethanol and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents). When the hemiasterlin derivative or synthetic intermediate thereof according to the present invention has an acidic functional group such as a carboxyl, optical resolution can also be carried out by using an optically active amine (for example, an organic amine such as 1-phenylethylamine, quinine, quinidine, cinchonidine, cinchonine and strychnine) to form a salt.

Examples of the temperature at which the salt is formed include the range from −50° C. to the boiling point of the solvent, preferably include the range from 0° C. to the boiling point, and more preferably include the range from room temperature to the boiling point of the solvent. In order to improve optical purity, it is desirable that the temperature be once raised to the vicinity of the boiling point of the solvent. Upon separating the precipitated salt by filtration, the yield may be improved by cooling as necessary. Examples of the amount of the optically active acid or amine to be used include the range of about 0.5 to about 2.0 equivalent to the substrate, and preferably include the range around 1 equivalent. As necessary, an optically active salt with high purity can be obtained by recrystallizing a crystal in an inert solvent (for example, an alcohol solvent such as methanol, ethanol and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents). In addition, a free form may be obtained by treating a salt that has been optically resolved with an acid or base through a conventional method, as necessary.

Among the raw materials or intermediates in the production methods described above, those for which the production method was not described, are either commercially available compounds or may be synthesized from commercially available compounds by methods known to a person having ordinary skill in the art or methods equivalent thereto.

EXAMPLES

Hereinafter, the present invention will be explained further specifically with reference to Reference Examples, Examples and Test Examples, but the present invention is not limited to them, of course. Note that the names of compounds shown in the following Reference Examples and Examples do not necessarily follow the IUPAC nomenclature of chemistry.

Compounds of Reference Examples and Examples may be obtained as an acid addition salt such as a TFA salt, depending on a method of treatment after the reaction and the like.

In order to simplify description of the specification, abbreviations as shown below may be used in Examples and the tables in Examples. As abbreviations used for substituents, Me represents a methyl group, Et represents an ethyl group, Boc represents a tert-butoxycarbonyl group, Fmoc represents a 9-fluorenylmethyloxycarbonyl group, trt represents a trityl group, Ph represents a phenyl group, and Bn represents a benzyl group. TFA represents trifluoroacetic acid, THF represents tetrahydrofuran, TCEP represents tris (2-carboxyethyl)phosphine, Tris-HCl represents trishydroxymethylaminomethane hydrochloride, PBS represents phosphate buffered saline, TBS represents Tris buffered saline, HEPES represents 2-[4-(2-hydroxyethyl)piperazin-1-yl]ethanesulfonic acid, and PIPES represents piperazine-1,4-bis(2-ethanesulfonic acid). For symbols used for NMR, s means a singlet, d means a doublet, dd means a doublet of doublets, t means a triplet, q means a quartet, m means a multiplet, br means broad, brs means a broad singlet, brd means a broad doublet, brm means a broad multiplet, and J means the binding constant.

High Performance Liquid Chromatography-Mass Spectrometer; measurement conditions for LCMS are as follows, and the observed value of mass spectrometry [MS (m/z)] is shown as $[M+nH]^{n+}/n$, $[M+Na]^+$ or $[M−nH]^−/n$, and the retention time is shown as Rt (min). Note that, for each found value, the measurement conditions used for the measurement are denoted by A to D or F to H.

Measurement Condition A
  Detection Equipment: Shimadzu LCMS-IT-TOF
  Column: Phenomenex Kinetex (1.7 μm C18, 50 mm×2.10 mm)
  Solvents: solution A: 0.1% HCOOH/CH$_3$CN, solution B: 0.1% HCOOH/H$_2$O
  Gradient Condition:
    0.0 min; A/B=1:99
    0.0 to 1.4 min; Linear gradient from 1% to 95% A
    1.4 to 1.6 min; A/B=95:5
    1.6 to 2.0 min; A/B=1:99
  Flow Rate: 1.2 mL/min
  UV: 220/254 nm
  Column Temperature: 40° C.
Measurement Condition B
  Detection Equipment: Shimadzu LCMS-IT-TOF
  Column: Phenomenex Kinetex (1.7 μm C18, 50 mm×2.10 mm)
  Solvents: solution A: 0.1% HCOOH/CH$_3$CN, solution B: 0.1% HCOOH/H$_2$O
  Gradient Condition:
    0.0 min; A/B=10:90
    0.0 to 1.4 min; Linear gradient from 10% to 90% A
    1.4 to 1.6 min; A/B=90:10
    1.6 to 2.0 min; A/B=10:90
  Flow Rate: 1.2 mL/min
  UV: 220/254 nm
  Column Temperature: 40° C.
Measurement Condition C
  Detection Equipment: Shimadzu LCMS-IT-TOF
  Column: Phenomenex Kinetex (1.7 μm C8, 50 mm×2.10 mm)
  Solvents: solution A: 0.1% HCOOH/CH$_3$CN, solution B: 0.1% HCOOH/H$_2$O
  Gradient Condition:
    0.0 min; A/B=1:99
    0.0 to 1.4 min; Linear gradient from 1% to 95% A
    1.4 to 1.6 min; A/B=95:5
    1.6 to 2.0 min; A/B=1:99
  Flow Rate: 1.2 mL/min
  UV: 220/254 nm
  Column Temperature: 40° C.
Measurement Condition D
  Detection Equipment: Shimadzu LCMS-IT-TOF
  Column: Phenomenex Kinetex (1.7 μm C8, 50 mm×2.10 mm)
  Solvents: solution A: 0.1% HCOOH/CH$_3$CN, solution B: 0.1% HCOOH/H$_2$O
  Gradient Condition:
    0.0 min; A/B=10:90
    0.0 to 1.4 min; Linear gradient from 10% to 90% A 1.4 to 1.6 min; A/B=90:10
1.6 to 2.0 min; A/B=10:90
Flow Rate: 1.2 mL/min
UV: 220/254 nm
Column Temperature: 40° C.
Measurement Condition F
  Detection Equipment: ACQUITY (registered Trademark) SQdetecter (Waters Corporation)
  HPLC: ACQUITY (registered Trademark) system
  Column: Waters ACQUITY UPLC (registered Trademark) BEH C18 (1.7 μm, 2.1 mm×30 mm)
  Solvents: solution A: 0.06% formic acid/$CH_3CN$, solution B: 0.06% formic acid/$H_2O$
  Gradient Condition: 0.0 to 1.3 min Linear gradient from 2% to 96% A
  Flow Rate: 0.8 mL/min
  UV: 220/254 nm
  Column Temperature: 25° C.
Measurement Condition G
  Detection Equipment: Shimadzu LCMS-IT-TOF
  Column: Phenomenex Kinetex (1.7 μm C8, 50 mm×2.10 mm)
  Solvents: solution A: 0.1% HCOOH/$CH_3CN$, solution B: 0.1% HCOOH/$H_2O$
  Gradient Condition:
    0.0 min; A/B=10:90
    0.0 to 1.4 min; Linear gradient from 10% to 95% A
    1.4 to 1.6 min; A/B=95:5
    1.6 to 2.0 min; A/B=10:90
  Flow Rate: 1.2 mL/min
  UV: 220/254 nm
  Column Temperature: 40° C.
Measurement Condition H
  Detection Equipment: Shimadzu LCMS-IT-TOF
  Column: Phenomenex Kinetex (1.7 μm C8, 50 mm×2.10 mm)
  Solvents: solution A: 0.1% HCOOH/$CH_3CN$, solution B: 0.1% HCOOH/$H_2O$
  Gradient Condition:
    0.0 min; A/B=40:60
    0.0 to 1.4 min; Linear gradient from 40% to 95% A
    1.4 to 1.6 min; A/B=95:5
    1.6 to 2.0 min; A/B=5:95
  Flow Rate: 1.2 mL/min
  UV: 220/254 nm
  Column Temperature: 40° C.

High Performance Liquid Chromatography; measurement conditions for determining the average drug antibody ratio (average DAR) are as follows, and the retention time is shown as Rt (min). Note that, for each found value, the measurement conditions used for the measurement are denoted by E.

Measurement Condition E
  HPLC: Shimadzu LC-10A series
  Column: nonporous TSKgel Butyl-NPR column (Tosoh Bioscience, 2.5 μm, 35 mm×4.6 mm)
  Solvents: solution A: 1.5 mol/L ammonium sulfate, 25 mmol/L aqueous sodium phosphate solution (pH 6.95), solution B: 25% isopropanol/25 mmol/L aqueous sodium phosphate solution (pH 6.95)
  Gradient Condition:
    0.0 min; A/B=100:0
    0.0 to 12.0 min; Linear gradient from 0% to 100% B
    12.1 to 18.0 min; A/B=100:0
  Flow Rate: 0.8 mL/min
  UV: 230 nm
  Column Temperature: 25° C.

Reference Example 1

(6S,9S,12S,13E,17R)-9-tert-butyl-17-(3-{[2-(2,5-dioxo-2,5-dihydro-1H-pyrrol-1-yl)ethyl]amino}-3-oxopropyl)-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaoctadec-13-en-18-oic Acid Tert-Butyl Ester

[Chemical Formula 44]

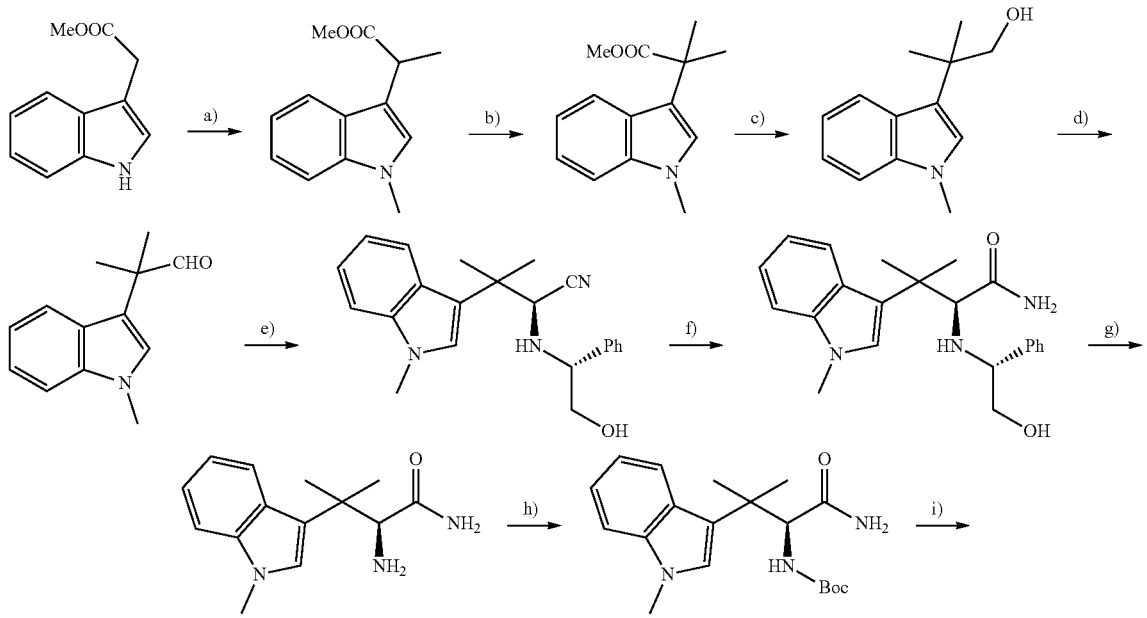

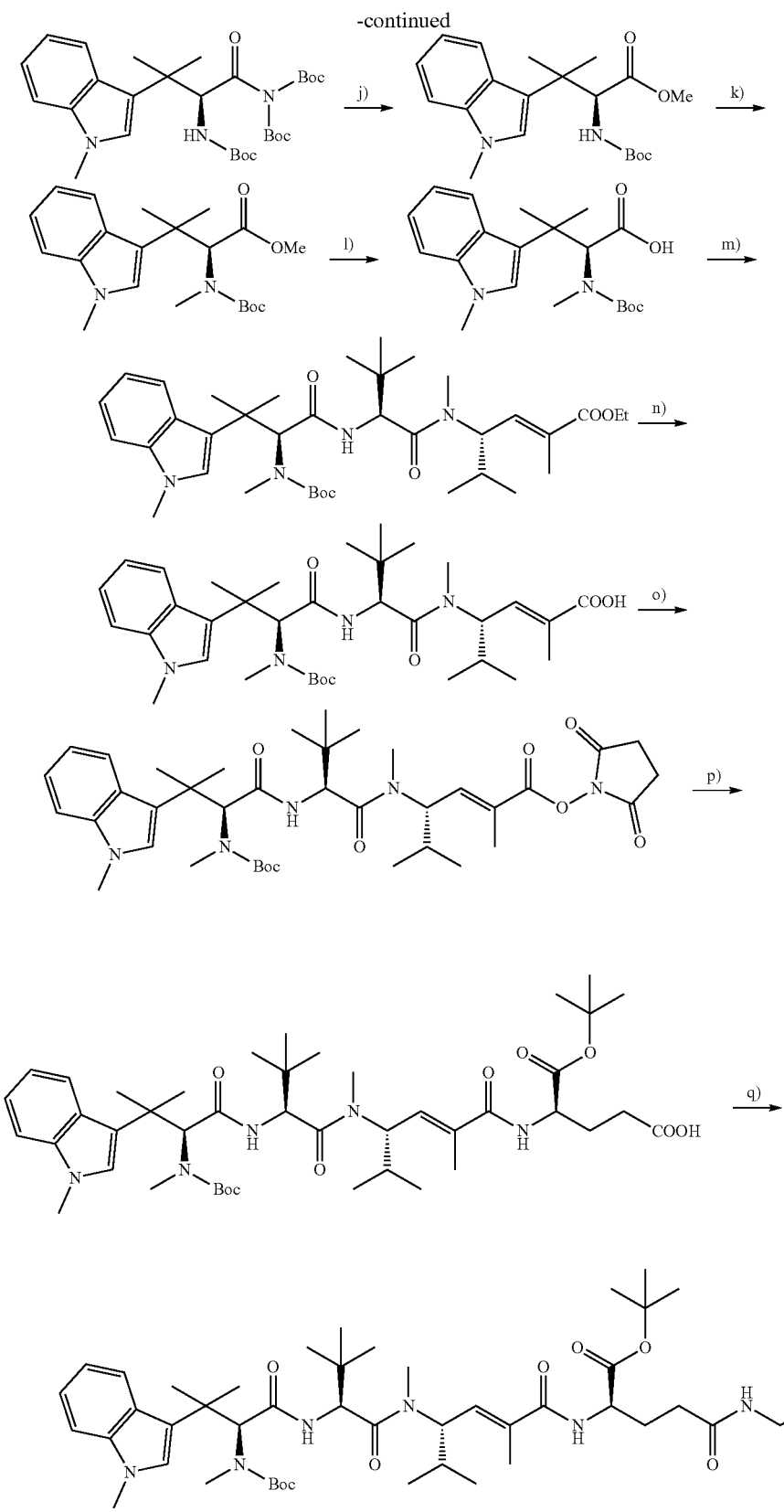
Reference Example 1 a) Production of Methyl 2-(1-methyl-1H-indol-3-yl)propanoate

Under nitrogen atmosphere, to a solution of indole-3-acetic acid methyl ester (3.8 g) in tetrahydrofuran (87 mL) at −78° C., potassium hexamethyldisilazide (1 mol/L tetrahydrofuran solution, 65.5 mL) was added dropwise, and the resultant mixture was then stirred at 0° C. for 2 hours. After cooling the reaction solution to −78° C., methyl iodide (23 g) was added dropwise thereto, and the reaction solution was then stirred at 0° C. for 3 hours. After the reaction ended, water was added and the resultant mixture was extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give methyl 2-(1-methyl-1H-indol-3-yl)propanoate (3.95 g).

$^1$H-NMR (400 MHz, CDCl$_3$):1.60 (3H, d, J=7.1 Hz), 3.67 (3H, s), 3.76 (3H, s), 4.02 (1H, q, J=7.1 Hz), 7.00 (1H, s), 7.12 (1H, t, J=7.8 Hz), 7.23 (1H, t, J=7.8 Hz), 7.29 (1H, d, J=7.8 Hz), 7.66 (1H, d, J=7.8 Hz).

b) Production of Methyl 2-methyl-2-(1-methyl-1H-indol-3-yl)propanoate

Under nitrogen atmosphere, to a solution of methyl 2-(1-methyl-1H-indol-3-yl)propanoate (3.94 g) in tetrahydrofuran (200 mL) at −78° C., potassium hexamethyldisilazide (1 mol/L tetrahydrofuran solution, 27.7 mL) was added dropwise, and the resultant mixture was then stirred at 0° C. for 2 hours. After cooling the reaction solution to −78° C., methyl iodide (15.4 g) was added dropwise thereto, and the reaction solution was then stirred at 0° C. for 3 hours. After the reaction ended, water was added and the resultant mixture was extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give methyl 2-methyl-2-(1-methyl-1H-indol-3-yl)propanoate (3.59 g).

$^1$H-NMR (400 MHz, CDCl$_3$):1.66 (6H, s), 3.61 (3H, s), 3.73 (3H, s), 6.91 (1H, s), 7.06 (1H, t, J=8.0 Hz), 7.19 (1H, t, J=8.0 Hz), 7.27 (1H, d, J=8.0 Hz), 7.61 (1H, d, J=7.9 Hz).

c) Production of 2-methyl-2-(1-methyl-1H-indol-3-yl)propan-1-ol

Under nitrogen atmosphere, to a solution of methyl 2-methyl-2-(1-methyl-1H-indol-3-yl)propanoate (3.59 g) in diethyl ether (169 mL) and dichloromethane (47 mL) at −78° C., diisobutylaluminum hydride (1 mol/L n-hexane solution, 38.8 mL) was added dropwise, and the resultant mixture was then stirred at 0° C. for 1 hour. After the reaction ended, water was added, and then, to the reaction mixture at 25° C., a saturated aqueous solution of potassium sodium tartrate was added, and the resultant mixture was then extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give 2-methyl-2-(1-methyl-1H-indol-3-yl)propan-1-ol (3.14 g).

$^1$H-NMR (400 MHz, CDCl$_3$):1.42 (6H, s), 3.74 (3H, s), 3.77 (2H, s), 6.87 (1H, s), 7.07 (1H, t, J=7.9 Hz), 7.20 (1H, t, J=7.9 Hz), 7.29 (1H, d, J=8.0 Hz), 7.75 (1H, d, J=8.0 Hz).

d) Production of 2-methyl-2-(1-methyl-1H-indol-3-yl)propanal

Under nitrogen atmosphere, a mixed solution of 2-methyl-2-(1-methyl-1H-indol-3-yl)propan-1-ol (3.14 g), tetrapropylammonium perruthenate (271 mg), N-methylmorpholine-N-oxide (3.26 g) and molecular sieve 4A (7.7 g) in dichloromethane (110 mL) was stirred at 25° C. for 1 hour. After the reaction ended, the reaction solution was filtered through celite and the solvent was then distilled off, and the residue was purified by silica gel column chromatography (eluting solvent; hexane:ethyl acetate) to give 2-methyl-2-(1-methyl-1H-indol-3-yl)propanal (2.4 g).

$^1$H-NMR (400 MHz, CDCl$_3$):1.53 (6H, s), 3.77 (3H, s), 6.94 (1H, s), 7.07 (1H, t, J=8.0 Hz), 7.22 (1H, t, J=8.0 Hz), 7.30 (1H, d, J=8.0 Hz), 7.53 (1H, d, J=8.0 Hz), 9.47 (1H, s).

e) Production of (2S)-2-{[(1R)-2-hydroxy-1-phenylethyl]amino}-3-methyl-3-(1-methyl-1H-indol-3-yl)butanenitrile Under nitrogen atmosphere, a solution of 2-methyl-2-(1-methyl-1H-indol-3-yl)propanal (2.4 g) and (R)-(−)-2-phenylglycinol (1.63 g) in toluene (47 mL) was subjected to heating reflux for 1.5 hours, and after distilling off water with a Dean-Stark apparatus, the solvent was distilled off. Under nitrogen atmosphere, dichloromethane (69 mL) at 0° C. was added to the residue and trimethylsilyl cyanide (2.36 g) was then added, and the resultant mixture was stirred at 25° C. for 96 hours. To the reaction solution, tetra-n-butylammonium fluoride (1 mol/L tetrahydrofuran solution, 1 mL) was added, and after stirring the solution for further 30 minutes, water was added and the resultant mixture was extracted with chloroform. The organic layer was dried over anhydrous sodium sulfate, and the solvent was distilled off under reduced pressure. The residue was purified by silica gel column chromatography (eluting solvent; hexane:ethyl acetate) to give (2S)-2-{[(1R)-2-hydroxy-1-phenylethyl]amino}-3-methyl-3-(1-methyl-1H-indol-3-yl)butanenitrile (2.74 g).

$^1$H-NMR (400 MHz, CDCl$_3$):1.64 (3H, s), 1.65 (3H, s), 3.49-3.55 (1H, m), 3.73 (1H, dd, J=10.9, 4.2 Hz), 3.79 (1H, s), 3.80 (3H, s), 4.05 (1H, dd, J=7.9, 3.6 Hz), 6.96-7.00 (2H, m), 7.11 (2H, d, J=8.0 Hz), 7.21-7.40 (6H, m).

f) Production of Nα-[(1R)-2-hydroxy-1-phenylethyl]-β,β,1-trimethyl-L-tryptophanamide To a suspension of (2S)-2-{[(1R)-2-hydroxy-1-phenylethyl]amino}-3-methyl-3-(1-methyl-1H-indol-3-yl)butanenitrile (2.74 g), dimethyl sulfoxide (6.16 g) and potassium carbonate (10.9 g) in methanol (50 mL) and water (2.1 mL), a 30% aqueous hydrogen peroxide solution (8.94 mL) was added at 0° C., and the resultant mixture was stirred at 45° C. for 1.5 hours. After the reaction ended, a saturated aqueous sodium thiosulfate solution was added, and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform:methanol) to give Nα-[(1R)-2-hydroxy-1-phenylethyl]-β,β,1-trimethyl-L-tryptophanamide (2.32 g).

$^1$H-NMR (400 MHz, CDCl$_3$):1.49 (3H, s), 1.51 (3H, s), 2.06-2.14 (1H, br), 2.37 (1H, dd, J=6.0, 6.0 Hz), 3.44-3.50 (1H, m), 3.50-3.54 (1H, m), 3.56-3.63 (m, 2H), 3.75 (3H, s), 5.52 (1H, brs), 6.14 (1H, brs), 6.71-6.73 (2H, m), 6.81-6.85 (2H, m), 6.97-7.00 (2H, m), 7.10-7.18 (2H, m), 7.24-7.28 (2H, m).

g) Production of β,β,1-trimethyl-L-tryptophanamide

To a solution of Nα-[(1R)-2-hydroxy-1-phenylethyl]-β,β,1-trimethyl-L-tryptophanamide (2.32 g) in methanol (65 mL), palladium hydroxide/carbon (2.8 g) was added, and the resultant mixture was stirred at room temperature for 3 hours under hydrogen atmosphere. The reaction solution was filtered through celite and the solvent was then distilled off, and the residue was purified by silica gel column chromatography (eluting solvent; chloroform:methanol) to give β,β,1-trimethyl-L-tryptophanamide (1.27 g).
$^1$H-NMR (400 MHz, DMSO-d6):1.24 (2H, brs), 1.28 (3H, s), 1.42 (3H, s), 3.68 (1H, s), 3.71 (3H, s), 6.93-7.00 (2H, m), 7.06 (1H, s), 7.11 (1H, t, J=7.7 Hz), 7.29 (1H, brs), 7.36 (1H, d, J=8.3 Hz), 7.88 (1H, d, J=8.2 Hz).

h) Production of Nα-(tert-butoxycarbonyl)-β,β,1-trimethyl-L-tryptophanamide

A mixed solution of β,β,1-trimethyl-L-tryptophanamide (1.27 g), sodium bicarbonate (522 mg), di-tert-butyl dicarbonate (1.35 g), tetrahydrofuran (13 mL), chloroform (13 mL) and water (6.5 mL) was stirred at 25° C. for 16 hours. After the reaction ended, water was added and the resultant mixture was extracted with chloroform. The organic layer was dried over anhydrous sodium sulfate, and the solvent was distilled off under reduced pressure. The residue was purified by silica gel column chromatography (eluting solvent; chloroform:methanol) to give Nα-(tert-butoxycarbonyl)-β,β,1-trimethyl-L-tryptophanamide (1.80 g). $^1$H-NMR (400 MHz, CDCl$_3$):1.33 (3H, s), 1.47 (9H, s), 1.50 (3H, s), 3.73 (3H, d, J=1.3 Hz), 4.51 (1H, brs), 4.86 (1H, brs), 5.02 (1H, brd, J=8.2 Hz), 5.59 (1H, brd, J=6.4 Hz), 6.83 (1H, d, J=1.8 Hz), 7.15 (1H, t, J=7.3 Hz), 7.21-7.25 (1H, m), 7.30 (1H, d, J=8.2 Hz), 8.05 (1H, brd, J=7.3 Hz).
LC-MS: 346 (M+H)$^+$ (1.211 min, Measurement Condition A)

i) Production of N,N,Nα-tris(tert-butoxycarbonyl)-β,β,1-trimethyl-L-tryptophanamide A mixed solution of Nα-(tert-butoxycarbonyl)-β,β,1-trimethyl-L-tryptophanamide (1.79 g), di-tert-butyl dicarbonate (2.8 g), N,N-diisopropylethylamine (2.68 g), 4-dimethylaminopyridine (0.19 g) and chloroform (20 mL) was stirred at 25° C. for 2.5 hours. After the reaction ended, water was added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; hexane:ethyl acetate) to give N,N,Nα-tris(tert-butoxycarbonyl)-β,β,1-trimethyl-L-tryptophanamide (1.99 g).
$^1$H-NMR (400 MHz, CDCl$_3$):1.08-1.58 (33H, m), 3.70 (3H, s), 4.67-4.90 (0.2H, m), 5.25-5.45 (0.8H, m), 6.00-6.03 (1H, m), 6.81-6.87 (1H, m), 7.04-7.09 (1H, m), 7.13-7.18 (1H, m), 7.21-7.27 (1H, m), 7.91-7.94 (1H, m).

LC-MS: 546 (M+H)$^+$ (1.630 min, Measurement Condition A)

j) Production of methyl N-(tert-butoxycarbonyl)-β,β,1-trimethyl-L-tryptophanate

Under nitrogen atmosphere, to a solution of N,N,Nα-tris(tert-butoxycarbonyl)-β,β,1-trimethyl-L-tryptophanamide (2.29 g) in methanol (21 mL), lithium methoxide (176 mg) was added at 0° C., and the resultant mixture was then stirred at 25° C. for 2 hours. After the reaction ended, a saturated aqueous ammonium chloride solution was added, and the reaction mixture was extracted with ethyl acetate. The organic layer was washed with saturated brine and then dried over anhydrous sodium sulfate, and the solvent was distilled off under reduced pressure. The residue was purified by silica gel column chromatography (eluting solvent; hexane:ethyl acetate) to give methyl N-(tert-butoxycarbonyl)-β,β,1-trimethyl-L-tryptophanate (927 mg).
$^1$H-NMR (400 MHz, CDCl$_3$):1.17-1.59 (15H, m), 3.45 and 3.58 (3H, 2brs), 3.71 (3H, s), 4.56-4.73 (1.2H, m), 5.06 (0.8H, brd, J=7.3 Hz), 6.81-6.82 (1H, m), 7.05-7.10 (1H, m), 7.16-7.21 (1H, m), 7.24-7.29 (1H, in), 7.73-7.80 (1H, m).
LC-MS: 361 (M+H)$^+$ (1.379 min, Measurement Condition A).

k) Production of Methyl N-(tert-butoxycarbonyl)-N,β,β,1-tetramethyl-L-tryptophanate Under nitrogen atmosphere, to a solution of methyl N-(tert-butoxycarbonyl)-β,β,1-trimethyl-L-tryptophanate (927 mg) in N,N-dimethylformamide (13 mL), sodium hydride 60% dispersion (168 mg) was added at 0° C., and the resultant mixture was then stirred at 25° C. for 15 minutes. After cooling the reaction suspension to 0° C., methyl iodide (1.1 g) was added thereto, and the reaction solution was then stirred at 25° C. for 1 hour. After the reaction ended, water was added and the resultant mixture was extracted with ethyl acetate. The organic layer was dried over anhydrous sodium sulfate, and the solvent was distilled off under reduced pressure. The residue was purified by silica gel column chromatography (eluting solvent; hexane:ethyl acetate) to give methyl N-(tert-butoxycarbonyl)-N,β,β,1-tetramethyl-L-tryptophanate (915 mg). $^1$H-NMR (400 MHz, CDCl$_3$):1.42 (9H, s), 1.52 and 1.64 (6H, 2s), 2.80 and 2.86 (3H, 2s), 3.46 (3H, s), 3.71 (3H, s), 5.27 and 5.52 (1H, 2s), 6.85 (1H, s), 7.07-7.27 (3H, m), 7.78 and 7.92 (1H, 2d, J=7.88 Hz). LC-MS: 397 (M+Na)$^+$ (1.406 min, Measurement Condition B)

l) Production of N-(tert-butoxycarbonyl)-N,β,β,1-tetramethyl-L-tryptophan

To a solution of methyl N-(tert-butoxycarbonyl)-N,β,β,1-tetramethyl-L-tryptophanate (639 mg) in water (11 mL)-methanol (44 mL), a 1 mol/L lithium hydroxide (13.5 mL) was added, and the resultant mixture was stirred at 60° C. for 24 hours. After the reaction ended, a 1 mol/L aqueous oxalic acid solution was added to change the pH of the reaction solution to 4, and water was then added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; chloroform:methanol) to give N-(tert-butoxycarbonyl)-N,β,β,1-tetramethyl-L-tryptophan (610 mg).

¹H-NMR (400 MHz, CDCl₃):1.43 (9H, s), 1.53 (3H, s), 1.63 (3H, s), 2.76 and 2.89 (3H, 2s), 3.71 (3H, s), 5.36 and 5.44 (1H, 2s), 6.85 and 6.87 (1H, 2s), 7.02-7.11 (1H, m), 7.18 (1H, t, J=7.3 Hz), 7.24-7.27 (1H, in), 7.81 and 7.96 (1H, 2d, J=7.9 Hz).

LC-MS: 361 (M+H)⁺, 359 (M−H)⁻ (1.300 min, Measurement Condition A).

m) Production of N-(tert-butoxycarbonyl)-N,β,β,1-tetramethyl-L-tryptophyl-N-[(3S,4E)-6-ethoxy-2,5-dimethyl-6-oxohex-4-en-3-yl]-N,3-dimethyl-L-valinamide A mixed solution of N-(tert-butoxycarbonyl)-N,β,β,1-tetramethyl-L-tryptophan (500 mg), ethyl (2E,4S)-2,5-dimethyl-4-[methyl(3-methyl-L-valyl)amino]hex-2-enoate (520 mg), 1-ethyl-3-(3-dimethylaminopropyl)carbodiimide hydrochloride (399 mg), 1-hydroxy-1H-benzotriazole monohydrate (425 mg) and N,N-dimethylformamide (5 mL) was stirred at 25° C. for 16 hours. After the reaction ended, water was added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; hexane:ethyl acetate) to give N-(tert-butoxycarbonyl)-N,β,β,1-tetramethyl-L-tryptophyl-N-[(3S,4E)-6-ethoxy-2,5-dimethyl-6-oxohex-4-en-3-yl]-N,3-dimethyl-L-valinamide (759 mg).

LC-MS: 655 (M+H)⁺ (1.714 min, Measurement Condition A)

n) Production of N-(tert-butoxycarbonyl)-N,β,β,1-tetramethyl-L-tryptophyl-N-[(3S,4E)-5-carboxy-2-methylhex-4-en-3-yl]-N,3-dimethyl-L-valinamide To a solution of N-(tert-butoxycarbonyl)-N,β,β,1-tetramethyl-L-tryptophyl-N-[(3S,4E)-6-ethoxy-2,5-dimethyl-6-oxohex-4-en-3-yl]-N,3-dimethyl-L-valinamide (127 mg) in water (1.55 mL)-methanol (4.65 mL), 1 mol/L lithium hydroxide (1.65 mL) was added, and the resultant mixture was stirred at 25° C. for 24 hours. After the reaction ended, a 1 mol/L aqueous oxalic acid solution was added to change the pH of the reaction solution to 4, and water was then added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; chloroform:methanol) to give N-(tert-butoxycarbonyl)-N,β,β,1-tetramethyl-L-tryptophyl-N-[(3S,4E)-5-carboxy-2-methylhex-4-en-3-yl]-N,3-dimethyl-L-valinamide (93 mg).

LC-MS: 627 (M+H)⁺ (1.508 min, Measurement Condition A)

o) Production of N-(tert-butoxycarbonyl)-N,β,β,1-tetramethyl-L-tryptophyl-N-{(3S,4E)-6-[(2,5-dioxopyrrolidin-1-yl)oxy]-2,5-dimethyl-6-oxohex-4-en-3-yl}-N, 3-dimethyl-L-valinamide A mixed solution of N-(tert-butoxycarbonyl)-N,β,β,1-tetramethyl-L-tryptophyl-N-[(3S,4E)-5-carboxy-2-methyl-hex-4-en-3-yl]-N,3-dimethyl-L-valinamide (185 mg), N-hydroxysuccinimide (97 mg), bromotripyrrolidinophosphonium hexafluorophosphate (391 mg), 4-dimethylaminopyridine (102 mg), N,N-diisopropylethylamine (108 mg) and N,N-dimethylformamide (2.8 mL) was stirred at 25° C. for 4 hours. After the reaction ended, water was added and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform:methanol) to give N-(tert-butoxycarbonyl)-N,β,β,1-tetramethyl-L-tryptophyl-N-{(3S, 4E)-6-[(2,5-dioxopyrrolidin-1-yl)oxy]-2,5-dimethyl-6-oxohex-4-en-3-yl}-N, 3-dimethyl-L-valinamide (166 mg).

¹H-NMR (400 MHz, CDCl₃):8.27 and 7.96 (1H, 2d, J=7.9 Hz), 7.16-7.04 (4H, m), 6.88 (1H, d, J=9.1 Hz), 6.17 and 6.09 (1H, 2d, J=8.5 Hz), 5.96 and 5.66 (1H, 2s), 5.07 (1H, t, J=9.3 Hz), 4.45 and 3.87 (1H, 2d, J=8.6 Hz), 3.74 and 3.73 (3H, 2s), 2.99 (3H, s), 2.95 (3H, s), 2.83 (4H, brs), 1.97 (3H, s), 1.92-1.86 (1H, m), 1.57-1.42 (14H, m), 0.89 (3H, d, J=6.1 Hz), 0.83-0.80 (3H, m), 0.48 and 0.41 (9H, 2s).

LC-MS: 724 (M+H)⁺ (1.573 min, Measurement Condition A)

p) Production of (6S,9S,12S,13E,17R)-17-(tert-butoxycarbonyl)-9-tert-butyl-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaicos-13-en-20-oic Acid A mixed solution of N-(tert-butoxycarbonyl)-N,β,β,1-tetramethyl-L-tryptophyl-N-{(3S,4E)-6-[(2,5-dioxopyrrolidin-1-yl)oxy]-2,5-dimethyl-6-oxohex-4-en-3-yl}-N, 3-dimethyl-L-valinamide (30 mg), D-glutamic acid α-tert-butyl ester hydrochloride (10.7 mg), N,N-diisopropylethylamine (49.7 mg) and N,N-dimethylformamide (1.0 mL) was stirred at 25° C. for 3 hours. After the reaction ended, water was added, and the resultant mixture was extracted with chloroform. The organic layer was washed with water and then dried over anhydrous sodium sulfate, and the solvent was distilled off under reduced pressure. The residue was purified by silica gel column chromatography (eluting solvent; chloroform:methanol) to give (6S,9S,12S,13E,17R)-17-(tert-butoxycarbonyl)-9-tert-butyl-2,2,5,11,14-pentamethyl-6-[2-(1-methyl-1H-indol-3-yl)propan-2-yl]-4,7,10,15-tetra oxo-12-(propan-2-yl)-3-oxa-5,8,11,16-tetraazaicos-13-en-20-oic acid (14.2 mg).

LC-MS 834 (M+Na)⁺ (1.574 min, Measurement Condition D)

q) Production of (6S,9S,12S,13E,17R)-9-tert-butyl-17-(3-{[2-(2,5-dioxo-2,5-dihydro-1H-pyrrol-1-yl)ethyl]amino}-3-oxopropyl)-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaoctadec-13-en-18-oic acid tert-butyl Ester (Reference Example 1)

A mixed solution of (6S,9S,12S,13E,17R)-17-(tert-butoxycarbonyl)-9-tert-butyl-2,2,5,11,14-pentamethyl-6-[2-(1-methyl-1H-indol-3-yl)propan-2-yl]-4,7,10,15-tetra oxo-12-(propan-2-yl)-3-oxa-5,8,11,16-tetraazaicos-13-en-20-oic acid (14 mg), N-(2-aminoethyl)maleimide hydrochloride (3.0 mg), 1-ethyl-3-(3-dimethylaminopropyl)carbodiimide hydrochloride (6.6 mg), 1-hydroxy-1H-benzotriazole monohydrate (5.2 mg), N,N-diisopropylethylamine (4.4 mg) and N,N-dimethylformamide (0.5 mL) was stirred at 25° C. for 2 hours. After the reaction ended, water was added, and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform:methanol) to give Reference Example 1 (11.6 mg).

LC-MS: 934 (M+H)$^+$ (1.597 min, Measurement Condition D)

Reference Example 2

N-(tert-Butoxycarbonyl)-N,β,β-trimethyl-L-phenylalanyl-N-{(3S,4E)-6-[(2,5-dioxopyrrolidin-1-yl)oxy]-2,5-dimethyl-6-oxohex-4-en-3-yl}-N,3-dimethyl-L-valinamide

[Chemical Formula 45]

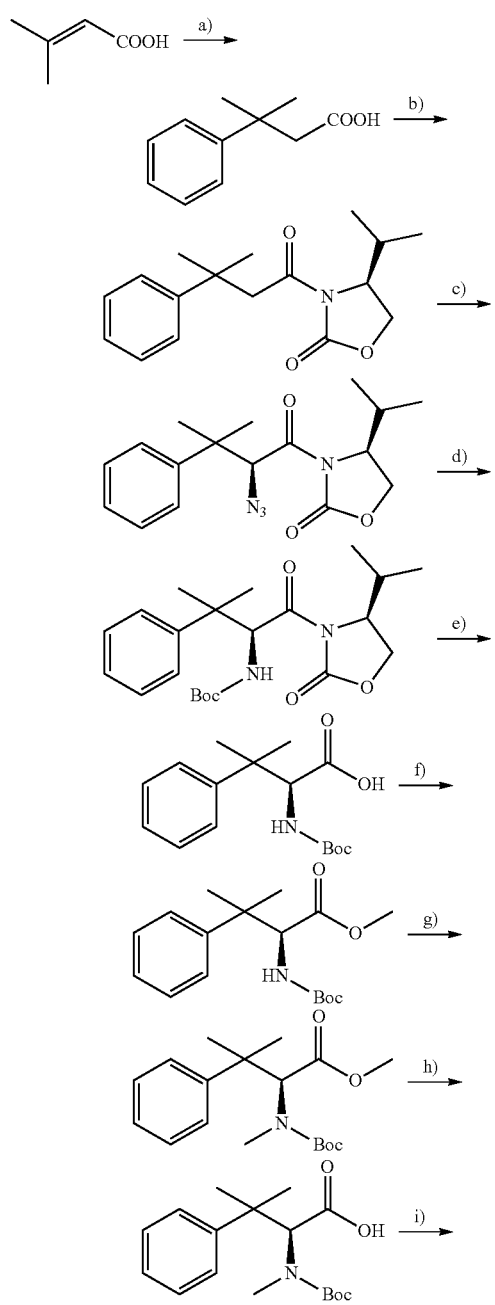

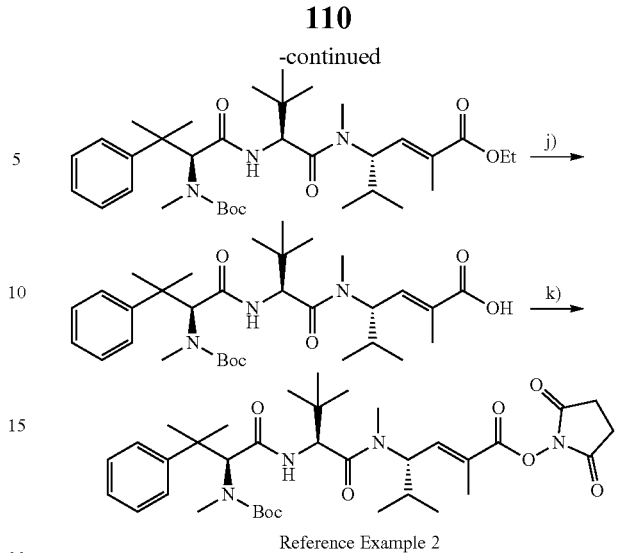

Reference Example 2 a) Production of 3-methyl-3-phenylbutanoic Acid

To a solution of 3-methyl-2-butenoic acid (15 g) in benzene (100 mL), aluminum chloride (24.1 g) was added at 10° C., and the resultant mixture was stirred for 30 minutes and then stirred at 40° C. for 1 hour. After cooling the reaction solution to 0° C., ice water was added, and the resultant mixture was extracted with tert-butyl methyl ether, concentrated to some extent, and the organic layer was extracted with a saturated aqueous sodium bicarbonate solution. The pH of the aqueous layer was changed to 2 with concentrated hydrochloric acid, and the resultant mixture was extracted with tert-butyl methyl ether. The organic layer was dried over anhydrous magnesium sulfate, and the solvent was distilled off under reduced pressure to give 3-methyl-3-phenylbutanoic acid (26.3 g).

$^1$H-NMR (400 MHz, CDCl$_3$):1.46 (6H, s), 2.65 (2H, s), 7.20 (1H, t, J=7.2 Hz), 7.31 (1H, t, J=7.2 Hz), 7.37 (2H, d, J=7.2 Hz).

b) Production of (4S)-3-(3-methyl-3-phenylbutanoyl)-4-(propan-2-yl)-1,3-oxazolidin-2-one To a solution of 3-methyl-3-phenylbutanoic acid (17.2 g) in THF (900 mL), triethylamine (23.7 mL) and pivaloyl chloride (15.3 mL) was added at −78° C. After raising the temperature to 0° C., the resultant mixture was stirred for 1 hour. Separately, to a solution of (S)-isopropyloxazolidinone (19.5 g) in THF (760 mL), n-butyllithium (1.64 mol/L hexane solution, 89.8 mL) was added at −78° C., the resultant mixture was stirred for 30 minutes to prepare a lithium salt. The previous reaction solution was cooled to −78° C., the lithium salt was added dropwise, the resultant mixture was stirred for 1 hour, and the temperature was then raised to 0° C. After stirring the mixture for further 30 minutes, water was added, and the resultant mixture was extracted with tert-butyl methyl ether. The organic layer was washed with saturated brine and dried over anhydrous magnesium sulfate. The solvent was distilled off under reduced pressure, and the residue was purified by silica gel column chromatography (eluting solvent; hexane:tert-butyl methyl ether) to give (4S)-3-(3-methyl-3-phenylbutanoyl)-4-(propan-2-yl)-1,3-oxazolidin-2-one (27.0 g).

$^1$H-NMR (400 MHz, CDCl$_3$):0.723 (3H, d, J=6.8 Hz), 0.80 (3H, d, J=6.8 Hz), 1.49 (s, 6H), 2.13-2.18 (m, 1H), 3.36

(s, 3H), 3.99-4.09 (m, 2H), 4.20-4.23 (m, 1H),7.16-7.20 (m, 1H), 7.28-7.32 (m, 2H), 7.38-7.40 (m, 2H)

c) Production of (4S)-3-[(2S)-2-azido-3-methyl-3-phenylbutanoyl]-4-(propan-2-yl)-1,3-oxazolidin-2-one A suspension of (4S)-3-(3-methyl-3-phenylbutanoyl)-4-(propan-2-yl)-1,3-oxazolidin-2-one (27.0 g) in THF (560 mL) was cooled to −78° C., potassium hexamethyldisilazide (1.06 mol/L tetrahydrofuran solution, 99.5 mL) was added, and the resultant mixture was stirred for 1.5 hours. A solution of 2,4,6-triisopropylbenzenesulfonyl azide (40 g) in THF (330 mL) at −78° C. was added, and after 10 minutes, acetic acid (24.5 mL) was added, the temperature was raised to 40° C., and the resultant mixture was stirred for 1 hour. Saturated brine was added, and the resultant mixture was extracted with tert-butyl methyl ether. The organic layer was washed with a saturated aqueous sodium bicarbonate solution and saturated brine, and the organic layer was then dried over anhydrous magnesium sulfate. The solvent was distilled off under reduced pressure, and the residue was purified by silica gel column chromatography (eluting solvent; hexane:chloroform) to give (4S)-3-[(2S)-2-azido-3-methyl-3-phenylbutanoyl]-4-(propan-2-yl)-1,3-oxazolidin-2-one (16.4 g).

$^1$H-NMR (400 MHz, CDCl$_3$):0.80 (3H, d, J=6.8 Hz), 0.84 (3H, d, J=7.2 Hz), 1.54 (3H, s), 1.56 (3H, s), 2.28-2.33 (1H, m), 3.54-3.59 (1H, m), 3.87-3.90 (1H, m), 3.95-3.98 (1H, m), 5.66 (1H, s), 7.23-7.420 (5H, m).

d) Production of Tert-butyl{(2S)-3-methyl-1-oxo-1-[(4S)-2-oxo-4-(propan-2-yl)-1,3-oxazolidin-3-yl]-3-phenylbutan-2-yl}carbamate To a solution of (4S)-3-[(2S)-2-azido-3-methyl-3-phenylbutanoyl]-4-(propan-2-yl)-1,3-oxazolidin-2-one (16.4 g) in ethyl acetate (1200 mL), di-tert-butyl dicarbonate (24.0 g) and 10% Pd—C (11.6 g, 50% wet) were added, and the resultant mixture was stirred for 2 hours under hydrogen atmosphere. The reaction solution was filtered through celite, and was washed with ethyl acetate. The solvent was distilled off under reduced pressure, and the residue was purified by silica gel column chromatography (eluting solvent; hexane:tert-butyl methyl ether) to give tert-butyl {(2S)-3-methyl-1-oxo-1-[(4S)-2-oxo-4-(propan-2-yl)-1,3-oxazolidin-3-yl]-3-phenylbutan-2-yl}carbamate (16.1 g).

$^1$H-NMR (400 MHz, CDCl$_3$):0.77 (3H, d, J=6.8 Hz), 0.82 (3H, d, J=6.8 Hz), 1.42 (3H, s), 1.43 (9H, s), 1.48 (3H, s), 2.20-2.29 (1H, m), 3.45 (1H, t, J=8.8 Hz), 3.80-3.83 (1H, m), 3.89-3.92 (1H, dd, J=2.0 Hz, J=8.4 Hz), 5.16 (1H, brs), 6.13 (1H, d, J=9.6 Hz), 7.21-7.26 (1H, m), 7.29-7.33 (2H, m). 7.42 (2H, d, J=7.2 Hz).

e) Production of N-(tert-butoxycarbonyl)-β,β-dimethyl-L-phenylalanine

To a solution of tert-butyl {(2S)-3-methyl-1-oxo-1-[(4S)-2-oxo-4-(propan-2-yl)-1,3-oxazolidin-3-yl]-3-phenylbutan-2-yl}carbamate (16.1 g) in THF (468 mL) and water (117 mL), a 30% aqueous hydrogen peroxide solution (32.5 mL) and an aqueous lithium hydroxide solution (1 mol/L, 119 mL) were added at 0° C., the temperature was raised to 25° C., and the resultant mixture was stirred for 3 hours. An aqueous sodium bisulfate solution (1.5 mol/L, 470 mL) was added at 0° C., the temperature was raised to 25° C., and the resultant mixture was stirred for 1 hour. The pH was changed to 3 with an aqueous citric acid solution (1 mol/L), and the resultant mixture was extracted with tert-butyl methyl ether. The organic layer was washed with saturated brine, and the organic layer was dried over anhydrous magnesium sulfate. The solvent was distilled off under reduced pressure to give N-(tert-butoxycarbonyl)-β,β-dimethyl-L-phenylalanine (14.2 g).

$^1$H-NMR (400 MHz, CDCl$_3$):1.38 (9H, s), 1.44 (3H, s), 1.46 (3H, s), 4.56 (1H, brd, J=11.6 Hz), 4.94 (1H, brd, J=14.4 Hz), 7.21-7.38 (5H, in).

f) Production of N-(tert-butoxycarbonyl)-β,β-dimethyl-L-phenylalanine Methyl Ester To a solution of N-(tert-butoxycarbonyl)-β,β-dimethyl-L-phenylalanine (14.2 g) in N,N-dimethylformamide (84 ml), sodium carbonate (8.44 g) and methyl iodide (9.91 mL) were added, and the resultant mixture was stirred at 25° C. for 15 hours. After cooling the mixture to 0° C., chilled water was added and the resultant mixture was extracted with tert-butyl methyl ether, and the organic layer thus obtained was washed with saturated brine and then dried over anhydrous magnesium sulfate. The solvent was distilled off under reduced pressure, and the residue was purified by silica gel column chromatography (eluting solvent; hexane:tert-butyl methyl ether) to give N-(tert-butoxycarbonyl)-β,β-dimethyl-L-phenylalanine methyl ester (11.1 g).

$^1$H-NMR (400 MHz, CDCl$_3$):1.36 (9H, s), 1.37 (3H, s), 1.41 (3H, s), 3.48 (3H, brs), 4.49 (1H, brd, J=9.8 Hz), 4.98 (1H, brd, J=9.1 Hz), 7.18-7.22 (1H, m), 7.27-7.33 (4H, m).

g) Production of N-(tert-butoxycarbonyl)-N,β,β-trimethyl-L-phenylalanine Methyl Ester By the same approach as Reference Example 1-k), from N-(tert-butoxycarbonyl)-β,β-dimethyl-L-phenylalanine methyl ester (307 mg), N-(tert-butoxycarbonyl)-N,β,β-trimethyl-L-phenylalanine methyl ester (245 mg) was obtained.

LC-MS: 344 (M+Na)$^+$ (1.589 min, Measurement Condition C)

h) Production of N-(tert-butoxycarbonyl)-N,β,β-trimethyl-L-phenylalanine

By the same approach as Reference Example 1-1), from N-(tert-butoxycarbonyl)-N,β,β-trimethyl-L-phenylalanine methyl ester (235 mg), N-(tert-butoxycarbonyl)-N,β,β-trimethyl-L-phenylalanine (195 mg) was obtained.

LC-MS: 330 (M+Na)$^+$ (1.420 min, Measurement Condition C)

i) Production of N-(tert-butoxycarbonyl)-N,β,β-trimethyl-L-phenylalanyl-N-[(3S,4E)-6-ethoxy-2,5-dimethyl-6-oxohex-4-en-3-yl]-N,3-dimethyl-L-valinamide By the same approach as Reference Example 1-m), from N-(tert-butoxycarbonyl)-N,β,β-trimethyl-L-phenylalanine (195 mg), N-(tert-butoxycarbonyl)-N,β,β-trimethyl-L-phenylalanyl-N-[(3S,4E)-6-ethoxy-2,5-dimethyl-6-oxohex-4-en-3-yl]-N,3-dimethyl-L-valinamide (307 mg) was obtained.

LC-MS: 624 (M+Na)$^+$ (1.797 min, Measurement Condition C)

j) Production of N-(tert-butoxycarbonyl)-N,β,β-trimethyl-L-phenylalanyl-N-[(3S,4E)-5-carboxy-2-methylhex-4-en-3-yl]-N,3-dimethyl-L-valinamide By the same approach as Reference Example 1-n), from N-(tert-butoxycarbonyl)-N,β,β-trimethyl-L-phenylalanyl-N-[(3S,4E)-6-ethoxy-2,5-dimethyl-6-oxohex-4-en-3-yl]-N,3-dimethyl-L-valinamide (307 mg), N-(tert-butoxycarbonyl)-N,β,β-trimethyl-L-phenylalanyl-N-[(3S,4E)-5-carboxy-2-methylhex-4-en-3-yl]-N,3-dimethyl-L-valinamide (286 mg) was obtained.

LC-MS: 596 (M+Na)$^+$, 572 (M−H)$^−$ (1.596 min, Measurement Condition C)

k) Production of N-(tert-butoxycarbonyl)-N,β,β-trimethyl-L-phenylalanyl-N-{(3S,4E)-6-[(2,5-dioxopyrrolidin-1-yl)oxy]-2,5-dimethyl-6-oxohex-4-en-3-yl}-N,3-dimethyl-L-valinamide (Reference Example 2)

By the same approach as Reference Example 1-o), from N-(tert-butoxycarbonyl)-N,β,β-trimethyl-L-phenylalanyl-N-[(3S,4E)-5-carboxy-2-methylhex-4-en-3-yl]-N,3-dimethyl-L-valinamide (286 mg), Reference Example 2 (227 mg) was obtained.

LC-MS: 693 (M+Na)$^+$ (1.658 min, Measurement Condition C)

Reference Example 3

(6S,9S,12S,13E,17R,22R)-9-tert-Butyl-28-(2,5-dioxo-2,5-dihydro-1H-pyrrol-1-yl)-2,2,5,11,14-pentamethyl-6-[2-(1-methyl-1H-indol-3-yl)propan-2-yl]-4,7,10,15,20,25-hexaoxo-12-(propan-2-yl)-3-oxa-5,8,11,16,21,26-hexaazaoctacos-13-en-17,22-dioic Acid Di-Tert-Butyl Ester

[Chemical Formula 46]

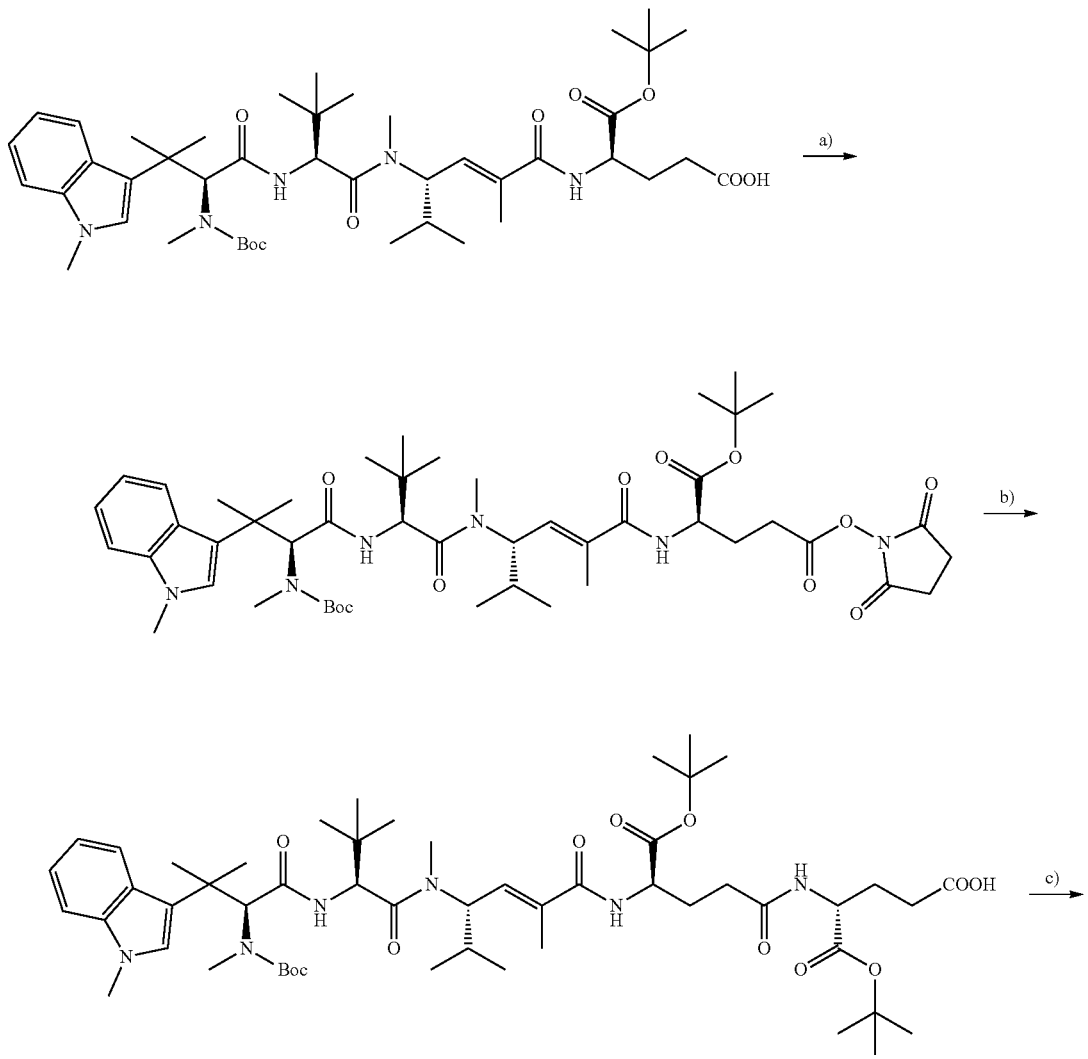

-continued

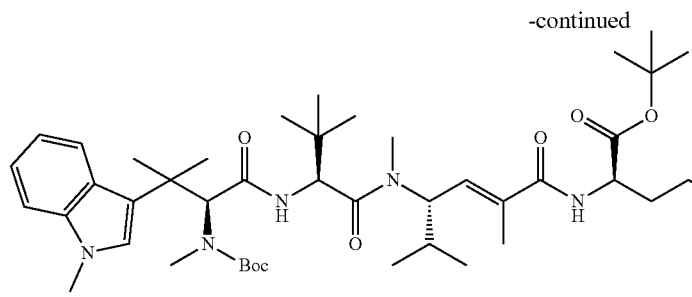 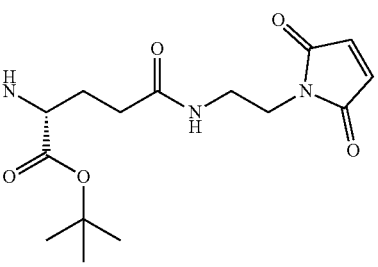

Reference Example 3 a) Production of (6S,9S,12S,13E,17R)-9-tert-butyl-17-{3-[(2,5-dioxopyrrolidin-1-yl)oxy]-3-oxopropyl}-2,2,5,11,14-pentamethyl-6-[2-(1-methyl-1H-indol-3-yl) propan-2-yl]-4,7,10,15-tetraoxo-12-(propan-2-yl)-3-oxa-5,8,11,16-tetraazaoctadec-13-en-18-oic Acid Tert-Butyl Ester By the same approach as Reference Example 1-o), from (6S,9S,12S,13E,17R)-17-(tert-butoxycarbonyl)-9-tert-butyl-2,2,5,11,14-pentamethyl-6-[2-(1-methyl-1H-indol-3-yl)propan-2-yl]-4,7,10,15-tetra oxo-12-(propan-2-yl)-3-oxa-5,8,11,16-tetraazaicos-13-en-20-oic acid (90.2 mg), (6S,9S,12S,13E,17R)-9-tert-butyl-17-{3-[(2,5-dioxopyrrolidin-1-yl)oxy]-3-oxopropyl}-2,2,5,11,14-pentamethyl-6-[2-(1-methyl-1H-indol-3-yl) propan-2-yl]-4,7,10,15-tetraoxo-12-(propan-2-yl)-3-oxa-5,8,11,16-tetraazaoctadec-13-en-18-oic acid tert-butyl ester (51.8 mg) was obtained.

LC-MS: 931 (M+Na)$^+$ (1.662 min, Measurement Condition D)

b) Production of (6S,9S,12S,13E,17R,22R)-17,22-bis(tert-butoxycarbonyl)-9-tert-butyl-2,2,5,11,14-pentamethyl-6-[2-(1-methyl-1H-indol-3-yl)propan-2-yl]-4,7,10,15,20-pentaoxo-12-(propan-2-yl)-3-oxa-5,8,11,16,21-pentaazapentacos-13-en-25-oic Acid By the same approach as Reference Example 1-p), from (6S,9S,12S,13E,17R)-9-tert-butyl-17-{3-[(2,5-dioxopyrrolidin-1-yl)oxy]-3-oxopropyl}-2,2,5,11,14-pentamethyl-6-[2-(1-methyl-1H-indol-3-yl) propan-2-yl]-4,7,10,15-tetraoxo-12-(propan-2-yl)-3-oxa-5,8,11,16-tetraazaoctadec-13-en-18-oic acid tert-butyl ester (51.8 mg), (6S,9S,12S,13E,17R,22R)-17,22-bis(tert-butoxycarbonyl)-9-tert-butyl-2,2,5,11,14-pentamethyl-6-[2-(1-methyl-1H-indol-3-yl)propan-2-yl]-4,7,10,15,20-pentaoxo-12-(propan-2-yl)-3-oxa-5,8,11,16,21-pentaazapentacos-13-en-25-oic acid (40 mg) was obtained.

LC-MS: 1019 (M+Na)$^+$ (1.422 min, Measurement Condition D)

c) Production of (6S,9S,12S,13E,17R,22R)-9-tert-butyl-28-(2,5-dioxo-2,5-dihydro-1H-pyrrol-1-yl)-2,2,5,11,14-pentamethyl-6-[2-(1-methyl-1H-indol-3-yl)propan-2-yl]-4,7,10,15,20,25-hexaoxo-12-(propan-2-yl)-3-oxa-5,8,11,16,21,26-hexaazaoctacos-13-ene-17,22-dioic Acid Di-Tert-Butyl Ester (Reference Example 3)

By the same approach as Reference Example 1-q), from (6S,9S,12S,13E,17R,22R)-17,22-bis(tert-butoxycarbonyl)-9-tert-butyl-2,2,5,11,14-pentamethyl-6-[2-(1-methyl-1H-indol-3-yl)propan-2-yl]-4,7,10,15,20-pentaoxo-12-(propan-2-yl)-3-oxa-5,8,11,16,21-pentaazapentacos-13-en-25-oic acid (40 mg), Reference Example 3 (14 mg) was obtained.

LC-MS: 1141 (M+Na)$^+$ (1.618 min, Measurement Condition D)

Reference Example 4

N-{(2E,4S)-2,5-Dimethyl-4-[methyl(N,β,β,1-tetramethyl-L-tryptophyl-3-methyl-L-valyl)amino]hex-2-enoyl}-D-γ-glutamyl-L-lysine

[Chemical Formula 47]

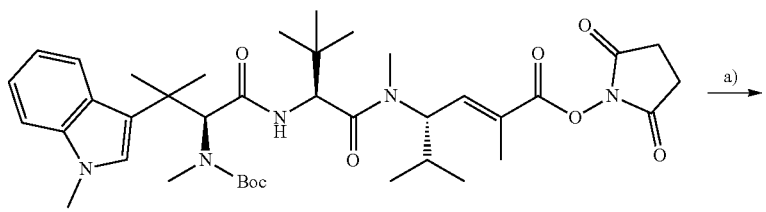

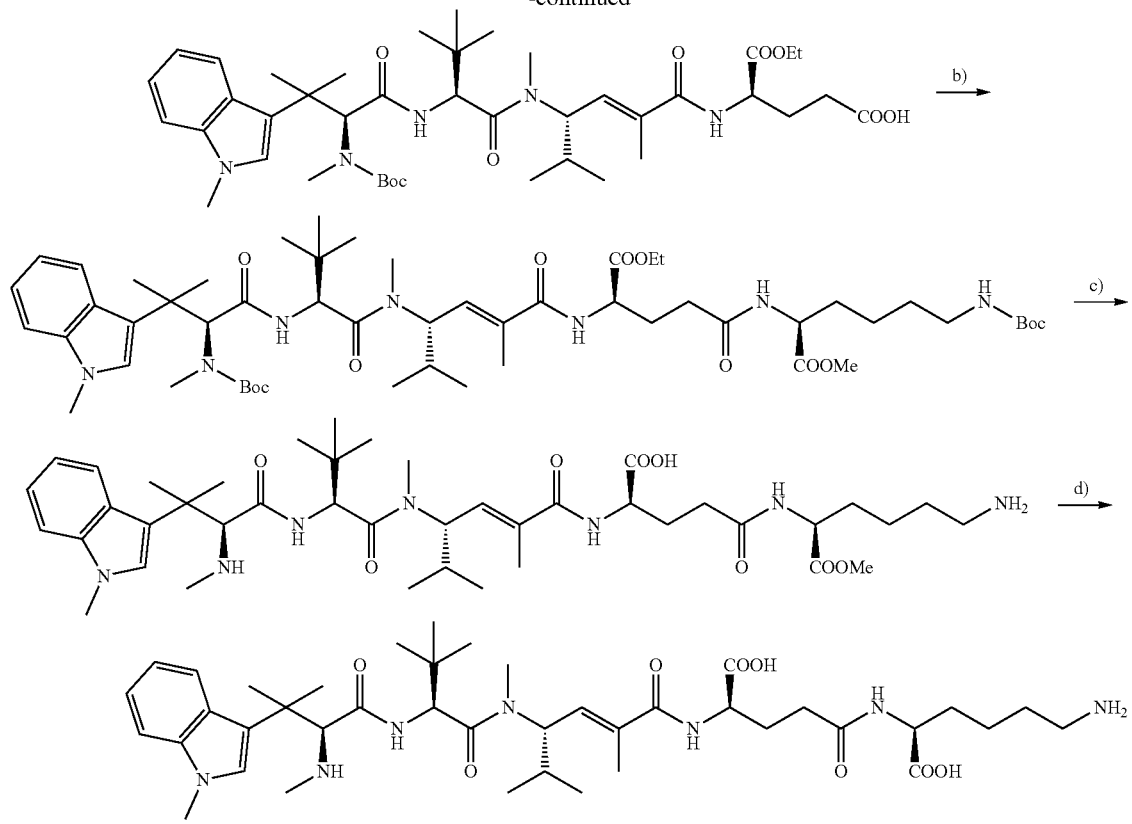

Reference Example 4 a) Production of (6S,9S,12S,13E,17R)-9-tert-butyl-17-(ethoxycarbonyl)-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaicos-13-en-20-oic Acid A mixed solution of N-(tert-butoxycarbonyl)-N,β,β,1-tetramethyl-L-tryptophyl-N-{(3S,4E)-6-[(2,5-dioxopyrrolidin-1-yl)oxy]-2,5-dimethyl-6-oxohex-4-en-3-yl}-N,3-dimethyl-L-valinamide (160 mg), D-glutamic acid α-ethyl ester trifluoroacetate (122 mg), N,N-diisopropylethylamine (100 mg) and N,N-dimethylformamide (2.2 mL) was stirred at 25° C. for 6 hours. After the reaction ended, a 1 mol/L aqueous oxalic acid solution was added to change the pH to 4, and the resultant mixture was extracted with chloroform. The organic layer was washed with water and saturated brine and then dried over anhydrous sodium sulfate, and the solvent was distilled off under reduced pressure. The residue was purified by silica gel column chromatography (eluting solvent; chloroform:methanol) to give (6S,9S,12S,13E,17R)-9-tert-butyl-17-(ethoxycarbonyl)-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaicos-13-en-20-oic acid (155 mg).

$^1$H-NMR (400 MHz, CDCl$_3$): 8.26 and 7.97 (1H, 2d, J=7.9 Hz), 7.32-7.05 (4H, m), 6.71 (1H, t, J=6.7 Hz), 6.45 (1H, d, J=8.6 Hz), 6.31-6.26 (1H, m), 5.95 and 5.63 (1H, 2s), 4.94-4.82 (1H, m), 4.64-4.59 (1H, m), 4.51 and 4.41 (1H, 2d, J=9.1 Hz), 4.21 (2H, q, J=7.3 Hz), 3.75 and 3.74 (3H, 2s), 3.00 (3H, s), 2.97 and 2.95 (3H, 2s), 2.52-2.38 (2H, m), 2.29-2.20 (1H, m), 2.10-2.00 (1H, m), 1.98-1.90 (1H, m), 1.90 (3H, s), 1.57-1.45 (14H, m), 1.28 (3H, t, J=7.3 Hz), 0.88 (3H, d, J=6.1 Hz), 0.82 (3H, d, J=6.7 Hz), 0.53 and 0.46 (9H,2s).

LC-MS 784 (M+H)$^+$, 782 (M−H)$^−$ (1.472 min, Measurement Condition A)

b) Production of (6S,9S,12S,13E,17R,22S)-9-tert-butyl-2,2,5,11,14,30,30-heptamethyl-6-[2-(1-methyl-1H-indol-3-yl)propan-2-yl]-4,7,10,15,20,28-hexaoxo-12-(propan-2-yl)-3,29-dioxa-5,8,11,16,21,27-hexaazahentriacont-13-ene-17,22-dioic acid 17-ethyl 22-methyl Ester By the same approach as Reference Example 1-m), from (6S,9S,12S,13E,17R)-9-tert-butyl-17-(ethoxycarbonyl)-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaicos-13-en-20-oic acid (20 mg), (6S,9S,12S,13E,17R,22S)-9-tert-butyl-2,2,5,11,14,30,30-heptamethyl-6-[2-(1-methyl-1H-indol-3-yl)propan-2-yl]-4,7,10,15,20,28-hexaoxo-12-(propan-2-yl)-3,29-dioxa-5,8,11,16,21,27-hexaazahentriacont-13-ene-17,22-dioic acid 17-ethyl 22-methyl ester (13 mg) was obtained.

LC-MS: 1026 (M+H)$^+$ (1.597 min, Measurement Condition D)

c) Production of (3S,6S,9S,10E,14R,19S)-23-amino-6-tert-butyl-8,11-dimethyl-3-[2-(1-methyl-1H-indol-3-yl)propan-2-yl]-4,7,12,17-tetraoxo-9-(propan-2-yl)-2,5,8,13,18-pentaazatricos-10-ene-14,19-dioic acid 14-ethyl 19-methyl Ester To a solution of (6S,9S,12S,13E,17R,22S)-9-tert-butyl-2,2,5,11,14,30,30-heptamethyl-6-[2-(1-methyl-1H-indol-3-yl)propan-2-yl]-4,7,10,15,20,28-hexaoxo-12-(propan-2-yl)-3,29-dioxa-5,8,11,16,21,27-hexaazahentriacont-13-ene-17,22-dioic acid 17-ethyl 22-methyl ester (13 mg) in chloroform (1.0 mL), trifluoroacetic acid (0.2 mL) was added, and the resultant mixture was stirred at 25° C. for 1 hour. After the reaction ended, the reaction solution was purified by silica gel column chromatography (eluting solvent; methanol:chloroform) to give (3S,6S,9S,10E,14R,19S)-23-amino-6-tert-butyl-8,11-dimethyl-3-[2-(1-methyl-1H-indol-3-yl)propan-2-yl]-4,7,12,17-tetraoxo-9-(propan-2-yl)-2,5,8,13,18-pentaazatricos-10-ene-14,19-dioic acid 14-ethyl 19-methyl ester (10 mg).

LC-MS: 826 (M+H)$^+$, 824 (M−H)$^−$ (0.978 min, Measurement Condition D)

d) Production of N-{(2E,4S)-2,5-dimethyl-4-[methyl(N,β,β,1-tetramethyl-L-tryptophyl-3-methyl-L-valyl)amino]hex-2-enoyl}-D-γ-glutamyl-L-lysine (Reference Example 4)

By carrying out production by the same approach as Reference Example 1-n), followed by purification by reversed phase column chromatography (eluting solvent; acetonitrile with 0.1% TFA:water), from (3S,6S,9S,10E,14R,19S)-23-amino-6-tert-butyl-8,11-dimethyl-3-[2-(1-methyl-1H-indol-3-yl)propan-2-yl]-4,7,12,17-tetraoxo-9-(propan-2-yl)-2,5,8,13,18-pentaazatricos-10-ene-14,19-dioic acid 14-ethyl 19-methyl ester (10 mg), Reference Example 4 (7.2 mg) was obtained.

LC-MS: 784 (M+H)$^+$, 782 (M−H)$^−$ (0.889 min, Measurement Condition D)

Reference Example 5 tert-Butyl N5-(2-(2,5-dioxo-2,5-dihydro-1H-pyrrol-1-yl)ethyl)-D-glutaminate

[Chemical Formula 48]

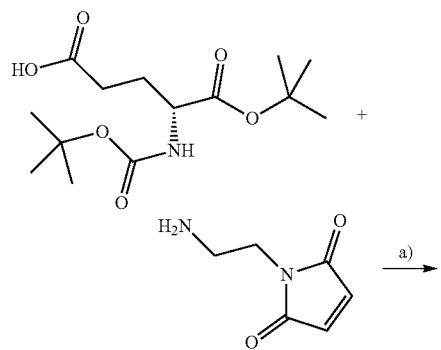

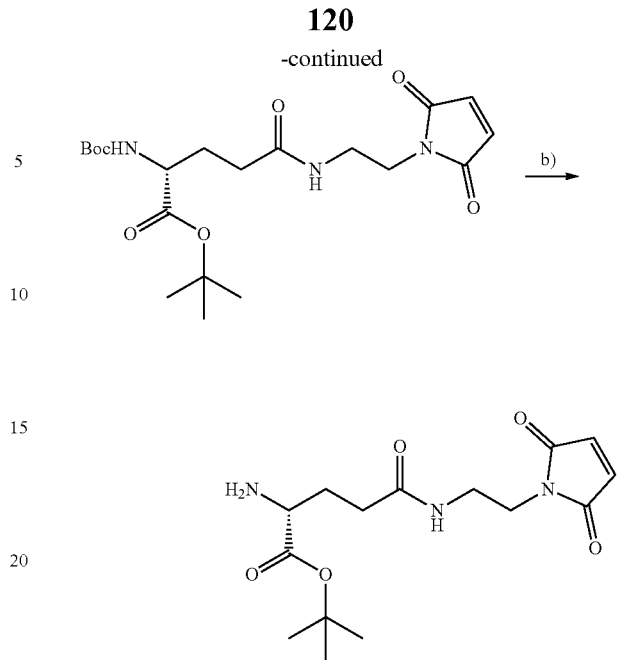

Reference Example 5 a) Production of tert-butyl N2-(tert-butoxycarbonyl)-N5-(2-(2,5-dioxo-2,5-dihydro-1H-pyrrol-1-yl)ethyl)-D-glutaminate A mixed solution of BOC-D-glutamic acid α-tert-butyl ester (2.061 g), 1-(2-amino-ethyl)-pyrrole-2,5-dione hydrochloride (1.20 g), 2-(1H-benzo[d][1,2,3]triazol-1-yl)-1,1,3,3-tetramethylisouronium hexafluorophosphate (V) (3.87 g), N,N-diisopropylethylamine (3.47 mL) and N,N-dimethylformamide (10 mL) was stirred at room temperature for 1 hour. After the reaction ended, ethyl acetate was added, the organic layer was washed with a saturated aqueous sodium bicarbonate solution and saturated brine and then dried over anhydrous sodium sulfate, and the solvent was distilled off under reduced pressure. The residue was purified by silica gel chromatography (eluting solvent; hexane:ethyl acetate) to give tert-butyl N2-(tert-butoxycarbonyl)-N5-(2-(2,5-dioxo-2,5-dihydro-1H-pyrrol-1-yl) ethyl)-D-glutaminate (2.8 g).

LC-MS: 426 (M+H)$^+$ (1.030 min, Measurement Condition F)

b) Production of tert-butyl N5-(2-(2,5-dioxo-2,5-dihydro-1H-pyrrol-1-yl)ethyl)-D-glutaminate (Reference Example 5)

A mixed solution of tert-butyl N2-(tert-butoxycarbonyl)-N5-(2-(2,5-dioxo-2,5-dihydro-1H-pyrrol-1-yl) ethyl)-D-glutaminate (51.8 mg) and TFA (1 mL) was stirred at room temperature for 1 hour 20 minutes. The reaction solution was ice-cooled, and then concentrated under reduced pressure to give Reference Example 5 (56.3 mg). The compound obtained was used for the subsequent reaction without purification.

LC-MS: 326 (M+H)$^+$ (0.496 min, Measurement Condition F)

Reference Example 6

N5-(2-(2,5-Dioxo-2,5-dihydro-1H-pyrrol-1-yl)ethyl)-D-glutamine

[Chemical Formula 49]

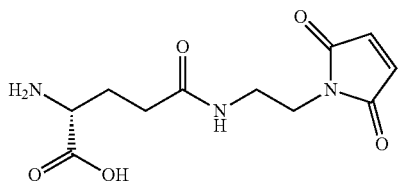

Reference Example 6

A mixed solution of tert-butyl N2-(tert-butoxycarbonyl)-N5-(2-(2,5-dioxo-2,5-dihydro-1H-pyrrol-1-yl) ethyl)-D-glutaminate (64.8 mg) and TFA (1 mL) was stirred at room temperature for 17 hours. After the reaction ended, the resultant mixture was concentrated under reduced pressure to give Reference Example 6. The compound obtained was used for the subsequent reaction without purification.

LC-MS: 270 (M+H)$^+$ (0.254 min, Measurement Condition F)

Reference Example 7

N5-[2-(2,5-Dioxo-2,5-dihydro-1H-pyrrol-1-yl)ethyl]-D-glutaminyl-D-glutamic Acid

[Chemical Formula 50]

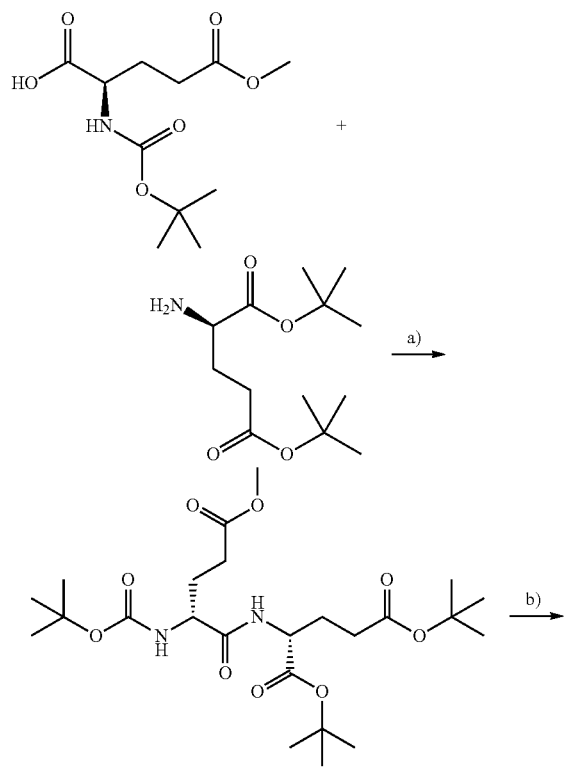

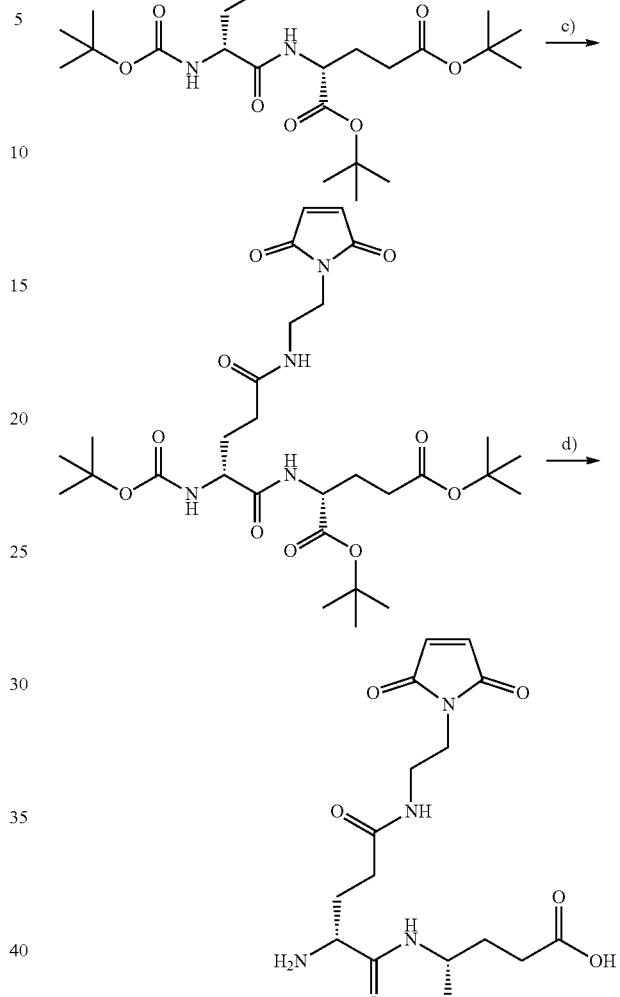

Reference Example 7 a) Production of di-tert-butyl ((R)-2-((tert-butoxycarbonyl)amino)-5-methoxy-5-oxopentanoyl)-D-glutamate A mixture of N-α-(tert-butoxycarbonyl)-D-glutamic acid γ-methyl ester (261 mg), D-glutamic acid di-tert-butyl ester hydrochloride (295 mg), O-(7-azabenzotriazol-1-yl)-N,N,N',N'-tetramethyluronium hexafluorophosphate (456 mg), N,N-diisopropylethylamine (0.446 mL) and N,N-dimethylformamide (4 mL) was stirred at room temperature for 2 hours. After the reaction ended, water was added, and the resultant mixture was extract with ethyl acetate. The organic layer was washed with water and a saturated aqueous sodium bicarbonate solution and then dried over anhydrous sodium sulfate, and the solvent was distilled off under reduced pressure. The residue was purified by silica gel chromatography (eluting solvent; hexane:ethyl acetate) to give di-tert-butyl ((R)-2-((tert-butoxycarbonyl)amino)-5-methoxy-5-oxopentanoyl)-D-glutamate (502 mg).

¹H-NMR (400 MHz, CDCl₃): 1.42 (18H, s), 1.44 (9H, s), 1.84-1.94 (2H, in), 2.12 (2H, dtt, J=22.5, 8.4, 3.0 Hz), 2.26 (2H, dtd, J=25.2, 10.0, 4.5 Hz), 2.43 (2H, tdd, J=24.8, 14.2, 7.5 Hz), 3.67 (3H, s), 4.14 (1H, t, J=6.1 Hz), 4.43 (1H, td, J=7.9, 4.9 Hz), 5.23 (1H, d, J=7.3 Hz), 6.81 (1H, d, J=7.3 Hz).

b) Production of (R)-4-((tert-butoxycarbonyl) amino)-5-(((R)-1,5-di-tert-butoxy-1,5-dioxopentan-2-yl)amino)-5-oxopentanoic Acid A mixture of di-tert-butyl ((R)-2-((tert-butoxycarbonyl) amino)-5-methoxy-5-oxopentanoyl)-D-glutamate (502 mg), a 1 mol/L aqueous lithium hydroxide solution (0.999 mL) and methanol (5 mL) was stirred at room temperature for 16 hours. After the reaction ended, a 1 mol/L aqueous citric acid solution was added to acidify (pH 4), methanol was distilled off under reduced pressure, and the resultant mixture was extracted with chloroform. The organic layer was dried over anhydrous sodium sulfate, and the solvent was distilled off under reduced pressure. The residue was purified by silica gel chromatography (eluting solvent; chloroform:methanol) to give (R)-4-((tert-butoxycarbonyl) amino)-5-(((R)-1,5-di-tert-butoxy-1,5-dioxopentan-2-yl)amino)-5-oxopentanoic acid (393 mg).

LC-MS: 489 (M+H)⁺ (1.417 min, Measurement Condition G)

c) Production of di-tert-butyl N2-(tert-butoxycarbonyl)-N5-(2-(2,5-dioxo-2,5-dihydro-1H-pyrrol-1-yl) ethyl)-D-glutaminyl-D-glutamate A mixed solution of (R)-4-((tert-butoxycarbonyl) amino)-5-(((R)-1,5-di-tert-butoxy-1,5-di oxopentan-2-yl)amino)-5-oxopentanoic acid (205 mg), 1-(2-amino-ethyl)-pyrrole-2,5-dione hydrochloride (89 mg), 2-(1H-benzo[d][1,2,3]triazol-1-yl)-1,1,3,3-tetramethylisouronium hexafluorophosphate (V) (191 mg), N,N-diisopropylethylamine (0.187 mL) and N,N-dimethylformamide (3 mL) was stirred at room temperature for 16 hours. After the reaction ended, water was added and the resultant mixture was extracted with chloroform. The organic layer was dried over anhydrous sodium sulfate, and the solvent was distilled off under reduced pressure. The residue was purified by silica gel chromatography (eluting solvent; chloroform:methanol) to give di-tert-butyl N2-(tert-butoxycarbonyl)-N5-(2-(2,5-dioxo-2,5-dihydro-1H-pyrrol-1-yl) ethyl)-D-glutaminyl-D-glutamate (13 mg).

LC-MS: 611 (M+H)⁺ (1.638 min, Measurement Condition G)

d) Production of N5-[2-(2,5-dioxo-2,5-dihydro-1H-pyrrol-1-yl)ethyl]-D-glutaminyl-D-glutamic Acid (Reference Example 7)

Reference Example 7 was synthesized through the same reaction and treatment as Example M1 for di-tert-butyl N2-(tert-butoxycarbonyl)-N5-(2-(2,5-dioxo-2,5-dihydro-1H-pyrrol-1-yl) ethyl)-D-glutaminyl-D-glutamate (13 mg). Reference Example 7 synthesized was directly used for the subsequent reaction without purification.

Reference Examples 8 to 18

In Accordance with the methods described in literatures (Bioorg. Med. Chem. Lett. 2004 Nov. 1; 14(21): 5317-22, J. Med. Chem. 2004 Sep. 9; 47(19): 4774-86, International Publication No. WO 2003/082268, and International Publication No. WO 2016/123582 and the like), the compounds shown in the following table 1 were obtained.

TABLE 1

| Reference Example | Structural Formula | LC-MS/Rt (min) | LC-MS Measurement Condition |
| --- | --- | --- | --- |
| 8 | | 438(M + H)⁺/0.886 | F |
| 9 | | 552(M + H)⁺/0.76 | H |
| 10 | | 552(M + H)⁺/0.76 | H |

TABLE 1-continued

| Reference Example | Structural Formula | LC-MS/Rt (min) | LC-MS Measurement Condition |
|---|---|---|---|
| 11 | | 542(M + H)⁺/1.46 | G |
| 12 | | 492(M + H)⁺/1.26 | G |
| 13 | | 480(M + H)⁺/1.25 | G |
| 14 | | 480(M + H)⁺/1.30 | G |
| 15 | | 502(M − H)⁻/1.18 | G |
| 16 | | 502(M + H)⁺/1.11 | G |
| 17 | | 480(M + H)⁺/1.13 | G |

| Reference Example | Structural Formula | LC-MS/Rt (min) | LC-MS Measurement Condition |
|---|---|---|---|
| 18 | 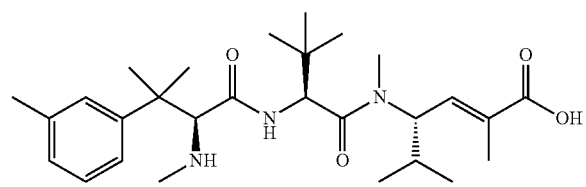 | 524(M + H)+/1.304 | G |

Reference Example 19

N,β,β,3-Tetramethyl-L-phenylalanyl-N-[(3S,4E)-5-carboxy-2-methylhex-4-en-3-yl]-N,3-dimethyl-L-valinamide

[Chemical Formula 51]

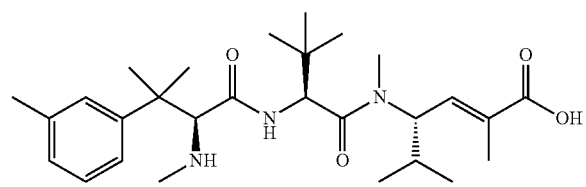

Reference Example 19

A mixed solution of (S,E)-4-((S)-2-((S)-3-(3-bromophenyl)-3-methyl-2-(methylamino)butan amido)-N,3,3-trimethylbutanamido)-2,5-dimethylhex-2-enoic acid (62.5 mg), tetrakis(triphenylphosphine)palladium(0) (13.07 mg), dimethylzinc (0.113 mL) and tetrahydrofuran (5 mL) was stirred at 60° C. for 2.5 hours. After the reaction ended, the solvent was distilled off under reduced pressure. The residue was purified by silica gel chromatography (eluting solvent; chloroform:methanol) to give Reference Example 19 (29.7 mg).

LC-MS: 488 (M+H)+ (0.68 min, Measurement Condition F)

Reference Example 20

(S,E)-4-((S)-2-((S)-3-(3-Cyanophenyl)-3-methyl-2-(methylamino)butan amido)-N,3,3-trimethylbutanamido)-2,5-dimethylhex-2-enoic acid

[Chemical Formula 52]

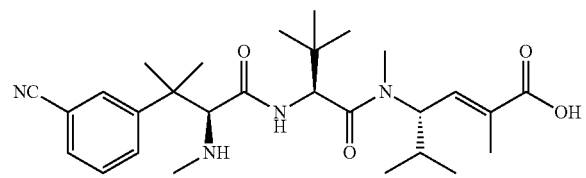

Reference Example 20

A mixed solution of (S,E)-4-((S)-2-((S)-3-(3-bromophenyl)-3-methyl-2-(methylamino)butan amido)-N,3,3-trimethylbutanamido)-2,5-dimethylhex-2-enoic acid (76.1 mg), tetrakis(triphenylphosphine)palladium(0) (15.92 mg), zinc (18.01 mg), zinc cyanide (32.3 mg) and N,N-dimethylformamide (1 mL) was stirred at 120° C. for 1 hour under microwave irradiation. After the reaction ended, the solvent was distilled off under reduced pressure. After partially purifying the residue by silica gel chromatography (eluting solvent; chloroform:methanol), through reversed phase HPLC (the mobile phase was water with 0.1% TFA/acetonitrile with 0.035% TFA solvent), Reference Example 20 (53.5 mg) was obtained. LC-MS: 499 (M+H)+ (0.99 min, Measurement Condition F)

Reference Example 21

(S,E)-4-((S)-2-((S)-3-([1,1'-Biphenyl]-3-yl)-3-methyl-2-(methylamino)butanamido)-N,3,3-trimethylbutanamido)-2,5-dimethylhex-2-enoic Acid

[Chemical Formula 53]

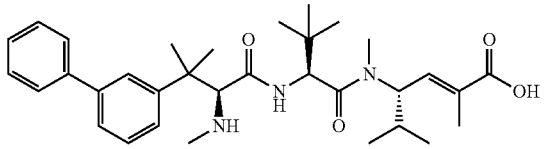

Reference Example 21

A mixed solution of (S,E)-4-((S)-2-((S)-3-(3-bromophenyl)-3-methyl-2-(methylamino)butan amido)-N,3,3-trimethylbutanamido)-2,5-dimethylhex-2-enoic acid (64.3 mg), tetrakis(triphenylphosphine)palladium(0) (13.45 mg), phenylboranic acid (28.4 mg), sodium carbonate (24.67 mg) and tetrahydrofuran (5 mL) was stirred at 80° C. for 3.5 hours. The solvent was distilled off under reduced pressure. Through reversed phase HPLC (the mobile phase was water with 0.1% TFA/acetonitrile with 0.035% TFA solvent), Reference Example 21 (10.7 mg) was obtained.

LC-MS: 550 (M+H)+ (0.88 min, Measurement Condition F)

Reference Example 22

4-(4-(((S)-1-(((S,E)-5-Carboxy-2-methylhex-4-en-3-yl)(methyl)amino)-3,3-dimethyl-1-oxabutan-2-yl)amino)-2-methyl-3-(methylamino)-4-oxo butan-2-yl)benzoic Acid

[Chemical Formula 54]

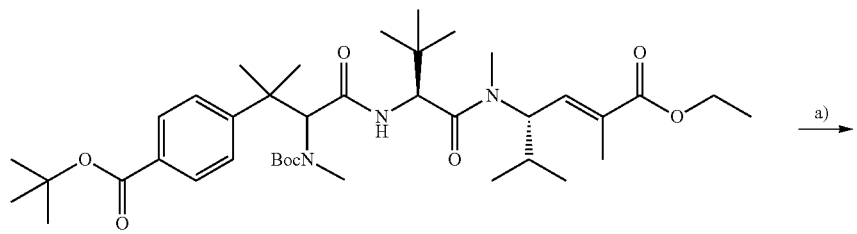

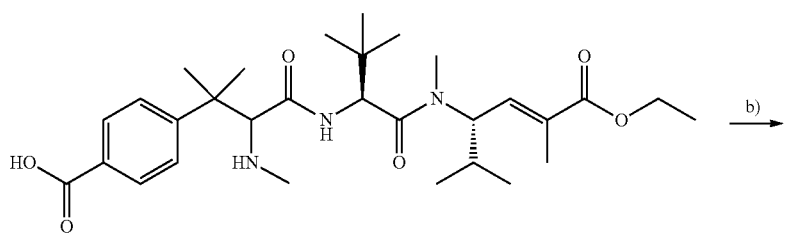

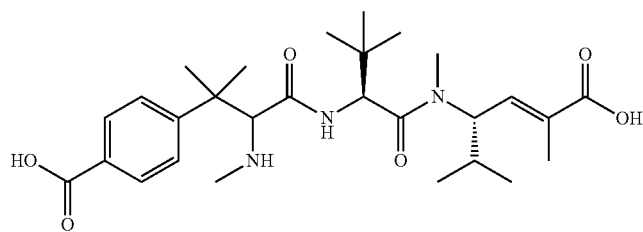

Reference Example 22 a) Production of 4-(4-(((S)-1-(((S,E)-6-ethoxy-2,5-dimethyl-6-oxohex-4-en-3-yl)(methyl)amino)-3,3-dimethyl-1-oxabutan-2-yl)amino)-2-methyl-3-(methylamino)-4-oxabutan-2-yl)benzoic Acid A mixed solution of ethyl (9S,12 S,E)-6-(2-(4-(tert-butoxycarbonyl)phenyl)propan-2-yl)-9-(tert-butyl)-12-isopropyl-2,2,5,11,14-pentamethyl-4,7,10-trioxo-3-oxa-5,8,11-triazapentadec-13-en-15-oate (400 mg), TFA (2 mL) and chloroform (8 mL) was stirred at room temperature for 4 hours. The solvent was distilled off under reduced pressure to give 4-(4-(((S)-1-(((S,E)-6-ethoxy-2,5-dimethyl-6-oxo-hex-4-en-3-yl)(methyl) amino)-3,3-dimethyl-1-oxabutan-2-yl)amino)-2-methyl-3-(methylamino)-4-oxabutan-2-yl)benzoic acid (376 mg). The compound obtained was used for the subsequent reaction without purification.

LC-MS: 546 (M+H)$^+$ (1.15 min, Measurement Condition F)

b) Production of 4-(4-(((S)-1-(((S,E)-5-carboxy-2-methylhex-4-en-3-yl)(methyl)amino)-3,3-dimethyl-1-oxabutan-2-yl)amino)-2-methyl-3-(methylamino)-4-oxo butan-2-yl)benzoic Acid (Reference Example 22)

While a mixed solution of 4-(4-(((S)-1-(((S,E)-6-ethoxy-2,5-dimethyl-6-oxohex-4-en-3-yl)(methyl) amino)-3,3-dimethyl-1-oxabutan-2-yl)amino)-2-methyl-3-(methylamino)-4-oxabutan-2-yl)benzoic acid (55.2 mg), methanol (3 mL) and water (1 mL) was stirred under ice cooling, lithium hydroxide (16.98 mg) was added. The resultant mixture was stirred at room temperature for 2 days. The solvent was distilled off under reduced pressure. The residue was subjected to reversed phase HPLC (the mobile phase was water with 0.1% TFA/acetonitrile with 0.035% TFA solvent) to give Reference Example 22 (21.1 mg).

LC-MS: 518 (M+H)$^+$ (1.18 min, Measurement Condition F)

Reference Example 23

(4 S,E)-4-((2S)-2-(3-(4-(tert-Butoxycarbonyl)phenyl)-3-methyl-2-(methylamino)butanamido)-N,3,3-trimethylbutanamido)-2,5-dimethylhex-2-enoic Acid

[Chemical Formula 55]

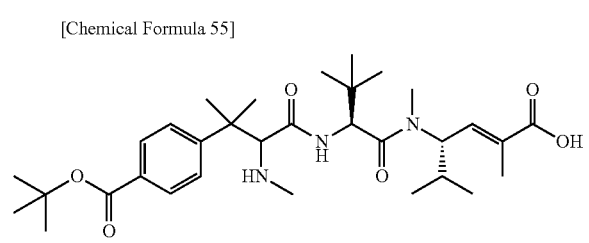

Reference Example 23

Reference Example 23 was obtained from tert-butyl 4-(4-(((S)-1-(((S,E)-6-ethoxy-2,5-dimethyl-6-oxohex-4-en-3-yl)(methyl) amino)-3,3-dimethyl-1-oxobutan-2-yl)amino)-2-methyl-3-(methyl amino)-4-oxobutan-2-yl)benzoate in the same manner as in n) step of Reference Example 1.

LC-MS: 574 (M+H)$^+$ (1.29 min, Measurement Condition G)

Reference Example 24

(S,E)-4-((S)-2-((S)-3-(4-(tert-Butoxycarbonyl)phenyl)-3-methyl-2-(methoxyamino)butanamido)-N,3,3-trimethylbutanamido)-2,5-dimethylhex-2-enoic Acid

[Chemical Formula 56]

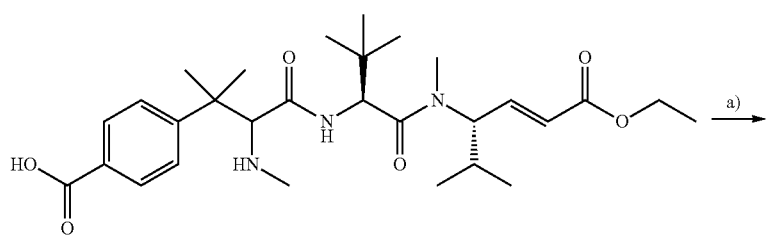
a)

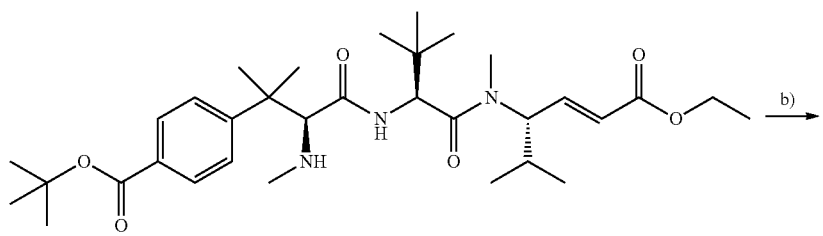
b)

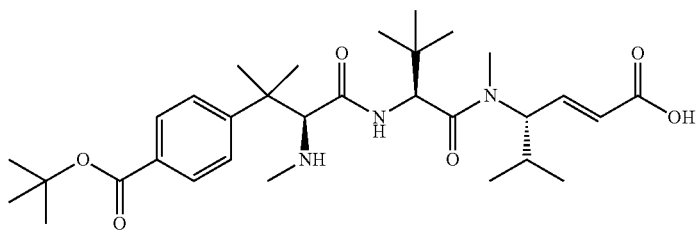

Reference Example 24 a) Production of tert-butyl 4-((S)-4-(((S)-1-(((S,E)-6-ethoxy-2,5-dimethyl-6-oxohex-4-en-3-yl)(methyl) amino)-3,3-dimethyl-1-oxobutan-2-yl)amino)-2-methyl-3-(methylamino)-4-oxobutan-2-yl)benzoate To a mixed solution of 4-(4-(((S)-1-(((S,E)-6-ethoxy-2,5-dimethyl-6-oxohex-4-en-3-yl)(methyl) amino)-3,3-dimethyl-1-oxobutan-2-yl)amino)-2-methyl-3-(methylamino)-4-oxobutan-2-yl)benzoic acid (104.0 mg) and toluene (1 mL), N,N-dimethylfluoroamido-di-tert-butyl acetate (0.456 mL) was added, and after the resultant mixture was subjected to heating reflux for 14 hours, distilling off the solvent under reduced pressure. The residue was purified by silica gel chromatography to give tert-butyl 4-((S)-4-(((S)-1-(((S,E)-6-ethoxy-2,5-dimethyl-6-oxohex-4-en-3-yl)(methyl) amino)-3,3-dimethyl-1-oxobutan-2-yl)amino)-2-methyl-3-(methylamino)-4-oxobutan-2-yl)benzoate (21.0 mg).

LC-MS: 602 (M+H)$^+$ (1.47 min, Measurement Condition F)

b) Production of (S,E)-4-((S)-2-((S)-3-(4-(tert-butoxycarbonyl)phenyl)-3-methyl-2-(methoxyamino) butanamido)-N,3,3-trimethylbutanamido)-2,5-dimethylhex-2-enoic Acid (Reference Example 24)

To a mixed solution of tert-butyl 4-((S)-4-(((S)-1-(((S,E)-6-ethoxy-2,5-dimethyl-6-oxohex-4-en-3-yl)(methyl) amino)-3,3-dimethyl-1-oxobutan-2-yl)amino)-2-methyl-3-(methylamino)-4-oxobutan-2-yl)benzoate (10.5 mg), methanol (3 mL) and water (1.000 mL), lithium hydroxide (4.39 mg) was added, and the resultant mixture was stirred at room temperature for 2 days. The solvent was distilled off under reduced pressure, and the residue was purified by reversed phase HPLC (the mobile phase was water with 0.1% TFA/acetonitrile with 0.035% TFA solvent) to give Reference Example 24 (7.0 mg).

LC-MS: 574 (M+H)$^+$ (1.49 min, Measurement Condition F)

Reference Example 25

4-((S)-4-(((S)-1-(((S,E)-5-Carboxy-2-methylhex-4-en-3-yl)(methyl)amino)-3,3-dimethyl-1-oxobutan-2-yl)amino)-2-methyl-3-(methylamino)-4-oxobutan-2-yl)benzoic Acid

[Chemical Formula 57]

Reference Example 25

To a mixed solution of tert-butyl 4-((S)-4-(((S)-1-((S,E)-6-ethoxy-2,5-dimethyl-6-oxohex-4-en-3-yl)(methyl) amino)-3,3-dimethyl-1-oxobutan-2-yl)amino)-2-methyl-3-(methylamino)-4-oxobutan-2-yl)benzoate (10.5 mg), methanol (3 mL) and water (1 mL), lithium hydroxide (4.39 mg) was added, and after the resultant mixture was stirred at room temperature for 5 days, distilling off the solvent under reduced pressure. The residue was dissolved in chloroform (4 mL), trifluoroacetic acid (1 mL) was added, and the resultant mixture was stirred at room temperature for 17 hours. After distilling off the solvent under reduced pressure, the residue was purified by reversed phase HPLC (the mobile phase was water with 0.1% TFA/acetonitrile with 0.035% TFA solvent) to give Reference Example 25 (7.40 mg).

LC-MS: 518 (M+H)$^+$ (1.08 min, Measurement Condition F)

Reference Example 26

(4S,E)-4-((2S)-2-(3-(4-Hydroxyphenyl)-3-methyl-2-(methylamino)butyl)-N,3,3-trimethylbutanamido)-2,5-dimethylhex-2-enoic Acid

[Chemical Formula 58]

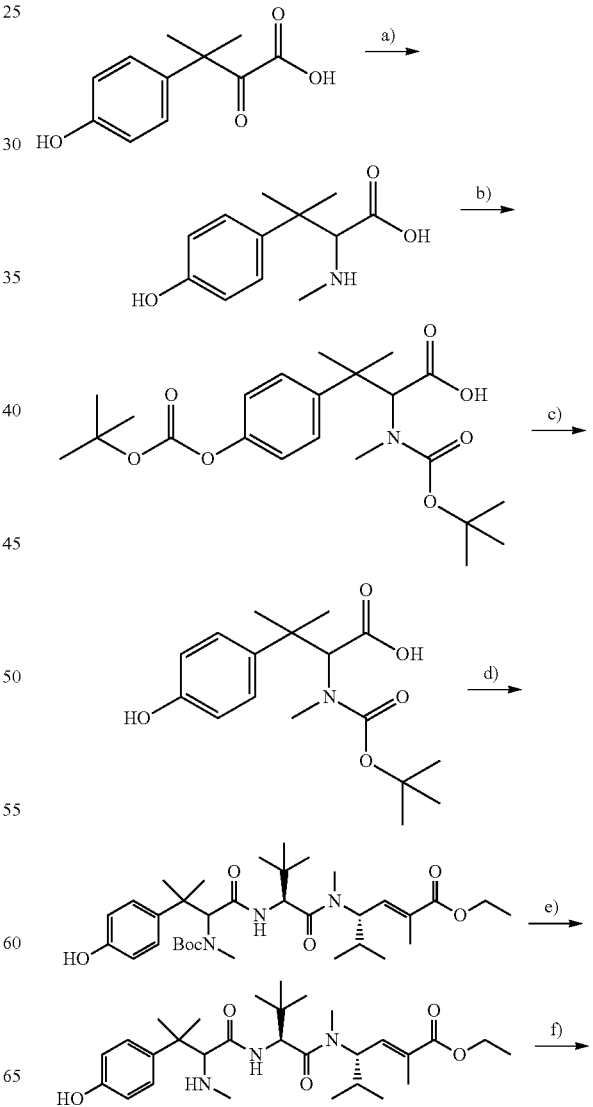

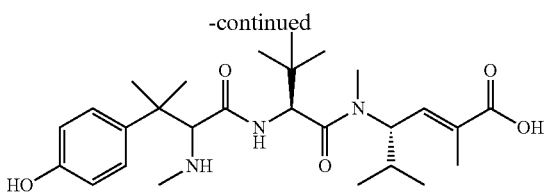

Reference Example 26 a) Production of 3-(4-hydroxyphenyl)-3-methyl-2-(methylamino)butanoic Acid

Under nitrogen atmosphere, a solution of 3-(4-hydroxyphenyl)-3-methyl-2-oxobutanoic acid (54.9 g) in anhydrous tetrahydrofuran (480 mL) was ice-cooled, and methylamine (280 mL) (2 mol/L tetrahydrofuran solution) was added dropwise. After stirring the mixture at room temperature for 1 hour, borane-pyridine complex (27.5 mL) was added dropwise, and the resultant mixture was stirred at 55° C. for 2.5 hours. Under ice cooling, methanol (240 mL) was added dropwise, and the mixture was stirred at room temperature for 2 hours. After distilling off the solvent under reduced pressure, tetrahydrofuran was added, and the suspension was subjected to suction filtration. The powder was washed with tetrahydrofuran to give 3-(4-hydroxyphenyl)-3-methyl-2-(methylamino)butanoic acid (40.7 g). $^1$H-NMR (400 MHz, D$_2$O): 1.21 (3H, s), 1.24 (3H, s), 2.04 (3H, s), 3.06 (1H, s), 6.52 (2H, d, J=8.8 Hz), 7.11 (2H, d, J=8.8).

b) Production of 2-((tert-butoxycarbonyl)(methyl)amino)-3-(4-((tert-butoxycarbonyl)oxy)phenyl)-3-methylbutanoic Acid Under nitrogen atmosphere, to a suspension of 3-(4-hydroxyphenyl)-3-methyl-2-(methylamino)butanoic acid (10.2 g) in 1,4-dioxane/water (1:1) (160 mL), di-tert-butyl carbonate (39.9 g) and potassium carbonate (25.4 g) were added, and the resultant mixture was stirred at 40° C. overnight. Ethyl acetate and water were added to the reaction solution, and after changing the pH to 2 to 3 with a 1 mol/L aqueous potassium bisulfate solution, the mixture was extracted with ethyl acetate. The organic layer was washed with saturated brine, followed by drying over anhydrous magnesium sulfate, and the solvent was then distilled off under reduced pressure. The residue was purified by silica gel chromatography (eluting solvent; chloroform:methanol) to give 2-((tert-butoxycarbonyl)(methyl)amino)-3-(4-((tert-butoxycarbonyl)oxy) phenyl)-3-methylbutanoic acid (15.7 g).
$^1$H-NMR (400 MHz, DMSO-D$_6$): 1.38 (12H, s), 1.48 (12H, s), 2.64 (3H, s), 7.09 (2H, d, J=8.4 Hz), 7.40 (2H, d, J=8.8).

c) Production of (S)-2-((tert-butoxycarbonyl)(methyl)amino)-3-(4-hydroxyphenyl)-3-methylbutanoic Acid Under nitrogen atmosphere, 2-((tert-butoxycarbonyl)(methyl)amino)-3-(4-((tert-butoxycarbonyl)oxy) phenyl)-3-methylbutanoic acid (15.7 g) was dissolved in dichloromethane (370 mL), a 28% sodium methoxide methanol solution (15.8 g) and methanol (14 mL) were added, and the resultant mixture was stirred at room temperature for 1.5 hours. Ethyl acetate and a 4% aqueous potassium bisulfate solution were added to the reaction solution, and the mixture was extracted. The organic layer was washed with saturated brine, followed by drying over anhydrous magnesium sulfate, and the solvent was distilled off under reduced pressure. The residue was purified by silica gel chromatography (eluting solvent; chloroform:methanol) to give (S)-2-((tert-butoxycarbonyl)(methyl)amino)-3-(4-hydroxyphenyl)-3-methylbutanoic acid (153.7 mg).
$^1$H-NMR (400 MHz, DMSO-D$_6$): 1.36 (12H, s), 1.42 (3H, s), 2.60 (3H, s), 6.66 (2H, d, J=8.0 Hz), 7.15 (2H, d, J=8.4).

d) Production of ethyl (9S,12S,E)-9-(tert-butyl)-6-(2-(4-hydroxyphenyl)propan-2-yl)-12-isopropyl-2,2,5,11,14-pentamethyl-4,7,10-trioxo-3-oxa-5,8,11-triazapentadec-13-en-15-oate A suspension of (S)-2-((tert-butoxycarbonyl)(methyl) amino)-3-(4-hydroxyphenyl)-3-methylbutanoic acid (153.7 mg), ethyl (S,E)-4-((S)-2-amino-N,3,3-trimethylbutanamido)-2,5-dimethylhex-2-enoate hydrochloride (117.6 mg), N-ethyl-N-isopropylpropan-2-amine (0.172 mL), 1-ethyl-3-(3-dimethylaminopropyl)carbodiimide hydrochloride (129 mg), 1-hydroxybenzotriazole (103 mg) and N,N-dimethylformamide (5 mL) was stirred at room temperature for 17 hours. After the solvent was distilled off under reduced pressure, chloroform was added, the organic layer was washed with a saturated aqueous sodium bicarbonate solution and then dried over anhydrous sodium sulfate, and the solvent was distilled off under reduced pressure. The residue was purified by silica gel chromatography (eluting solvent; hexane:ethyl acetate) to give ethyl (9S,12S,E)-9-(tert-butyl)-6-(2-(4-hydroxyphenyl)propan-2-yl)-12-isopropyl-2,2,5,11,14-pentamethyl-4,7,10-trioxo-3-oxa-5,8,11-triazapentadec-13-en-15-oate (206.3 mg).
LC-MS: 618 (M+H)$^+$ (1.69 min, Measurement Condition F)

e) Production of ethyl (4S,E)-4-((2S)-2-(3-(4-hydroxyphenyl)-3-methyl-2-(methylamino)butan amido)-N,3,3-trimethylbutanamido)-2,5-dimethylhex-2-enoate To a mixed solution of ethyl (9S,12S,E)-9-(tert-butyl)-6-(2-(4-hydroxyphenyl)propan-2-yl)-12-isopropyl-2,2,5,11,14-pentamethyl-4,7,10-trioxo-3-oxa-5,8,11-triazapentadec-13-en-15-oate (189.2 mg) and chloroform (4 mL), TFA (1 mL) was added, and after the resultant mixture was stirred at room temperature for 1 hour, the solvent was distilled off under reduced pressure. Chloroform was added to the residue, and the organic layer was washed with a saturated aqueous sodium bicarbonate solution and then dried over anhydrous sodium sulfate, and the solvent was distilled off under reduced pressure. The residue was purified by silica gel chromatography (eluting solvent; hexane:ethyl acetate) to give ethyl (4S,E)-4-((2S)-2-(3-(4-hydroxyphenyl)-3-methyl-2-(methylamino)butan amido)-N,3,3-trimethylbutanamido)-2,5-dimethylhex-2-enoate (110.1 mg).
LC-MS: 518 (M+H)$^+$ (1.09 min, Measurement Condition F)

f) Production of (4S,E)-4-((2S)-2-(3-(4-hydroxyphenyl)-3-methyl-2-(methylamino)butyl)-N,3,3-trimethylbutanamido)-2,5-dimethylhex-2-enoic Acid (Reference Example 26)

To a mixed solution of ethyl (4S,E)-4-((2S)-2-(3-(4-hydroxyphenyl)-3-methyl-2-(methylamino)butanamido)-N,3,3-trimethylbutanamido)-2,5-dimethylhex-2-enoate (110.1 mg), methanol (3 mL) and water (1 mL), lithium hydroxide (35.7 mg) was added under ice cooling, and the resultant mixture was stirred at room temperature for 2 days. The solvent was distilled off under reduced pressure, and the residue was purified by reversed phase HPLC (the mobile phase was water with 0.1% TFA/acetonitrile with 0.035% TFA solvent) to give Reference Example 26 (113.2 mg).

LC-MS: 490 (M+H)$^+$ (1.03 min, Measurement Condition F)

Reference Example 27

((4 S,E)-4-((2S)-2-(3-(4-Hydroxyphenyl)-3-methyl-2-(methylamino)butanamido)-N,3,3-trimethylbutanamido)-2,5-dimethylhex-2-enoyl)-D-glutamic Acid mg) and N,N-dimethylformamide (1 mL) was stirred at room temperature for 15 hours. Ethyl acetate was added to the reaction solution, the resultant mixture was washed with saturated brine, the organic layer was then dried over anhydrous sodium sulfate, and the solvent was distilled off under reduced pressure. The residue was purified by silica gel chromatography (eluting solvent; chloroform/methanol) to give dimethyl ((4 S,E)-4-((2S)-2-(3-(4-hydroxyphenyl)-3-methyl-2-(methylamino)buta namido)-N,3,3-trimethylbutanamido)-2,5-dimethylhex-2-enoyl)-D-glutamate (21.6 mg).

LC-MS: 647 (M+H)$^+$ (1.21 min, Measurement Condition F)

[Chemical Formula 59]

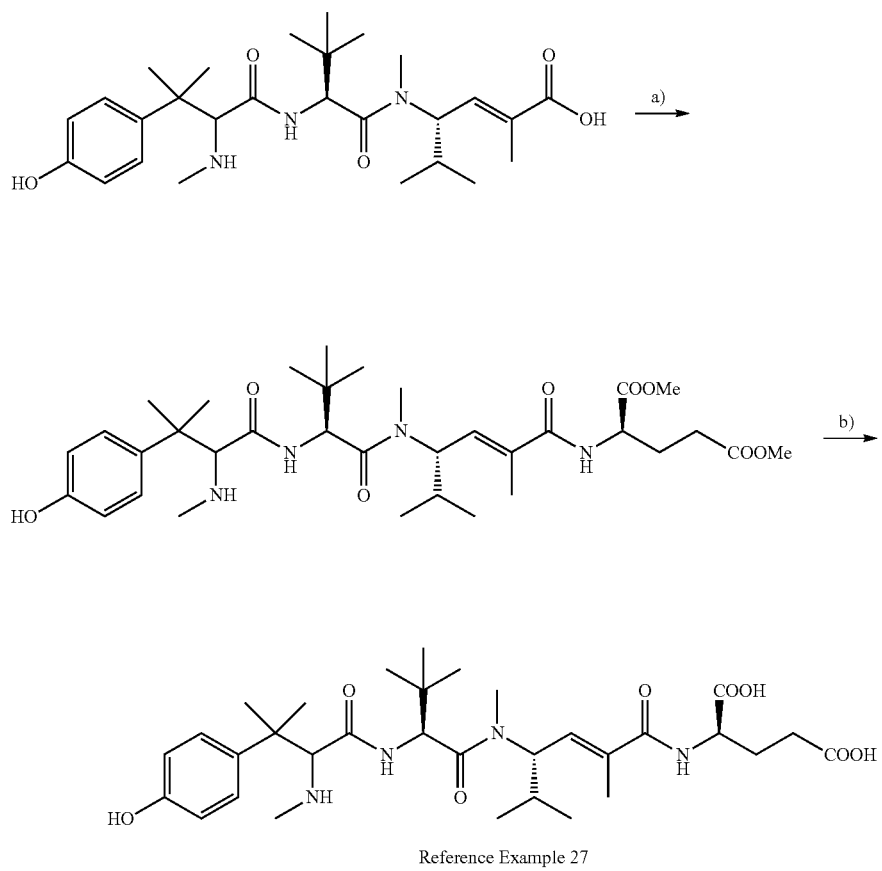

Reference Example 27 a) Production of dimethyl ((4 S,E)-4-((2S)-2-(3-(4-hydroxyphenyl)-3-methyl-2-(methylamino)butanamdo)-N,3,3-trimethylbutanamido)-2,5-dimethylhex-2-enoyl)-D-glutamate A mixture of (4S,E)-4-((2S)-2-(3-(4-hydroxyphenyl)-3-methyl-2-(methylamino)butan amido)-N,3,3-trimethylbutanamido)-2,5-dimethylhex-2-enoic acid trifluoroacetate (21.4 mg), N-ethyl-N-isopropylpropan-2-amine (22.91 mg), dimethyl D-glutamate hydrochloride (15.01 mg), 3-(((ethylimino)methylene)amino)-N,N-dimethylpropan-1-amine hydrochloride (13.59 mg), 1-hydroxybenzotriazole (9.58 b) Production of ((4S,E)-4-((2S)-2-(3-(4-hydroxyphenyl)-3-methyl-2-(methylamino)butanamido)-N,3,3-trimethylbutanamido)-2,5-dimethylhex-2-enoyl)-D-glutamic Acid (Reference Example 27)

To a mixed solution of dimethyl ((4S,E)-4-((2S)-2-(3-(4-hydroxyphenyl)-3-methyl-2-(methylamino)butanamido)-N,3,3-trimethylbutanamido)-2,5-dimethylhex-2-enoyl)-D-glutamate (21.6 mg), methanol (3 mL) and water (1 mL), lithium hydroxide (5.61 mg) was added at room temperature, and the resultant mixture was stirred. The solvent was distilled off under reduced pressure. The residue was purified by high performance liquid chromatography to give Reference Example 27 (15.8 mg).

LC-MS: 619 (M+H)$^+$ (1.04 min, Measurement Condition F)

Reference Example 28

N6-(tert-Butoxycarbonyl)-N2-((R)-4-((S,E)-4-((S)-2-((S)-2-((tert-butoxycarbonyl)(methyl)amino)-3-(5-fluoro-1-methyl-1H-indol-3-yl)-3-methylbutanamido)-N,3,3-trimethylbutanamido)-2,5-dimethylhex-2-enamido)-4-carboxybutanoyl)lysine

[Chemical Formula 60]

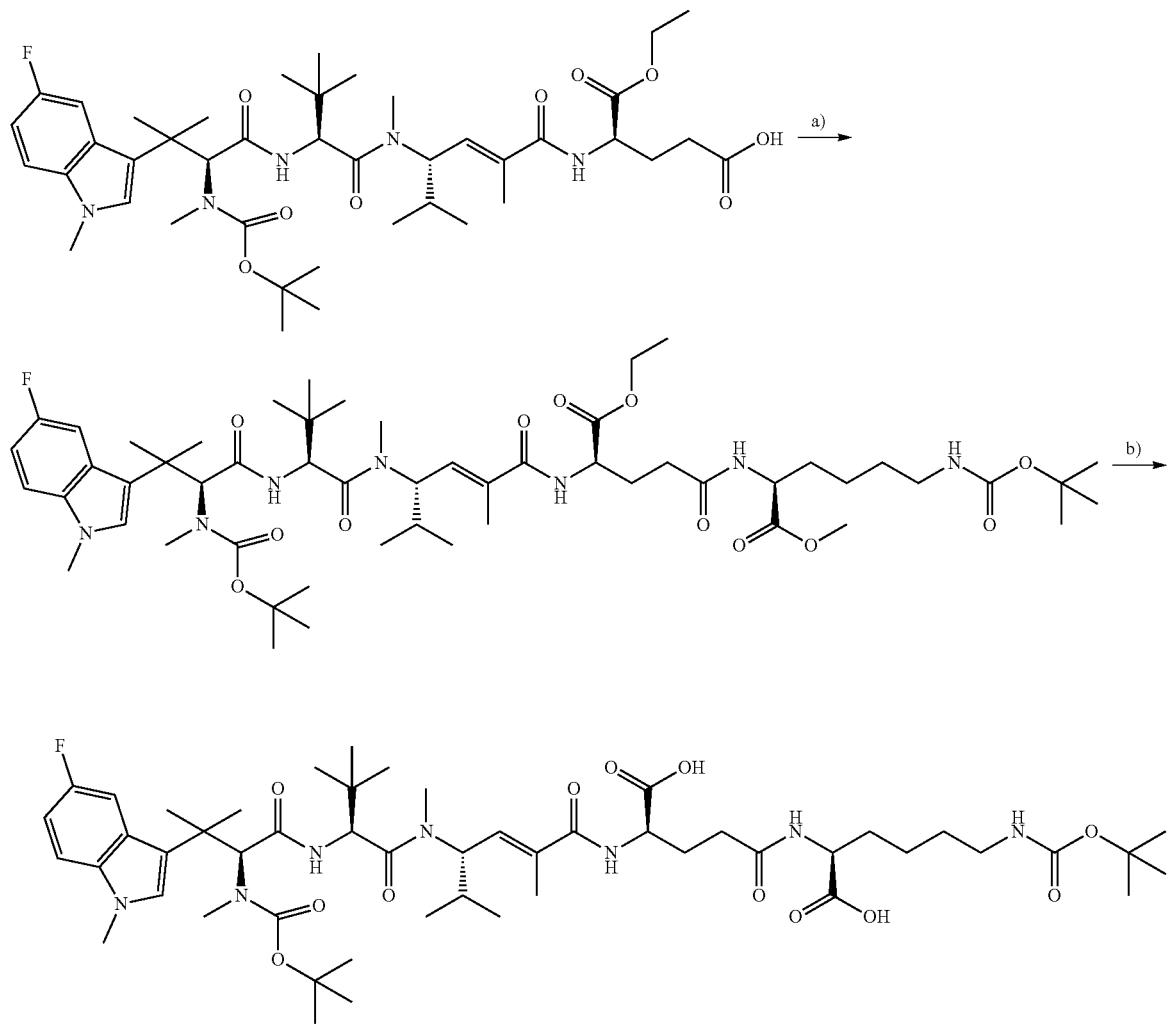

Reference Example 28 a) Production of methyl N6-(tert-butoxycarbonyl)-N2-((R)-4-((S,E)-4-((S)-2-((S)-2-((tert-butoxycarbonyl)(methyl)amino)-3-(5-fluoro-1-methyl-1H-indol-3-yl)-3-methylbutanamido)-N,3,3-trimethylbutanamido)-2,5-dimethylhex-2-enamido)-5-ethoxy-5-oxopentanoyl)lysinate To a mixed solution of (6S,9S,12S,17R,E)-9-(tert-butyl)-17-(ethoxycarbonyl)-6-(2-(5-fluoro-1-methyl-1H-indol-3-yl)propan-2-yl)-12-isopropyl-2,2,5,11,14-pentamethyl-4,7,10,15-tetraoxo-3-oxa-5,8,11,16-tetraazaicos-13-en-20-oic acid (54.5 mg) and N,N-dimethylformamide (2 mL), 1-[bis(dimethylamino)methylene]-1H-1,2,3-triazole[4,5-b]pyridinium 3-oxide hexafluorophosphate (31.0 mg) was added under ice cooling, and the resultant mixture was stirred for 30 minutes. N-(tert-Butoxycarbonyl)-L-lysine methyl ester hydrochloride (24.20 mg) and N-ethyl-N-isopropylpropan-2-amine (0.028 mL) were added, the resultant mixture was stirred at room temperature for 17 hours, and the solvent was then distilled off under reduced pressure. The residue was purified by silica gel chromatography (eluting solvent; chloroform:methanol) to give methyl N6-(tert-butoxycarbonyl)-N2-((R)-4-((S,E)-4-((S)-2-((S)-2-((tert-butoxy carbonyl)(methyl)amino)-3-(5-fluoro-1-methyl-1H-indol-3-yl)-3-methyl butanamido)-N,3,3-trimethylbutanamido)-2,5-dimethylhex-2-enamido)-5-ethoxy-5-oxopentanoyl)lysinate (71 mg).

LC-MS: 1067 (M+Na)$^+$ (1.557 min, Measurement Condition G)

b) Production of N6-(tert-butoxycarbonyl)-N2-((R)-4-((S,E)-4-((S)-2-((S)-2-((tert-butoxy carbonyl)(methyl)amino)-3-(5-fluoro-1-methyl-1H-indol-3-yl)-3-methylbutanamido)-N,3,3-trimethylbutanamido)-2,5-dimethylhex-2-enamido)-4-carboxybutanoyl)lysine (Reference Example 28)

A mixed solution of methyl N6-(tert-butoxycarbonyl)-N2-((R)-4-((S,E)-4-((S)-2-((S)-2-((tert-butoxy carbonyl)(methyl)amino)-3-(5-fluoro-1-methyl-1H-indol-3-yl)-3-methylbutanamido)-N,3,3-trimethylbutanamido)-2,5-dimethylhex-2-enamido)-5-ethoxy-5-oxopentanoyl)lysinate (71 mg), methanol (4 mL) and a 1 mol/L aqueous lithium hydroxide solution (4 mL) was stirred at 60° C. for 17 hours. A saturated aqueous citric acid solution was added to the reaction solution to acidify, and the resultant mixture was then extracted with ethyl acetate. The organic layer was dried over anhydrous magnesium sulfate, and the solvent was distilled off under reduced pressure. The residue was purified by ODS column chromatography (eluting solvent; water:acetonitrile) to give Reference Example 28 (49.0 mg).

LC-MS: 1024 (M+Na)$^+$ (1.416 min, Measurement Condition G)

Reference Example 29

Di-tert-butyl ((S,E)-4-((S)-2-((R)-1-(tert-butoxycarbonyl)piperidine-2-carboxamido)-N,3,3-trimethylbutanamido)-2,5-dimethylhex-2-enoyl)-D-glutamate

[Chemical Formula 61]

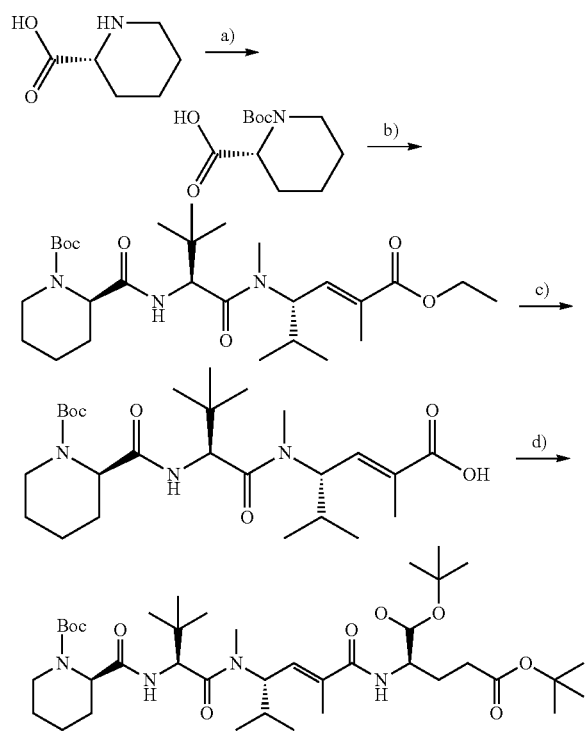

Reference Example 29 a) Production of (R)-1-(tert-butoxycarbonyl)piperidine-2-carboxylic Acid

A mixed solution of D-pipecolic acid (3.10 g), di-tert-butyl dicarbonate (7.86 g), a 5 mol/L aqueous sodium hydroxide solution (19.20 mL), tetrahydrofuran (10 mL) and water (10 mL) was stirred at room temperature for 8 hours, and the solvent was then distilled off under reduced pressure. After the aqueous phase was washed with diethyl ether, the aqueous phase was neutralized (pH 7) with a 0.1 mol/L hydrochloric acid solution, and the resultant mixture was extracted with diethyl ether. After drying over anhydrous sodium sulfate, the solvent was distilled off under reduced pressure to give (R)-1-(tert-butoxycarbonyl)piperidine-2-carboxylic acid (4.16 g). LC-MS: 228 (M−H)$^−$ (1.51 min, Measurement Condition F)

b) Production of Tert-butyl (R)-2-(((S)-1-(((S,E)-6-ethoxy-2,5-dimethyl-6-oxohex-4-en-3-yl)(methyl)amino)-3,3-dimethyl-1-oxobutan-2-yl)carbamoyl)piperidine-1-carboxylate A suspension of (R)-1-(tert-butoxycarbonyl)piperidine-2-carboxylic acid (432.3 mg), ethyl (S,E)-4-((S)-2-amino-N,3,3-trimethylbutanamido)-2,5-dimethylhex-2-enoate (393 mg), o-(benzotriazol-1-yl)-N,N,N',N'-tetramethyluronium hexafluorophosphate (953 mg), N-ethyl-N-isopropylpropan-2-amine (0.659 mL) and N,N-dimethylformamide (3 mL) was stirred at room temperature for 15 hours, and then extracted with ethyl acetate. The organic layer was washed with a saturated aqueous sodium bicarbonate solution and saturated brine, and then dried over anhydrous sodium sulfate. The solvent was distilled off under reduced pressure. The residue was purified by silica gel chromatography (eluting solvent; hexane:ethyl acetate) to give tert-butyl (R)-2-(((S)-1-(((S,E)-6-ethoxy-2,5-dimethyl-6-oxohex-4-en-3-yl)(methyl)amino)-3,3-dimethyl-1-oxobutan-2-yl)carbamoyl)piperidine-1-carboxylate (658 mg).

LC-MS: 546 (M+Na)$^+$ (1.51 min, Measurement Condition F)

c) Production of (S,E)-4-((S)-2-((R)-1-(tert-butoxycarbonyl)piperidine-2-carboxamido)-N,3,3-trimethylbutanamido)-2,5-dimethylhex-2-enoic Acid A mixed solution of tert-butyl (R)-2-(((S)-1-(((S,E)-6-ethoxy-2,5-dimethyl-6-oxohex-4-en-3-yl)(methyl)amino)-3,3-dimethyl-1-oxobutan-2-yl)carbamoyl)piperidine-1-carboxylate (508.1 mg), methanol (8 mL), water (2 mL) and lithium hydroxide (204 mg) was stirred at room temperature for 4 days, and then extracted with ethyl acetate. The organic layer was washed with saturated brine and then dried over anhydrous sodium sulfate, and the solvent was distilled off under reduced pressure to give (S,E)-4-((S)-2-((R)-1-(tert-butoxycarbonyl)piperidine-2-carboxamido)-N,3,3-trimethylbutanamido)-2,5-dimethylhex-2-enoic acid. The compound obtained was directly used for the subsequent reaction without purification.

LC-MS: 518 (M+Na)$^+$ (1.19 min, Measurement Condition F)

d) Production of Di-tert-butyl ((S,E)-4-((S)-2-((R)-1-(tert-butoxycarbonyl)piperidine-2-carboxamido)-N,3,3-trimethylbutanamido)-2,5-dimethylhex-2-enoyl)-D-glutamate (Reference Example 29)

A mixed solution of (S,E)-4-((S)-2-((R)-1-(tert-butoxycarbonyl)piperidine-2-carboxamido)-N,3,3-trimethylbutanamido)-2,5-dimethylhex-2-enoic acid (481 mg), N-ethyl-N-isopropylpropan-2-amine (0.501 mL), 3-(((ethylamino)methylene)amino)-N,N-dimethylpropan-1-amine hydrochloride (372 mg), 1H-benzo[d][1,2,3]triazol-1-ol (262 mg), D-glutamic acid di-tert-butyl ester hydrochloride (287 mg) and N,N-dimethylformamide (10 mL) was stirred at room temperature for 20 hours, and then extracted with ethyl acetate. The organic layer was washed with a saturated aqueous sodium bicarbonate solution and saturated brine, and then dried over anhydrous sodium sulfate. The residue was purified by silica gel chromatography (eluting solvent; hexane:ethyl acetate) to give Reference Example 29 (673.0 mg).

LC-MS: 759 (M+Na)+ (1.35 min, Measurement Condition H)

Reference Examples 30 to 52

The compounds shown in the following Table 2 were obtained through the same reaction and treatment as step p) of Reference Example 1, using the A15 intermediate of Reference Example 1, Reference Example 2 and Reference Example 53 as raw material compounds.

TABLE 2

| Reference Example | Structural Formula | LC-MS/Rt (min) | LC-MS Measurement Condition |
|---|---|---|---|
| 30 | | 7.45(M + H)+/1.594 | G |
| 31 | | 745(M + H)+/1.526 | G |
| 32 | | 759(M + H)+/1.693 | G |

TABLE 2-continued

| Reference Example | Structural Formula | LC-MS/Rt (min) | LC-MS Measurement Condition |
|---|---|---|---|
| 33 | | 759(M + H)+/1.732 | G |
| 34 | | 745(M + H)+/1.439 | G |
| 35 | | 745(M + H)+/1.400 | G |
| 36 | | 759(M + H)+/1.413 | G |

TABLE 2-continued

| Reference Example | Structural Formula | LC-MS/Rt (min) | LC-MS Measurement Condition |
|---|---|---|---|
| 37 | | 759(M + H)⁺/1.475 | G |
| 38 | | 812(M + H)⁺/1.560 | G |
| 39 | | 798(M + H)⁺/1.415 | G |
| 40 | | 798(M + H)⁺/1.474 | G |

TABLE 2-continued

| Reference Example | Structural Formula | LC-MS/Rt (min) | LC-MS Measurement Condition |
|---|---|---|---|
| 41 | | 798(M + H)⁺/1.470 | G |
| 42 | | 812(M + H)⁺/1.460 | G |
| 43 | | 812(M + H)⁺/1.450 | G |
| 44 | | 798(M + H)⁺/1.420 | G |

TABLE 2-continued

| Reference Example | Structural Formula | LC-MS/Rt (min) | LC-MS Measurement Condition |
|---|---|---|---|
| 45 | | 812(M + H)⁺/1.457 | G |
| 46 | | 944(M + H)⁺/1.407 | G |
| 47 | | 1129(M + H)⁺/1.30 | F |
| 48 | | 911(M + H)⁺/1.709 | G |

TABLE 2-continued

| Reference Example | Structural Formula | LC-MS/Rt (min) | LC-MS Measurement Condition |
|---|---|---|---|
| 49 | | 802(M + H)+/1.390 | G |
| 50 | | 855(M + H)+/1.588 | G |
| 51 | | 952(M − H)−/1.399 | G |
| 52 | | 802(M + H)+/1.452 | G |

Reference Example 53

The compounds shown in the following table 3 were obtained through the same reaction and treatment as Reference Example 1, using corresponding raw material compounds.

TABLE 3

| Reference Example | Structural Formula | LC-MS/Rt (min) | LC-MS Measurement Condition |
|---|---|---|---|
| 53 | [structure] | 742(M + H)+/1.488 | G |

Reference Examples 54 to 73

The compounds shown in the following table 4 were obtained through the same reaction and treatment as step c) of Reference Example 3, using corresponding raw material compounds.

TABLE 4

| Reference Example | Structural Formula | LC-MS/Rt (min) | LC-MS Measurement Condition |
|---|---|---|---|
| 54 | [structure] | 889(M + Na)+/1.498 | G |
| 55 | [structure] | 867(M + H)+/1.433 | G |

TABLE 4-continued

| Reference Example | Structural Formula | LC-MS/ Rt (min) | LC-MS Measurement Condition |
|---|---|---|---|
| 56 | | 881(M + H)+/ 1.701 | G |
| 57 | | 881(M + H)+/ 1.710 | G |
| 58 | | 867(M + H)+/ 1.447 | G |
| 59 | | 867(M + H)+/ 1.413 | G |

TABLE 4-continued

| Reference Example | Structural Formula | LC-MS/ Rt (min) | LC-MS Measurement Condition |
|---|---|---|---|
| 60 | | 881(M + H)+/ 1.422 | G |
| 61 | | 895(M + H)+/ 1.419 | G |
| 62 | | 909(M + H)+/ 1.475 | G |
| 63 | | 934(M + H)+/ 1.441 | G |
| 64 | | 920(M + H)+/ 1.498 | G |

TABLE 4-continued

| Reference Example | Structural Formula | LC-MS/ Rt (min) | LC-MS Measurement Condition |
|---|---|---|---|
| 65 | | 920(M + H)+/ 1.443 | G |
| 66 | | 942(M + Na)+/ 1.440 | G |
| 67 | | 934(M + H)+/ 1.475 | G |
| 68 | | 970(M + Na)+/ 1.503 | G |

TABLE 4-continued
| Reference Example | Structural Formula | LC-MS/ Rt (min) | LC-MS Measurement Condition |
|---|---|---|---|
| 69 | 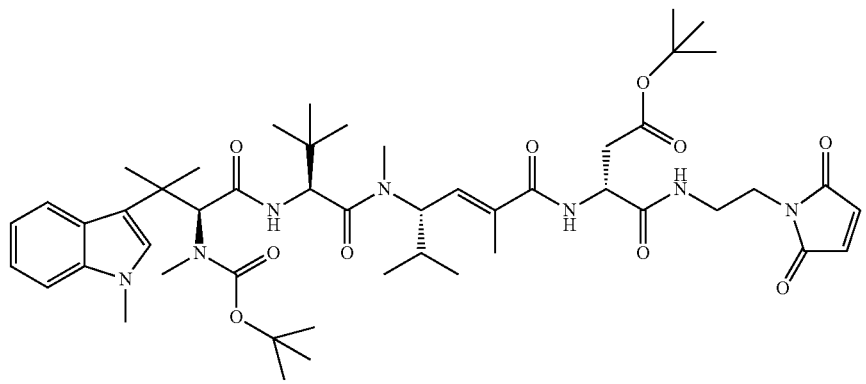 [SMILES: C/C(=C\[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)N[C@H](CC(=O)OC(C)(C)C)C(=O)NCCN1C(=O)C=CC1=O] | 920(M + H)+/ 1.459 | G |
| 70 | 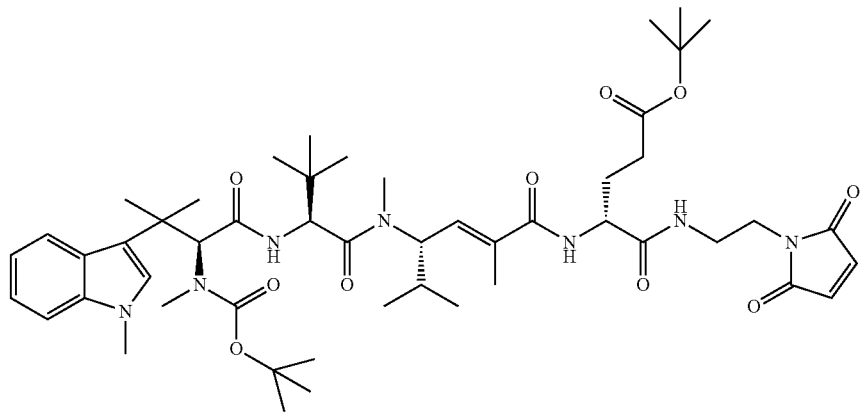 [SMILES: C/C(=C\[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)N[C@H](CCC(=O)OC(C)(C)C)C(=O)NCCN1C(=O)C=CC1=O] | 934(M + H)+/ 1.497 | G |
| 71 | 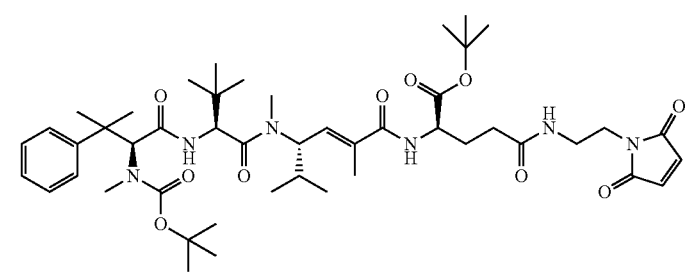 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)N[C@H](CCC(=O)NCCN1C(=O)C=CC1=O)C(=O)OC(C)(C)C] | 881(M + H)+/ 1.373 | G |
| 72 | 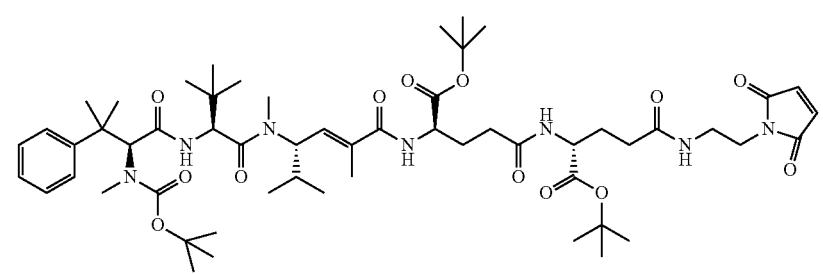 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)N[C@H](CCC(=O)N[C@H](CCC(=O)NCCN1C(=O)C=CC1=O)C(=O)OC(C)(C)C)C(=O)OC(C)(C)C] | 1066 (M + H)+/ 1.415 | G |

TABLE 4-continued

| Reference Example | Structural Formula | LC-MS/ Rt (min) | LC-MS Measurement Condition |
|---|---|---|---|
| 73 | | 1273 (M + Na)+/ 1.624 | G |

Reference Examples 74 to 78

The compounds shown in the following Table 5 were obtained through the same reaction and treatment as Reference Example M1, using corresponding raw material compounds.

TABLE 5

| Reference Example | Structural Formula | LC-MS/RT (min) | LC-MS Measurement Condition |
|---|---|---|---|
| 74 | | 800 (M − H)−/ 0.923 | G |
| 75 | | 653 (M − H)−/ 0.853 | G |
| 76 | | 653 (M − H)−/ 0.952 | G |
| 77 | | 600 (M − H)−/ 0.853 | G |

TABLE 5-continued

| Reference Example | Structural Formula | LC-MS/RT (min) | LC-MS Measurement Condition |
|---|---|---|---|
| 78 | [structure] | 525 (M + H)+/ 0.82 | G |

Reference Examples 79 to 88

The compounds shown in the following Table 6 were obtained through the same reaction and treatment as step in) of Reference Example 1, using corresponding raw material compounds and Reference Example 5.

TABLE 6

| Reference Example | Structure Formula | LC-MS/ Rt (min) | LC-MS Measurement Condition |
|---|---|---|---|
| 79 | [structure] | 849 (M + H)+/1.138 | G |
| 80 | [structure] | 799 (M + H)+/0.976 | F |
| 81 | [structure] | 787 (M + H)+/1.387 | G |

TABLE 6-continued
| Reference Example | Structure Formula | LC-MS/ Rt (min) | LC-MS Measurement Condition |
|---|---|---|---|
| 82 | 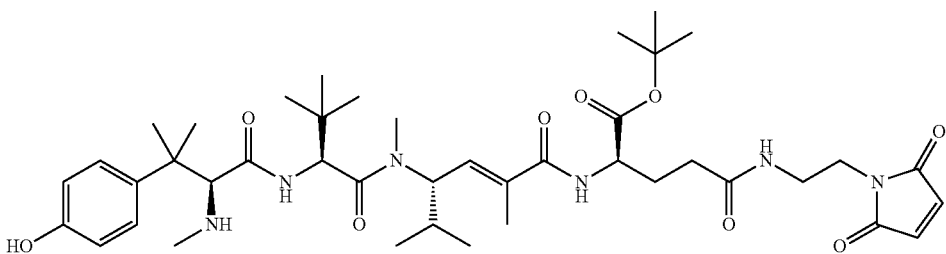 [SMILES: CN[C@H](C(=O)N[C@H](C(=O)N(C)[C@H](/C=C(\C)C(=O)N[C@H](CCC(=O)NCCN1C(=O)C=CC1=O)C(=O)OC(C)(C)C)C(C)C)C(C)(C)C)C(C)(C)c1ccc(O)cc1] | 795 (M − H)−/1.24 | G |
| 83 | 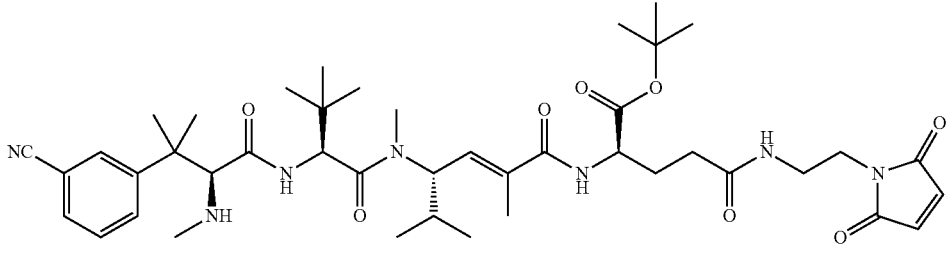 [SMILES: CN[C@H](C(=O)N[C@H](C(=O)N(C)[C@H](/C=C(\C)C(=O)N[C@H](CCC(=O)NCCN1C(=O)C=CC1=O)C(=O)OC(C)(C)C)C(C)C)C(C)(C)C)C(C)(C)c1cccc(C#N)c1] | 806 (M + H)+/1.34 | G |
| 84 | 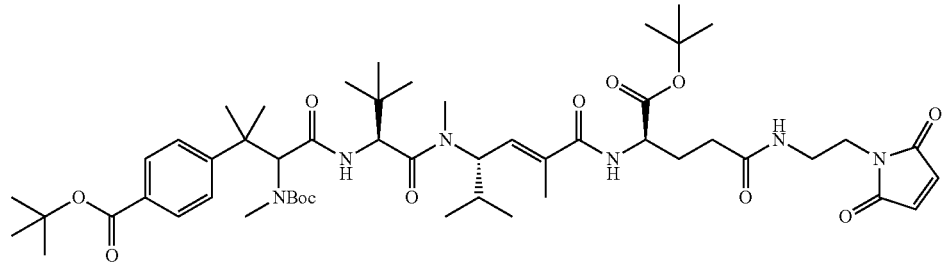 [SMILES: C/C(=C\[C@H](C(C)C)N(C)C(=O)[C@@H](NC(=O)C(N(C)C(=O)OC(C)(C)C)C(C)(C)c1ccc(C(=O)OC(C)(C)C)cc1)C(C)(C)C)C(=O)N[C@H](CCC(=O)NCCN1C(=O)C=CC1=O)C(=O)OC(C)(C)C] | 981 (M + H)+/1.702 | G |
| 85 | 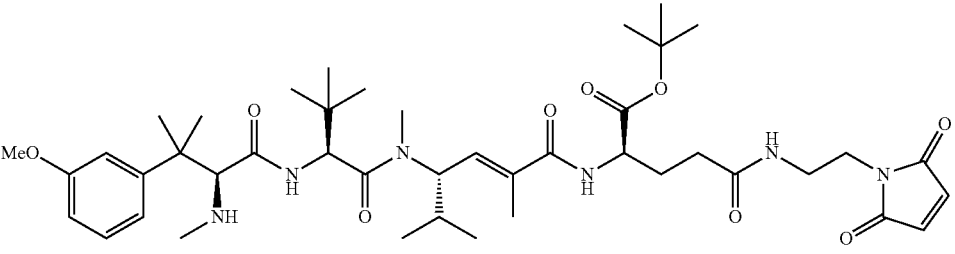 [SMILES: CN[C@H](C(=O)N[C@H](C(=O)N(C)[C@H](/C=C(\C)C(=O)N[C@H](CCC(=O)NCCN1C(=O)C=CC1=O)C(=O)OC(C)(C)C)C(C)C)C(C)(C)C)C(C)(C)c1cccc(OC)c1] | 811 (M + H)+/1.10 | G |
| 86 | 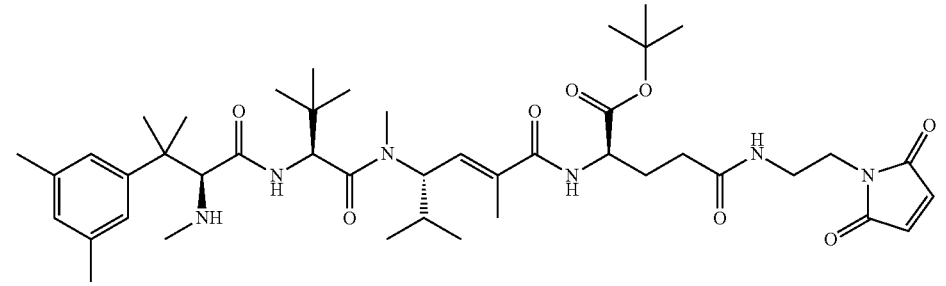 [SMILES: CN[C@H](C(=O)N[C@H](C(=O)N(C)[C@H](/C=C(\C)C(=O)N[C@H](CCC(=O)NCCN1C(=O)C=CC1=O)C(=O)OC(C)(C)C)C(C)C)C(C)(C)C)C(C)(C)c1cc(C)cc(C)c1] | 809 (M + H)+/1.17 | G |

TABLE 6-continued

| Reference Example | Structure Formula | LC-MS/ Rt (min) | LC-MS Measurement Condition |
|---|---|---|---|
| 87 | 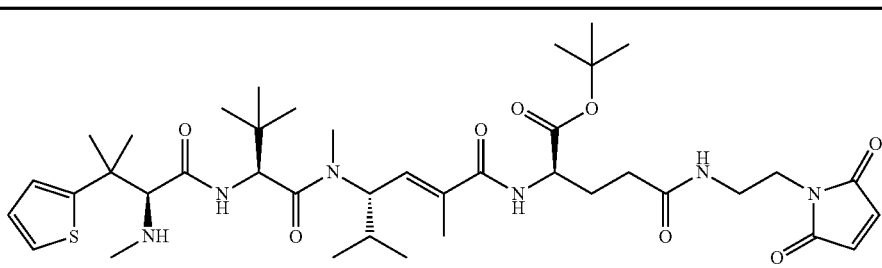 | 787 (M + H)+/1.060 | G |
| 88 | 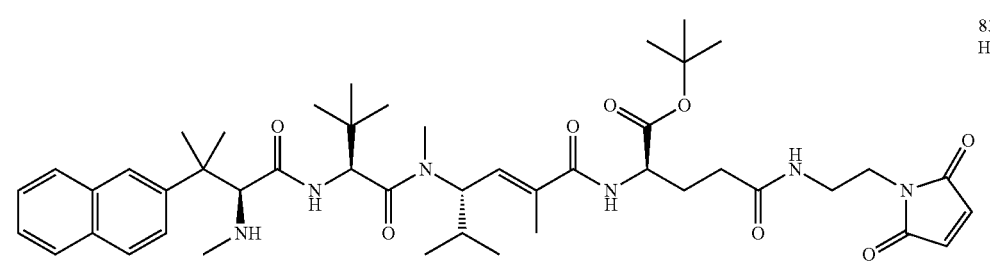 | 831 (M + H)+/1.173 | G |

Reference Examples 89 to 95

The compounds shown in the following Table 7 were obtained through the same reaction and treatment as step o) of Reference Example 1, using corresponding raw material compounds.

TABLE 7

| Reference Example | Structural Formula | LC-MS/ Rt (min) | LC-MS Measurement Condition |
|---|---|---|---|
| 89 | 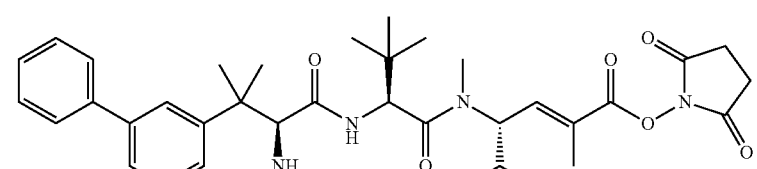 | 647 (M + H)+/ 0.89 | G |
| 90 | 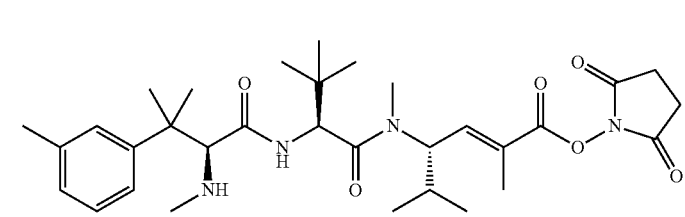 [SMILES: CN[C@H](C(=O)N[C@H](C(=O)N(C)[C@H](/C=C(\C)C(=O)ON1C(=O)CCC1=O)C(C)C)C(C)(C)C)C(C)(C)c1cccc(C)c1] | 585 (M + H)+/ 0.67 | G |
| 91 | 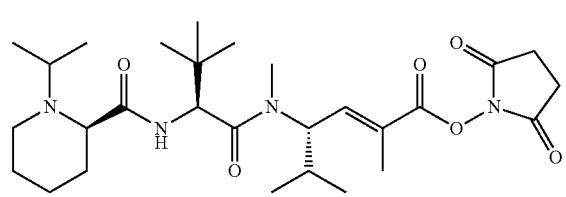 [SMILES: C/C(=C\[C@H](C(C)C)N(C)C(=O)[C@@H](NC(=O)[C@H]1CCCCN1C(C)C)C(C)(C)C)C(=O)ON1C(=O)CCC1=O] | 535 (M + H)+/ 0.707 | F |

TABLE 7-continued

| Reference Example | Structural Formula | LC-MS/ Rt (min) | LC-MS Measurement Condition |
|---|---|---|---|
| 92 | 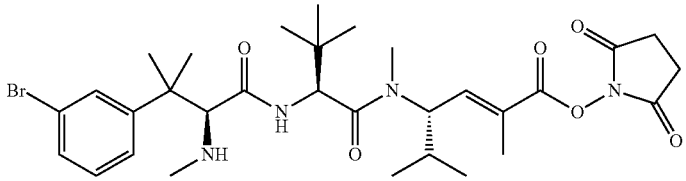 [SMILES: CN[C@H](C(=O)N[C@H](C(=O)N(C)[C@H](/C=C(\C)C(=O)ON1C(=O)CCC1=O)C(C)C)C(C)(C)C)C(C)(C)c1cccc(Br)c1] | 649 (M + H)+/ 0.81 | G |
| 93 | 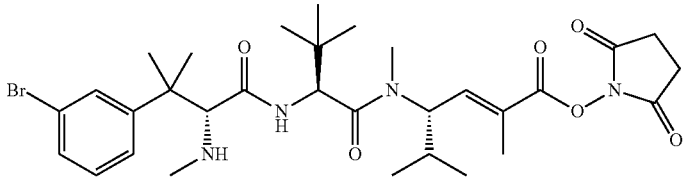 [SMILES: CN[C@@H](C(=O)N[C@H](C(=O)N(C)[C@H](/C=C(\C)C(=O)ON1C(=O)CCC1=O)C(C)C)C(C)(C)C)C(C)(C)c1cccc(Br)c1] | 649 (M + H)+/ 0.86 | G |
| 94 | 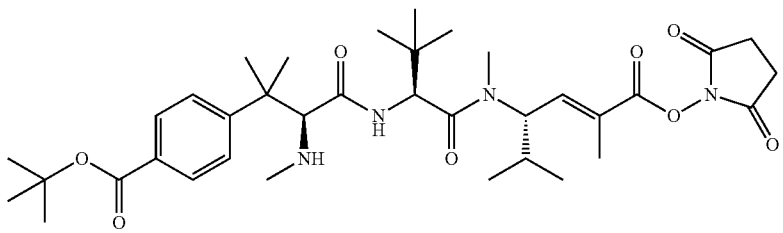 [SMILES: CN[C@H](C(=O)N[C@H](C(=O)N(C)[C@H](/C=C(\C)C(=O)ON1C(=O)CCC1=O)C(C)C)C(C)(C)C)C(C)(C)c1ccc(C(=O)OC(C)(C)C)cc1] | 671 (M + H)+/ 1.08 | G |
| 95 | 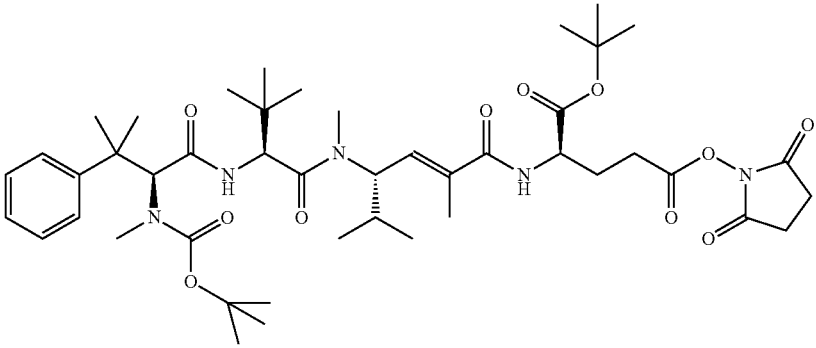 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)N[C@H](CCC(=O)ON1C(=O)CCC1=O)C(=O)OC(C)(C)C] | 878 (M + Na)+/ 1.426 | G |

Reference Example 96

The compound shown in the following Table 8 was obtained through the same reaction and treatment as Reference Example M1, using corresponding raw material compounds.

TABLE 8

| Reference Example | Structural Formula | LC-MS/ Rt (min) | LC-MS Measurement Condition |
|---|---|---|---|
| 96 | 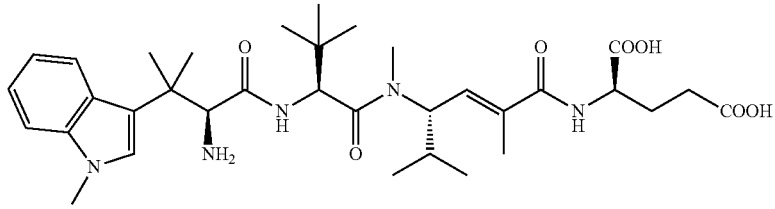 [SMILES: C/C(=C\[C@H](C(C)C)N(C)C(=O)[C@@H](NC(=O)[C@@H](N)C(C)(C)c1cn(C)c2ccccc12)C(C)(C)C)C(=O)N[C@H](CCC(=O)O)C(=O)O] | 642 (M + H)+/ 1.056 | D |

Reference Example 97
(R)-4-((R)-4-((R)-4-Amino-5-(tert-butoxy)-5-oxo-pentanamido)-5-(tert-butoxy)-5-oxopentanamido)-5-(tert-butoxy)-5-oxopentanoic Acid
[Chemical Formula 62]
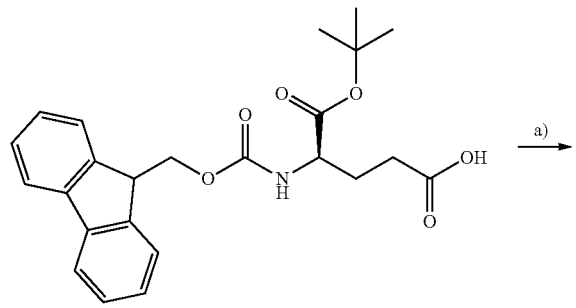
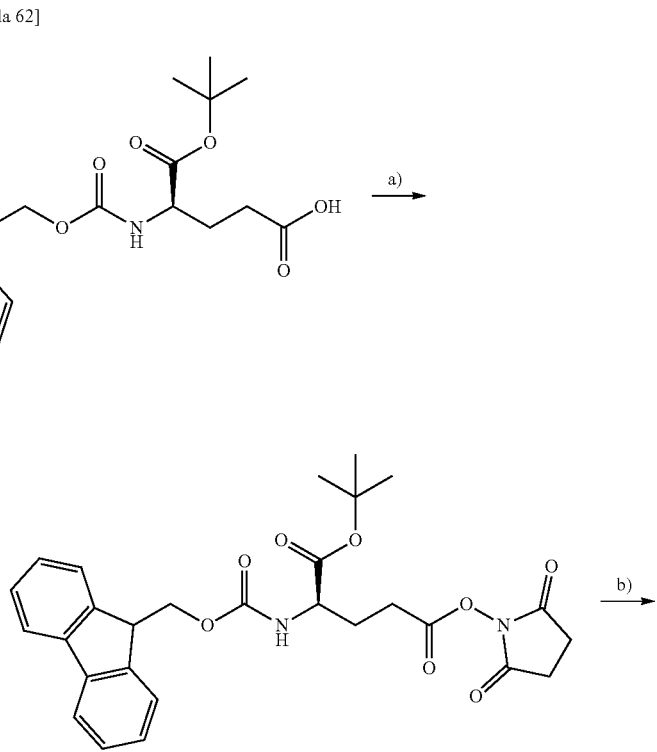
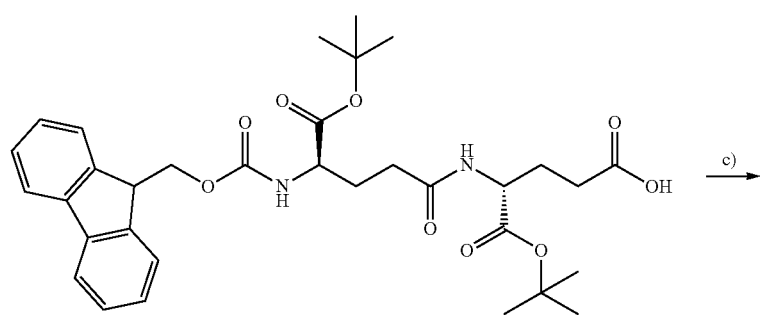
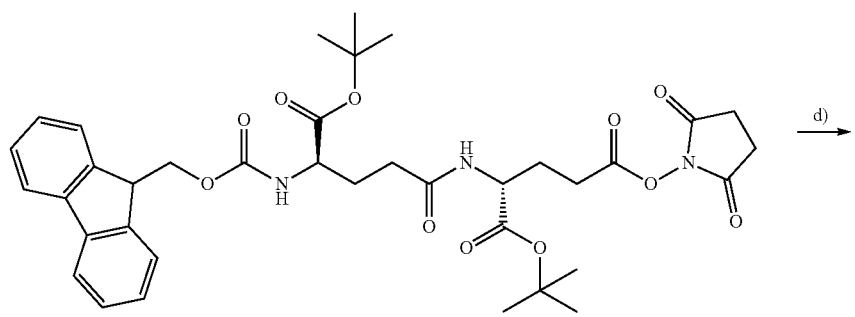

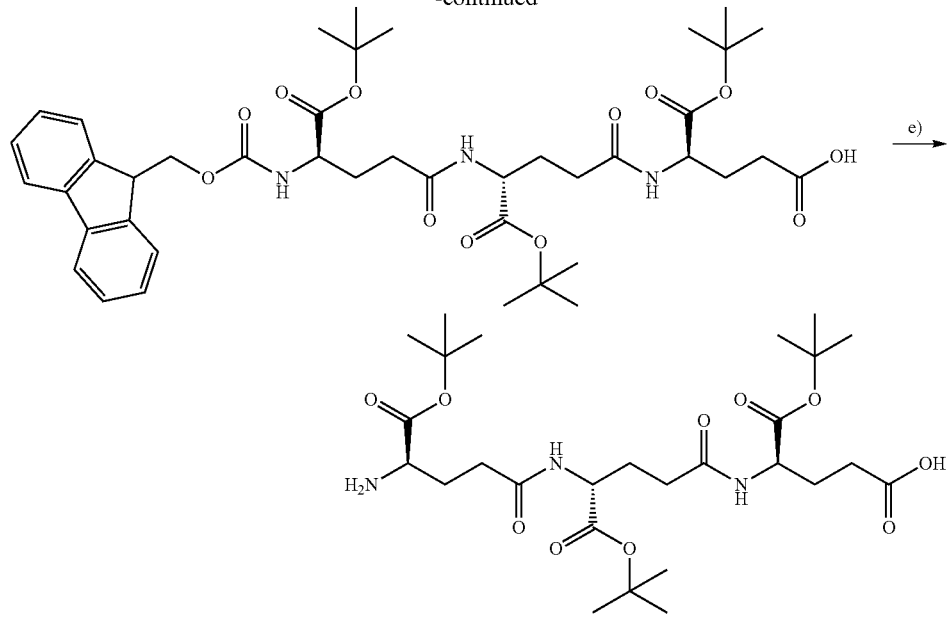

Reference Example 97 a) Production of 1-(tert-butyl) 5-(2,5-dioxopyrrolidin-1-yl) (((9H-fluoren-9-yl)methoxy)carbonyl)-D-glutamate By the same approach as Reference Example 3-a), from (R)-4-((((9H-fluoren-9-yl)methoxy)carbonyl)amino)-5-(tert-butoxy)-5-oxopentanoic acid (500 mg), 1-(tert-butyl) 5-(2,5-dioxopyrrolidin-1-yl) (((9H-fluoren-9-yl)methoxy)carbonyl)-D-glutamate (520 mg) was obtained.

LC-MS: 523 (M+H)$^+$ (1.324 min, Measurement Condition G)

b) Production of (R)-4-((R)-4-((((9H-fluoren-9-yl)methoxy)carbonyl)amino)-5-(tert-butoxy)-5-oxopentanamido)-5-(tert-butoxy)-5-oxopentanoic Acid By the same approach as Reference Example 3-b), from 1-(tert-butyl) 5-(2,5-dioxopyrrolidin-1-yl) (((9H-fluoren-9-yl)methoxy)carbonyl)-D-glutamate (520 mg), (R)-4-((R)-4-((((9H-fluoren-9-yl)methoxy)carbonyl)amino)-5-(tert-butoxy)-5-oxopentanamido)-5-(tert-butoxy)-5-oxopentanoic acid (428.7 mg) was obtained.

LC-MS: 611 (M+H)$^+$ (1.551 min, Measurement Condition G)

c) Production of 1-(tert-butyl) 5-(2,5-dioxopyrrolidin-1-yl) ((R)-4-((((9H-fluoren-9-yl)methoxy)arbonyl)amino)-5-(tert-butoxy)-5-oxopentanoyl)-D-glutamate By the same approach as Reference Example 3-a), from (R)-4-((R)-4-((((9H-fluoren-9-yl)methoxy)carbonyl)amino)-5-(tert-butoxy)-5-oxopentanamido)-5-(tert-butoxy)-5-oxopentanoic acid (100 mg), 1-(tert-butyl) 5-(2,5-dioxopyrrolidin-1-yl) ((R)-4-((((9H-fluoren-9-yl)methoxy)carbonyl)amino)-5-(tert-butoxy)-5-oxopentanoyl)-D-glutamate (33 mg) was obtained.

LC-MS: 708 (M+H)$^+$ (1.598 min, Measurement Condition G)

d) Production of (5R,10R,15R)-5,10,15-tris(tert-butoxycarbonyl)-1-(9H-fluoren-9-yl)-3,8,13-trioxo-2-oxa-4,9,14-triazaoctadecan-18-oic Acid By the same approach as Reference Example 3-b), from 1-(tert-butyl) 5-(2,5-dioxopyrrolidin-1-yl) ((R)-4-((((9H-fluoren-9-yl)methoxy)carbonyl)amino)-5-(tert-butoxy)-5-oxopentanoyl)-D-glutamate (33 mg), (5R,10R,15R)-5,10,15-tris(tert-butoxycarbonyl)-1-(9H-fluoren-9-yl)-3,8,13-trioxo-2-oxa-4,9,14-triazaoctadecan-18-oic acid (16.6 mg) was obtained.

LC-MS: 796 (M+H)$^+$ (1.119 min, Measurement Condition F)

e) Production of (R)-4-((R)-4-((R)-4-amino-5-(tert-butoxy)-5-oxopentanamido)-5-(tert-butoxy)-5-oxopentanamido)-5-(tert-butoxy)-5-oxopentanoic Acid (Reference Example 97)

A mixed solution of (5R,10R,15R)-5,10,15-tris(tert-butoxycarbonyl)-1-(9H-fluoren-9-yl)-3,8,13-trioxo-2-oxa-4,9,14-triazaoctadecan-18-oic acid (16.6 mg) in piperidine (0.3 mL) and N,N-dimethylformamide (1.5 mL) was stirred at 25° C. for 7 hours, and the reaction solution was then purified by reversed phase column chromatography (eluting solvent; acetonitrile with 0.1% TFA:water) to give Reference Example 97 (7.5 mg). LC-MS: 574 (M+H)$^+$ (0.698 min, Measurement Condition F)

Reference Example 98

The compound shown in the following Table 9 was obtained through the same reaction and treatment as Reference Example 2, using corresponding raw material compounds.

TABLE 9

| Reference Example | Structural Formula | LC-MS/ Rt (min) | LC-MS Measurement Condition |
|---|---|---|---|
| 98 | 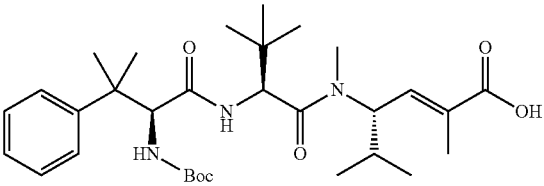 [SMILES: C/C(=C\[C@H](C(C)C)N(C)C(=O)[C@@H](NC(=O)[C@@H](NC(=O)OC(C)(C)C)C(C)(C)c1ccccc1)C(C)(C)C)C(=O)O] | 560 (M + H)⁺/ 1.480 | G |

Reference Example 99

The compound shown in the following Table 10 was obtained through the same reaction and treatment as step in) of Reference Example 1, using Reference Example 98 and Reference Example 5.

TABLE 10

| Reference Example | Structural Formula | LC-MS/ Rt (min) | LC-MS Measurement Condition |
|---|---|---|---|
| 99 | 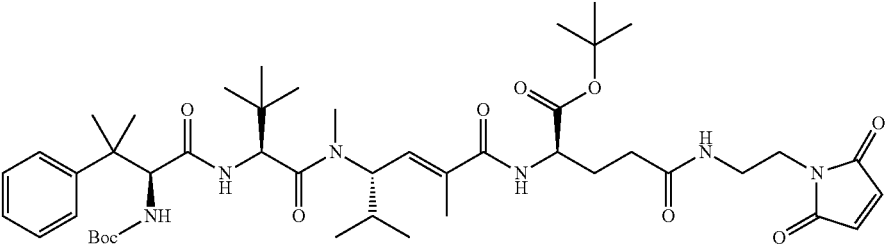 [SMILES: C/C(=C\[C@H](C(C)C)N(C)C(=O)[C@@H](NC(=O)[C@@H](NC(=O)OC(C)(C)C)C(C)(C)c1ccccc1)C(C)(C)C)C(=O)N[C@H](CCC(=O)NCCN1C(=O)C=CC1=O)C(=O)OC(C)(C)C] | 889 (M + Na)⁺/1.524 | G |

Reference Example 100

Di-tert-butyl ((4S,E)-4-((2S)-2-(3-(4-((2-(2,5-dioxo-2,5-dihydro-1H-pyrrol-1-yl)ethyl) carbamoyl)phenyl)-3-methyl-2-(methylamino)butanamido)-N,3,3-trim ethylbutanamido)-2,5-dimethylhex-2-enoyl)-D-glutamate

[Chemical Formula 63]

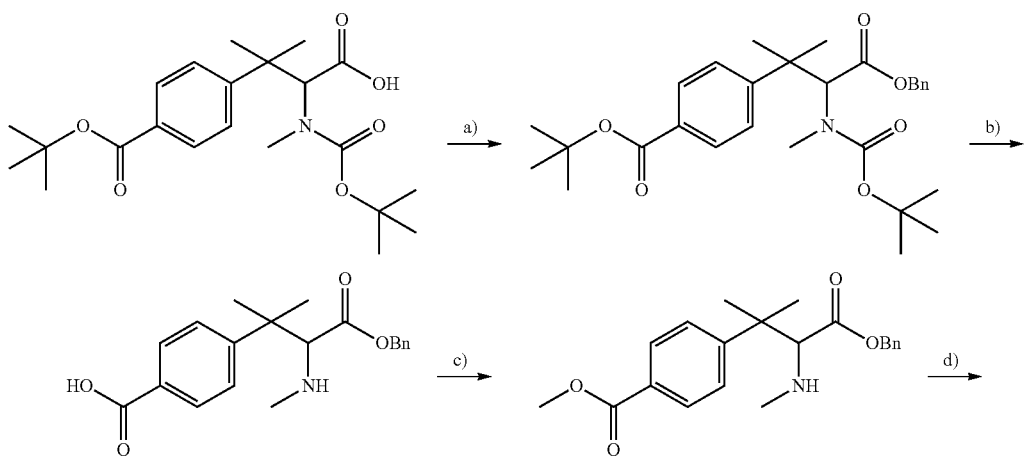

-continued
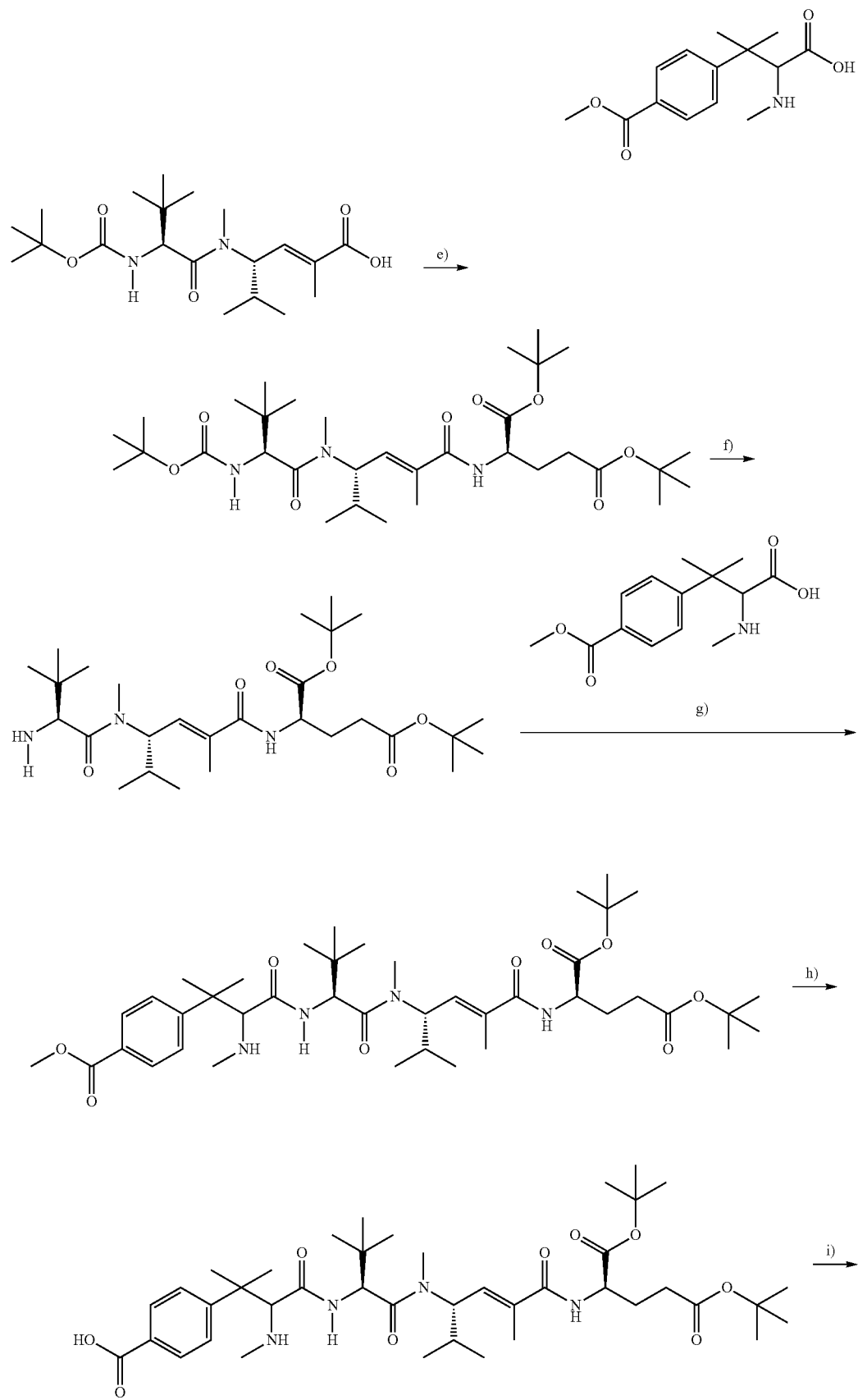

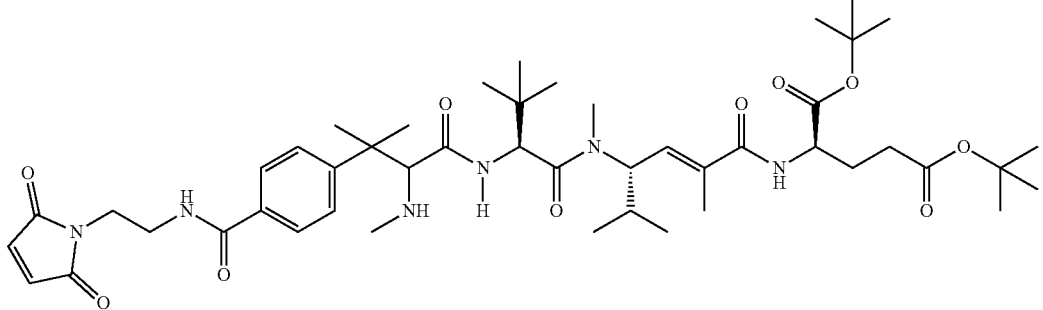

Reference Example 100 a) Production of Tert-butyl 4-(4-(benzyloxy)-3-((tert-butoxycarbonyl)(methyl)amino)-2-methyl-4-oxobutan-2-yl)benzoate To a suspension of 2-((tert-butoxycarbonyl)(methyl)amino)-3-(4-(tert-butoxycarbonyl)phenyl)-3-methylbutanoic acid (1.48 g), sodium carbonate (0.77 g) and N,N-dimethylformamide (7 mL), benzyl bromide (0.647 mL) was added, and the resultant mixture was stirred at room temperature for 17 hours. Ethyl acetate was added to the reaction solution. The organic layer was washed with water and saturated brine and then dried over anhydrous sodium sulfate, and the solvent was distilled off under reduced pressure. The residue was purified by silica gel chromatography (eluting solvent; hexane:ethyl acetate) to give tert-butyl 4-(4-(benzyloxy)-3-((tert-butoxycarbonyl)(methyl)amino)-2-methyl-4-oxobutan-2-yl)benzoate (1.78 g).

LC-MS: 520 (M+Na)$^+$ (1.778 min, Measurement Condition G)

b) Production of 4-(4-(benzyloxy)-2-methyl-3-(methylamino)-4-oxobutan-2-yl)benzoic Acid Trifluoroacetate To a mixed solution of tert-butyl 4-(4-(benzyloxy)-3-((tert-butoxycarbonyl)(methyl)amino)-2-methyl-4-oxobutan-2-yl)benzoate (1.78 g) and chloroform (40 mL), trifluoroacetic acid (10 mL) was added, and the resultant mixture was stirred at room temperature for 5 hours. The solvent was distilled off under reduced pressure to give 4-(4-(benzyloxy)-2-methyl-3-(methylamino)-4-oxobutan-2-yl)benzoic acid trifluoroacetate. The compound obtained was used for the subsequent reaction without purification.

LC-MS: 342 (M+H)$^+$ (1.05 min, Measurement Condition F)

c) Production of methyl 4-(4-(benzyloxy)-2-methyl-3-(methylamino)-4-oxobutan-2-yl)benzoate To a suspension of 4-(4-(benzyloxy)-2-methyl-3-(methylamino)-4-oxobutan-2-yl)benzoic acid trifluoroacetate, sodium carbonate (379 mg) and N,N-dimethylformamide (9 mL), iodomethane (0.169 mL) was added, and the resultant mixture was stirred at room temperature. Ethyl acetate was added to the reaction solution. The organic layer was washed with water and saturated brine and then dried over anhydrous sodium sulfate, and the solvent was distilled off under reduced pressure. The residue was purified by silica gel chromatography (eluting solvent; hexane:ethyl acetate) to give methyl 4-(4-(benzyloxy)-2-methyl-3-(methylamino)-4-oxobutan-2-yl)benzoate (362.3 mg).

LC-MS: 356 (M+H)$^+$ (1.08 min, Measurement Condition F)

d) Production of 3-(4-(methoxycarbonyl)phenyl)-3-methyl-2-(methylamino)butanoic Acid Under hydrogen atmosphere, a suspension of methyl 4-(4-(benzyloxy)-2-methyl-3-(methylamino)-4-oxobutan-2-yl)benzoate (362.3 mg), palladium-carbon (85.5 mg) and ethyl acetate (10 mL) was stirred at room temperature for 10 hours. After the reaction solution was filtered through filter paper, the solvent was distilled off under reduced pressure to give 3-(4-(methoxycarbonyl)phenyl)-3-methyl-2-(methylamino)butanoic acid. The compound obtained was used for reaction of Reference Example 100-g) without purification.

LC-MS: 266 (M+H)$^+$ (0.82 min, Measurement Condition F)

e) Production of di-tert-butyl ((S,E)-4-((S)-2-((tert-butoxycarbonyl)amino)-N,3,3-trimethylbutanamido)-2,5-dimethylhex-2-enoyl)-D-glutamate A mixed solution of (S,E)-4-((S)-2-((tert-butoxycarbonyl)amino)-N,3,3-trimethylbutanamido)-2,5-dimethylhex-2-enoic acid (220.2 mg), di-tert-butyl D-glutamate hydrochloride (254 mg), N-ethyl-N-isopropylpropan-2-amine (0.300 mL), 1-ethyl-3-(3-dimethyl aminopropyl)carbodiimide hydrochloride (220 mg), 1-hydroxybenzotriazole (175 mg) and N,N-dimethylformamide was stirred at room temperature for 17 hours. Ethyl acetate was added to the reaction solution. The organic layer was washed with water and saturated brine and then dried over anhydrous sodium sulfate, and the solvent was distilled off under reduced pressure. Di-tert-butyl ((S,E)-4-((S)-2-((tert-butoxycarbonyl)amino)-N,3,3-trimethylbutanamido)-2,5-dimethylhex-2-enoyl)-D-glutamate (232.4 mg) was obtained.

LC-MS: 626 (M+H)$^+$ (1.76 min, Measurement Condition F)

f) Production of Di-tert-butyl ((S,E)-4-((S)-2-amino-N,3,3-trimethylbutanamido)-2,5-dimethylhex-2-enoyl)-D-glutamate To a mixed solution of di-tert-butyl ((S,E)-4-((S)-2-((tert-butoxycarbonyl)amino)-N,3,3-trimethylbutanamido)-2,5-dimethylhex-2-enoyl)-D-glutamate (232.4 mg) and ethyl acetate (3.7 mL), a solution of hydrochloric acid (13.54 mg)

in ethyl acetate was added under ice cooling, and the resultant mixture was stirred at room temperature for 1 hour 20 minutes. The reaction solution was ice-cooled, 28% aqueous ammonia was added, and the resultant mixture was extracted with ethyl acetate. The organic layer was dried over anhydrous sodium sulfate, and the solvent was distilled off under reduced pressure to give di-tert-butyl ((S,E)-4-((S)-2-amino-N,3,3-trimethylbutanamido)-2,5-dimethylhex-2-enoyl)-D-glutamate (62.2 mg). The compound obtained was used for the subsequent reaction without purification.

LC-MS: 526 (M+H)$^+$ (1.14 min, Measurement Condition F)

g) Production of di-tert-butyl ((4S,E)-4-((2S)-2-(3-(4-(methoxycarbonyl)phenyl)-3-methyl-2-(methylamino)butanamido)-N,3,3-trimethylbutanamido)-2,5-dimethylhex-2-enoyl)-D-glutamate A suspension of 3-(4-(methoxycarbonyl)phenyl)-3-methyl-2-(methylamino)butanoic acid (31.4 mg), di-tert-butyl ((S,E)-4-((S)-2-amino-N,3,3-trimethylbutanamido)-2,5-dimethylhex-2-enoyl)-D-glutamate (62.2 mg), 1-ethyl-3-(3-dimethylaminopropyl)carbodiimide hydrochloride (45.4 mg), 1-hydroxybenzotriazole (32.0 mg), N-ethyl-N-isopropylpropan-2-amine (0.062 mL) and N,N-dimethylformamide (2 mL) was stirred at room temperature for 17 hours. The solvent was distilled off under reduced pressure. Ethyl acetate was added to the residue, the resultant mixture was washed with water, a saturated aqueous sodium bicarbonate solution and saturated brine, the organic layer was then dried over anhydrous sodium sulfate, and the solvent was distilled off under reduced pressure. The residue was purified by silica gel chromatography (eluting solvent; hexane:ethyl acetate) to give di-tert-butyl ((4 S,E)-4-((2S)-2-(3-(4-(methoxycarbonyl)phenyl)-3-methyl-2-(methylamino)butanamido)-N,3,3-trimethylbutanamido)-2,5-dimethylhex-2-enoyl)-D-glutamate (60.1 mg).

LC-MS: 774(M+H)$^+$ (1.341 min, Measurement Condition G)

h) Production of 4-((7R,12S,15S,E)-7-(tert-butoxycarbonyl)-15-(tert-butyl)-12-isopropyl-2,2,10,13,19-pentamethyl-18-(methylamino)-4,9,14,17-tetraoxo-3-oxa-8,13,16-triazaicos-10-en-19-yl)benzoic Acid To a mixed solution of tert-butyl ((4 S,E)-4-((2S)-2-(3-(4-(methoxycarbonyl)phenyl)-3-methyl-2-(methylamino)butanamido)-N,3,3-trimethylbutanamido)-2,5-dimethylhex-2-enoyl)-D-glutamate (56.3 mg), methanol (4 mL) and water (1 mL), lithium hydroxide (9.17 mg) was added under ice cooling, and the resultant mixture was stirred at room temperature for 17 hours. The solvent was distilled off under reduced pressure. The residue was purified by reversed phase HPLC (the mobile phase was water with 0.1% TFA/ acetonitrile with 0.035% TFA solvent) to give 4-((7R,12S,15S,E)-7-(tert-butoxycarbonyl)-15-(tert-butyl)-12-isopropyl-2,2,10,13,19-pentamethyl-18-(methylamino)-4,9,14,17-tetraoxo-3-oxa-8,13,16-triazaicos-10-en-19-yl)benzoic acid (14.8 mg).

LC-MS: 759(M+H)$^+$ (1.334 min, Measurement Condition G)

i) Production of Di-tert-butyl ((4S,E)-4-((2S)-2-(3-(4-((2-(2,5-dioxo-2,5-dihydro-1H-pyrrol-1-yl)ethyl)carbamoyl)phenyl)-3-methyl-2-(methylamino)butanamido)-N,3,3-trimethylbutanamido)-2,5-dimethylhex-2-enoyl)-D-glutamate (Reference Example 100)

A mixed solution of 4-((7R,12S,15S,E)-7-(tert-butoxycarbonyl)-15-(tert-butyl)-12-isopropyl-2,2,10,13,19-pentamethyl-18-(methylamino)-4,9,14,17-tetraoxo-3-oxa-8,13,16-triazaicos-10-en-19-yl)benzoic acid (14.8 mg), 3-(((ethylimino)methylene)amino)-N,N-dimethylpropan-1-amine hydrochloride (7.48 mg), 1-hydroxybenzotriazole (5.97 mg), N-ethyl-N-isopropylpropan-2-amine (0.014 mL), 1-(2-aminoethyl)-pyrrole-2,5-dione hydrochloride (6.86 mg) and N,N-dimethylformamide (2 mL) was stirred at room temperature for 3 hours. Ethyl acetate was added, the resultant mixture was washed with a saturated aqueous sodium bicarbonate solution and saturated brine, the organic layer was then dried over anhydrous sodium sulfate, and the solvent was distilled off under reduced pressure. The residue was purified by silica gel chromatography (eluting solvent; chloroform:methanol) to give Reference Example 100 (9.00 mg).

LC-MS: 881(M+H)$^+$ (1.287 min, Measurement Condition G)

Reference Example M1

(3S,6S,9S,10E,14R)-6-tert-Butyl-14-(3-{[2-(2,5-dioxo-2,5-dihydro-1H-pyrrol-1-yl)ethyl]amino}-3-oxopropyl)-8,11-dimethyl-3-[2-(1-methyl-1H-indol-3-yl)propan-2-yl]-4,7,12-trioxo-9-(propan-2-yl)-2,5,8,13-tetraazapentadec-10-en-15-oic Acid

[Chemical Formula 64]

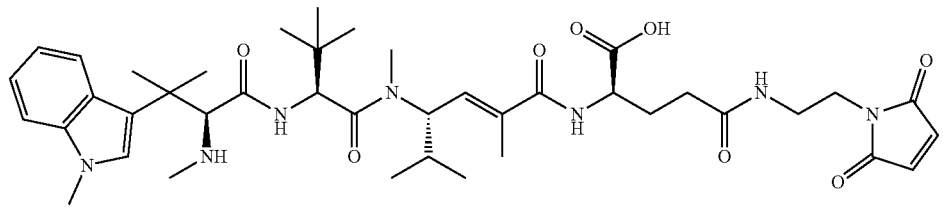

Reference Example M1

To a solution of Reference Example 1 (14 mg) in chloroform (1.0 mL), trifluoroacetic acid (0.2 mL) was added, and the resultant mixture was stirred at 25° C. for 4 hours. Thereafter, trifluoroacetic acid (0.2 mL) was further added, and the resultant mixture was additionally stirred at 25° C. for 2 hours. After the reaction ended, the solvent was distilled off under reduced pressure, and the residue was purified by reversed phase column chromatography (eluting solvent; acetonitrile with 0.1% TFA:water) to give Reference Example M1 (2.8 mg).

LC-MS: 778 (M+H)$^+$, 776 (M−H)$^−$ (1.081 min, Measurement Condition D)

Reference Example M2

N-{(2E,4S)-2,5-Dimethyl-4-[methyl(N,β,β,1-tetramethyl-L-tryptophyl-3-methyl-L-valyl)amino]hex-2-enoyl}-D-γ-glutamyl-N$^6$-[6-(2,5-dioxo-2,5-dihydro-1H-pyrrol-1-yl)hexanoyl]-L-lysine

[Chemical Formula 65]

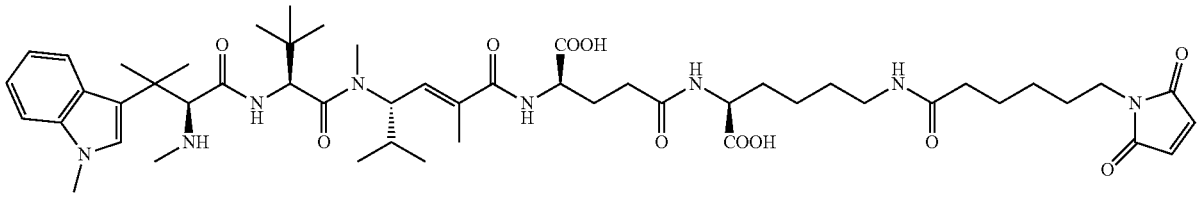

Reference Example M2

A mixed solution of Reference Example 4 (7.2 mg), N-succinimidyl 6-maleimidehexanoate (2.8 mg), N,N-diisopropylethylamine (2.3 mg) and N,N-dimethylformamide (1 mL) was stirred at 25° C. for 18 hours. After the reaction ended, the reaction solution was purified by reversed phase column chromatography (eluting solvent; acetonitrile with 0.1% TFA:water) to give Reference Example M2 (2.8 mg).

LC-MS: 977 (M+H)$^+$, 975 (M−H)$^−$ (1.061 min, Measurement Condition D)

Reference Examples M3 to M51

The compounds shown in the following Table 11 were obtained through the same reaction and treatment as Reference Example M1, Reference Example M2 or step p) of Reference Example 1, using corresponding raw material compounds.

TABLE 11

| Reference Example | Structural Formula | LC-MS/ Rt (min) | LC-MS Measurement Condition |
|---|---|---|---|
| M3 | | 907 (M + H)⁺ 1.045 | D |
| M4 | | 725 (M + H)⁺ 0.821 | D |
| M5 | | 854 (M + H)⁺ 0.902 | D |
| M6 | | 983 (M + H)⁺ 1.003 | D |

TABLE 11-continued

| Reference Example | Structural Formula | LC-MS/ Rt (min) | LC-MS Measurement Condition |
|---|---|---|---|
| M7 | | 843 (M + H)+ 1.005 | D |
| M8 | | 820 (M + H)+ 1.014 | D |
| M9 | | 711 (M + H)+ 0.979 | G |
| M10 | | 711 (M + H)+ 0.924 | G |

TABLE 11-continued

| Reference Example | Structural Formula | LC-MS/ Rt (min) | LC-MS Measurement Condition |
|---|---|---|---|
| M11 | | 725 (M + H)+ 1.120 | G |
| M12 | | 725 (M + H)+ 0.896 | G |
| M13 | | 711 (M + H)+ 0.839 | G |
| M14 | | 711 (M + H)+ 0.838 | G |

TABLE 11-continued
| Reference Example | Structural Formula | LC-MS/ Rt (min) | LC-MS Measurement Condition |
|---|---|---|---|
| M15 | 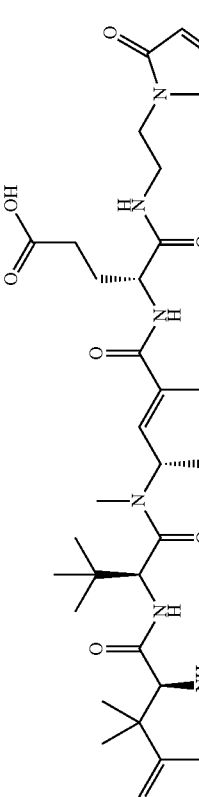 | 725 (M + H)+/ 0.847 | G |
| M16 | 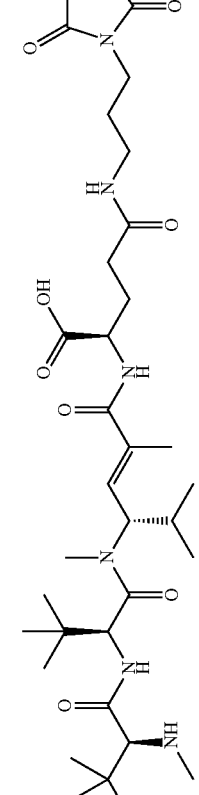 | 739 (M + H)+/ 0.852 | G |
| M17 | 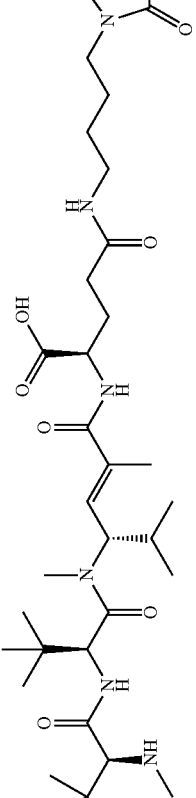 | 753 (M + H)+/ 1.059 | G |
| M18 | 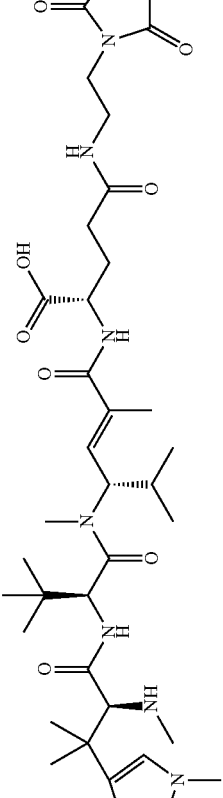 | 778 (M + H)+/ 1.174 | G |

TABLE 11-continued

| Reference Example | Structural Formula | LC-MS/ Rt (min) | LC-MS Measurement Condition |
|---|---|---|---|
| M19 | | 764 (M + H)+ 1.108 | G |
| M20 | | 764 (M + H)+ 1.077 | G |
| M21 | | 764 (M + H)+ 1.023 | G |
| M22 | | 778 (M + H)+ 1.043 | G |

TABLE 11-continued
| Reference Example | Structural Formula | LC-MS/ Rt (min) | LC-MS Measurement Condition |
|---|---|---|---|
| M23 | 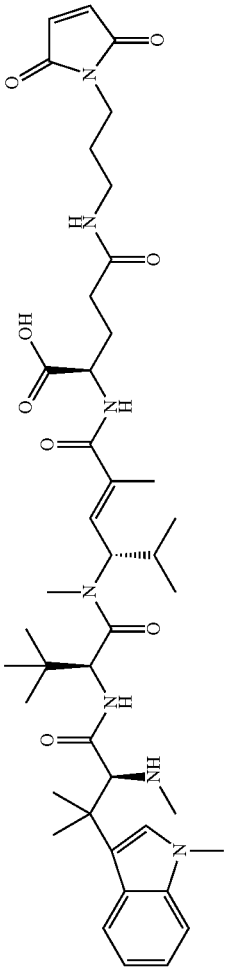 | 792 (M + H)+ / 1.122 | G |
| M24 | 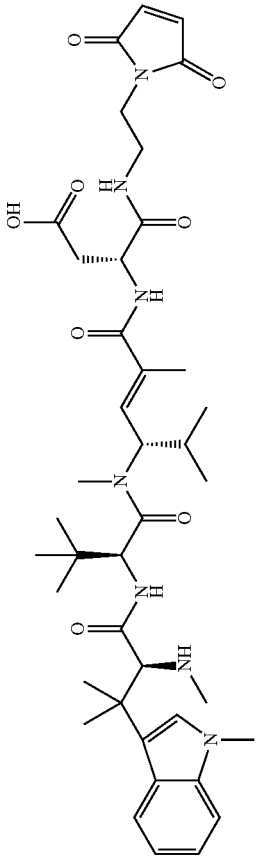 | 764 (M + H)+ / 1.086 | G |
| M25 | 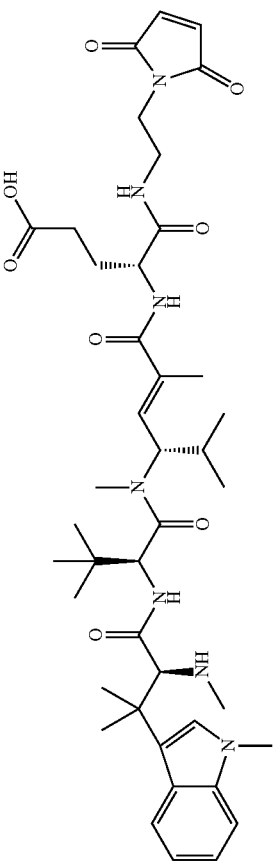 | 778 (M + H)+ / 1.081 | G |
| M26 | 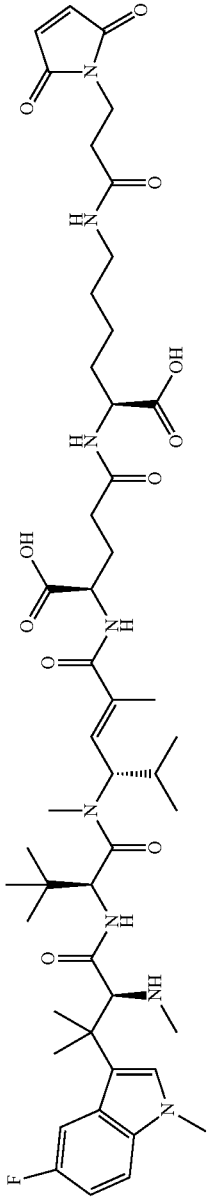 | 951 (M − H)− / 1.011 | G |

TABLE 11-continued

| Reference Example | Structural Formula | LC-MS/ Rt (min) | LC-MS Measurement Condition |
|---|---|---|---|
| M27 | | 820 (M + H)+ 1.027 | G |
| M28 | | 767 (M + H)+ 0.969 | G |
| M29 | | 674 (M − H)− 1.02 | G |

TABLE 11-continued

| Reference Example | Structural Formula | LC-MS/ Rt (min) | LC-MS Measurement Condition |
|---|---|---|---|
| M30 | | 770 (M + H)+ / 0.997 | G |
| M31 | | 791 (M − H)− / 1.07 | G |
| M32 | | 741 (M − H)− / 0.99 | G |
| M33 | | 729 (M − H)− / 1.18 | G |

TABLE 11-continued

| Reference Example | Structural Formula | LC-MS/Rt (min) | LC-MS Measurement Condition |
|---|---|---|---|
| M34 | | 739 (M − H)⁻/1.05 | G |
| M35 | | 748 (M − H)⁻/1.03 | G |
| M36 | | 767 (M − H)⁻/0.98 | G |
| M37 | | 755 (M + H)⁺/0.99 | G |
| M38 | | 753 (M + H)⁺/1.05 | G |

TABLE 11-continued

| Reference Example | Structural Formula | LC-MS/ Rt (min) | LC-MS Measurement Condition |
|---|---|---|---|
| M39 | | 731 (M + H)+ 0.94 | G |
| M40 | | 775 (M + H)+ 1.019 | G |
| M41 | | 799 (M − H)− 1.13 | G |
| M42 | | 737 (M − H)− 0.96 | G |
| M43 | | 687 (M − H)− 0.82 | G |

TABLE 11-continued

| Reference Example | Structural Formula | LC-MS/ Rt (min) | LC-MS Measurement Condition |
|---|---|---|---|
| M44 | | 801 (M − H)⁻/ 0.96 | F |
| M45 | | 801 (M − H)⁻/ 1.02 | G |
| M46 | | 823 (M − H)⁻/ 1.28 | G |
| M47 | | 769 (M + H)⁺/ 0.919 | G |

TABLE 11-continued

| Reference Example | Structural Formula | LC-MS/ Rt (min) | LC-MS Measurement Condition |
|---|---|---|---|
| M48 | | 835 (M + H)+ 1.396 | D |
| M49 | | 711 (M + H)+ 1.263 | G |
| M50 | | 649 (M + H)+ 0.981 | G |
| M51 | | 596 (M + H)+ 1.203 | G |

Reference Example M52

N²—((S,E)-4-((S)-2-((S)-2-(Dimethyl amino)-3-methyl-3-phenylbutanamido)-N,3,3-trimethylbutanamido)-2,5-dimethylhex-2-enoyl)-N⁵-(2-(2,5-dioxo-2,5-dihydro-1H-pyrrolo-1-yl)ethyl)-D-glutamine

[Chemical Formula 66]

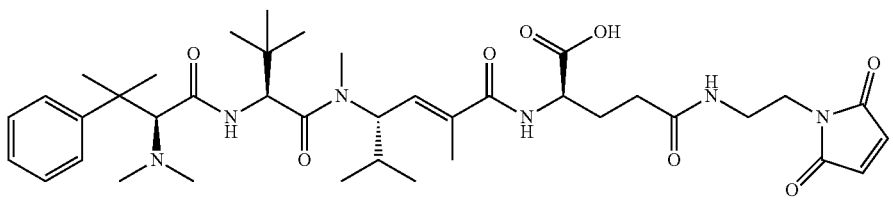

Reference Example M52

To a solution of monotrifluoroacetate of Reference Example M4 (10 mg) in acetonitrile (1 mL), an aqueous formaldehyde solution (1 mL) was added, sodium triacetoxyborate (15 mg) was added, and the resultant mixture was stirred at room temperature for 3 hours. The reaction solution was concentrated, and then purified by reversed phase HPLC (the mobile phase was water with 0.1% TFA/acetonitrile with 0.035% TFA solvent) to give Reference Example M52 (5.4 mg). LC-MS: 739 (M+H)⁺ (1.007 min, Measurement Condition G)

Reference Example ADC1

Brentuximab-Reference Example M4 Conjugate (Average Drug Antibody Ratio: 8.00)

[Chemical Formula 67]

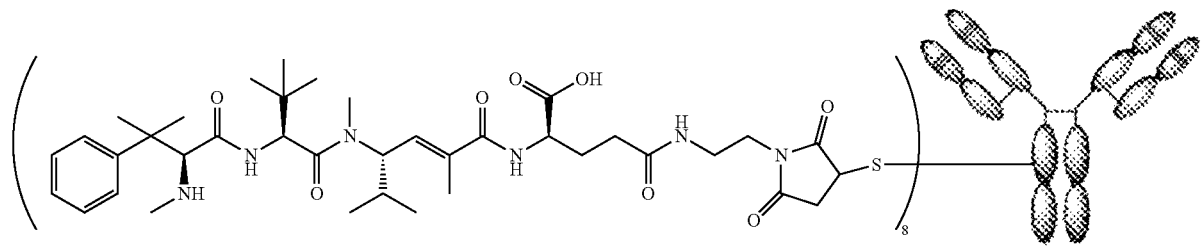

Reference Example ADC1

To a phosphate buffered saline solution (1.4 mL) of brentuximab (100 mg), a trishydroxymethylaminomethane hydrochloride buffered solution (13.3 mL) of 1 mmol/L tris(2-carboxyethyl)phosphine (TCEP) was added, and the resultant solution was incubated at 37° C. for 45 minutes. After cooling the antibody solution to 0° C., through treatment with a PD-10 desalination column pre-equilibrated with a phosphate buffered saline solution, a phosphate buffered saline solution of the reduced brentuximab was obtained. After cooling this to 0° C., a 1 mmol/L DMSO solution (6.6 mL) of Reference Example M4 10 times diluted with a phosphate buffered saline solution was added and completely mixed, and the resultant solution was incubated at 4° C. for 17 hours. Thereafter, through purification by a PD-10 desalination column pre-equilibrated with a phosphate buffered saline solution and subsequent centrifugal concentration, Reference Example ADC1 (68.7 mg) was obtained.

The average DAR of the ADC thus obtained was measured by reducing or non-reducing SDS-PAGE, or HPLC-HIC. Alternatively, the average DAR may be measured qualitatively or quantitatively by ultraviolet-visible absorption spectroscopy (UV-Vis), reducing or non-reducing SDS-PAGE, HPLC-HIC, SEC, RP-HPLC, LC-MS or the like. These techniques are described in Antibody Drug Conjugates, Methods in Molecular Biology vol. 1045, 2013. pp 267-284. L. Ducry, Ed.

HPLC-HIC analysis (measurement condition E) was carried out for Reference Example ADC1 obtained through the above protocol, and the result was that Rt of the peak of Reference Example ADC1, the DAR of which was 8, was 4.89 min.

Reference Examples ADC2 to ADC46

The ADCs shown in the following Table 12 were obtained through the same reaction and treatment as Reference Example ADC1, using corresponding antibodies and modifying agents (compounds of Reference Examples).

[Chemical Formula 68]

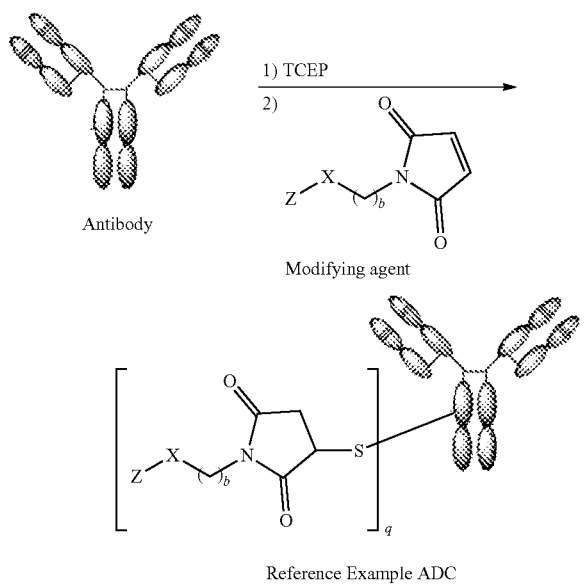

Reference Example ADC

TABLE 12

| Compound | Antibody (mAb) | Modifying agent | Average DAR (q) | HIC retention time (min) |
|---|---|---|---|---|
| Comparative Example ADC1 | Brentuximab | Comparative Example compound 1 | 7.65 | 7.30 |
| Reference Example ADC2 | Brentuximab | Reference Example M1 | 8 | 5.94 |
| Reference Example ADC3 | Brentuximab | Reference Example M2 | 7.31 | 5.45 |
| Reference Example ADC4 | Brentuximab | Reference Example M3 | 7.55 | 5.67 |
| Reference Example ADC5 | Brentuximab | Reference Example M5 | 8 | 4.75 |
| Reference Example ADC6 | Brentuximab | Reference Example M6 | 8 | 4.66 |
| Reference Example ADC7 | Brentuximab | Reference Example M7 | 8 | 4.42 |
| Reference Example ADC8 | Brentuximab | Reference Example M8 | 6.79 | 6.01 |
| Reference Example ADC9 | Trastuzumab | Reference Example M1 | 7.30 | 5.41 |
| Reference Example ADC10 | Trastuzumab | Reference Example M4 | 7.70 | 5.94 |
| Reference Example ADC11 | Brentuximab | Reference Example M9 | 8 | 5.72 |
| Reference Example ADC12 | Brentuximab | Reference Example M27 | 8 | 7.08 |
| Reference Example ADC13 | Brentuximab | Reference Example M10 | 8 | 5.77 |
| Reference Example ADC14 | Brentuximab | Reference Example M11 | 8 | 6.02 |
| Reference Example ADC15 | Brentuximab | Reference Example M12 | 8 | 5.45 |
| Reference Example ADC16 | Brentuximab | Reference Example M13 | 8 | 5.88 |
| Reference Example ADC17 | Brentuximab | Reference Example M14 | 8 | 5.69 |
| Reference Example ADC18 | Brentuximab | Reference Example M15 | 7.03 | 5.89 |
| Reference Example ADC19 | Brentuximab | Reference Example M16 | 8 | 6.03 |
| Reference Example ADC20 | Brentuximab | Reference Example M17 | 7.76 | 6.08 |
| Reference Example ADC21 | Brentuximab | Reference Example M18 | 7.70 | 6.80 |
| Reference Example ADC22 | Brentuximab | Reference Example M19 | 7.82 | 6.56 |
| Reference Example ADC23 | Brentuximab | Reference Example M20 | 7.73 | 6.6 |
| Reference Example ADC24 | Brentuximab | Reference Example M21 | 7.75 | 6.54 |
| Reference Example ADC25 | Brentuximab | Reference Example M22 | 7.74 | 6.57 |
| Reference Example ADC26 | Brentuximab | Reference Example M23 | 7.8 | 6.86 |
| Reference Example ADC27 | Brentuximab | Reference Example M24 | 7.64 | 6.67 |
| Reference Example ADC28 | Brentuximab | Reference Example M25 | 7.7 | 6.73 |
| Reference Example ADC 29 | Brentuximab | Reference Example M28 | 7.5 | 6.79 |
| Reference Example ADC 30 | Brentuximab | Reference Example M42 | Production of ADC was confirmed by SDS-PAGE | |
| Reference Example ADC 31 | Brentuximab | Reference Example M26 | Production of ADC was confirmed by SDS-PAGE | |
| Reference Example ADC 32 | Brentuximab | Reference Example M41 | Production of ADC was confirmed by SDS-PAGE | |
| Reference Example ADC 33 | Brentuximab Example M36 | Reference | 8 | 4.02 |
| Reference Example ADC 34 | Brentuximab | Reference Example M35 | 7.72 | 5.38 |
| Reference Example ADC 35 | Brentuximab | Reference Example M34 | 8 | 4.62 |
| Reference Example ADC 36 | Brentuximab | Reference Example M33 | 7.79 | 4.95 |
| Reference Example ADC 37 | Brentuximab | Reference Example M45 | 7.7 | 6.98 |
| Reference Example ADC 38 | Brentuximab | Reference Example M43 | 8 | 3.80 |
| Reference Example ADC 39 | Brentuximab | Reference Example M31 | 7.7 | 7.38 |
| Reference Example ADC 40 | Brentuximab | Reference Example M32 | 7.76 | 5.32 |
| Reference Example ADC 41 | Brentuximab | Reference Example M47 | 8 | 3.83 |
| Reference Example ADC 42 | Brentuximab | Reference Example M29 | 8 | 3.94 |
| Reference Example ADC 43 | Brentuximab | Reference Example M46 | Production of ADC was confirmed by SDS-PAGE | |
| Reference Example ADC 44 | Brentuximab | Reference Example M30 | Production of ADC was confirmed by SDS-PAGE | |
| Reference Example ADC 45 | Brentuximab | Reference Example M48 | 8 | 5.75 |
| Reference Example ADC 46 | Brentuximab | Reference Example M50 | Production of ADC was confirmed by SDS-PAGE | |

The Rt (min) of the Example ADCs in the above Table 12 is that of the peak of ADCs with a DAR of 8, observed by HPLC-HIC analysis (measurement condition E). The Rt (min) of the ADC of Comparative Example 3 is that of the peak of ADC with a DAR of 8.

Comparative Example compound 1 in the above Table 12 refers to the following compound disclosed in International Publication No. WO 2014/057436 (Patent Literature 8).

[Chemical Formula 69]

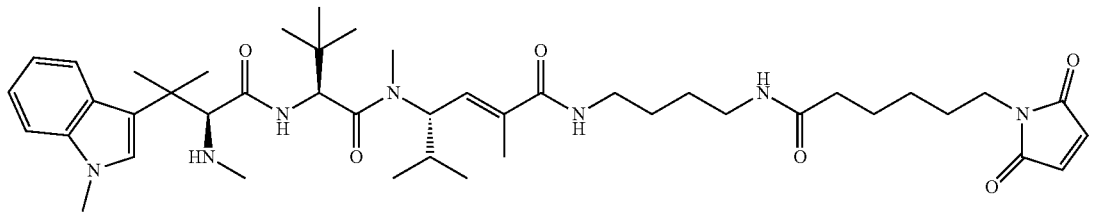

Comparative Example coupound 1

"Production of ADC was confirmed by SDS-PAGE" means that bands were strongly detected in the vicinity of a molecular weight of 50 kDa and a molecular weight of 25 kDa as a result of SDS-PAGE analysis for Reference Example ADC under disulfide non-reducing conditions, using SeeBlue (R) Plus2 (Thermo Fisher Scientific K.K.) as a marker. This indicates that the modifying agent conjugates to the cysteine residues involved in the disulfide bonds between the light chains and heave chains and of the hinge of the antibody, which means that an ADC is obtained.

Example MM1

(3S,6S,9S,10E,14R)-14-(3-{[2-(3-{[(2R)-2-Amino-2-carboxyethyl]sulfanyl}-2,5-dioxopyrrolidin-1-yl)ethyl]amino}-3-oxopropyl)-6-tert-butyl-8,11-dimethyl-4,7,12-trioxo-3-(2-phenylpropan-2-yl)-9-(propan-2-yl)-2,5,8,13-tetraazapentadec-10-en-15-oic Acid

[Chemical Formula 70]

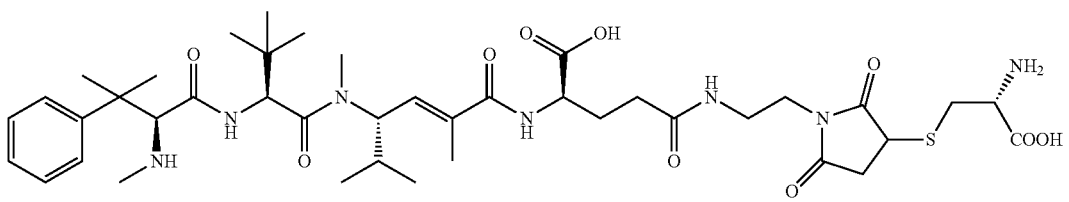

To an aqueous solution (1.0 mL) of Reference Example M4 (10 mg), cysteine (1.73 mg) was added, and the resultant mixture was stirred at 4° C. for 1 hour. Thereafter, the reaction solution was purified by reversed phase column chromatography (eluting solvent; acetonitrile with 0.1% TFA:water) to give Example MM1 (10 mg).

LC-MS: 846 (M+H)$^+$, 844 (M−H)$^-$ (0.855 min, Measurement Condition B)

Examples MM2 to MM47

The compounds shown in the following Table 13 were obtained through the same reaction and treatment as Example MM1, using corresponding raw material compounds.

TABLE 13

| Example | Structural Formula | LC-MS/ Rt (min) | LC-MS Measurement Condition |
|---|---|---|---|
| MM2 | | 1096 (M − H)⁻/0.894 | B |
| MM3 | | 1026 (M − H)⁻/0.890 | B |
| MM4 | | 897 (M − H)⁻/0.879 | B |
| MM5 | | 939 (M − H)⁻/1.255 | B |

TABLE 13-continued

| Example | Structural Formula | LC-MS/Rt (min) | LC-MS Measurement Condition |
|---|---|---|---|
| MM6 | | 973 (M−H)/0.810 | B |
| MM7 | | 1102 (M−H)/0.835 | B |
| MM8 | | 973 (M−H)/0.813 | B |
| MM9 | | 830 (M−H)/0.800 | B |

TABLE 13-continued

| Example | Structural Formula | LC-MS/Rt (min) | LC-MS Measurement Condition |
|---|---|---|---|
| MM10 | | 830 (M − H)/0.823 | B |
| MM11 | | 844 (M − H)/0.805 | B |
| MM12 | | 844 (M − H)/0.837 | B |
| MM13 | | 830 (M − H)/0.829 | B |

TABLE 13-continued

| Example | Structural Formula | LC-MS/Rt (min) | LC-MS Measurement Condition |
|---|---|---|---|
| MM14 | | 830 (M−H)⁻/0.830 | B |
| MM15 | | 844 (M−H)⁻/0.808 | B |
| MM16 | | 858 (M−H)⁻/0.819 | B |
| MM17 | | 872 (M−H)⁻/0.819 | B |

TABLE 13-continued

| Example | Structural Formula | LC-MS/ Rt (min) | LC-MS Measurement Condition |
|---|---|---|---|
| MM18 | | 897 (M − H)⁻/0.866 | B |
| MM19 | | 883 (M − H)⁻/0.853 | B |
| MM20 | | 883 (M − H)⁻/0.843 | B |
| MM21 | | 883 (M − H)⁻/0.863 | B |

TABLE 13-continued

| Example | Structural Formula | LC-MS/Rt (min) | LC-MS Measurement Condition |
|---|---|---|---|
| MM22 | | 897 (M − H)−/0.865 | B |
| MM23 | | 911 (M − H)−/0.868 | B |
| MM24 | | 883 (M − H)−/0.876 | B |

TABLE 13-continued

| Example | Structural Formula | LC-MS/Rt (min) | LC-MS Measurement Condition |
|---|---|---|---|
| MM25 | | 897 (M−H)/0.877 | B |
| MM26 | | 1072 (M−H)/0.873 | B |
| MM27 | | 939 (M−H)/1.264 | B |
| MM28 | | 886 (M−H)/0.842 | B |

TABLE 13-continued
| Example | Structural Formula | LC-MS/Rt (min) | LC-MS Measurement Condition |
|---|---|---|---|
| MM29 | 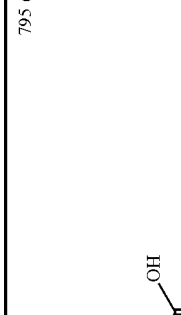 | 795 (M − H)⁻/0.825 | B |
| MM30 | 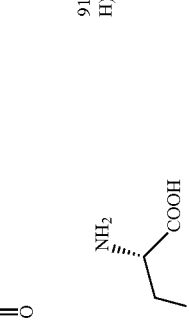 | 912 (M − H)⁻/0.888 | B |
| MM31 |  | 862 (M − H)⁻/0.838 | B |
| MM32 |  | 850 (M − H)⁻/0.859 | B |

TABLE 13-continued

| Example | Structural Formula | LC-MS/Rt (min) | LC-MS Measurement Condition |
|---|---|---|---|
| MM33 | | 860 (M − H)/0.788 | B |
| MM34 | | 869 (M − H)/0.806 | B |
| MM35 | | 888 (M − H)/0.785 | B |
| MM36 | | 874 (M − H)/0.823 | B |

TABLE 13-continued

| Example | Structural Formula | LC-MS/Rt (min) | LC-MS Measurement Condition |
|---|---|---|---|
| MM37 | | 872 (M − H)⁻/0.868 | B |
| MM38 | | 894 (M − H)⁻/0.899 | B |
| MM39 | | 920 (M − H)⁻/0.929 | B |
| MM40 | | 858 (M − H)⁻/0.836 | B |

TABLE 13-continued

| Example | Structural Formula | LC-MS/Rt (min) | LC-MS Measurement Condition |
|---|---|---|---|
| MM41 | | 808 (M − H)−/0.741 | B |
| MM42 | | 922 (M − H)−/0.877 | B |
| MM43 | | 888 (M − H)−/0.791 | B |
| MM44 | | 954 (M − H)−/1.014 | B |

TABLE 13-continued

| Example | Structural Formula | LC-MS/Rt (min) | LC-MS Measurement Condition |
|---|---|---|---|
| MM45 | | 830 (M − H)⁻/0.807 | B |
| MM46 | | 858 (M − H)⁻/0.826 | B |
| MM47 | | 1030 (M − H)⁻/0.837 | B |

Examples MM48 to MM67

The compounds shown in the following Table 14 were obtained through the same reaction and treatment as Example MM1, using corresponding raw material compounds.

[Chemical Formula 71]

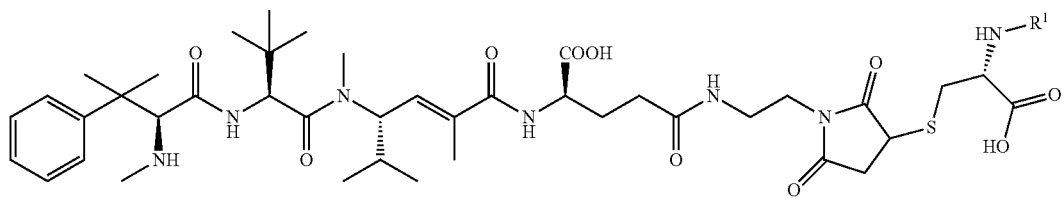

TABLE 14

| Example | R¹ | LC-MS/ RT (min) | LC-MS Measurement Condition |
|---|---|---|---|
| MM48 |  | 915 (M − H)⁻/0.780 | B |
| MM49 |  | 1000 (M − H)⁻/0.919 | B |
| MM50 |  | 958 (M − H)⁻/0.940 | B |
| MM51 |  | 959 (M − H)⁻/0.792 | B |
| MM52 |  | 972 (M − H)⁻/0.847 | B |
| MM53 |  | 973 (M − H)⁻/0.801 | B |
| MM54 |  | 901 (M − H)⁻/0.826 | B |
| MM55 |  | 981 (M − H)⁻/0.806 | B |
| MM56 |  | 957 (M − H)⁻/0.919 | B |
| MM57 |  | 957 (M − H)⁻/0.954 | B |
| MM58 |  | 972 (M − H)⁻/0.936 | B |
| MM59 |  | 975 (M − H)⁻/0.820 | B |

TABLE 14-continued

| Example | R¹ | LC-MS/ RT (min) | LC-MS Measurement Condition |
|---|---|---|---|
| MM60 | (S)-2-amino-3-phenylpropanoyl | 991 (M − H)⁻/0.828 | B |
| MM61 | prolyl | 941 (M − H)⁻/0.844 | B |
| MM62 | seryl | 931 (M − H)⁻/0.770 | B |
| MM63 | threonyl | 945 (M − H)⁻/0.810 | B |
| MM64 | tryptophyl | 1030 (M − H)⁻/0.846 | B |
| MM65 | tyrosyl | 1007 (M − H)⁻/0.803 | B |
| MM66 | valyl | 943 (M − H)⁻/0.839 | B |
| MM67 | (glycyl-glutamyl) | 1030 (M − H)⁻/1.002 | B |

Examples MM68 to MM70

The compounds shown in the following Table 15 were obtained through the same reaction and treatment as Example MM1, using corresponding raw material compounds.

[Chemical Formula 72]

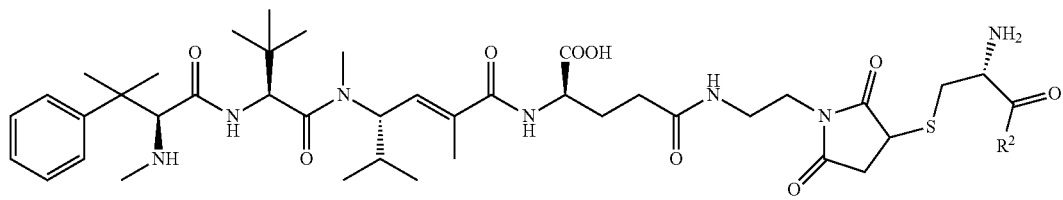

TABLE 15

| Example | R² | LC-MS/ Rt (min) | LC-MS Measurement Condition |
|---|---|---|---|
| MM68 | 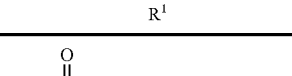 | 959 (M − H)⁻/0.959 | B |

TABLE 15-continued

| Example | R² | LC-MS/ Rt (min) | LC-MS Measurement Condition |
|---|---|---|---|
| MM69 | (structure) | 941 (M − H)⁻/ 1.008 | B |
| MM70 | (structure) | 931 (M − H)⁻/ 0.965 | B |

Comparative Example compound 2 refers to the following compound obtained through the same reaction and treatment as Example MM1, using a compound disclosed in International Publication No. WO 2014/057436 (Patent Literature 8).

[Chemical Formula 73]

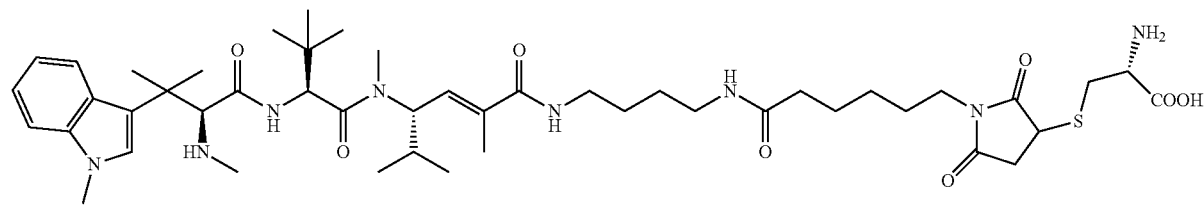

Comparative Example compound 2

Test Examples

Hereinafter, results of pharmacological tests with respect to particular Examples of the hemiasterlin derivative according to the present invention will be shown and their pharmacological actions will be explained, but the present invention is not limited to compounds shown in these Test Examples.

Test Example 1: Evaluation of Activity for Inhibiting Microtubule Polymerization Using Porcine Tubulins (1)

Using a tubulin polymerization inhibition assay kit (catalog number: BK006P) purchased from Cytoskeleton Inc., the polymerization inhibitory activity of compounds of Examples with a concentration of 9.1 μM was evaluated in accordance with the protocol appended to the kit. In summary of the protocol, to a 96 well microplate, 80 mM PIPES pH 6.9, 2 mM MgCl, 0.5 mM EGTA and 5% DMSO buffered solution of the compound to be evaluated was added in an amount of 10 μL for each well, and to these wells, 3 mg/ml porcine tubulin 80 mM PIPES pH 6.9, 2 mM MgCl, 0.5 mM EGTA, 1 mM GTP and 10.2% glycerol solution was added in an amount of 100 μL for each well. In order to examine a state in which tubulins polymerize over time, the absorbance at 340 nm was measured at 37° C., using a microplate reader. As the polymerization of tubulins progresses, the absorbance at 340 nm rises. The results are shown in FIG. 1.

As shown in FIG. 1, Examples MM1 and MM47 exhibited activities for inhibiting microtubule polymerization in the microtubule polymerization inhibition evaluation test.

Test Example 2: Evaluation of Activity for Inhibiting Microtubule Polymerization Using Porcine Tubulins (2)

Using a tubulin polymerization inhibition assay kit (catalog number: BK006P) purchased from Cytoskeleton Inc., the polymerization inhibitory activity of compounds of Examples with a concentration of 9.1 μM was evaluated in accordance with the protocol appended to the kit. To a 96 well microplate, 80 mM PIPES pH 6.9, 2 mM MgCl, 0.5 mM EGTA and 5% DMSO buffered solution of the compound to be evaluated was added in an amount of 10 μL for each well, and to these wells, 3 mg/mL porcine tubulin 80 mM PIPES pH 6.9, 2 mM MgCl, 0.5 mM EGTA, 1 mM GTP and 10.2% glycerol solution was added in an amount of 100 μL for each well. In order to examine a state in which tubulins polymerize over time, the absorbance at 340 nm was measured at 37° C., using a microplate reader. As the polymerization of tubulins progresses, the absorbance at 340 nm rises.

The tubulin polymerization inhibitory activity was evaluated based on the proportion of polymerized tubulins 60 minutes after the assay initiation. Specifically, the microtubule polymerization rate (%) was calculated by dividing the absorbance of tubulins that had polymerized at wells to which the compound had been added by the absorbance of tubulins that had polymerized at wells to which the compound had not been added, and multiplying the obtained value by 100. The results are shown in Table 16.

TABLE 16

| Compound | Microtubule polymerization rate (%) |
|---|---|
| Comparative Example compound 2 | 0 |
| Example MM1 | 9 |
| Example MM5 | 2 |
| Example MM11 | 0 |
| Example MM15 | 0 |
| Example MM17 | 0 |
| Example MM18 | 0 |
| Example MM23 | 0 |
| Example MM28 | 0 |
| Example MM30 | 12 |
| Example MM32 | 0 |
| Example MM45 | 56 |

TABLE 16-continued

| Compound | Microtubule polymerization rate (%) |
|---|---|
| Example MM46 | 0 |
| Example MM47 | 6 |

It is indicated that the lower value the microtubule polymerization rate is, the more strongly the compound inhibits polymerization of microtubules.

Test Examples 3: Cellular Toxicity Test (1)

Karpas-299 cells (European Collection of Authenticated Cell Cultures, hereinafter, ECACC), which are human lymphoma cell lines, were cultured in RPMI 1640 (GIBCO) containing 10% fetal bovine serum (MP Biomedicals) (hereinafter, referred to as the "culture medium"). Cells were prepared to be $2 \times 10^5$ cells/mL in the culture medium, and were added to a 96 well microplate for cell culturing in an amount of 50 μL for each well. Compounds of Examples or the Comparative Example compound 4 times diluted with the culture medium in 8 stages were added to the microplate in an amount of 50 μL for each well. These were cultured at 37° C. under 5% $CO_2$ for 4 days. After culturing, the microplate was taken out from the incubator, and was left at rest at room temperature for 10 minutes. To each well, 50 μL of CellTiter-Glo Luminescent Cell Viability Assay (Promega) was added, and the resultant mixture was stirred. This mixture was incubated at a dark place for 20 minutes. Using a microplate luminometer, luminescence at each well was measured, thereby calculating the cell viability. From the value of the cell viability, the $IC_{50}$ value was calculated. The results are shown in Table 17.

The $IC_{50}$ value was calculated by the following formula:

$IC_{50}(nM) = \text{antilog}(\text{LOG}_{10}(a/b) \times (e-d)/(c-d) + \text{LOG}_{10}b)$ a: concentration a of test substance
b: concentration b of test substance
c: cell viability upon adding test substance with concentration a
d: cell viability upon adding test substance with concentration b
e: intermediate value between maximum and minimum among cell viabilities upon adding test substances with different concentrations (a and b are concentrations crossing the cell viability e, and a>b is indicated).

The cell viability at each concentration was calculated by the following formula:

Cell Viability (%) = a'/b' × 100 a': mean value of luminescence amount of wells to which test substance was added (n=6)
b': mean value of luminescence amount of wells to which test substance was not added (n=6)
(n represents the number of evaluations performed per test substance concentration).

TABLE 17

| Cell | Compound | IC$_{50}$ (nM) |
|---|---|---|
| Karpas-299 | Comparative Example compound 2 | 30 |
| | Example MM1 | >1000 |
| | Example MM2 | 459 |
| | Example MM3 | 387 |
| | Example MM4 | 289 |
| | Example MM5 | >1000 |
| | Example MM6 | >1000 |
| | Example MM7 | >1000 |
| | Example MM8 | 284 |
| | Example MM9 | >1000 |
| | Example MM10 | >1000 |
| | Example MM11 | >1000 |
| | Example MM13 | >1000 |
| | Example MM14 | >1000 |
| | Example MM15 | >1000 |
| | Example MM16 | 867 |
| | Example MM17 | 850 |
| | Example MM18 | 541 |
| | Example MM19 | 303 |
| | Example MM20 | 337 |
| | Example MM21 | 471 |
| | Example MM22 | 740 |
| | Example MM23 | 942 |
| | Example MM24 | 521 |
| | Example MM25 | 555 |
| | Example MM26 | 384 |
| | Example MM27 | >1000 |
| | Example MM28 | >1000 |
| | Example MM29 | >1000 |
| | Example MM30 | >1000 |
| | Example MM31 | >1000 |
| | Example MM32 | >1000 |
| | Example MM33 | 36 |
| | Example MM35 | >1000 |
| | Example MM36 | >1000 |
| | Example MM37 | >1000 |
| | Example MM38 | 726 |
| | Example MM39 | 118 |
| | Example MM40 | 146 |
| | Example MM43 | >1000 |
| | Example MM44 | >1000 |
| | Example MM45 | >1000 |
| | Example MM46 | >1000 |
| | Example MM47 | >1000 |
| | Example MM48 | 935 |
| | Example MM49 | >1000 |
| | Example MM50 | >1000 |
| | Example MM51 | 473 |
| | Example MM52 | >1000 |
| | Example MM53 | 416 |
| | Example MM54 | 453 |
| | Example MM55 | 554 |
| | Example MM56 | 581 |
| | Example MM57 | 686 |
| | Example MM58 | 712 |
| | Example MM59 | >1000 |
| | Example MM60 | 679 |
| | Example MM61 | >1000 |
| | Example MM62 | 512 |
| | Example MM63 | 768 |
| | Example MM64 | 370 |
| | Example MM65 | 311 |
| | Example MM66 | 955 |
| | Example MM67 | 684 |
| | Example MM68 | 443 |
| | Example MM69 | >1000 |
| | Example MM70 | 723 |

As shown in the above Table 17, the Comparative Example compound exhibited strong cellular toxicity to Karpas-299 cells. By contrast, compounds of Examples exhibited weak cellular toxicity to Karpas-299 cells.

Test Example 4: Lysosomal Metabolism Test for ADCs

Using human liver lysosomes (catalog number: H0610.L) and 10× catabolic buffer (catalog number: K5200) purchased from SEKISUI Xeno Tech, metabolism tests for Reference Example ADCs were evaluated in accordance with a protocol recommended by SEKISUI Xeno Tech. To a 1.5 mL Eppendorf tube, 70 µL of ultrapure water, 20 µL of 10× catabolic buffer, and 100 µL of human liver lysosomes 10 times diluted with ultrapure water were added, and 10 µL of the compound to be evaluated in phosphate buffered saline was added to this. The reaction solution was incubated at 37° C. for 16 hours, 200 µL of acetonitrile was then added, the resultant mixture was further incubated at 25° C. for 16 hours, and this was then analyzed by LC-MS. The analysis condition is as follows. The results for detected compounds are shown in Table 18.

(Analysis Condition)
  Mass spectrometer: 6500Qtrap (AB Sciex Pte. Ltd.) or Orbitrap Elite (Thermo Fisher Scientific K.K.)
  Spray Voltage: 3500 V
  Capillary Temperature: 400° C.
  HPLC: Ultimate3000 UPLC (Thermo Fisher Scientific K.K.)
  Column: InertSustain $C_{18}$ (GL Sciences, Inc., 3 µm, 2.1 mm×100 mm)
  Solvent: solution A: 0.1% $HCOOH/CH_3CN$, solution B: 0.1% $HCOOH/H_2O$
  Gradient Condition:
    0.0 min to 1.5 min; A/B=5:95
    1.5 to 11.0 min; Linear gradient from 5% to 95% A
    11.0 to 12.0 min; A/B=95:5
    12.0 to 15.0 min; A/B=5:95
  Flow Rate: 0.2 mL/min
  Column Temperature: 40° C.

TABLE 18

| Compound | Detected compound | LC-MS/min | Theoretical MS value |
|---|---|---|---|
| Reference Example ADC1 | Example MM1 | 423.7253 $(M + 2H)^{2+}/4.80$ | 423.7251 $(M + 2H)^{2+}$ |

As shown in the above Table 18, it was demonstrated that the hemiasterlin derivative according to the present invention is produced through metabolism of the antibody moiety of ADC by lysosomes.

Test Example 5: Metabolism Test for Anti-CD30 ADC Using Cells

Karpas-299 cells (European Collection of Authenticated Cell Cultures, hereinafter, ECACC), which are human lymphoma cell lines, were cultured in RPMI 1640 (GIBCO) containing 10% fetal bovine serum (MP Biomedicals) (hereinafter, referred to as the "culture medium"). Cells were prepared to be $2\times10^6$ cells/mL in the culture medium, and were added to a plate for cell culturing in an amount of 3 mL, and 1.5 µL of Reference Example ADC1 in a concentration of 30 mg/mL was then added. This was cultured at 37° C. under 5% $CO_2$ for 1 day. After culturing, the cell suspension was separated into cell pellets and culture solution by centrifugation (at 2000 g for 5 minutes). To the culture solution collected, 4 mL of acetonitrile was added, and the resulting mixture was then incubated at 25° C. for 18 hours. After the incubation, the acetonitrile suspension was centrifuged (at 2500 g for 5 minutes) to collect the supernatant, the pH of this was changed to about 4 with acetic acid, and this was then lyophilized to give a white solid. On the other hand, the cell pellets were washed twice with 3 mL of phosphate buffered saline, 0.3 mL of Tris buffered saline and 0.6 mL of acetonitrile were then added, and this was incubated at 25° C. for 18 hours. After the incubation, the acetonitrile suspension was centrifuged (at 2500 g for 5 minutes) to collect the supernatant, the pH of this was changed to about 4 with acetic acid, and this was then lyophilized to give a white solid. The resultant sample was dissolved in an aqueous solution (3 mL) with 0.1% formic acid/10% acetonitrile, and 5 µL thereof was analyzed by LC-MS. The analysis condition is as follows. The results for detected compounds are shown in Table 19.

(Analysis Condition)
  Mass spectrometer: Q-Exactive (Thermo Fisher Scientific K.K.)
  Spray Voltage: 3500 V
  Capillary Temperature: 400° C.
  HPLC: Ultimate3000 UPLC (Thermo Fisher Scientific K.K.)
  Column: Acquity UPLC HSS T3 column (Waters Corporation, 1.8 µm, 2.1 mm×50 mm)
  Solvent: solution A: 0.1% $HCOOH/CH_3CN$, solution B: 0.1% $HCOOH/H_2O$
  Gradient Condition:
    0.0 min; A/B=10:90
    0.0 to 2.0 min; Linear gradient from 10% to 90% A
    2.0 to 6.0 min; A/B=90:10
    6.0 to 8.0 min; A/B=10:90
  Flow Rate: 0.2 mL/min
  Column Temperature: 40° C.

TABLE 19

| Compound | Compound obtained | Theoretical value $(M + H)^+$ | Found value detected $(M + H)^+/min$ |
|---|---|---|---|
| Comparative Example ADC1 | Comparative Example compound 2 | 911.5429 | 911.5418/0.76 |
| Reference Example ADC1 | Example MM1 | 846.4435 | 846.4465/2.61 |

A test was separately conducted under the same conditions as in Test Example 5 using brentuximab, and the result was that the hemiasterlin derivative according to the present invention was not detected as a metabolite.

As shown in the above Table 19, it was confirmed that the hemiasterlin derivative according to the present invention is produced by allowing ADC to act on cells expressing an antigen.

Test Example 6: Cellular Toxicity Test for ADCs

Karpas-299 cells (ECACC), which are CD30 antigen-positive and HER2 antigen-negative, were cultured in RPMI 1640 (GIBCO) containing 10% fetal bovine serum (MP Biomedicals) (hereinafter, referred to as "culture medium A" in this test). In addition, SK-BR-3 cells (ATCC), which are CD30 antigen-negative and HER2 antigen-positive, were cultured in McCoy's 5A (GIBCO) containing 10% fetal bovine serum (MP Biomedicals) (hereinafter, referred to as "culture medium B" in this test). Karpas-299 cells and SK-BR-3 cells were prepared to be $2\times10^6$ cells/mL in culture medium A or culture medium B, and were added to a 96 well microplate for cell culturing in an amount of 50 µL for each well. After the addition, SK-BR-3 cells were cultured at 37° C. under 5% $CO_2$ overnight. ADCs 4 times diluted with culture medium A or culture medium B in 8 stages were added to the microplate in an amount of 50 μL for each well, and Karpas-299 cells and SK-BR-3 cells were cultured at 37° C. under 5% $CO_2$ for 4 days and 3 days, respectively. After culturing, the microplate was taken out from the incubator, and was left at rest at room temperature for 10 minutes. To each well, 50 μL of CellTiter-Glo Luminescent Cell Viability Assay (Promega) was added, and the resultant mixture was stirred. This mixture was incubated at a dark place for 20 minutes. Using a microplate luminometer, luminescence was measured, thereby calculating the cell viability for each concentration of the ADC. The $IC_{50}$ value was calculated in accordance with the method described in Test Example 3. The results are shown in Table 20.

TABLE 20

| Cell | Compound | IC50 (nM) |
| --- | --- | --- |
| Karpas-299 | Comparative Example ADC1 | 0.056 |
| (CD30 antigen-positive | Reference Example ADC1 | 0.020 |
| cell line) | Reference Example ADC2 | 0.020 |
| (HER2 antigen-negative | Reference Example ADC3 | 0.019 |
| cell line) | Reference Example ADC4 | 0.019 |
|  | Reference Example ADC5 | 0.036 |
|  | Reference Example ADC6 | 0.034 |
|  | Reference Example ADC7 | 0.046 |
|  | Reference Example ADC8 | 0.034 |
|  | Reference Example ADC9 | 3.77 |
|  | Reference Example ADC10 | >6.6 |
|  | Reference Example ADC11 | 0.114 |
|  | Reference Example ADC12 | 0.034 |
|  | Reference Example ADC13 | 0.588 |
|  | Reference Example ADC14 | 0.050 |
|  | Reference Example ADC15 | 0.495 |
|  | Reference Example ADC16 | 0.029 |
|  | Reference Example ADC19 | 0.004 |
|  | Reference Example ADC20 | 0.008 |
|  | Reference Example ADC21 | 0.022 |
|  | Reference Example ADC22 | 0.029 |
|  | Reference Example ADC23 | 0.029 |
|  | Reference Example ADC24 | 0.043 |
|  | Reference Example ADC25 | 0.046 |
|  | Reference Example ADC26 | 0.0098 |
|  | Reference Example ADC27 | 0.040 |
|  | Reference Example ADC28 | 0.036 |
|  | Reference Example ADC29 | 0.028 |
|  | Reference Example ADC30 | 0.015 |
|  | Reference Example ADC31 | 0.0072 |
|  | Reference Example ADC32 | 0.083 |
|  | Reference Example ADC33 | 0.011 |
|  | Reference Example ADC34 | 0.061 |
|  | Reference Example ADC35 | 0.018 |
|  | Reference Example ADC36 | 0.098 |
|  | Reference Example ADC37 | 0.030 |
|  | Reference Example ADC38 | 0.021 |
|  | Reference Example ADC39 | 0.042 |
|  | Reference Example ADC40 | 0.022 |
|  | Reference Example ADC45 | 1.98 |
| SK-BR-3 | Reference Example ADC1 | >6.6 |
| (CD30 antigen-negative | Reference Example ADC4 | >6.6 |
| cell line) | Reference Example ADC9 | 0.21 |
| (HER2 antigen-positive | Reference Example ADC10 | 0.18 |
| cell line) |  |  |

As shown in the above Table 20, the antibody-drug conjugate with brentuximab, which is a CD30 antigen-specific antibody, exhibited strong cytotoxic activity to Karpas-299 cells, which are CD30 antigen-positive cells, and exhibited weak cytotoxic activity to SK-BR-3 cells, which are CD30 antigen-negative cells. The antibody-drug conjugate with trastuzumab, which is a HER2 antigen-specific antibody, exhibited strong cytotoxic activity to SK-BR-3 cells, which are HER2 antigen-positive cells, and exhibited weak cytotoxic activity to Karpas-299 cells, which are HER2 antigen-negative cells.

Even a compound with weak cellular toxicity selectively exhibited strong cytotoxic activity by being produced through metabolism of an antibody-drug conjugate in antigen-positive cells that specifically bind to an antibody. That is, the Example compounds were revealed to selectively exhibit strong cytotoxic activity to positive cells that specifically bind to an antibody if being present in the cells through metabolism of an antibody-drug conjugate.

Test Example 7: Efficacy Test for Antibody-Drug Conjugates in Karpas-299 Tumor Type Using CB-17SCID Mice This test is a representative test for evaluating antitumor actions of drugs. Karpas human anaplastic giant cell lymphoma models are made by subcutaneously transplanting $5 \times 10^6$ cells to CB-17SCID mice. In such tumor models, treatment was initiated after the tumor reached a mean volume of 90 to 110 $mm^3$. To mice, a solution formed by dissolving Reference Example ADC in phosphate buffered saline is injected intravenously once. The tumor volume is calculated using the formula: 0.5 (longest dimension×vertical $dimension^2$). When the tumor reached about 2000 $mm^3$, the mouse was excluded from the test and the mean tumor size is no longer plotted. Note that the method of this test is described in Hamblett K. J. et al., Clin. Cancer Res., 2004, 10, 7063-7070 and the like.

Test Example 8: Toxicity (Safety) Test of Drug or Antibody-Drug Conjugate Using Mice or Rats This test is a representative test for evaluating toxicity (safety) of drugs or antibody-drug conjugates. The toxicity may be confirmed by single or repetitive tail intravenous administration of a drug or antibody-drug conjugate to mice or Sprague-Dawley rats and by performing general symptom observation, hematologic test, blood chemistry study, bone marrow examination, autopsy, organ weight, histopathologic examination and the like. Note that this test is described in New Edition Toxicology, edited by Board of Education in The Japanese Society of Toxicology, Asakura Publishing Co., Ltd., (2009).

From the above results, it was found that the Examples compounds exhibit lower activities in the cellular toxicity tests, compared to the Comparative Example compounds. On the other hand, the Example compounds did not lose tubulin polymerization inhibitory activity originating from the hemiasterlin structure. In addition, the antibody-drug conjugates that provide an Example compound by the action of protease expressed in target cells exhibited high activity in the cellular toxicity tests. As such, according to antibody-drug conjugates containing the Example compounds as a part of structure, it is suggested that, even if a drug moiety containing an antibody moiety is generated in the systemic blood and extracellularly released through metabolism of the antibody-drug conjugate, the induction of cellular toxicity to normal cells by the Example compounds can be suppressed, thereby reducing side effects.

INDUSTRIAL APPLICABILITY

As explained above, the hemiasterlin derivatives according to the present invention exhibits cytotoxic activity selectively in antigen-expressing cells and has low cytotoxicity in normal cells, and therefore, is expected to be an anticancer agent excellent in safety.

The invention claimed is:
1. A compound represented by formula (1) or (1'):
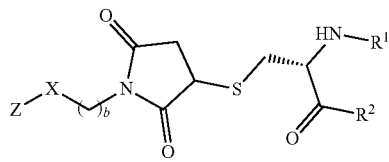
(1)
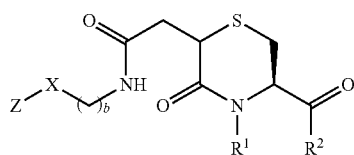
(1')
wherein
b represents an integer of 1 to 5;
X represents —NH— or —CO—;
Z represents a group represented by formula (Z-1), formula (Z-2), formula (Z-3), formula (Z-4), formula (Z-5), formula (Z-6), formula (Z-7), formula (Z-8), formula (Z-9), formula (Z-10) or formula (Z-11):
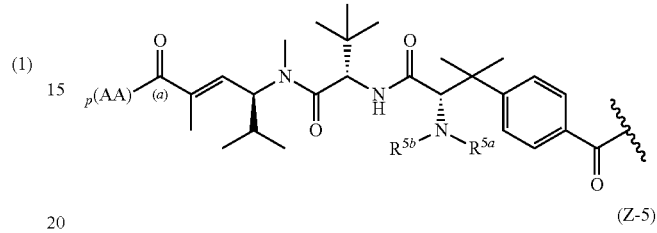
(Z-1)
(Z-2)
(Z-3)
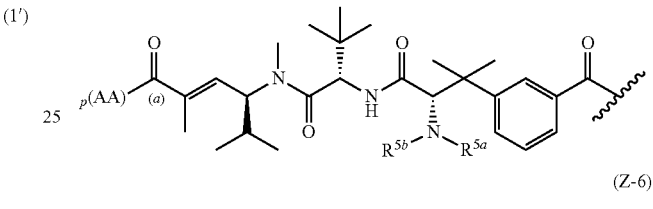
(Z-4)
(Z-5)
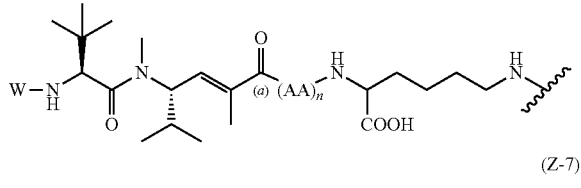
(Z-6)
(Z-7)
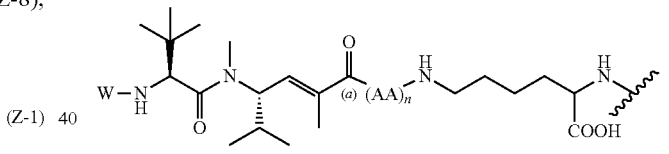
(Z-8)
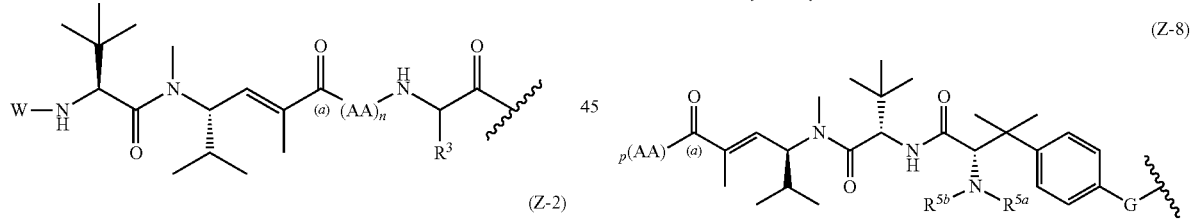
(Z-9)
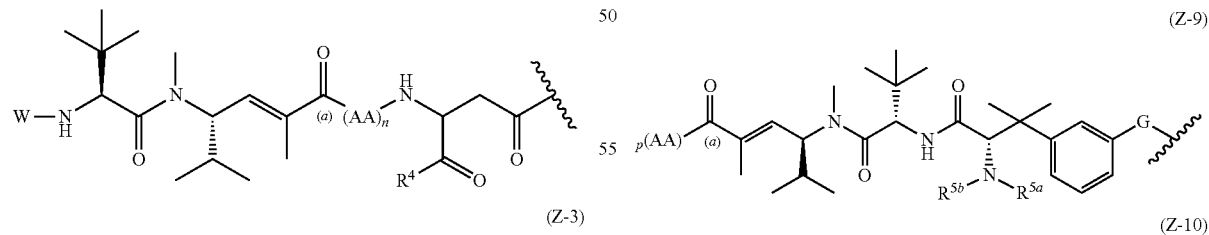
(Z-10)
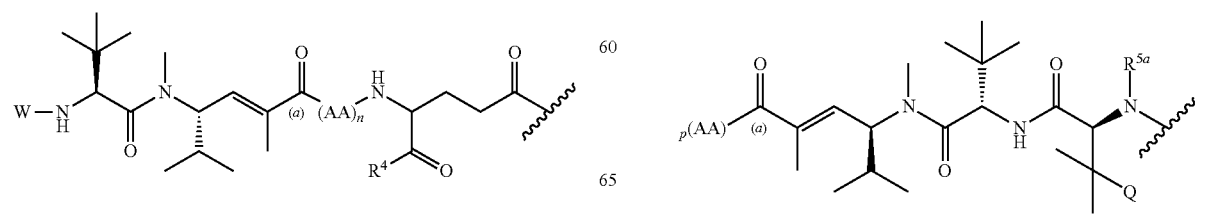

-continued (Z-11)

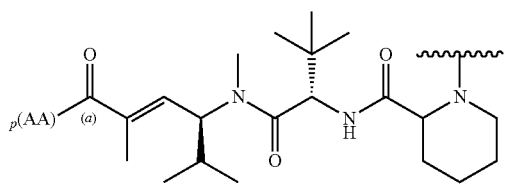

where
n represents an integer of 0 to 2;
p represents an integer of 1 to 3;
AA represents a glutamic acid residue (Glu), an aspartic acid residue (Asp) or a lysine residue (Lys), and when there is a plurality of AAs, each AA may be the same as or different from each other and AAs are bonded to each other via an amide bond, and an N-terminal nitrogen atom of $(AA)_n$ or $(AA)_p$ forms an amide bond together with carbonyl group (a);
G represents —O— or —NH—; and
W represents a group represented by formula (W-1) or formula (W-2):

(W-1)

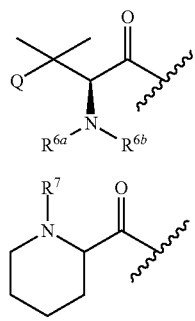

(W-2)

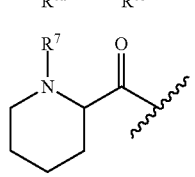

where
$R^{6a}$ and $R^{6b}$ each independently represent a hydrogen atom or a methyl group;
$R^7$ represents a $C_{1-6}$ alkyl group; and
Q represents a group represented by formula (Q-1), formula (Q-2), formula (Q-3), formula (Q-4), formula (Q-5), formula (Q-6) or formula (Q-7):

(Q-1)

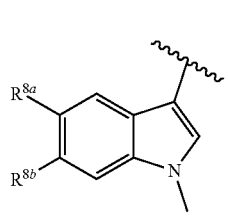

(Q-2)

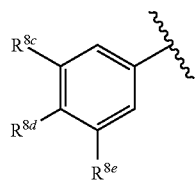

-continued (Q-3)

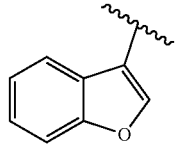

(Q-4)

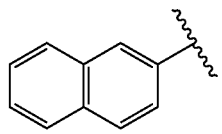

(Q-5)

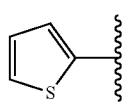

(Q-6)

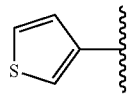

(Q-7)

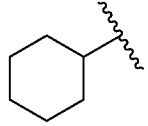

where
$R^{8a}$ and $R^{8b}$ each independently represent a hydrogen atom, a halogen atom, a $C_{1-6}$ alkyl group or a $C_{1-6}$ alkoxy group; and
$R^{8c}$, $R^{8d}$ and $R^{8e}$ each independently represent a hydrogen atom, a halogen atom, a hydroxy group, a cyano group, an amino group, a carboxyl group, a phenyl group, or a $C_{1-6}$ alkyl group, a $C_{1-6}$ alkoxy group or a $C_{1-6}$ alkyl ester group optionally substituted with 1 to 3 fluorine atoms;
$R^3$ represents —$(CH_2)_u$—$COR^9$;
u represents 1 or 2;
$R^4$ and $R^9$ each independently represent a hydroxy group or AD;
AD represents Glu, Asp or Lys, and an N-terminal nitrogen atom of AD forms an amide bond together with a neighboring carbonyl group;
with a proviso that when $R^4$ or $R^9$ is AD, n is 0 or 1; and
$R^{5a}$ and $R^{5b}$ each independently represent a hydrogen atom or a methyl group;
with a proviso that when X is —NH—, Z is formula (Z-1), formula (Z-2), formula (Z-3), formula (Z-4) or formula (Z-5), and when X is —CO—, Z is formula (Z-6), formula (Z-7), formula (Z-8), formula (Z-9), formula (Z-10) or formula (Z-11);
$R^1$ represents a hydrogen atom or $(AB)_m$;
AB represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ABs, each AB may be the same as or different from each other and ABs are bonded to each other via an amide bond;

m represents an integer of 1 to 9;

$R^2$ represents a hydroxy group or $(AC)_g$;

AC represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ACs, each AC may be the same as or different from each other and ACs are bonded to each other via an amide bond; and g represents an integer of 1 to 9;

with a proviso that when $R^1$ is $(AB)_m$ and $R^2$ is $(AC)_g$, a sum of m and g is an integer of 2 to 10, or a salt thereof.

2. The compound according to claim 1, wherein formula (1) and (1') are represented by formula (1-1) and (1'-1), respectively:

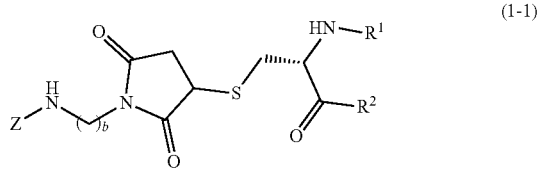

(1-1)

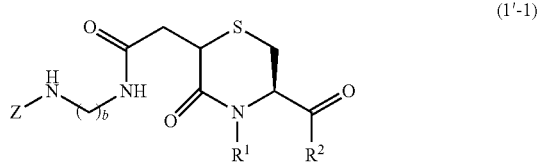

(1'-1)

wherein b represents an integer of 1 to 5;

Z represents a group represented by formula (Z-1), formula (Z-2), formula (Z-3), formula (Z-4) or formula (Z-5):

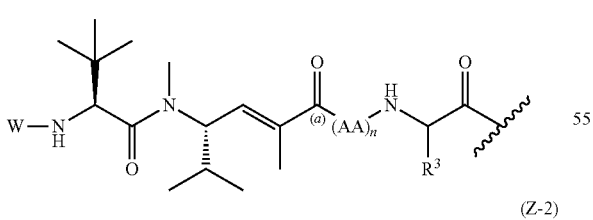

(Z-1)

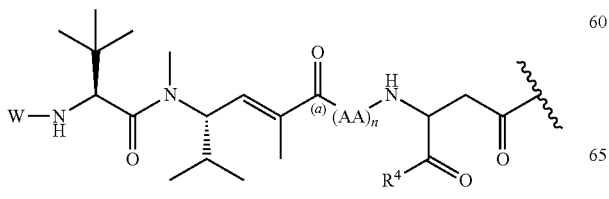

(Z-2)

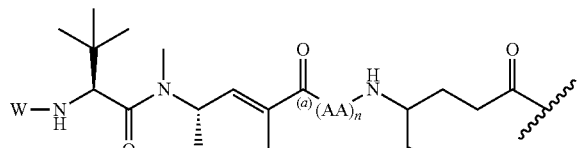

(Z-3)

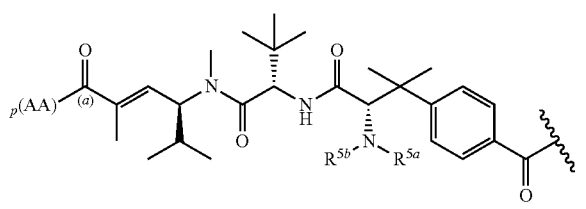

(Z-4)

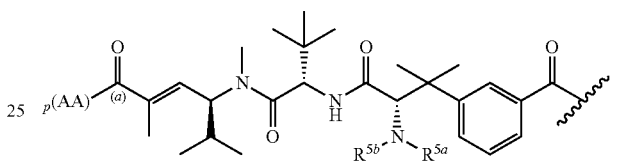

(Z-5)

where n represents an integer of 0 to 2;

p represents an integer of 1 to 3;

AA represents a glutamic acid residue (Glu), an aspartic acid residue (Asp) or a lysine residue (Lys), and when there is a plurality of AAs, each AA may be the same as or different from each other and AAs are bonded to each other via an amide bond, and an N-terminal nitrogen atom of $(AA)_n$ or $(AA)_p$ forms an amide bond together with carbonyl group (a); and W represents a group represented by formula (W-1) or formula (W-2):

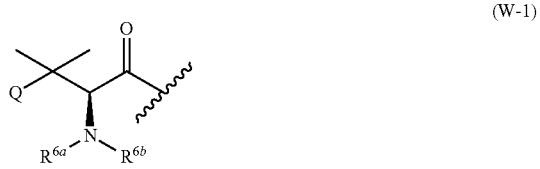

(W-1)

(W-2)

where $R^{6a}$ and $R^{6b}$ each independently represent a hydrogen atom or a methyl group;

$R^7$ represents a $C_{1-6}$ alkyl group; and

Q represents a group represented by formula (Q-1), formula (Q-2), formula (Q-3), formula (Q-4), formula (Q-5), formula (Q-6) or formula (Q-7):

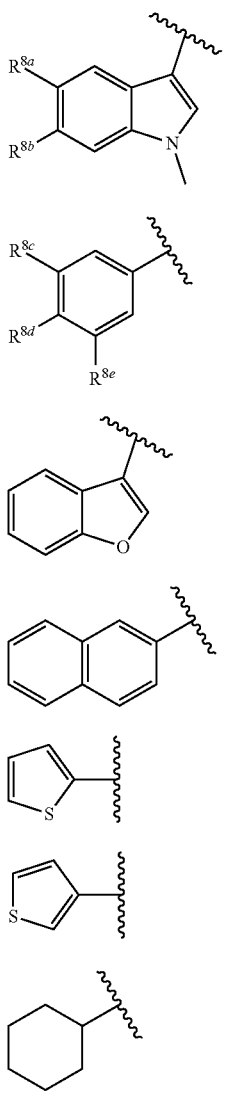

where
R$^{8a}$ and R$^{8b}$ each independently represent a hydrogen atom, a halogen atom, a C$_{1-6}$ alkyl group or a C$_{1-6}$ alkoxy group; and
R$^{8c}$, R$^{8d}$ and R$^{8e}$ each independently represent a hydrogen atom, a halogen atom, a hydroxy group, a cyano group, an amino group, a carboxyl group, a phenyl group, or a C$_{1-6}$ alkyl group, a C$_{1-6}$ alkoxy group or a C$_{1-6}$ alkyl ester group optionally substituted with 1 to 3 fluorine atoms;
R$^3$ represents —(CH$_2$)$_u$—COR$^9$;
u represents 1 or 2;
R$^4$ and R$^9$ each independently represent a hydroxy group or AD;
AD represents Glu, Asp or Lys, and an N-terminal nitrogen atom of AD forms an amide bond together with a neighboring carbonyl group;
with a proviso that when R$^4$ or R$^9$ is AD, n is 0 or 1; and
R$^{5a}$ and R$^{5b}$ each independently represent a hydrogen atom or a methyl group;
R$^1$ represents a hydrogen atom or (AB)$_m$;
AB represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ABs, each AB may be the same as or different from each other and ABs are bonded to each other via an amide bond;
m represents an integer of 1 to 9;
R$^2$ represents a hydroxy group or (AC)$_g$;
AC represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ACs, each AC may be the same as or different from each other and ACs are bonded to each other via an amide bond; and
g represents an integer of 1 to 9;
with a proviso that when R$^1$ is (AB)$_m$ and R$^2$ is (AC)$_g$, a sum of m and g is an integer of 2 to 10, or a salt thereof.

3. The compound according to claim 2, wherein
R$^7$ is a methyl group or an isopropyl group; and
Q is formula (Q-1), formula (Q-2), formula (Q-4), formula (Q-6) or formula (Q-7),
or a salt thereof.

4. The compound according to claim 2, wherein
p is 1;
W is formula (W-1);
Q is formula (Q-1) or formula (Q-2);
R$^{8a}$ and R$^{8b}$ are each independently a hydrogen atom, a fluorine atom or a methoxy group;
R$^{8c}$, R$^{8d}$ and R$^{8e}$ are each independently a hydrogen atom, a fluorine atom, a hydroxy group, a cyano group, an amino group, a carboxyl group, a methyl group, a trifluoromethyl group or a methoxy group; and
R$^4$ and R$^9$ are each a hydroxy group,
or a salt thereof.

5. The compound according to claim 2, wherein
Z is formula (Z-1), formula (Z-2) or formula (Z-3);
W is formula (W-1);
Q is formula (Q-1) or formula (Q-2);
R$^{8a}$ and R$^{8b}$ are each a hydrogen atom;
R$^{8c}$, R$^{8d}$ and R$^{8e}$ are each a hydrogen atom; and
R$^4$ and R$^9$ are each a hydroxy group,
or a salt thereof.

6. The compound according to claim 2, wherein b is 2, or a salt thereof.

7. The compound according to claim 1, wherein formula (1) and (1') are represented by formula (1-2) and (1'-2), respectively:

(1-2)

(1'-2)

wherein b represents an integer of 1 to 5;

Z represents a group represented by formula (Z-6), formula (Z-7), formula (Z-8), formula (Z-9), formula (Z-10) or formula (Z-11):

(Z-6)

(Z-7)

(Z-8)

(Z-9)

(Z-10)

(Z-11)

where n represents an integer of 0 to 2;

p represents an integer of 1 to 3;

AA represents a glutamic acid residue (Glu), an aspartic acid residue (Asp) or a lysine residue (Lys), and when there is a plurality of AAs, each AA may be the same as or different from each other and AAs are bonded to each other via an amide bond;

an N-terminal nitrogen atom of (AA) n or (AA) p forms an amide bond together with carbonyl group (a);

G represents —O— or —NH—; and

W represents a group represented by formula (W-1) or formula (W-2):

(W-1)

(W-2)

where $R^{6a}$ and $R^{6b}$ each independently represent a hydrogen atom or a methyl group;

$R^7$ represents a $C_{1-6}$ alkyl group; and

Q represents a group represented by formula (Q-1), formula (Q-2), formula (Q-3), formula (Q-4), formula (Q-5), formula (Q-6) or formula (Q-7):

(Q-1)

(Q-2)

-continued (Q-3)
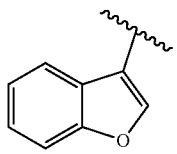

(Q-4)
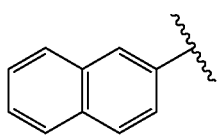

(Q-5)
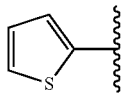

(Q-6)
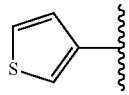

(Q-7)
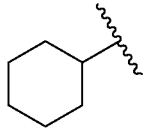

where
$R^{8a}$ and $R^{8b}$ each independently represent a hydrogen atom, a halogen atom, a C1-6 alkyl group or a C1-6 alkoxy group; and
$R^{8c}$, $R^{8d}$ and $R^{8e}$ each independently represent a hydrogen atom, a halogen atom, a hydroxy group, a cyano group, an amino group, a carboxyl group, a phenyl group, or a $C_{1-6}$ alkyl group, a $C_{1-6}$ alkoxy group or a $C_{1-6}$ alkyl ester group optionally substituted with 1 to 3 fluorine atoms; and
$R^{5a}$ and $R^{5b}$ each independently represent a hydrogen atom or a methyl group; and
$R^1$ represents a hydrogen atom or (AB) m;
AB represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ABs, each AB may be the same as or different from each other and ABs are bonded to each other via an amide bond;
m represents an integer of 1 to 9;
$R^2$ represents a hydroxy group or $(AC)_g$;
AC represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val), and when there is a plurality of ACs, each AC may be the same as or different from each other and ACs are bonded to each other via an amide bond; and
g represents an integer of 1 to 9;
with a proviso that when $R^1$ is (AB) m and $R^2$ is $(AC)_g$, a sum of m and g is an integer of 2 to 10,
or a salt thereof.

8. The compound according to claim 7, wherein
Z is formula (Z-6), formula (Z-7), formula (Z-8) or formula (Z-9);
$R^7$ is a methyl group or an isopropyl group; and
Q is formula (Q-1), formula (Q-2), formula (Q-4), formula (Q-6) or formula (Q-7),
or a salt thereof.

9. The compound according to claim 7, wherein
Z is formula (Z-6) or formula (Z-7);
W is formula (W-1);
Q is formula (Q-1) or formula (Q-2);
$R^{8a}$ and $R^{8b}$ are each independently a hydrogen atom, a fluorine atom or a methoxy group; and
$R^{8c}$, $R^{8d}$ and $R^{8e}$ are each independently a hydrogen atom, a fluorine atom, a hydroxy group, a cyano group, an amino group, a carboxyl group, a methyl group, a trifluoromethyl group or a methoxy group,
or a salt thereof.

10. The compound according to claim 7, wherein
$R^{8a}$ and $R^{8b}$ are each a hydrogen atom; and
$R^{8c}$, $R^{8d}$ and $R^{8e}$ are each a hydrogen atom,
or a salt thereof.

11. The compound according to claim 7, wherein b is 3, or a salt thereof.

12. The compound according to claim 1, wherein
$(AB)_m$ is an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr), a valine residue (Val), *¹-(Glu)-(Gly), *¹-(Glu)-(Gly)-(Arg), *¹-(Glu)-(Gly)-(Arg)-(Asn), *¹-(Glu)-(Gly)-(Arg)-(Asn)-(Phe), *¹-(Glu)-(Gly)-(Arg)-(Asn)-(Phe)-(Ser), *¹-(Glu)-(Gly)-(Arg)-(Asn)-(Phe)-(Ser)-(Lys), *¹-(Glu)-(Gly)-(Arg)-(Asn)-(Phe)-(Ser)-(Lys)-(Thr) or *¹-(Glu)-(Gly)-(Arg)-(Asn)-(Phe)-(Ser)-(Lys)-(Thr)-(Val), where
terminus *¹ represents amide bonding to a cysteine residue; and
$(AC)_g$ is a glycine residue (Gly) or a proline residue (Pro), or a salt thereof.

13. The compound according to claim 1, wherein
$(AB)_m$ is an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr) or a valine residue (Val); and (AC)$_g$ is a glycine residue (Gly),
or a salt thereof.

14. The compound according to claim 1, wherein R$^1$ is a hydrogen atom; and R$^2$ is a hydroxy group,
or a salt thereof.

15. The compound according to claim 1, wherein (AA)$_n$ is a group represented by formula (A-1):

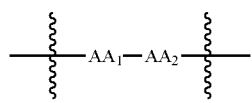
(A-1)

where
AA$_1$ and AA$_2$ each independently represent Glu, Asp or Lys,
or a salt thereof.

16. The compound according to claim 1, wherein (AA)$_n$ is a group represented by formula (A-2):

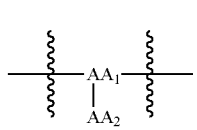
(A-2)

where
AA$_1$ and AA$_2$ each independently represent Glu, Asp or Lys,
or a salt thereof.

17. The compound according to claim 1, wherein n is 0 or 1, or a salt thereof.

18. The compound according to claim 1, wherein the compound is selected from the following:

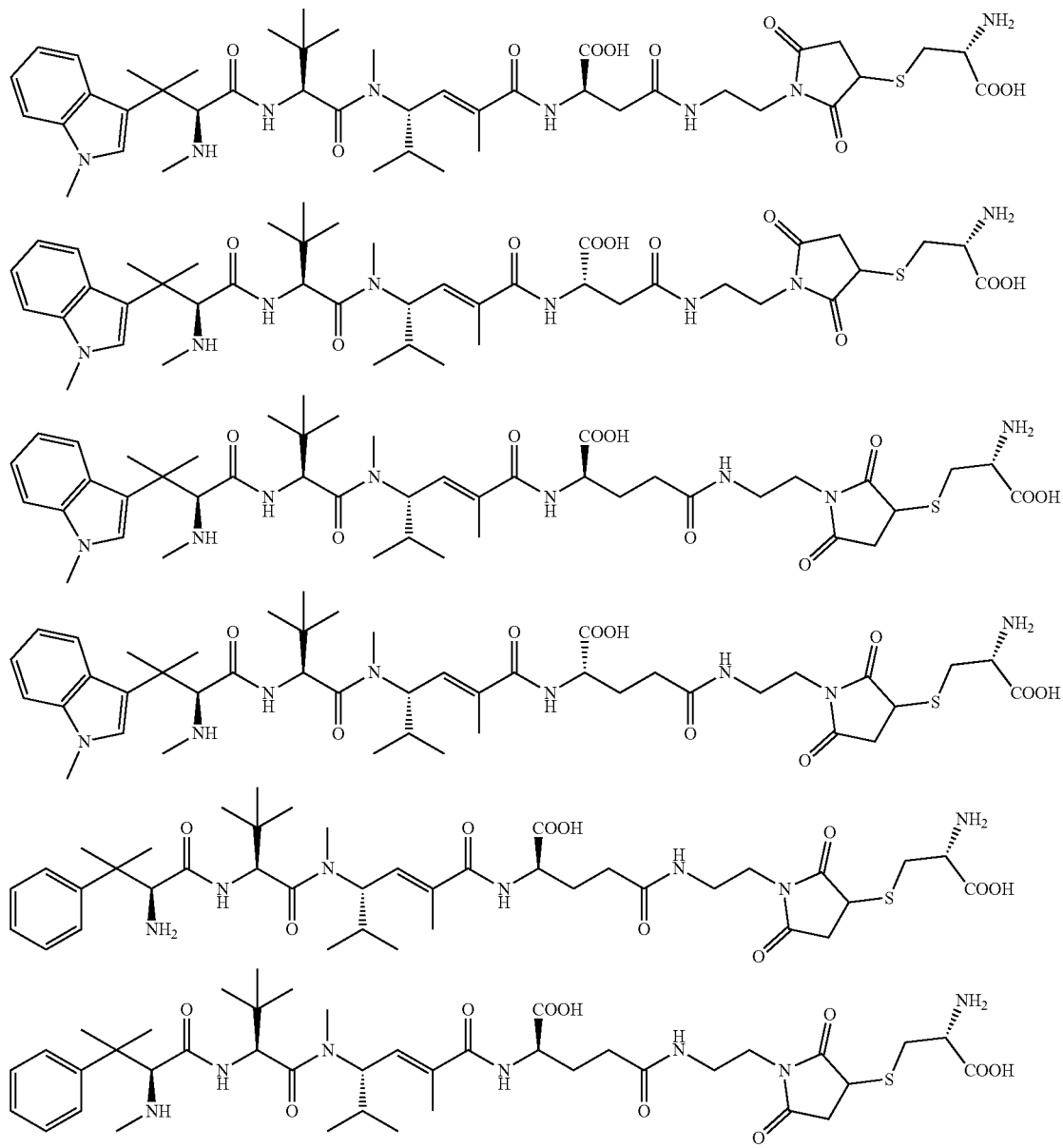

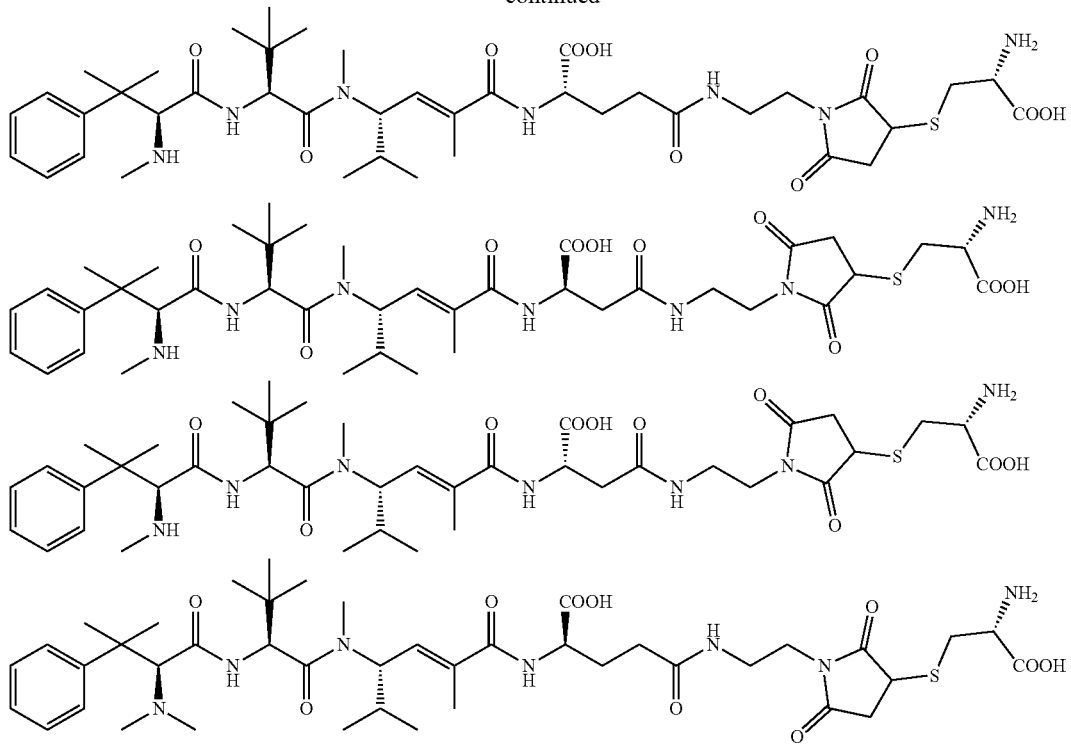
or a salt thereof.
19. The compound according to claim 1, wherein the compound is selected from the following:
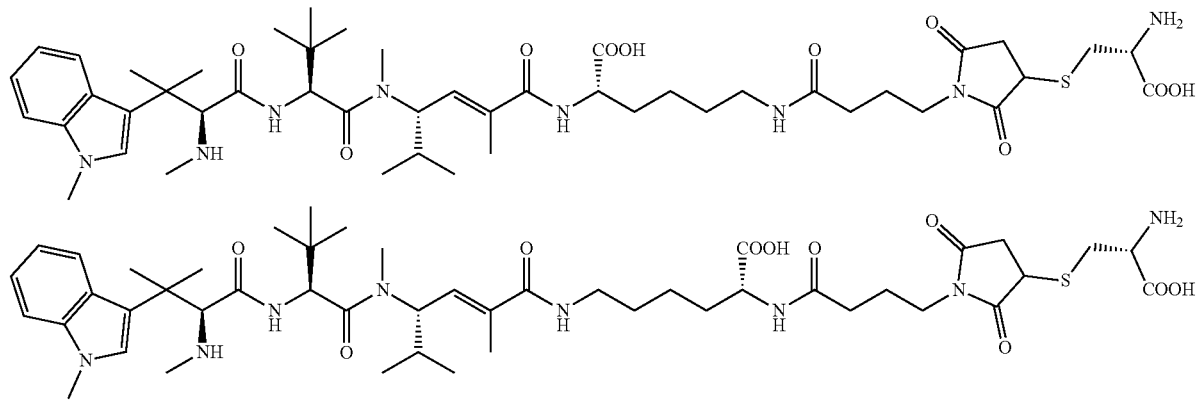
or a salt thereof.
20. The compound according to claim 1, wherein the compound is:
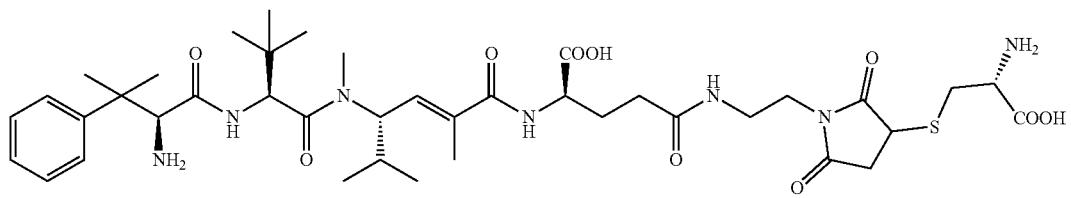 [SMILES: C/C(=C\[C@H](C(C)C)N(C)C(=O)[C@@H](NC(=O)[C@@H](N)C(C)(C)c1ccccc1)C(C)(C)C)C(=O)N[C@H](CCC(=O)NCCN1C(=O)CC(SC[C@H](N)C(=O)O)C1=O)C(=O)O]
or a salt thereof.

21. The compound according to claim 1, wherein the compound is:

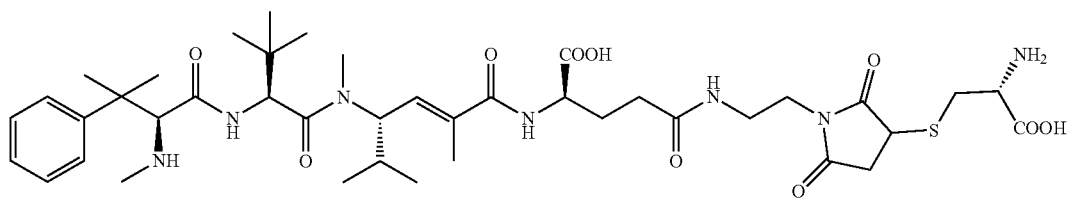 [SMILES: CN[C@H](C(=O)N[C@H](C(=O)N(C)[C@H](/C=C(\C)C(=O)N[C@H](CCC(=O)NCCN1C(=O)CC(SC[C@H](N)C(=O)O)C1=O)C(=O)O)C(C)C)C(C)(C)C)C(C)(C)c1ccccc1]

or a salt thereof.

22. The compound according to claim 1, wherein the compound is:

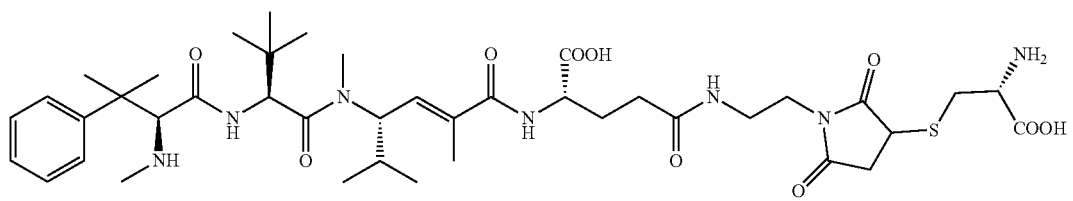 [SMILES: CN[C@H](C(=O)N[C@H](C(=O)N(C)[C@H](/C=C(\C)C(=O)N[C@@H](CCC(=O)NCCN1C(=O)CC(SC[C@H](N)C(=O)O)C1=O)C(=O)O)C(C)C)C(C)(C)C)C(C)(C)c1ccccc1]

or a salt thereof.

23. The compound according to claim 1, wherein the compound is:

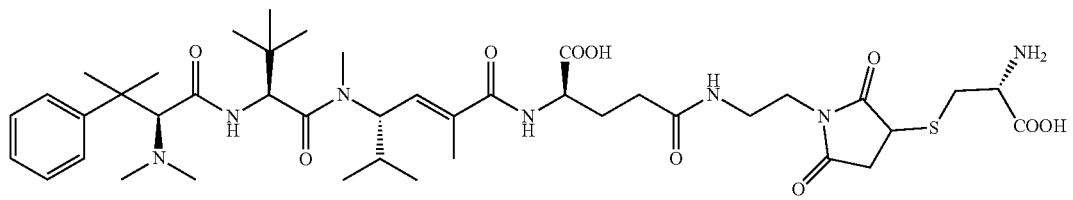 [SMILES: C/C(=C\[C@H](C(C)C)N(C)C(=O)[C@@H](NC(=O)[C@@H](N(C)C)C(C)(C)c1ccccc1)C(C)(C)C)C(=O)N[C@H](CCC(=O)NCCN1C(=O)CC(SC[C@H](N)C(=O)O)C1=O)C(=O)O]

or a salt thereof.

24. A pharmaceutical composition comprising the compound according to claim 1 or a pharmaceutically acceptable salt thereof.

25. An anticancer agent comprising the compound according to claim 1 or a pharmaceutically acceptable salt thereof.

26. A method of treating cancer, comprising administering an antibody-drug conjugate which releases the compound according to claim 1 or a pharmaceutically acceptable salt thereof in cells through metabolism to a patient in need thereof.

* * * * *

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Example of (AB)m

<400> SEQUENCE: 1

Asn Arg Gly Glu
1

<210> SEQ ID NO 2
<211> LENGTH: 5
<212> TYPE: PRT
<213> ORGANISM: Artificial Sequence
<220> FEATURE:
<223> OTHER INFORMATION: Example of (AB)m

<400> SEQUENCE: 2

Phe Asn Arg Gly Glu
1               5

<210> SEQ ID NO 3
<211> LENGTH: 6
<212> TYPE: PRT
<213> ORGANISM: Artificial Sequence
<220> FEATURE:
<223> OTHER INFORMATION: Example of (AB)m

<400> SEQUENCE: 3

Ser Phe Asn Arg Gly Glu
1               5

<210> SEQ ID NO 4
<211> LENGTH: 7
<212> TYPE: PRT
<213> ORGANISM: Artificial Sequence
<220> FEATURE:
<223> OTHER INFORMATION: Example of (AB)m

<400> SEQUENCE: 4

Lys Ser Phe Asn Arg Gly Glu
1               5

<210> SEQ ID NO 5
<211> LENGTH: 8
<212> TYPE: PRT
<213> ORGANISM: Artificial Sequence
<220> FEATURE:
<223> OTHER INFORMATION: Example of (AB)m

<400> SEQUENCE: 5

Thr Lys Ser Phe Asn Arg Gly Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Example of (AB)m
```

```
<400> SEQUENCE: 6
Val Thr Lys Ser Phe Asn Arg Gly Glu
1               5
```